(12) United States Patent
Frueh et al.

(10) Patent No.: US 10,995,121 B2
(45) Date of Patent: *May 4, 2021

(54) HUMAN CYTOMEGALOVIRUS COMPRISING EXOGENOUS ANTIGENS

(71) Applicant: Oregon Health & Science University, Portland, OR (US)

(72) Inventors: Klaus Frueh, Portland, OR (US); Scott G. Hansen, Portland, OR (US); Jay Nelson, Lake Oswego, OR (US); Louis Picker, Portland, OR (US); Patrizia Caposio, Beaverton, OR (US)

(73) Assignee: Oregon Health & Science University, Portland, OR (US)

(*) Notice: Subject to any disclaimer, the term of this patent is extended or adjusted under 35 U.S.C. 154(b) by 0 days.

This patent is subject to a terminal disclaimer.

(21) Appl. No.: 16/545,561

(22) Filed: Aug. 20, 2019

(65) Prior Publication Data

US 2020/0102354 A1  Apr. 2, 2020

Related U.S. Application Data

(63) Continuation of application No. 15/326,444, filed as application No. PCT/US2015/040807 on Jul. 16, 2015, now Pat. No. 10,428,118.

(60) Provisional application No. 62/025,348, filed on Jul. 16, 2014.

(51) Int. Cl.
| | |
|---|---|
| *C07K 14/045* | (2006.01) |
| *A61K 39/12* | (2006.01) |
| *C12N 15/86* | (2006.01) |
| *A61K 35/33* | (2015.01) |
| *A61K 39/00* | (2006.01) |
| *A61K 39/39* | (2006.01) |
| *C12N 15/85* | (2006.01) |
| *A61K 39/21* | (2006.01) |
| *C07K 14/16* | (2006.01) |
| *A61P 35/00* | (2006.01) |

(52) U.S. Cl.
CPC ............ *C07K 14/045* (2013.01); *A61K 35/33* (2013.01); *A61K 39/0011* (2013.01); *A61K 39/12* (2013.01); *A61K 39/39* (2013.01); *C12N 15/85* (2013.01); *C12N 15/86* (2013.01); *A61K 39/21* (2013.01); *A61K 2039/5254* (2013.01); *A61K 2039/5256* (2013.01); *A61K 2039/572* (2013.01); *A61P 35/00* (2018.01); *C07K 14/161* (2013.01); *C12N 2710/16143* (2013.01); *C12N 2740/15034* (2013.01); *C12N 2740/16234* (2013.01)

(58) Field of Classification Search
CPC .. C07K 14/005; C07K 16/088; C07K 14/045; C12N 15/86; C12N 15/869; C12N 7/00; C12N 2710/00011; C12N 2710/16111; C12N 2710/16143; A61K 39/245; A61K 39/12; A61K 35/763; A61K 38/162; A61K 2039/525; A61K 2039/5256; A61K 2039/6075

See application file for complete search history.

(56) References Cited

U.S. PATENT DOCUMENTS

| | | |
|---|---|---|
| 5,168,062 A | 12/1992 | Stinski |
| 5,273,876 A | 12/1993 | Hock et al. |
| 5,385,839 A | 1/1995 | Stinski |
| 5,720,957 A | 2/1998 | Jones et al. |
| 5,830,745 A | 11/1998 | Hock et al. |
| 5,833,993 A | 11/1998 | Wardley et al. |
| 6,033,671 A | 3/2000 | Frueh et al. |
| 7,537,770 B2 | 5/2009 | Kemble et al. |
| 7,892,822 B1 | 2/2011 | Koszinowski et al. |
| 9,249,427 B2* | 2/2016 | Picker ............... A61K 39/08 |
| 9,541,553 B2 | 1/2017 | Picker et al. |
| 9,783,823 B2 | 10/2017 | Picker et al. |
| 9,862,972 B2 | 1/2018 | Picker et al. |
| 9,982,241 B2 | 5/2018 | Picker et al. |
| 10,101,329 B2 | 10/2018 | Picker et al. |
| 10,167,321 B2 | 1/2019 | Carfi et al. |
| 10,316,334 B2 | 6/2019 | Picker et al. |
| 10,428,118 B2* | 10/2019 | Frueh ............... A61P 31/00 |
| 10,532,099 B2 | 1/2020 | Picker et al. |
| 10,688,164 B2 | 6/2020 | Nelson et al. |
| 10,760,097 B2 | 9/2020 | Picker et al. |
| 2002/0176870 A1* | 11/2002 | Schall ............... C12N 15/86 |
| | | 424/230.1 |
| 2003/0118568 A1 | 6/2003 | Crew |

(Continued)

FOREIGN PATENT DOCUMENTS

| | | |
|---|---|---|
| EP | 0521427 A1 | 1/1993 |
| WO | WO-8810311 A1 | 12/1988 |

(Continued)

OTHER PUBLICATIONS

Murphy E, Shenk T. Human cytomegalovirus genome. Curr Top Microbiol Immunol. 2008;325:1-19. (Year: 2008).*

(Continued)

*Primary Examiner* — Rachel B Gill

(74) *Attorney, Agent, or Firm* — Sterne, Kessler, Goldstein & Fox P.L.L.C.

(57) ABSTRACT

Human cytomegalovirus vectors comprising heterologous antigens are disclosed. The vectors derived from the TR strain, are ganciclovir-sensitive, include active US2, US3, US6, US7 and UL131A genes, and have a deleterious or inactivating mutation in the UL82 gene preventing the expression of pp71.

30 Claims, 19 Drawing Sheets

Specification includes a Sequence Listing.

(56) References Cited

U.S. PATENT DOCUMENTS

| | | |
|---|---|---|
| 2003/0138454 A1 | 7/2003 | Hill et al. |
| 2004/0086489 A1 | 5/2004 | Schall et al. |
| 2004/0110188 A1 | 6/2004 | Hahn et al. |
| 2004/0248300 A1 | 12/2004 | Preston |
| 2005/0064394 A1 | 3/2005 | Liu et al. |
| 2005/0118192 A1 | 6/2005 | Boursnell et al. |
| 2006/0019369 A1 | 1/2006 | Hahn |
| 2008/0071037 A1 | 3/2008 | Carr et al. |
| 2008/0199493 A1 | 8/2008 | Picker et al. |
| 2009/0148435 A1 | 6/2009 | Lebreton et al. |
| 2009/0148447 A1 | 6/2009 | Ledbetter et al. |
| 2009/0148477 A1 | 6/2009 | Bruder et al. |
| 2009/0203144 A1 | 8/2009 | Beaton et al. |
| 2009/0297555 A1 | 12/2009 | Kemble et al. |
| 2010/0142823 A1 | 6/2010 | Wang et al. |
| 2013/0089559 A1 | 4/2013 | Grawunder et al. |
| 2013/0136768 A1 | 5/2013 | Picker et al. |
| 2013/0142823 A1 | 6/2013 | Picker et al. |
| 2013/0156808 A1 | 6/2013 | Jonjic |
| 2013/0202638 A1 | 8/2013 | Thirion et al. |
| 2014/0141038 A1 | 5/2014 | Picker et al. |
| 2016/0010112 A1 | 1/2016 | Picker et al. |
| 2016/0114027 A1 | 4/2016 | Hahn et al. |
| 2016/0354461 A1 | 12/2016 | Picker et al. |
| 2017/0143809 A1 | 5/2017 | Nelson et al. |
| 2017/0350887 A1 | 12/2017 | Picker et al. |
| 2018/0016599 A1 | 1/2018 | Evans et al. |
| 2018/0087069 A1 | 3/2018 | Picker et al. |
| 2018/0133321 A1 | 5/2018 | Picker et al. |
| 2018/0282378 A1 | 10/2018 | Frueh et al. |
| 2018/0298404 A1 | 10/2018 | Frueh et al. |
| 2019/0099479 A1 | 4/2019 | Picker et al. |
| 2020/0140888 A1 | 5/2020 | Picker et al. |
| 2020/0237915 A1 | 7/2020 | Picker et al. |

FOREIGN PATENT DOCUMENTS

| | | |
|---|---|---|
| WO | WO-9503399 A2 | 2/1995 |
| WO | WO-9604383 A1 | 2/1996 |
| WO | WO-9631241 A1 | 10/1996 |
| WO | WO-9906582 A1 | 2/1999 |
| WO | WO-9907869 A1 | 2/1999 |
| WO | WO-02062296 A2 | 8/2002 |
| WO | WO-2003093455 A2 | 11/2003 |
| WO | WO-2006031264 A2 | 3/2006 |
| WO | WO-2006125983 A1 | 11/2006 |
| WO | WO-2010101663 A2 | 9/2010 |
| WO | WO-2011093858 A1 | 8/2011 |
| WO | WO-2011119920 A2 | 9/2011 |
| WO | WO-2011138040 A2 | 11/2011 |
| WO | WO-2011143650 A2 | 11/2011 |
| WO | WO-2011143653 A2 | 11/2011 |
| WO | WO-2012170765 A2 | 12/2012 |
| WO | WO-2014138209 A1 | 9/2014 |
| WO | WO-2016011293 A1 | 1/2016 |
| WO | WO-2016130693 A1 | 8/2016 |
| WO | WO-2017087921 A1 | 5/2017 |
| WO | WO-2018005559 A1 | 1/2018 |

OTHER PUBLICATIONS

Michel D, Miloti´cI, Wagner M, Vaida B, Holl J, Ansorge R, Mertens T. The human cytomegalovirus UL78 gene is highly conserved among clinical isolates, but is dispensable for replication in fibroblasts and a renal artery organ-culture system. J Gen Virol. Feb. 2005;86(Pt 2):297-306. (Year: 2005).*

Montaner S, Kufareva I, Abagyan R, Gutkind JS. Molecular mechanisms deployed by virally encoded G protein-coupled receptors in human diseases. Annu Rev Pharmacol Toxicol. 2013;53:331-54. Epub Oct. 22, 2012. (Year: 2012).*

Basta, S., et al., "Inhibitory Effects of Cytomegalovirus Proteins Us2 and Us11 Point to Contributions From Direct Priming and Cross-priming in Induction of Vaccinia Virus-specific Cd8(+) T Cells," Journal of Immunology 168(11):5403-5408, American Association of Immunologists, United States (Jun. 2002).

Besold, K., et al., "Immune Evasion Proteins GpUS2 and GpUS11 of Human Cytomegalovirus Incompletely Protect Infected Cells From CD8 T Cell Recognition," Virology 391(1):5-19, Academic Press, United States (Aug. 2009).

Borst, E and Messerle, M, "Development of a Cytomegalovirus Vector for Somatic Gene Therapy," Bone Marrow Transplant 25 Suppl 2:S80-S82, Nature Publishing Group (May 2000).

Borst, E.M and Messerle, M, "Construction of a Cytomegalovirus-based Amplicon: a Vector With a Unique Transfer Capacity," Human Gene Therapy 14(10):959-970, M.A. Liebert, United States (Jul. 2003).

Bresnahan, W.A and Shenk, T.E, "UL82 Virion Protein Activates Expression of Immediate Early Viral Genes in Human Cytomegalovirus-infected Cells," Proceedings of the National Academy of Sciences of the United States of America 97(26):14506-14511, National Academy of Sciences, United States (Dec. 2000).

Bresnahan, W.A., et al., "Replication of Wild-type and Mutant Human Cytomegalovirus in Life-extended Human Diploid Fibroblasts," Journal of Virology 74(22):10816-10818, American Society for Microbiology, United States (Nov. 2000).

Brondke, H. "Human Herpesvirus 5, Towne Strain," US3 (NCBI GenBank Acc. No. AAS49002), Dep. Apr. 8, 2004.

Brondke, H. "Human Herpesvirus 5, Towne Strain," US6 (NCBI GenBank Acc. No. AAS49004), Dep. Apr. 8, 2004.

Brown, B.D and Naldini.L, "Exploiting and Antagonizing MicroRNA Regulation for Therapeutic and Experimental Applications," Nature reviews Genetics 10(8):578-585, Nature Publishing Group, England (Aug. 2009).

Campadelli-Flume, et al., Editors, "Chapter 15: Betaherpes Viral Genes and Their Functions" Human Herpesviruses: Biology, Therapy, and Immunoprophylaxis. Cambridge: Cambridge University Press, 2007.

Cantrell, S.R and Bresnahan, W.A, "Human Cytomegalovirus (Hcmv) UL82 Gene Product (pp71) Relieves hDaxx-mediated Repression of Hcmv Replication," Journal of Virology 80(12):6188-6191, American Society for Microbiology, United States (Jun. 2006).

Cantrell, S.R and Bresnahan, W.A, "Interaction Between the Human Cytomegalovirus UL82 Gene Product (pp71) and HDaxx Regulates Immediate-early Gene Expression and Viral Replication," Journal of Virology 79(12):7792-7802, American Society for Microbiology, United States (Jun. 2005).

Chang, W.L and Barry, P.A, "Cloning of the Full-length Rhesus Cytomegalovirus Genome as an Infectious and Self-Excisable Bacterial Artificial Chromosome for Analysis of Viral Pathogenesis," Journal of Virology 77(9):5073-5083, American Society for Microbiology, United States (May 2003).

Chau, N.H., et al., "Transcriptional Regulation of the Human Cytomegalovirus Us11 Early Gene," Journal of Virology 73(2):863-870, American Society for Microbiology, United States (Feb. 1999).

Davison, A.J and Stow, N.D, "New Genes From Old: Redeployment of DUTPase by Herpesviruses," Journal of Virology 79(20):12880-12892, American Society for Microbiology, United States (Oct. 2005).

Dudek, T and Knipe, D.M, "Replication-defective Viruses as Vaccines and Vaccine Vectors," Virology 344(1):230-239, Academic Press, United States (Jan. 2006).

Dunn, W., et al., "Functional Profiling of a Human Cytomegalovirus Genome," Proceedings of the National Academy of Sciences of the United States of America 100(24):14223-14228, National Academy of Sciences, United States (Nov. 2003).

European Search Report for EP Application No. EP16200334, The Hague, dated May 18, 2017.

European Search Report for EP Application No. EP17197412, Munich, Germany, dated Apr. 23, 2018.

Prod'Homme, V., et al., "Human Cytomegalovirus UL40 Signal peptide Regulates Cell Surface Expression of the NK Cell Ligands HLA-E and gpUL18," J. Immunology 188(6):2794-2804, American Society of Immunologist, United States (2012).

Goodrum, F., et al., "Human Cytomegalovirus Persistence," Cellular Microbiology 14(5):644-655, Wiley-Blackwell, England (May 2012).

(56) References Cited

OTHER PUBLICATIONS

Gorman, S., et al., "Prior Infection with Murine Cytomegalovirus (Mcmv) Limits the Immunocontraceptive Effects of an MCMV Vector Expressing the Mouse Zona-Pellucida-3 Protein," Vaccine 26(31):3860-3869, Elsevier Science, Netherlands (Jul. 2008).
Grimwood, J., et al. "NCBI GenBank Direct Submission," Ace. No. AC146906, Sub. Nov. 5, 2003.
Hagemier, S.C., "Functional Analysis of the Human Cytomegalovirus UL82 gene product PP71 protein during Virus Replication," Doctoral Dissertation, The University of Texas Southwestern Medical Center at Dallas, May 2007, pp. 1-181.
Hahn, G., et al., "Human Cytomegalovirus UL131-128 Genes are Indispensable for Virus Growth in Endothelial Cells and Virus Transfer to Leukocytes," Journal of Virology 78(18):10023-10033, American Society for Microbiology, United States (Sep. 2004).
Halary, F., et al., "Human Cytomegalovirus Binding to DC-SIGN is Required for Dendritic Cell Infection and Target Cell Trans-Infection," Immunity 17(5):653-664, Cell Press, United States (Nov. 2002 ).
Hansen, S.G., et al., "Complete Sequence and Genomic Analysis of Rhesus Cytomegalovirus," Journal of Virology 77(12):6620-6636, American Society for Microbiology, United States (Jun. 2003).
Hansen, S.G., et al., "Effector Memory T Cell Responses are Associated With Protection of Rhesus Monkeys From Mucosal Simian Immunodeficiency Virus Challenge," Nature Medicine 15(3):293-299, Nature Publishing Company, United States (Mar. 2009).
Hansen, S.G., et al., "Evasion of Cd8+ T Cells Is Critical for Superinfection by Cytomegalovirus," Science 328(5974):102-106, American Association for the Advancement of Science, United States (Apr. 2010).
Hansen, S.G., et al., "Profound Early Control of Highly Pathogenic SIV by an Effector Memory T-cell Vaccine," Nature 473(7348):523-527, Nature Publishing Group, England (May 2011).
International Search Report and Written opinion for International Application No. PCT/US2011/036657, Korean Intellectual Property Office, Republic of Korea, dated Mar. 2012, 12 pages.
Jones, T.R., et al., "Multiple Independent Loci Within the Human Cytomegalovirus Unique Short Region Down-regulate Expression of Major Histocompatibility Complex Class I Heavy Chains," Journal of Virology 69(8):4830-4841, American Society for Microbiology, United States (Aug. 1995).
Jones, T.R., et al., "Replacement Mutagenesis of the Human Cytomegalovirus Genome: US10 and US11 Gene Products are Nonessential," Journal of Virology 65(11):5860-5872, American Society for Microbiology, United States (Nov. 1991).
Kaech, S.M., et al., "Effector and Memory T-cell Differentiation: Implications for Vaccine Development," Nature Reviews. Immunology 2(4):251-262, Nature Pub. Group, England (2002).
Kalejta, R.F, "Human Cytomegalovirus PP71: a New Viral Tool to Probe the Mechanisms of Cell Cycle Progression and Oncogenesis Controlled by the Retinoblastoma Family of Tumor Suppressors," Journal of Cellular Biochemistry 93(1):37-45, Wiley-Liss, United States (Sep. 2004).
Karrer, U., et al., "Expansion of Protective CD8+ T-Cell Responses Driven by Recombinant Cytomegaloviruses," Journal of Virology 78(5):2255-2264, American Society for Microbiology, United States (Mar. 2004).
Kropff, B and Mach, M, "Identification of the Gene Coding for Rhesus Cytomegalovirus Glycoprotein B and Immunological Analysis of the Protein," 78(Pt 8):1999-2007, Microbiology Society, England (Aug. 1997).
Lilja, A.E., et al., "Functional Genetic Analysis of Rhesus Cytomegalovirus: Rh01 Is an Epithelial Cell Tropism Factor," Journal of Virology 82(5):2170-2181, American Society for Microbiology, United States (Mar. 2008).
Mahmood, K., et al., "Human Cytomegalovirus Plasmid-based Amplicon Vector System for Gene Therapy," Genetic vaccines and therapy 3(1):1, BioMed Central, England (Jan. 2005).

Marshall, K.R., et al., "Activity and Intracellular Localization of the Human Cytomegalovirus Protein PP71," The Journal of general virology 83(Pt 7):1601-1612, Microbiology Society, England (Jul. 2002).
Maussang, D., et al., "Human Cytomegalovirus-encoded Chemokine Receptor US28 Promotes Tumorigenesis," Proceedings of the National Academy of Sciences of the United States of America 103(35):13068-13073, National Academy of Sciences, United States (Aug. 2006).
McGregor, A., et al., "Molecular, Biological, and in Vivo Characterization of the Guinea Pig Cytomegalovirus (CMV) Homologs of the Human Cmv Matrix Proteins pp71 (UL82) and pp65 (UL83)," Journal of virology 78(18):9872-9889, American Society for Microbiology, United States (Sep. 2004).
Mohr, C.A., et al., "A Spread-deficent Cytomegalovirus for Assessment of First-target Cells in Vaccination," Journal of virology 84(15):7730-7742, American Society for Microbiology, United States (Aug. 2010 ).
Mohr, C.A., et al., "Engineering of Cytomegalovirus Genomes for Recombinant Live Herpesvirus Vaccines," International Journal of Medical Microbiology 298(1-2):115-125, Urban & Fischer Verlag, Germany (Jan. 2008).
Moutaftsi, M., et al., "Human Cytomegalovirus Inhibits Maturation and Impairs Function of Monocyte-derived Dendritic Cells," Blood 99(8):2913-2921, American Society of Hematology, United States (Apr. 2002).
Murphy, C.G., et al., "Vaccine Protection Against Simian Immunodeficiency Virus by Recombinant Strains of Herpes Simplex Virus," Journal of virology 74(17):7745-7754, American Society for Microbiology, United States (Sep. 2000).
Murphy, E., et al., "Coding Potential of Laboratory and Clinical Strains of Human Cytomegalovirus," Proceedings of the National Academy of Sciences of the United States of America 100(25):14976-14981, National Academy of Sciences, United States (Dec. 2003).
Wu., H.L., et al., "Cytomegalovirus vaccine vector 68-1 elicits universal, MHC-E-restricted CD8 T-cell responses against SIV," Journal of Medical Primatology 44(5):313, Wiley Online Library, United States (2014).
Olaleye, O.D., et al., "Cytomegalovirus Infection Among Tuberculosis Patients in a Chest Hospital in Nigeria," Comparative Immunology, Microbiology and Infectious Diseases 13(2):101-106, Elsevier Science Ltd, England (1990).
Onuffer, J.J and Horuk, R, "Chemokines, Chemokine Receptors and Small-molecule Antagonists: Recent Developments," Trends in Pharmacological Sciences 23(10):459-467, Published by Elsevier in Association with the International Union of Pharmacology, England (Oct. 2002).
Oxford, K.L., et al., "Protein Coding Content of the ULb' Region of Wild-Type Rhesus Cytomegalovirus," Virology 373(1):181-188, Academic Press, United States (Mar. 2008).
Plotkin, S.A., et al., "Vaccines for the Prevention of Human Cytomegalovirus Infection," Reviews of Infectious Diseases 12 Suppl 7:S827-S838, University of Chicago Press, United States (Sep.-Oct. 1990).
Powers, C and Fruh, K, "Rhesus CMV: an Emerging Animal Model for Human CMV," Medical Microbiology and Immunology 197(2):109-115, Springer-Verlag, Germany (Jun. 2008).
Redwood, A.J., et al., "Use of a Murine Cytomegalovirus K181-derived Bacterial Artificial Chromosome as a Vaccine Vector for Immunocontraception," Journal of virology 79(5):2998-3008, American Society for Microbiology, United States (Mar. 2005).
Rizvanov, A.A., et al., "Generation of a Recombinant Cytomegalovirus for Expression of a Hantavirus Glycoprotein," Journal of virology 77(22):12203-12210, American Society for Microbiology, United States (Nov. 2003).
Ryckman, B.J., et al., "Characterization of the Human Cytomegalovirus Gh/gl/ul128-131 Complex That Mediates Entry Into Epithelial and Endothelial Cells," Journal of virology 82(1):60-70, American Society for Microbiology, United States (Jan. 2008).
Schleiss, M.R., et al., "Genetically Engineered Live-attenuated Cytomegalovirus (CMV) Vaccines Improve Pregnancy Outcome in the Guinea-pig Model of Congenital CMV Infection," Retrovirology 5(1):1-3, (Apr. 2008).

(56) References Cited

OTHER PUBLICATIONS

European Search Report for EP Application No. EP11008462, Munich, Germany, dated Jul. 26, 2012.
GenBank Report, Accession No. NP_057850, (published Aug. 1, 2000).
Pietra, G., et al., "The Emerging Role of HLA-E-restricted CD8+ T Lymphocytes in the Adaptive Immune Response to Pathogens and Tumors," Journal of Biomedicine and Biotechnology 2010(9070921):1-8, Hindawi, India (2010).
Oxxon Terapeutics Licenses Rights to Xenova's DISC-HSV and DISC-GM-CSF Vector Technolgies, BusinessWire, Jan. 13, 2005.
Tessmer, M.S., et al., "Salivary Gland NK Cells Are Phenotypically and Functionally Unique," PLoS Pathogens 7(1):e1001254, Public Library of Science, United States (Jan. 2011).
Ulmer, J.B, "Tuberculosis DNA Vaccines," Scandinavian Journal of Infectious Diseases 33(4):246-248, Informa Healthcare, England (2001).
Wang, X., et al., "Murine Cytomegalovirus Abortively Infects Human Dendritic Cells, Leading to Expression and Presentation of Virally Vectored Genes," Journal of virology 77(13):7182-7192, American Society for Microbiology, United States (Jul. 2003).
Wiertz, E.J., et al., "The Human Cytomegalovirus US11 Gene Product Dislocates Mhc Class I Heavy Chains From the Endoplasmic Reticulum to the Cytosol," Cell 84(5):769-779, Cell Press, United States (Mar. 1996).
Altschul, S.F. and Gish W., "Local Alignment Statistics," Methods in Enzymology 266:460-480, Academic Press, United States (1996).
Altschul, S.F., et al., "Basic Local Alignment Search Tool," Journal of Molecular Biology 215(3):403-410, Elsevier, England (Oct. 1990).
Andre, S., et al., "Increased Immune Response Elicited by DNA Vaccination With a Synthetic gp120 Sequence With Optimized Codon Usage," Journal of Virology 72(2):1497-1503, American Society for Microbiology, United States (Feb. 1998).
Barsov, E.V., et al., "Transduction of Siv-specific Tcr Genes Into Rhesus Macaque Cd8+ T Cells Conveys the Ability to Suppress Siv Replication," PLoS One 6(8):e23703, Public Library of Science, United States ( Aug. 2011).
Do, J.S., et al., "Unexpected Role for MHC II-Peptide Complexes in Shaping CD8 T-Cell Expansion and Differentiation in Vivo," Proceedings of the National Academy of Sciences 109(31):12698-12703, National Academy of Sciences, United States (Jul. 2012).
Felgner, J.H., et al., "Enhanced Gene Delivery and Mechanism Studies With a Novel Series of Cationic Lipid Formulaitons," Journal of Biological Chemistry 269(4):2550-2561, American Society for Biochemistry and Molecular Biology, United States (Jan. 1994).
Gilicze, A.B., et al., "Myeloid-Derived microRNAs, miR-223, miR27a, and miR-652, Are Dominant Players in Myeloid Regulation," BioMed Research International 2014:870267, Hindawi Publishing Corporation, United States (Aug. 2014).
Gill, R.B., et al., "Coding Potential of Ul/b' From the Initial Source of Rhesus Cytomegalovirus Strain 68-1," Virology 447(1-2):208-212, Academic Press, United States (Dec. 2013).
Gish, W and States, D.J, "Identification of Protein Coding Regions by Database Similarity Search," Nature Genetics 3(3):266-272, Nature Publishing Group, United States (Mar. 1993).
Goodman-Snitkoff, G., et al., "Role of Intrastructural/intermolecular Help in Immunization With Peptide-phospholipid Complexes," Journal of Immunology 147(2):410-415, American Association of Immunologists, United States (Jul. 1991).
Wang, D and Shenk,T ., "Human cytomegalovirus UL131 Open Reading Frame is Required for Epithelial Cell Tropism," Journal of Virology, 79(16):10330-10338, American Society for Microbiology, United States (Aug. 2005).
Hancock, M.H., et al., "Rhesus Cytomegalovirus Encodes Seventeen Micrornas that are Differentially Expressed In Vitro and In Vivo," Virology 425(2):133-142, Academic Press, United States (Apr. 2012).

Hansen, S.G., et al., "Broadly Targeted $Cd8^+T$ Cell Responses Restricted by Major Histocompatibility Complex E," Science 351(6274):714-720, American Association for the Advancement of Science, United States (Feb. 2016).
Hansen, S.G., et al., "Cytomegalovirus Vectors Violate CD8+ T Cell Epitope Recognition Paradigms," Science 340(6135):1237874, American Association for the Advancement of Science, United States (May 2013).
Hansen, S.G., et al., "Immune Clearance of Highly Pathogenic SIV Infection," Nature 502(7469):100-104, Nature Publishing Group, United Kingdom (Oct. 2013).
Higgins, D.G and Sharp, P.M, "CLUSTAL: A Package for Performing Multiple Sequence Alignment on a Microcomputer," Gene 73(1):237-244, Elsevier/North-Holland, Netherlands (Dec. 1988).
Higgins, D.G., and Sharp, P.M., "Fast and Sensitive Multiple Sequence Alignments on a Microcomputer," Computer Applications in the Biosciences 5(2):151-153, Oxford University Press, United Kingdom (Apr. 1989).
Huang, X., et al., "Parallelization of a Local Similarity Algorithm," Computer Applications in the Biosciences 8(2):155-165, Oxford University Press, England (Apr. 1992).
International Preliminary Report on Patentability for International Application No. PCT/US2016/017373, The International Bureau of WIPO, Geneva, Switzerland, dated Aug. 15, 2017, 8 pages.
International Search Report and Written Opinion for International Application No. PCT/US2015/040807, European Patent Office, HV Rijswijk, dated Oct. 28, 2015, 6 pages.
International Search Report and Written opinion for International Application No. PCT/US2016/017373, Korean Intellectual Property Office, Republic of Korea, dated May 23, 2016.
International Search Report for International Application No. PCT/US2012/041475, Korean Intellectual Property Office, Republic of Korea, dated Dec. 14, 2012.
Karlin, S. and Altschul, S.E., "Methods for Assessing the Statistical Significance of Molecular Sequence Features by using General Scoring Schemes," Proceedings of the National Academy of Sciences USA 87(6):2264-2268, National Academy of Sciences, United States (Mar. 1990).
Karlin, S, and Altschul, S.F., "Applications and Statistics for Multiple High-scoring Segments in Molecular Sequences," Proceedings of the National Academy of Sciences USA 90(12):5873-5877, National Academy of Sciences, United States (Jun. 1993).
Malouli, D., et al., "Reevaluation of the Coding Potential and Proteomic Analysis of the Bac-derived Rhesus Cytomegalovirus Strain 68-1," Journal of Virology 86(17):8959-8973, American Society for Microbiology, United States (Sep. 2012).
McGregor, A., et al., "Expression of the Human Cytomegalovirus UL97 Gene in a Chimeric Guinea Pig Cytomegalovirus (GPCMV) Results in Viable Virus with Increased Susceptibility to Ganciclovir and Maribavir," Antiviral Research 78(3):250-259, Elsevier, Netherlands (Jun. 2008).
Miller, M.D., et al., "Vaccination of Rhesus Monkeys With Synthetic Peptide in a Fusogenic Proteoliposome Elicits Simian Immunodeficiency Virus-specific Cd8+ Cytotoxic T Lymphocytes," Journal of Experimental Medicine 176(6):1739-1744, Rockefeller University Press, United States (Dec. 1992).
Murrell, L., et al., "Impact of Sequence Variation in the UL128 Locus on Production of Human Cytomegalovirus in Fibroblast and Epithelial Cells," Journal of Virology 87(19):10489-10500, American Society for Microbiology, United States (Oct. 2013).
Myers, E.W., and Miller, W., "Optimal Alignment in Linear Space," Computer Applications in the Biosciences 4(1):1-13, Oxford University Press, England (Mar. 1988).
Kim, S., et al., "Human Cytomegalovirus MicroRNA miR-US4-1 Inhibits CD8(+) T cell Responses by Targeting the Aminopeptidase ERAP1," Nature Immunology 12(10):984-991, Nature America Inc, United States (Sep. 2011).
Needleman, S.B. And Wunsch, C.D., "A General Method Applicable to the Search for Similarities in the Amino Acid Sequence of Two Proteins," Journal of Molecular Biology 48(3):443-453, Academic Press, England (Mar. 1970).

(56) References Cited

OTHER PUBLICATIONS

Oxford, K.L., et al., "Protein Coding Content of the UL)b' Region of Wild-type Rhesus Cytomegalovirus," Virology, 373(1):181-183, Academic Press, United States (Mar. 2008).
Pearce, E.L., et al., "Functional Characterization of MHC Class II-Restricted CD8+CD4- and CD8-CD4- T cell Responses to Infection in CD4-/- Mice," Journal of Immunology 173(4):2494-2499, American Association of Immunologists, United States (Aug. 2004).
Pearson, W.R. and Lipman, D.J., "Improved Tools for Biological Sequence Comparison," Proceedings of the National Academy of Sciences of the United States of America 85(8):2444-2448, National Academy of Sciences, United States (Apr. 1988).
Pearson, W.R., "Using the FASTA Program to Search Protein and DNA Sequence Databases," Methods in Molecular Biology 24:307-331, Humana Press, United States (Feb. 1994).
Hanley, P.J., et al., "Controlling cytomegalovirus: helping the immune system take the lead, "Viruses, 6(6):2242-2258, MDPI, Switzerland (May 2014).
Picker, L.J., et al., "New paradigms for HIV/AIDS vaccine development," Annual Review of Medicine 63:95-111, Annual Reviews, United States (Feb. 2012).
Pietra, G., et al., "HLA-E-Restricted Recognition of Cytomegalovirus-derived Peptides by Human CD8+ Cytolytic T Lymphocytes," Proceedings of the National Academy of Sciences of the United States of America 100(19):10896-10901, National Academy of Sciences, United States (Sep. 2003).
International Preliminary Report on Patentability for International Application No. PCT/US2015/040807 , The International Bureau of WIPO, Geneva, Switzerland, dated Jan. 17, 2017, 8 pages.
Joosten, S.A., et al., "Characteristics of HLA-E Restricted T-Cell Responses and Their Role in Infectious Diseases, " Journal of Immunology Research, 2016:2695396, Hindawi Publishing Corporation, Egypt (Sep. 2016).
Wu, F., et al., "Role of Specific MicroRNAs for Endothelial Function and Angiogenesis," Biochemical and Biophysical Research Communications 386(4):549-553, Elsevier, United States (Sep. 2009).
Sambrook, J., et al., "Molecular Cloning: A Laboratory Manual," Second Edition, Cold Spring Harbor Laboratory Press, United States (1989).
Schuessler, A., et al., "Charge Cluster-to-Alanine Scanning of UL 12B for Fine Tuning of the Endothelial Cell Tropism of Human Cytomegalovirus," Journal of Virology, 82(22):11239-11246, American Society for Microbiology, United States (Nov. 2008).
Schuessler, A., et al., "Mutational Mapping of UL130 of Human Cytomegalovirus Defines Peptide Motifs within the C-Terminal Third as Essential for Endothelial Cell Infection," Journal of Virology, 84(18): 9019-9026, American Society for Microbiology, United States (Sep. 2010).
Smith, T.F. and Waterman, M.S., "Comparison of Biosequences," Advances in Applied Mathematics 2(4):482-489, Academic Press, Inc., United States (Dec. 1981).
Michaelson, J.S and Leder, P., "RNAi Reveals Anti-Apoptotic and Transcriptionally Repressive Activities of DAXX," Journal of Cell Science 116(Pt 2):345-352, Company of Biologists, London (Jan. 2003).
Nicholson J.P., et al., "Properties of Virion Transactivator Proteins encoded by Primate Cytomegaloviruses," Journal of Virology, 6:65, BioMed Central, England (May 2009).
Ulmer, J.B., et al., "Heterologous Protection against Influenza by injection of DNA Encoding a Viral Protein," Science 259(5102):1745-1749, American Association for the Advancement of Science, United States (Mar. 1993).
Cranage, M., et al., "Carriers for the delivery of a vaccine against respiratory syncytial virus," Expert Opinion on Biological therapy 5(7):939-952, Taylor & Francis, United States (2005).
Antonis, A.F., "Vaccination with recombinant modified vaccinia virus Ankara expressing bovine respiratory syncytial virus (bRSV) proteins protects calves against RSV challenge." Vaccine 15(25):4818-4827, Elsevier, Netherlands (2007).

Kovarik, J., et al., "Induction of adult-like antibody, Th1, and CTL responses to measles hemagglutinin by early life murine immunization with an attenuated vaccinia-derived NYVAC (K1L) viral vector," Virology 285(1):12-20, Elsevier, Netherlands (2001).
Welter, J., et al., "Mucosal vaccination with recombinant poxvirus vaccines protects ferrets against symptomatic CDV infection," Vaccine 17(4):308-318, Elsevier, Netherlands (1999).
Guillaume, V., et al., "Nipah Virus: Vaccination and passive protection studies in a hamster model," Journal of Virology 78(2):834-840, American Society for Microbiology, United States (2004).
Wyatt, L.S., et al., "Development of a replication-deficient recombinant vaccinia virus vaccine effective against parainfluenza virus 3 infection in an animal model," Vaccine 14(15):1451-1458, Elsevier, Netherlands (1996).
Kenjiro, I., et al., "Long-term protective immunity to rinderpest in cattle following a single vaccination with recombinant vaccinia virus expressing the virus haemagglutinin protein," Journal of General Virology 81(6):1439-1446.
Grey, F., et al., "A human cytomegalovirus-encoded microRNA regulates expression of multiple viral genes involved in replication," PLOS pathogens 3(11):1593-1602, Public Library of Science, United States (2007.).
Ojha, M., et al., "Spatial and cellular localization of calcium-dependent protease (CDP II) in Allomyces arbuscula," Journal of Cell Science 116:1095-1105, The Company of Biologists, United Kingdom (2003).
Powers, C.J., et al., "Signal peptide-Dependent Inhibition of MHC Class I Heavy Chain Translation by Rhesus Cytomegalovirus," PLOS Pathogens 4(10):e1000150, Public Library of Science, United States.
Powers, C., et al., "The US2-11 region of RhCMV is both necessary and sufficient to counteract CD8+ T-cell immunity during re-infection of rhesus macaques," $34^{th}$ Annual International Herpesvirus Workshop, Jul. 25, 2009, Ithaca, New York.
Smith, M.S., et al., "Roles of Phosphatidylinositol 3-Kinase and NF-B in Human Cytomegalovirus-Mediated Monocyte Diapedesis and Adhesion: Strategy for Viral Persistence," Journal of Virology 81(14):7683-7694, American Society for Microbiology, United States (2007).
Bentz, G.L., et al., "Human Cytomegalovirus (HCMV) Infection of endothelial Cells Promotes Naïve Monocyte Extravasation and transfer of Productive Virus to Enhance Hematogenous Dissemination of HCMV," Journal of Virology 80(23):11539-15555, American Society for Microbiology, United States (2006).
Fruh, K., et al., "CD8+ T cell programming by cytomegalovirus vectors: applications in prophylactic and therapeutic vaccination," Current Opinion in Immunology 47:52-56, Elsevier, Netherlands (2017).
Office Action dated Aug. 2, 2018, in U.S. Appl. No. 15/326,444, inventor Frueh, K., et al., § 371(c) filed May 16, 2017, 13 pages.
Heineman, T.C., et al., "Chapter 71: Human Cytomegalovirus vaccines," in Arvin, Campadelli-Flume G., Human Herpesviruses: Biology, therapy, and Immunoprophylaxis.
James. S.H., et al., "The genetic basis of human cytomegalovirus resistance and current trends in antiviral resistance analysis," Infect Disord drug Targets 11(5):504-513.
Lauron, E., et al., "Human Cytomegaloviruses infection of Langerhans-type dendritic cells does not require the presence of the gH/gL/UL 128-131A complex and is blocked after nuclear deposition of viral genomes in immature cells," J. Virol 88(1):403-416, American society for Microbiology, United States (2014).
Smith, I.L., et al., "High-level resistance of cytomegalovirus to ganciclovir is associated with alternations in both the UL97 and DNA polymerase genes," J. Infect Dis. 176(1):69-77, Oxford Academic, United Kingdom (1988).
Bego, M., et al., "Characterization of an Antisense Transcript Spanning the Ul81-82 Locus of Human Cytomegalovirus," Journal of Virology, 79(17):11022-11034, American Society for Microbiology, United States (Sep. 2005).
Bowman, J.J., et al., "Rhesus and Human Cytomegalovirus Glycoprotein L are Required for Infection and Cell-to-Cell Spread of Virus but

(56) References Cited

OTHER PUBLICATIONS

Cannot Complement Each Other," Journal of Virology, 85(5):2089-2099, American Society for Microbiology, United States (Mar. 2011).

Corpet, F, "Multiple Sequence Alignment With Hierarchical Clustering," Nucleic Acids Research 16(22):10881-10890, Oxford University Press, England (Nov. 1988).

Dhuruvasan, K., et al., "Roles of Host and Viral MicroRNAs in Human Cytomegalovirus Biology,"Virus Research, 157(2):180-192, Elsevier Science, Netherlands (May 2011).

Dolan, A., et al., "Genetic Content of Wild-Type Human Cytomegalovirus," Journal of General Virology, 85(Pt 5):1301-1312, Microbiology Society, England (May 2004).

Geisler, A., et al., "MicroRNA-Regulated Viral Vectors for Gene Therapy," World Journal of Experimental Medicine, 6(2):37-54, Baishideng Publishing Group, United States (May 2016).

Guo, X.Z., et al., "Rapid Cloning, Expression, and Functional Characterization of Paired αβ and γδ T-Cell Receptor Chains from Single-Cell Analysis," Molecular Therapy: Methods & Clinical Development, 3:15054, Cell Press, United States (Jan. 2016).

Hahn, G., et al., "The Human Cytomegalovirus Ribonucleotide Reductase Homolog Ul45 Is Dispensable for Growth in Endothelial Cells, as Determined by a Bac-Cloned Clinical Isolate of Human Cytomegalovirus With Preserved Wild-Type Characteristics," Journal of Virology, 76(18):9551-9555, American Society for Microbiology, United States (Sep. 2002).

Hancock, J.M and Armstrong, J.S., "SIMPLE34: an Improved and Enhanced Implementation for Vax and Sun Computers of the Simple Algorithm for Analysis of Clustered Repetitive Motifs in Nucleotide Sequences,"Computer Applications in the Biosciences, 10(1):67-70, Oxford University Press, England (Feb. 1994).

Hobom, U., et al., "Fast Screening Procedures for Random Transposon Libraries of Cloned Herpesvirus Genomes: Mutational Analysis of Human Cytomegalovirus Envelope Glycoprotein Genes," Journal of Virology, 74(17):7720-7729, American Society for Microbiology (Sep. 2000).

Jarvis, M.A and Nelson, J.A., "Mechanisms of Human Cytomegalovirus Persistence and Latency," Frontiers in Bioscience 7:d1575-d1582, Frontiers in Bioscience Publications, United States (Jun. 2002).

Kenneson, A and Cannon, M.J., "Review and Meta-analysis of the Epidemiology of Congenital Cytomegalovirus (CMV) Infection, " Reviews in Medical Virology 17(4):253-276, Wiley, England (Jul.-Aug. 2007).

Khan, N., et al., "Identification of Cytomegalovirus-Specific Cytotoxic T Lymphocytes in Vitro Is Greatly Enhanced by the Use of Recombinant Virus Lacking the Us2 to Us11 Region or Modified Vaccinia Virus Ankara Expressing Individual Viral Genes, " Journal of Virology, 79(5):2869-2879, American Society for Microbiology, United States (Mar. 2005).

Matthews, T.J., et al., "Prospects for Development of a Vaccine against HTLV-III-related Disorders," AIDS Research and Human Retroviruses, 3(1):197-206, Mary Ann Liebert, United States (1987).

Noriega, V., et al., "Diverse Immune Evasion Strategies by Human Cytomegalovirus," Immunologic Research, 54(1-3):140-151, Humana Press, United States (Dec. 2012).

O'Connor, C.M and Shenk, T., "Human Cytomegalovirus pUL78 G Protein-Coupled Receptor Homologue Is Required for Timely Cell Entry in Epithelial Cells but Not Fibroblasts," Journal of Virology, 86(21):11425-11433, American Society for Microbiology, United States (Nov. 2012).

O'Connor, C.M., et al., "Host microRNA Regulation of Human Cytomegalovirus Immediate Early Protein Translation Promotes Viral Latency,"Journal of Virology, 88(10):5524-5532, American Society for Microbiology, United States (May 2014).

Retrieved from the Internet: (URL: http://www.microma.org/microma/getTargets.do?matureName=hsa-miR-142-3p&organism=9606), last accessed Oct. 6, 2015.

Snyder, C.M., et al., "Cross-presentation of a Spread-defective MCVM is Sufficient to Prime the Majority of Virus-specific CD8+T Cells," PLoS One, 5(3):e9681, Public Library of Science, United States (Mar. 2010).

Supplementary European Search Report for EP Application No. EP 16749813, Munich, Germany, dated Aug. 29, 2018.

Terhune, S., et al., "Human Cytomegalovirus Ul38 Protein Blocks Apoptosis," Journal of Virology, 81(7):3109-3123, American Society for Microbiology, United States (Apr. 2007).

Wagner, S., et al., "The 7-transmembrane Protein Homologue Ul78 of the Human Cytomegalovirus Forms Oligomers and Traffics Between the Plasma Membrane and Different Intracellular Compartments," Archives of Virology, 157(5):935-949, Springer-Verlag, Austria (May 2012).

\* cited by examiner

Fig. 17B

```
HIVgag    MAARASILSGGKLDAWEKIRLRPGGKKKYRLKHLVWASRELDRFALNPSLLETTEGCQQI  60
#3D6 p4   MAARASILSGGKLDAWEKIRLRPGGKKKYRLKHLVWASRELDRFALNPSLLETTEGCQQI  60
#3D6 p5   MAARASILSGGKLDAWEKIRLRPGGKKKYRLKHLVWASRELDRFALNPSLLETTEGCQQI  60
#3D6 p6   MAARASILSGGKLDAWEKIRLRPGGKKKYRLKHLVWASRELDRFALNPSLLETTEGCQQI  60
          ************************************************************

HIVgag    MNQLQPAVKTGTEEIKSLFNTVATLYCVHQRIDVKDTKEALDKIEEIQNKSKQKTQQAAA  120
#3D6 p4   MNQLQPAVKTGTEEIKSLFNTVATLYCVHQRIDVKDTKEALDKIEEIQNKSKQKTQQAAA  120
#3D6 p5   MNQLQPAVKTGTEEIKSLFNTVATLYCVHQRIDVKDTKEALDKIEEIQNKSKQKTQQAAA  120
#3D6 p6   MNQLQPAVKTGTEEIKSLFNTVATLYCVHQRIDVKDTKEALDKIEEIQNKSKQKTQQAAA  120
          ************************************************************

HIVgag    DTGDSSKVSQNYPIIQNAQGQMIHQNLSPRTLNAWVKVIEEKAFSPEVIPMFSALSEGAT  180
#3D6 p4   DTGDSSKVSQNYPIIQNAQGQMIHQNLSPRTLNAWVKVIEEKAFSPEVIPMFSALSEGAT  180
#3D6 p5   DTGDSSKVSQNYPIIQNAQGQMIHQNLSPRTLNAWVKVIEEKAFSPEVIPMFSALSEGAT  180
#3D6 p6   DTGDSSKVSQNYPIIQNAQGQMIHQNLSPRTLNAWVKVIEEKAFSPEVIPMFSALSEGAT  180
          ************************************************************

HIVgag    PQDLNVMLNIVGGHQAAMQMLKDTINEEAAEWDRLHPVQAGPIPPGQIREPRGSDIAGTT  240
#3D6 p4   PQDLNVMLNIVGGHQAAMQMLKDTINEEAAEWDRLHPVQAGPIPPGQIREPRGSDIAGTT  240
#3D6 p5   PQDLNVMLNIVGGHQAAMQMLKDTINEEAAEWDRLHPVQAGPIPPGQIREPRGSDIAGTT  240
#3D6 p6   PQDLNVMLNIVGGHQAAMQMLKDTINEEAAEWDRLHPVQAGPIPPGQIREPRGSDIAGTT  240
          ************************************************************

HIVgag    STPQEQLQWMTGNPPIPVGNIYKRWIILGLNKIVRMYSPVSILDIKQGPKEPFRDYVDRF  300
#3D6 p4   STPQEQLQWMTGNPPIPVGNIYKRWIILGLNKIVRMYSPVSILDIKQGPKEPFRDYVDRF  300
#3D6 p5   STPQEQLQWMTGNPPIPVGNIYKRWIILGLNKIVRMYSPVSILDIKQGPKEPFRDYVDRF  300
#3D6 p6   STPQEQLQWMTGNPPIPVGNIYKRWIILGLNKIVRMYSPVSILDIKQGPKEPFRDYVDRF  300
          ************************************************************

HIVgag    FKALRAEQATQDVKGWMTETLLVQNANPDCKSILKALGSGATLEEMMTACQGVGGPGHKA  360
#3D6 p4   FKALRAEQATQDVKGWMTETLLVQNANPDCKSILKALGSGATLEEMMTACQGVGGPGHKA  360
#3D6 p5   FKALRAEQATQDVKGWMTETLLVQNANPDCKSILKALGSGATLEEMMTACQGVGGPGHKA  360
#3D6 p6   FKALRAEQATQDVKGWMTETLLVQNANPDCKSILKALGSGATLEEMMTACQGVGGPGHKA  360
          ************************************************************

HIVgag    RVLAEAMSQAQQTNIMMQRGNFRGQKRIKCFNCGKEGHLARNCRAPRKKGCWKCGKEGHQ  420
#3D6 p4   RVLAEAMSQAQQTNIMMQRGNFRGQKRIKCFNCGKEGHLARNCRAPRKKGCWKCGKEGHQ  420
#3D6 p5   RVLAEAMSQAQQTNIMMQRGNFRGQKRIKCFNCGKEGHLARNCRAPRKKGCWKCGKEGHQ  420
#3D6 p6   RVLAEAMSQAQQTNIMMQRGNFRGQKRIKCFNCGKEGHLARNCRAPRKKGCWKCGKEGHQ  420
          ************************************************************

HIVgag    MKDCTERQANFLGKIWPSSKGRPGNFPQSRPEPTAPPAELFGMGEGIASLPKQEQKDREQ  480
#3D6 p4   MKDCTERQANFLGKIWPSSKGRPGNFPQSRPEPTAPPAELFGMGEGIASLPKQEQKDREQ  480
#3D6 p5   MKDCTERQANFLGKIWPSSKGRPGNFPQSRPEPTAPPAELFGMGEGIASLPKQEQKDREQ  480
#3D6 p6   MKDCTERQANFLGKIWPSSKGRPGNFPQSRPEPTAPPAELFGMGEGIASLPKQEQKDREQ  480
          ************************************************************

HIVgag    VPPLVSLKSLFGNDPLSQ  498
#3D6 p4   VPPLVSLKSLFGNDPLSQ  498
#3D6 p5   VPPLVSLKSLFGNDPLSQ  498
#3D6 p6   VPPLVSLKSLFGNDPLSQ  498
          ******************!
```

Fig. 18

Next generation sequencing of RhCMV 68-1.2 SIV-gag ΔUL36 viral DNA

Premature Stop codon due to G → T substitution in SIV gag in 37.9% of the population

SEQUENCE LISTING

```
<160> NUMBER OF SEQ ID NOS: 7

<210> SEQ ID NO 1
<211> LENGTH: 244443
<212> TYPE: DNA
<213> ORGANISM: Human cytomegalovirus

<400> SEQUENCE: 1
ggtggtgttg cctgcggcgg ggacgggggt tgcgctggga tcgggggtgg cgccggggac      60
gggggctttt cgcagcgggg aacacacacc gcctatttaa cctccacccg ctacaacaca     120
cacatgccgc acaatcatgc cagccacaga cacaaacagc acccacacca cgccgcttca     180
cccagaggac caacacacgt tacccgtaca ccacagtaac acacaaccgc aagtccaaac     240
ctcggacaaa cgcgccgccg aagaccaccg cacgcagatg gagctcgacg ccgcggacta     300
cgctgcttgc tcacaggccc gccaacacct ctacggtcaa acacaacccc aactacacgc     360
```

-continued

```
atacccaac gccaacccac aggaaagcgc tcatttttc acagagaatc aacatcaagt    420
cacgcatcta cttcacaaca ttggcgaggg cgcagcgctc ggctacccg tcccccgcgc    480 ggaaatccgc cgtggcggtg gcgactgggc cgacagcgca agcgacttcg acgccgactg   540
ctggtgcatg tggggacgct tcggaaccat gggccgccaa cctgtcgtga ccttactgtt   600
ggcgcgccaa cgcgacggcc tcgctgactg gaacgtcgta cgctgccgcg gcacaggctt   660
tcgcgcacac gattccgagg acggcgtctc tgtctggcgt cagcacctgg ttttttact    720 cggaggccac ggccgccgtg tacagttaga acgtccatcc gcgggagaag cccaagctcg   780
aggcctattg ccacgcatcc ggatcacccc cctctccaca tctccacgcc caaaaccacc   840
ccagcccacc acatccaccg cctcgcaccc acatgctacg gctcggccag atcacacgct   900 cttcctgtc ccttccacac cctcaaccac ggttcacaat ccccgaaact acgccgtcca    960
acttcacgcc gaaacgaccc gcacatggcg ctgggcacga cgccggtgaac gtggcgcgtg  1020 gatgccggcc gagacattta cgtgtcccaa ggataaacgt ccctggtaga cggggtaggg   1080
ggatctacca gcccagggct cgcgtatttc gccgccacgc tgcttcaccg atatccaata   1140
aacccatccc ctcgccacga cgtctccgcg tatctttgta gcctcaggaa tccgtccca    1200 cgtccaccca tcccgagcac tccacacgct ataacagacc acggacacgg caaatgcatg   1260
caaacttctc atttattgtg tctactactc tgtgttgcta caggggtga aggcaaagaa    1320 aaaaaaaagg aacaaaataa tagattagca gaaggaataa tccgtgcgac cgagcttgtg   1380
cttcttttct tataaggagg caaatatact agggaaaaca taagaatagg aagaaaccga   1440
ggtttgggag aaaagctgag ataaaatagc gcatttccca tacagaggtt gttgtttttg   1500
tggatcctaa gaggtttcaa gtgcgaatct taaagttctc acgagaatat tgtcttcaag   1560
aatcgacaac tgtggtccaa gatttttttt tggtcttttt aggttctgcg agggacatca   1620
cgatggatcg ttgcgatgaa gtcacgcgta cgcctctggt gtggcgcggt gtcgtgacag   1680
gagagtgtgt tttcagtgca gagctgtctt gattcctata tccgagtatc tgttttctcg   1740
taaggacggt aatcttcttt ggtgtaagta catctaaaag ctgcaaacta tattttaagg   1800
gctgtctcta ggtgtacttt gatgctggag tttttcgctg tgttgatgtg aataaatcta   1860
ctactactat tatatgcaga aagagtgatt atgccgagac aagattgcat tggctgaact   1920
gtttcaaaaa cgcctacact ctacttatcc gtaaacctaa ggtaatacta tgtgtaagtt   1980
gttttttttt tcttttttgta gtaaaatggt gatacgtgca attaaaactg tattccatgt   2040
ttccatcctt tcatttcaac tttaaaggcg gctttgagag cgaagaagtg cgaggataaa   2100
aatggatgac tccttcgtgt ccagggagtc gactactgca acgctgattg attaaaagat   2160
ggtctccgat gatgatgttg ttattgatcg aatcatggtg cagaacggcg acggagagga   2220
gcgtgtccgc cgccgggaag gtggtctctt tctcttttct ttttcaaga aatcttccat    2280 gtgtttatcg tagtgatcga aatcgactga tctcgggtc ttttgttgg tttcttttcg     2340 gttaatcatg tattgttttc ttttttaca gaaagatact ttttcatga gcaattcctc     2400 gcccggcgcc ggcatgccga ggtggggcca ctgcgatcag cggcatgccg acgccgaccc   2460
ggggatcttg gattcaccgt tttctctctt ctctctctac atacagaccg ggtggcagga   2520
gcggtaagga atcatcgtcg tctttcattc ttcgatgatt atggtaatac taaatcttat    2580
ctaggagcat atacatctaa gattggagta ctagtagtcg tttgtggttt ctattttttt   2640
ttatatttat ctatgacagt ttttctgttt ttcgttttga taataatata ataaaaactc   2700
atggacgtga aatctggctt ggttgtggtg atttcattct cattattgtt gtttcttt     2760
```

```
cgtcttgcgg atgaagatgt tgcgatgcgg ttgttgttgg tgttgctata caccgagaga   2820
gatgatcttt ttgttcttct ggttcatttc ctatgattgt ttggctgctg accgacgcgt   2880
caggatgtgc agggcatgcg gggaatcagg accggacacg ggataatttc atctacctat   2940
acggagatcg cggtcctcgc catgaggatc gcgacaggcg cgtcgagggg gcaggaacac   3000
ccttgcggat tgacattctt ggtggtgttt cgttgttgtc ggtagttgtt gttgacgatg   3060
aggataaata aaaatgacct tgttttttgtt ctgttttctc ttgttgggaa tcgtcgactt   3120
tgaattcttc gagttatcgg aaagctgagg tacccaaatg tctgtagctt ttttctttttt  3180 accctcttgt ttatcatctg cgattcgtgg taggtaggag agggaaatga taatccgaga   3240
ttaaggaaag gagaagataa aataaaaaaa aaataaaaca gaagccgacc ggccgccgac   3300
ccgttcccca ggaccagcct acgaggaacg gataacgcgg tggcgacggc agcggtggtg   3360
gcgctggggg tggcggtagt ggtactgctg atggtagtcg ggacggagga gagacgatgc   3420
atacatacac gcgtgcatgc tgcatgggtg gatggtccga ccgggagacg cggaagagaa   3480
actcacataa aaaggtgaca aaaagagcgg ttgaaaaaag aaaacgagat tcgaccagac   3540
agaagaggag gaccggggct tggcgaccct tccacgactg ctgttgtcat ctcggctcct   3600
ccgtcttctc ccggccacgg gcggctaagt caccgccgtt ctccccatcc gtccgagcgc   3660
cgaccgacca gccggccgat tcgcccgccg gggcttctgg agaacgccgg ggcagcagcg   3720
atctggagaa gccgctaaac ccctgcgttt ttatatggta gctctgccga gcgcgggctg   3780
acgcgttaag taagcggaaa gacgtgtgtg acgaaaaggg gtcccatggt atttcacgtg   3840
acgatgagga gatgcggttt ggagcacata cggtttagaa aaagggagtt gtcgtgacaa   3900
gggctgaggg acctctgtct ccatgtgtgt ataaaaagca aggcacgttc ataatgtaaa   3960
aaagaacacg ttgtaaacaa gctattgctg tatcattcgg ctgactatgc ttcattcgga   4020
ctgattttct tttcctaacg gcgtaactta aagtgattaa cgtatgatat ttgttcccca   4080
gagttatact atagtcatca tcctaaaatt cagatataaa tgaacacatg tcgtatgaga   4140
ttattaagaa accgaaacca cccatagttc accatcctct tcatcattca gccgatgacc   4200
cactccgtac aacgactcag tctgcttcgt catattgcaa agcacaagcg acgtatgtga   4260
acaacttgaa acacagactg tgttattaat gaccgttgta ccattactag tcacattgca   4320
taaagatcct ccgccgtcgt cccatctttt ccactcggtg gaaaaccggt cgctatcatc   4380
aactatggtg agattttcac cctgcgtggt attcagtttc ttcatattca taccttggat   4440
tccattatta aaccccaata ttaagcacgt tattagtacc ccccccccc accaaggaat    4500 gtgactggac cggttcctag cagctctggg agccatgttc aggttgaacc acagctacag   4560
cgaaaccgag tccagtgacc ggtaaccacg tccagcccct gcgtatgtac cagtccaagc   4620
acgtccggtc attgttctac acaggaaatc taactaggtc aacgtaattt tattccaccg   4680
ttacgcagaa tactaacaaa aaactacaca aatgtaacgg attacacata atttattacg   4740
tgaaaactgt aagaaagcca attcaccaag cgatacattt atttgacttc caagtgccac   4800
acatcaccac tatattcatc catgttttca ccgaaccaac gagacagatc gaagaagcca   4860
gaatcttccg actttaaatt acataaatcc aacgtattat gaccacagct cgacacacaa   4920
atagttgcgt tactattcac agtggcatta cctatacccg taacgttgca caaccactga   4980
tcaccattgt caccaaaaac ggttttccac ttagttgtca acggatcttt cctatgcgta   5040
atggtaaaat tactaccagt cgtcgctttt agctcattac gagtattatc cgcatccaca   5100
```

-continued

```
tatatcaacg tcatagctag gcacgctata agtaccccc ccccacaatg gaatgttgcc      5160
aaaccggttc tttcccgtta tagccatagc gttcccaggc aaaagcaaac gccgaaccta      5220
atgcagtaaa aagcgcttgc agccagaacc agcttatgta ccagccacga taacatccgg      5280
tcactgtttc cacaggaaac cctaccaggg tagagccccg cttgtttttt cctgtctatc      5340
ttgtttagca actcgtaaac tgtcagtcta gccacgtccg tttagatcaa aagtcacgta      5400
tactgcgacg ttgttttccac ccgtttcccc gtcccgccgt ttccgaacaa cccacccggg    5460
ttcagacaac cgaccaccaa cagaaatata cacacagacc accgggagtt cagttaaaga      5520
tttcatcagg tttatttttgg ctgctgctag tcttttgctt cttagaaaaa aaatacccat    5580
atagagaaat aatgatagtt tgacaacaca tatggcaggg atttcttctt catcaataag      5640
atatgcaatt ccccccaggga gagactttca acaattgaat ttacaaaaac aaaattacat    5700
caggagaaag agaggataca ttaataaata tattatatct ggtgtatata ctgaatgctg      5760
ctggttcata agtaacgat gctacttttt ttaattccaa gatggttttt ctttgttagt      5820
cttttgttga cttgctggtt cctaaaagtt ctcaaaaacg attgtgtgaa gattttatga      5880
cgttggttga ctagttcatg agattctgct gtacgtgtga tggttattcg ctggttcgtt      5940
ctaagatgag tatcgtactg tgtctgcgat ggtcgtctct tactggcatt ctctcggctg      6000
cctcttgctt tcatgattga aaaggaaaaa aggactccga gggcgcggtc atctttact      6060
tttcggtttt ttcgttggcg ggtcagaggt agtcagatca tgagactgtc gtggtcgatg      6120
aaactgtgtc tgctcaagtg acgtccattt cttgtacgga gaaaaaagtc atcgggataa      6180
ataaggctat acaaggcgtt gtcaagcgtg cggctctaaa caaattaagc gatacaaaat      6240
tacagtaata cgaataataa gttacccccct cccctgtgg tcccccgag acgagagcca      6300
cccatcgtgt actctcgcac cacccacgac cacagaggga gacgggacga agagacgacg      6360
cagagcgcca tctccttctg gaggccggcg gcgttaactg ctacagctgc ggcggcgaca      6420
acagctgcga tttgtcggcc gacatgccga tggtatgggc ggcggcggca gtggccgcgg      6480
cagcggggag gagaggagag agaagaggag cggggcgtcc gaaggcgagg atggcatggt      6540
ctcgccggag cgcccggctt ttatggaacg ctcgcgtccg gtcgggcagc gcccacagga      6600
agatgagtca aaactttttaa accatcctga gacccgagta gcggtttaca ggccgcacgc      6660
cagtcttagc taaaaacagc ggacagtccc acgctgtttc tgttgtggct ctctccagtt      6720
tcctcatcgc cgtcccgatc tccgtcgtca tcggaagaat accaccgct ctcatgcggc      6780
agtcgatcga cctcgacgaa cgagacgcgg cgacgcctct ctacggccga ctggttgtgg      6840
tggtgaaaga agagcaccag caatcccagg aggagcaaca agccctcaca tgtccaggag      6900
gtcggggaga gggcctgtcg gagatggccg tgaggcatca cgtacggcag ctgaggagaa      6960
acggagaaga aaggaaaatt accgtcaggg gccggggttc ttattagaga aacagcacgt      7020
aggtcaggat ccagatgcta atggcaatca tgatgacgat gatcatgcag gccaagacgc      7080
ggcgcaccaa tgccgaatcc aatagccgcc gtgcctccgg ttggtggccg gcggcatcta      7140
gagacatgat ttgggggga ccggcggcgc gaaaagacag ggagatggac agtgtcacgg      7200
tgttttgtta tgattaggac atggggaccg gaagccgaga cagagtacta cagggtgttg      7260
aagggtaacg tgagggagat catgtcatgg gcgggctgaa gaccgtgcgg ggaggattgg      7320
cgtgtgcggt gcttgtggaa cacggtgttt taatatgtat ccgcgtgtaa tgcacgcggt      7380
gtgcttttta gcactcggct tgataagcta cgtggccgtt tgcgccgaaa acacggttac      7440
caccaactgt ctcgtgaaaa cagaaaatac ccacctaaca tgtaagtgca atccgaatag      7500
```

```
cacatctacc aatggcagca agtgccacgc gatgtgcaaa tgccgggtca cagaacccat   7560
taccatgcta ggcgcatact cggcctgggg cgcgggctcg ttcgtggcca cgctgatagt   7620
cctgctggtg gtcttcttcg taatttacgc gcgcgaggag gagaaaaaca acacgggcac   7680
cgaggtagat caatgtctgg cctatcggag cctgacacgc aaaaagctgg aacaacacgc   7740
ggctaaaaag cagaacatct acgaacggat tccataccgg ccctccagac agaacgacaa   7800
ctccccgttg atcgaaccga cgggcacaga cgacgaagag gacgaggacg acgacgtctg   7860
ataaggaagg cgagaacgtg ttttgcacca tgcagaccta cagcaccccc ctcacgcttg   7920
tcatagtcac gtcgctgttt ttgttcacaa ctcagggaaa tttatcgaac gccgtcgaac   7980
caaccaaaaa acccctaaag ctcgccaact accgtgccac ctgcgaggac cgtacacgca   8040
cgctggttac caggcttaac actagtcatc acagcgtagt ctggcaacgt tatgatatct   8100
acagcagata catgcgtcgt atgccgccac tttgcatcat tacagacgcc tataaagaaa   8160
ccacgcatca gggtggcgca actttcacgt gcacgcgcca aaatctcacg ctgtacaatc   8220
ttacgattaa agatacggga gtctatcttc tacaggatca gtgtaccggc gatgtcgagg   8280
ctttctacct catcatccac ccacgtagct tctgccgagc tttggaaacg cgtcgatgct   8340
tttatccggg accagggaga gttgtggtta cggattccca agaggcagac cgagcaatta   8400
tctcggattt aaaacgccag tggtccggcc tctcactcca ttgcgcctgg gtttcgggac   8460
tgatgatctt tgttggcgca ctggtcatct gcttcctgcg atcacaacga atcggggaac   8520
aggacgctga acagctgcgg acggacctgg atacggaacc tttgttgttg acggtggacg   8580
gagatttgga ataaaagatg cgcgtcaacc gtcaaagacg caacaaccaa acgtaccgac   8640
aaacggtata tgtaattctg accttctaca ttgtacatag gggcatatgt aacagcaccg   8700
ataccaacaa ttctacatct acttcaaata gcaccgtctc tgatactaat gtatattcta   8760
ctccaaatcc tcccagtgta tcttctacaa ctcttgatac atctaccgac tcacagatat   8820
caatcgcctc aaacaccata tccagcacta caaatacatt gaccgcatat tctataacta   8880
cgttaaacac ctcgacttca tcttcaactc ttactgctgt ctctagtacc catacaagat   8940
cctcaatact ctccaacaac gcatcataca ccacatcatt ggataataca actacagaca   9000
taacgtccag cgaaagttca atcaacgtgt cgacagttta caacaccacg tacattcctg   9060
taacatcgct tgctattaat tgtactgcta caattaacgg aacaaataat tctagttcaa   9120
aaacttgcca acaagacatt gaaacaatac ctgtgaaatc aactccacta acggcagaag   9180
aaggaacaaa tattcaaata catggcaatg acacgtggga ttgtcccgac gtggtttggt   9240
atcgacatta taattggtct acacatggac accacattta tcccaataca cattacaaaa   9300
ctttgataca tcgacgcaag atcctaacgt cacatcctat atgttattct gatcgctcat   9360
cacctaccgc gtatcatgat ctatgccgtt catgtaataa aacagaacta cgcctttacg   9420
atttaaacac caccaattct ggtagatata gccgacggtg ttacaaacag taccatcacc   9480
agggaccaca cgaggatgaa aatttcggac taactgtaaa tcccaggaac aacactgaca   9540
attataccat cccagtatgt cccagatacg tagaaacaca atcacaggaa gatgaacaag   9600
acgacgatta tacactaagc actaccataa ataataatct tatgcgcaaa acaggtcact   9660
atgacatctc acatggcacg cacactacat gggctcttat actaatttgc atagcctgca   9720
tgcttctttt ttttgttcga cgagccctca ataaaaaata tcgtccacta cgagatgata   9780
ttagtgaatc tagccttgtt gtgcaatatc atcctgaaca tgaagactaa cgtttccgga   9840
```

```
catgcaacac ataaaattaa gtaacatatc taccatgaag tacagcaaat atctactaat    9900
gtctatccat ccaacagtga taccatgcac tggcatcttg cgattacatg gacggtaatc    9960
atatccacgt tttcggaatg ttgtaaccaa acttgtccgt gttcctgcgt ttgtgtcaat   10020
tctacaacag tcaacatatc cacaaatgaa acaacgtcta aagccatcac tccaactgct   10080
acgacaaata ccgcaaaaac aacgtcaagc cttgttatta ctacaccgtc atcagtaacg   10140
attagcaaag ccgtgtctac tgcagcttca tcaaccatac tatctcaaac caatcgcagt   10200
catacaagta atgtcatcac aaccccaaaa acgcggtttg aatataatat cacgggatat   10260
gttggccaag aagtgacttt caacttcagt ggatcatttt ggagctacat tgaatggttc   10320
cggtacagtt ctccaggctg gctttattcc tcggaaccaa tatgcaccgt taccaacagt   10380
tatcatcata ctttccctcg tggtacctta tgtttcgatt gtaacatgac aaaatttgtt   10440
atttacgatc taacgttaaa cgattctgga aagtacgttg tcaagagaac acgtcatgac   10500
aatcaatacg aagaagcatg ctacaatctc acggtaattt atgccaacac gacagccata   10560
gttaccaaca ggacgtgtga tagaagacaa acaaaaaata cagacactac taaccatgga   10620
atcgggaaac atattattga aactattaaa aaagccaaca ttcccctggg gattcatgct   10680
gtgtgggcgg gcatagtggt atcagtggca ctcatagcac tatatatggg taaccgtcgt   10740
aggcccagga aaccgcgtta taccagactt cctaaatacg acccggatga gttttggact   10800
aaaacctgat atgcacatca ataaactttt ttgtatcttt agttattaat gtctgtgtgt   10860
ttattcagaa taactcattt ataatataag acggaatatt catatacatt aaaaacatgg   10920
gtgtacaata taacactaaa ctgttattag ccgtattagc aattatccca gctggcattc   10980
tagtacaggc aatttcacat gagcaaaaaa catcctaccg gcaacttttg ctgcaaagtg   11040
aacgtgtgca ataccccatc acaacagtcg agggagatac aatttgcttt aacgttagta   11100
acaacccctg caacttttcc agttattgga atcacaataa ttgtgaactt tgcggttgga   11160
caccgttttt ctttgaatat gctggatata ctgaaaacac gtcgtgtcac ccacgattta   11220
cctgtattca tgatactaaa ggtctaaaac tatacaatgt aaccatgaat gactcgggaa   11280
tttatacaca acacgtttat cactgtgata ttccatgtaa catcagcgat gatcgtaaat   11340
ataacgtaga tgacattgat aactgcaacg ctactataaa tgtaaccgac tatattatta   11400
ccgtgttgtc ttcacgttat tctaaacgca ccgattacca cgtagatact tacattggtt   11460
atgcaaccac tgtggtgaca atagtattta tctgtgtttt aacttgcatt aacgtctcag   11520
caactctaag gcacagacta cgaactgaaa acaacgttaa cagcataacg tgattacaaa   11580
gtatcaacgc tagtttatcc aagagaaact ttcatgaagg atcgcaataa agcattgcta   11640
tgtatcatct ttattttaat catgtacctc atttatattt atttttaaacg tcgttgtatt   11700
cctactccgt ccccagacaa agcggatctg cgagtggaat ttccctcatt accccgtgt    11760
gtcggcatac agtgcgctgc ataagaacac gcatgacaca tagcgtacct ctggacggta   11820
cagtatatga taacatgatt caaggaaagt atggattcct accgacatgt tatgacagaa   11880
cacacaggtt ttctgcgtgt tttataaaag agcgtctcga agcagcttga gccacactac   11940
ggtccagata acgagcgttg caaaaaatat gccgcgcagt agtcgaaagc cgtactgagc   12000
gtgcgaagcg ggtagggtgc cgaacgacgg atatgcgccg ttgtcatctt cgactataag   12060
gatcgcgacc gagtcttcgg gcatggtaaa agccacacgg tgtggttgat atgtagcgta   12120
tccggtttgg aatcgttcgg ctccggctca ggggatagtg aggaattctc agggggacgat   12180
atgggaccca atgactggat aaaagaaggg ttttttcccag taagatgatc cccgtatcac   12240
```

```
atgaggtctg gatatatata aatgaggagt gaaataggca aagggtatca gacaccagcc    12300
tcgtcatgca gccgttggtt ctctcagcgg aggaactatc gtctctgcta atttgcaaat    12360
acatcccacc ttaagcgacg agtccataaa gcaccgttgt ccgggtacgg tgaaagtgac    12420
ccggattgta gcacgtccct tttttgtttt tgcatcgttt atcgtcacca ctagtgcaat    12480
attttgatcg taaggctgaa agagtattgt tatgatgctt agaacgtgga gattattaca    12540
gatggtactg cttgccacgt actgttatta tgttttgcg aattgttcaa tcagcacgac    12600
gactgctcct gtggaatgga agtctcccaa ccgtcagatt cccaagaata ttacctgcgc    12660
taattactca gggaccgtcg gcggtaacgt tactttcag ggtctcaaga ataaaacgga    12720
agacttttta tcttggctac tcgggtctgg ctataagtcc atttgctcgt tcttcccaca    12780
actccctggt gattctaatg agcagcatta cagatatgaa gtaaccaacc tcacgtacaa    12840
ttgtacctat gaccgcctaa cgttactgaa tctgacaatg gaaaacagca ggaattacta    12900
tttcagaaga gaagatgcga attccacctt ctactactct tgttacaatc tgaccgtgtc    12960
ctagagaacg cacgtgaagt tccacagagc cgcgtggctg tagctattgt ttacgttgct    13020
tttgaaatgt taagcgtccc tacgcgcta acatgtttct aggctactct gactgtgtag    13080
atcccggctt tgctgtatat cgtgtatcta gatcacgctt gaagctcgtg ttgtcttttg    13140
tgtggttggt cggtttgcgt ctccatgatt gtgccacgtt cgaatcctgc tgttacgaca    13200
tcaccgaggc ggagagtaac aaggctatat caagggacga agcagtattc acctccagcg    13260
tgagcacccg cacaccgtcc ctggcgatcg cgccgcctcc tgaccgatcg atgctgttat    13320
cacgggagga agaactcgtt ccgtggagtc gtctcatcat cactaagcag ttctacggag    13380
gcctgatttt ccacaccacc tgggttaccg gcttcgtttt gctaggactc ttgacgcttt    13440
tcgccagcct gtttcgtgtg ccgcaatcca tctgtcgttt ctgcatagac cgtctccggg    13500
acatcgcccg tcctttgaaa taccgctatc aacgtctcgt cgccaccgtg tagctagtta    13560
gccagctgtg tatagtttgt tgtgtttgc ttttgcgtat ttgttttcag tcagagagtc    13620
tgaaacgggg tgggagggac ttttgcgggt aatgcatgct aaaataaacg ggtgggctgg    13680
ggtgtgcttg gtaactcact gtttgaatac gcgctcacgc acatatgtag cactcaacat    13740
gttagctttt gcccgcacgc cccgggggcgt gccgagctgc ctttttaata aagtctgggt    13800
ttccagatac gcgctggttc tgattttgat gatttgtgcc tctgaaagct ctacgagctg    13860
ggccgtgaca tccaatcgac tgcctaactg tagcacggta actacaacag cgggtcaaga    13920
cgctgaattg cacggtccgg caccgttaag ctgtaatgtg acccagtggg gacgttacga    13980
gaatgaaagc acaccgtat tatggtgcac tttatgggga tcacgcatgc gagtctcatt    14040
aggacaccgt gtagcgtttg gctgttcttg gaaaacattt tttatttata acgtttctga    14100
aagtagcggt ggcacttact atcaaaaagg ttacaactgc accgacaaac atataacact    14160
atcttgtttc aacctaacgg tggttcctcg agcggttcaa agcacaacca ccgtaatgac    14220
acccacggtg gttacaaact ccacattcag tgtgtcactt attgcgttga gactgacgac    14280
aaattccagc gcggttggac acgctagtta tcaacgacaa cagcgtgttg aaaacgggac    14340
gttatccaag aacataacta acttggcatt cacctatggc agctggggcg ttgcgatgct    14400
gctgtttgcc gccgtgatgg tgctcgttga tttgggtttg cctcaatcgg cttggcgacg    14460
ctggcaaagc cacgtggacg atgaagaacg tggtttgtta atataggaag taaaaggcac    14520
tgttttagca tgactgtttc caaaccgtaa cgtggtaaat aaatcatggc ttccgacgtg    14580
```

-continued

```
ggttctcatc ctctgacagt tacacgattc cgctgcagag tgcatcatgt gtacaataaa    14640
ctgttgattt tagctttgtt tgcccccgtg attctggaat ccgtcatcta cgtgtccggg    14700
ccacagggag ggaacgttac cctgatatcc aacttcactt caaacatcag cgtacggtgg    14760
tttcgctggg acggcaacga tagccatctc atttgctttt acaaacgtgg agagggtctt    14820
tctacgccct atgtgggttt aagcttaagt tgtgcggcta accagatcac catcttcaac    14880
ctcacgttaa acgactccgg tcgttacgga gcagaaggtt ttacgagaag cggcgaaaat    14940
gaaacgtttc tgtggtataa tttgaccgtg aaacccaaac ctttggaaac tactccagct    15000
agtaacgtaa caaccatcgt cacgacgaca tcgacggtga ccggcgcgaa aagtaacgtt    15060
acggggaacg ccagtttagc accacaacta cgtgccgtcg ctggattctc caatcagacg    15120
cctttggaaa acaacacgca catggccttg gtaggtgttg tcgtgtttct agccctaata    15180
gttgtttgta ttatggggtg gtggaagttg ttgtgtagta aaccagagtt atagtaatgt    15240
gtttttatc agggagaagg ttttgtacca acaatgacta catcggggct atctgtgtcg    15300
gaaaattatg acgaaaatta tggactcacg gaaaccgcca atacaacgcg tacaaatagc    15360
agtgactggg taacgttagg aaccagtacg ccactgttgg gaagcacgga gactgcgatc    15420
aatttcggca acgcaactac ggttattcca caacctgtgg aacacccggc tggagaagta    15480
cagtaccaaa gaacgacaac gcattactct tggatgctga ttatcgttat cattttcatc    15540
atttttatta tcatctgtct acgagcacct cgaaaagttt atgatcgttg aaagacagc    15600
agagagtacg gacaagtgtt tatgacggat acagaactgt aatatactat gatgtctaag    15660
aagtgtttgc ggttatttcc atggatgaca attttgtttt gcataccaaa agcacaacat    15720
tggaactata tgacaatacc atgcgttctt aaaattggac gcggcggtca aaatatgagt    15780
ttgcctcccc ttaacaattc attgtacgga aacgatattt ttcaatggta tacagacaga    15840
ccgacagtca ccaacacgtt atgtctttat caaaacaatg agtactacac acaatccaat    15900
gaagatattt caaacatcaa atggcaatgt acaaaaaacc atacgttaat tcttattaac    15960
ctaaccgcaa catatagtag gaactattac tttcaatctc ttaaaactct tgggcaagga    16020
ataccgagac cgagcagctt atgttataat gttagtgtac accttaccca ccaaacacat    16080
tgtcatacaa ccacattatc cctgtatcca cctacacctg tacacaattc attaacaata    16140
tcaccgtcat tagcttcaac caactttaca catgttgcgg tccatcatgc cgcaggtaac    16200
gttgaagcac aacacaacac tgccactcca catacaacgt ggatcatacc cctggttatc    16260
attataacaa tcatcatttt aatttgtttc aaatttcccc agaaagcttg gaataaattc    16320
acacaatacc gatacaacag tatgctcgcc gccgcttaaa gaatcaccgt cgaggaaact    16380
aaaagctatg tacgtttatt tttcagctca ctgtttgaat accgtaaaca taatgacgta    16440
catatacgtg gttatacaac aggtgtttgt gttatgcggc gactgattaa ccatatcgtg    16500
aaccatgatc ttttccgatg gtctgtcgtg accgcaatga tattttacaa gtattccgaa    16560
acctgtatgg aggtcactgt cagagtaggt gatccagtta ccctcggtag tggacatggt    16620
tatcatccag gacaaaaagt acactggtat aaccagtcat gcgtcggcat cagcaacggc    16680
gaaaatacgc atcctatctg cacctacgac cctcctaaac ctggtagaca aaagacaatg    16740
aaaccactc cgttgccatc accactgttg tatgaatgtc acaattccac attaagcatt    16800
cttcatgtaa acgtctcaga tcccagaaac tattgcaggc gaaaatgtcc accaagggt    16860
aactgtgagt ttcccacatg ttttacatta tcgctgattt ctagaacgac aaccaccaga    16920
agacccggac aaaaaaactac gctgtcgcga ttaaaaacta cgccaaataa acatacgcag    16980
```

```
cacaaaagat ccacgcgaag aacgtcactt aaagattaca atgtaacggg tctgccgaaa   17040
ggctttgcgg actcgtttac cggtaacgta gaggcacata gagccaaaga tgccgcacac   17100
agcgcatgga ttctcattgt catcatcatt atcatagtcg tcattctgtt tttcttcaag   17160
attcctcaaa gactccgaga gaaatgggac accaagggat acctttacaa agggaccgat   17220
ggcctgccca ctacggacta attatcgtga gcggacggat atgtccggtt tcaaactcac   17280
tgtttgaata tagggacagt ccctacgaaa cctgagaaca tgtggaaatc acctgtggta   17340
gaatgctgct caggtacatt acctttcatc gcgaaaaggt actttaccta acggctgcat   17400
gcatctttgg tgtctacatc agcctccatg atgcctgcat accggtggtt ggcaagatag   17460
gtaccaacgt tacgttgaac gcggtagatg ttctttcccc tcgcgatcaa gttcgttggt   17520
catacggtcc aggcgggcaa ggctacatgt tatgcatttt cactggcaca tcaacaacaa   17580
cgtttaacag cacgcgcttt aattttcat gtctgagtaa ttacagcctc ctcctcatta   17640
acgttaccgc gcagtatagt actacctatc gtactatgac atcgctagac gattggcgtc   17700
accaaaaaca taaccatggt tttcgatgga ctttagacac atgttacaat ctgacagtga   17760
acgaaaacgg tacattcccc actaccacca ccaaaaagcc cactacgact acgaaaacga   17820
caactaccac aacacaaaaa acaaccacca cgagaacaac caccaccgcc aagaagacga   17880
cgataagcac tacccatcat aaacactcca gtcccaaaaa atccaccacc cctaacagtc   17940
acgtagaaca tcacgttggt tttgaagcca cagcagcgga aacaccgtta caaccaagcc   18000
cacagcacca acacgtggct acacacgccc tctgggtttt agcggtcgta atcgttatta   18060
tcatcattat cattttctac tttcgaatac cgcaaaagct gtggctgctc tggcagcatg   18120
acaagcacgg catcgtgctc atcccccaaa ccgatctgtg agcaagtcgc gtaggaaacg   18180
attgcatgaa atcactgtga aacgccaact ccgtgccaac tggcacggcg acaggcctt   18240 tgacgtattt gaagccaggc gcgctcttga taccgaaagg atccgagggg gctttccaaa   18300
gccgacgtcc ctgattccct tcataaagct gttgaccggc cctagaaaga ccaagagcat   18360
gctgtgggcc cactgcggtc gcttcttgcg ttatcatctg ctcccgctgc tgctgtgtag   18420
actgccattc ttactccttt ttcagcggcc gcagtgggcc cacggcttgg acattgtcga   18480
ggaggacgag tggctacggg agatacaagg agcgacgtac cagctgtcca tagtgcgcca   18540
agctatgcag cacgccggat tccaagtcag agcggcgtcg gtcatgacac ggcgaaacgc   18600
cgttgacctg gaccgaccgc cgctttggtc gggatcgctc ccgcatttgc ccgtctacga   18660
tgtgcgttcc ccgcggccgt tgagaccgcc gtcatcacag catcacgccg tatcacccga   18720
actgccgtcg cgaaacggga tacgttggca gtaccaagag ttgcagtata tggtggaaga   18780
acaacgcgcg cgaaatcagt cgcgtaatgc gattccgaga ccctcgttcc ccccccgga   18840 tccaccatcg cagccggcag aggatgcacg agacgcggac gcagaacgtg ccgaatcacc   18900
acatagtgca gaaagcaccg tcaggcacga cgcgagtgag aacgcagtgc ggcaacggcg   18960
cgaaagacgg cgctataacg ctctgacggt ccgcagccgg gactcgctgc tcctgacgcg   19020
aatacgcttc tccaaccaac ggtgtttcgg acgcgggcgt ttgagacatc ccgcgggaag   19080
tggtcccaac accggcggac cgcgaccgg cggtgcggga ctccgtcaac tacgccaaca   19140
actgacggtc cgctggcagc tgttccgcct acggtgccac ggttggacac agcaagtctc   19200
tagccagatc agaacccgct gggaggaaag caacgtcgtg agccagacgg ccacgcgagt   19260
acgtacgtgg tttgtggaaa gaaccacgtt ttggcgtcgc acgtggattc cgggacagaa   19320
```

```
cccggcggcc gaagcgcaag aactggccgt cataccgctg gcacccacgg tgctccagca    19380
gaacgaggaa ccacgtcaac agcttacggg agaggagaca agaaattcaa cgcacactca    19440
acgtgaagaa gtggaggacg tttcgagaga ggacgcgaga gaagggaatg atgggagccg    19500
agcaagtgga aacgacgaga gaaggaataa tgcgggaaga tatgatgatc acgaggttca    19560
agagccgcag gtcacttatc cagcgggaca aggagaactg aacaggaggt cacaggagga    19620
gaacgaggaa ggtggaccgt gtgaatcgcc gccaatgacg acaaatacgc tgaccgtggc    19680
ctgtccgccc cgcgaacccc cgcatcgtgc cctgtttcgt ctatgcttag gactgtgggt    19740
ctcgagctac ctggttcgac ggcccatgac gatttagaat acaccgagcc attcctttat    19800
ttcccccccc cccatccccg gtcgcttatg cgtgtcaaac actaccaata aagataatct    19860
gccaatagca ccttatatat aatatgtggt cgcgtgtggt cttttaagg agccctgaaa     19920
cacagacagg tatgggcggt ggccggctgc cgccgctgtg gctgccgcta ctgatcgcct    19980
ggagcgagtg gggcaactgc tgcctcgatg cgcctccggt ggtgcgttcg ccctgtctgc    20040
agccggtgcg cgaccgcaac cgcgagcgga acccgggctc accgcagttg ctgccttacg    20100
gcgaccgtct ggaggtggcc tgcatcttcc ccgcgcacga ctggccagag gtctctatcc    20160
gagtccacct ctgctactgg cccgagatcg tgcgttcgct ggtggtggac gcacgcagcg    20220
gtcaggtgtt acacaacgac gccagctgtt acatcgccgg cgggcgctgg cgttttgagg    20280
acggcggcgc ggcgcagcgg ctgagcctct cgtttcgtct catcaccgag accgcgggca    20340
cctacacctg cgtgctgggc aacgagaccc acagcctggc gaccgagacc acggcgctgg    20400
tggccgacgt gcacgacctg cgccactcgg accgctcctg cgacctggct ttcggatcgc    20460
gctcacagac gcggtacctg tggacgcccg atccctccag gttgcgcagt ataaactgcg    20520
gttgggaggg tgaacggcac cgcgtagtcc actacatccc cggcacctcg ggtctgctgc    20580
cctcgtgcga ggaggacgag cgcgaactgt gcgtgcccct catcagccat agcatcgccg    20640
acaacaactg cagccgccgg catcgagtag acggcgctag gcggcgctat catctgcgga    20700
gggattactg gctgacggat ccgaagatcg ggctgctggc cgcgggatcg gtggccctga    20760
cctccctctg ccacctgctg tgctactggt gttccgaatc gtaccggcgc ctgaacaccg    20820
aagaggaaaa cgaggcggcg gaggaaactg ccgcgggaga agcctctgcg gtagcggcgg    20880
cggccgtctc tgaggaagag cagcagcggg agtaaacggg gagagccatg aagcggatga    20940
ttcgcagtca cggcaggaaa acggaatgtc agatgacggg cgccggcgag cgacgcggct    21000
ccgccgtcgg tgcgctcatc tgcgacacgc gtacccgacg cggcagcggc gccaacgaac    21060
gccgcgactc cgacgtcggt cccatcgccc acagtagcgg taccagacgc ggttcggcaa    21120
atgaaacgtc cgcctgtacg cggaccgatc accagaaggc ggacattggg ctgtggttca    21180
tgtttctgtt ttttggactg tgttcgtggt tagcgatgcg gtatcgcgca caataaattt    21240
tgaatccata tcaaggaacg cgtgttttgt atttttattgg gaatattggc ggggataaac    21300
cggtttcgga tgtttaccct taatcttacc ggggacctcg ttgtcctctc cccttcttc    21360
ctcggacacc gggcttcatg ctgacgtagg taccgactgg ggtcaaaagc ctgggtactt    21420
atggggagcg cgcacaaagg accgtcaggc gccggcatgg agcgtcgccg aggtacggta    21480
ccgctgggat gggtgttttt tattctttgc ttatctgcct cttccccgtg tgctgttgac    21540
ctgggtagca agtcctcaaa ctctacctgc cgcttgaatg tgacggagtt ggcctcgatc    21600
cgtcctgggg aaacgtggac gttacacgga atgtgtatct ctatctgcta ctacgagaat    21660
gtgaccgagg acgagatcat cggcgtggct tttacttggc agcataacga gtctgtggtt    21720
```

```
gacctgtggt tgtaccagaa cgatacggtg atccgcaatt tcagcgacat caccaccaac    21780
atcttgcaag acggactgaa aatgcgaacc gtccctgtga ctaaactgta caccagccgc    21840
atggtcacta atcttaccgt gggccgttat gactgtttac gctgcgagaa cggtacgatg    21900
aaaataatcg agcgcctcca cgtccgattg ggctcgctat atccgagacc gcccggatcc    21960
gggctcgcca aacacccctc cgtaagagcc gacgaggaac tgtccgcgac cttggcgaga    22020
gacatcgtgt tggtctcggc catcactctg ttcttcttct tgctggccct acggatcccc    22080
cagcgactgt gtcagcggct gcgcattcgc ctgccgcatc gataccagcg gttacgcacc    22140
gaggactgaa cggataaccg caaaggccac gtgcaacgtt cacgctgcta taagaaggcc    22200
atgtcccccg tggacgggtc tctttgacac gagcgcggca cgccgttgcc acgagcatgg    22260
atcacgcgct cctcacacac ttcgtcggcc ggccccgtca ctgtcggttg gaaatgttga    22320
ttctggacga acaggtgtct aagagatcct gggacaccac ggtttaccac aggcgccgca    22380
aacatctacc tcgacgtcgc gctccgtgcg gcccccagag gccgccgag attcccaaaa    22440 gaagaaaaaa ggcggccgtc cttctgtttt ggcacgattt gtgctggctg tttcgacgac    22500 tttctttcc tcgggaggac tcggagccac tgatgtcgga tccggcacgg tctcccgaag    22560
aggaggagta acaacacac ggctaagagg atacatcatc aaagaagata ggaggggtca    22620
aaacgcggac tgaaagtata taacgccgat catgtccgag gaactgttaa taaaacgcca    22680
tgatgacaat gtggtgtctg acgttgtttg tgctgtggat gttgagagtg gtgggaatgc    22740
acgtgttgcg ttacgggtac acggggattt tcgatgatac atcgcatatg acgttgaccg    22800
ttgtggggat ttttgacggg caacactttt ttacctatca cgttaattcc agcgataaag    22860
cgtcaagtcg ggccaacggt accatttctt ggatggctaa cgtctcggcg gcctacccca    22920
cctacctgga cggggaaaga gccaaaggtg accttatttt taaccaaacc gagcaaaacc    22980
tgttagagct ggaaattgcg ttgggttacc ggtcacagag cgtgctgacg tggacgcacg    23040
agtgtaatac cacggaaaac ggtagttttg tagccggtta cgagggattt gggtgggacg    23100
gggaaacttt aatggagctc aaggataacc tgacactatg gacgggcccc aattacgaaa    23160
ttagttggtt gaagcaaaac aaaacgtaca tcgacgtaa aattaaaaac atcagcgagg    23220
gggatactac aatacaaagg aactatctca agggtaattg cactcaatgg tccgtcattt    23280
atagcgggtt tcaaaccccc gtcacccacc cagtggtaaa gggcggtgtc cgaaaccaga    23340
atgacaacag agctgaagca ttctgtacat cttacgggtt cttttccaggg gaaattaata    23400 ttactttat ccattacggt aataaggcgc ccgatgatag cgagcctcaa tgcaatccgc    23460
tacttcccac cttcgatggg actttccatc agggatgtta cgtagccatc ttttgcaatc    23520
aaaactacac ctgccgcgtt acacacggta attggacggt ggaaatcccc atcagcgtta    23580
cctcacctga cgacagttcc tcggggagg tccctgatca cccgacagct aacaaacgct    23640
ataacaccat gaccatcagc agtgtcctcc tagccctgct tttatgcgct ttgctattcg    23700
cgttcctgca ctactttacc accttgaaac aataccctacg taacctggcc tttgcgtggc    23760
gctatcgcaa ggtccggtcg tcatgaccag caacgccctg tatgagctgt ttcgacgtcg    23820
gttaccgcgt gcccccgtca acacggtcat gtttctcacg cgacgcactc gtgatgggtt    23880
ctgcggtcgg ttgacgtcca tcgccacgaa ttcccactac actatgttcg tgttagatca    23940
cggatccgtg cgcatcgagc gaccgagtca gtcagaagtg gattgcgcca gtttaatgga    24000
aacgctgaag cggattcggt tacgaaattc gtgggtagcg tcagaagacg agctagatgt    24060
```

```
gagtcgcagg gacgcgtgac acgaaacgcg ttcaggatta acgtaggttt tcgaaataac   24120
ctacgtccgt gagtgacgcg gtttcgtgtt gaaacccgcg cccgcttctc acggtggttt   24180
atgatgaaac cggcgttgcg gatccacgcg ggttcctcat tcaacctgcg aaaagaggaa   24240
gttgcggtaa aaccacgtca ataaagacgt caatgacacc tcaatgttgc gttggaacgg   24300
tctttatata tacaaacgcc gttatgatca gtgtccggca agatgctcgg gatacgggct   24360
atgctggtga tgctggatta ctactggata cagttgataa cgaacaatgg cactcgaagc   24420
aacaataccg ataccatctt tgtatctctc cttaccgggc ccaacggagt tactcgcaca   24480
gccatcggag gtctgtattc aaactacacc aacttaactg gagcatttgg cttcacttca   24540
acaaatatgt cagcaaccaa ctcttccgct gaggataatt ggagcgtaac caacctgacg   24600
gagagttgca tcaaccgcgg tgagtcctat gtgactacca tctggcttct ggactgcact   24660
aaaaacgata cttattggta ctatggaaat gcctacaatc atacatgtga aggtacaatt   24720
tcgggatatc tcctgggcat gtgcaagcta tggaaaagtt gggtcaataa tattacttct   24780
tataacactg tcagagtcga atcgctggga aatgaaaaca ggtgcatgct gctccctaga   24840
cagtatactc tcaacgccac ggtggaatgg tacaacaaat ctgaaggtga cgtaccagaa   24900
gaattcatgg actatgttat cctgacccccc ttggctgtgc ttacatgcgg actgcaggaa   24960
gcttatatac tcgacaaagg tcgtagatac atgtatttgt tttccgtgtc ctgcgtggga   25020
atcacaggta ccgtatctat tatactcgtc tccctatcgc tgctcatcct catctgttac   25080
tatcgctgtg gccggcttct gatatgccca cgcggctttg aactcttgcc agaattcact   25140
gaggaagagg aggaaaaaga aaattgtta acgcataatg acattgaagt ccaagtgcct   25200
attcgcacgc ggcgactact cgtcccttgg atccgggaga gcaaaatgtg ggtactacca   25260
cccccgttgc ctccacgacc tccccactta atagaattcc cgccgtctcc tccgtcatcg   25320
cctgggccca tgcacatggt ggtctgcatg ccagcatgac gaactttgga ctctgagccc   25380
caagcggtac gaactacata ttttccataa atctacactg aacttgagca caaagatact   25440
gacaatagac tggatataca gacttttata tgatccctgt acagatgtaa ataaaatgct   25500
tttatttaaa actggtccca atgttcttcg ggaatcatgg ggtggggacg ggggacgcgg   25560
tagggagcaa aaccgggtac atgggggggga acatcgtcca acagtagcac cagcggattg   25620
ggtaggggtt gctgcggagg tcggtcgatg acgatgtcga tctccatcgg cagatccggc   25680
aacatctctt catctccctc accgaccagc actcggcgct gttctggatg tatatgattc   25740
tggaaaagcc tccgacgagc tcgcggcgcg tagaaagcca agcggcgcaa gggccggcga   25800
gcccgaaagt ccatgcgcac agatggcatg agtccttgag tgacggtggt gagctgggga   25860
acagggctac ctcccatcgc gacggtgaca gtggatccat gagagaggcg ccgcacgctg   25920
catggctaaa taccgtgaat cccctgacgt cgtctttcgt cccgaacgcg tcatgttggg   25980
ggcgaggcgt aaaccgtcga ggttgaaaaa ccgcgtatct gcgacccgtc cggactacgt   26040 tgtttttag aagcggccac atgacctcga gatgtcgtca cccaaggtat ttaacggcac   26100
acagccagac gcgttcgtca gcagcgacgc cgacaagacc tcagcatggc tcggaggcta   26160
tggatcttga gcttactagc cgtgaccttg acggtggctt tggcggcacc ttctcagaaa   26220
tcgaagcgca ggtaaacgga atctggggaa ttcaacacag gtaagaaata taaaaaaata   26280
acgtgattgt gaacgcggtt atcgtgtttt tgcagcgtga cggtggaaca acccagtacc   26340
agcactaact ccgatggtaa taccacccccc agcaagaacg taactctcag tcagggggg   26400 tccaccaccg acggagatga agattactcc ggggggagact atgacgtttt gattacggat   26460
```

```
acagatggag gtaaccatca gcaaccacaa gagaagaccg acgaacacaa gggagaacac    26520
accaaagaaa atgaaaagac ccagtagcag cagcagatcc caagggttaa agaccatgtt    26580
gactattttg ttttttatta aaaagctgta aggttttgct ctaaaaacac cccgcctccg    26640
gtcttttttc ttttgtattc ggcacgcgaa acacggtttc ttcccatagc ctgtctaact    26700
agccttcccg tgagagttta tgaacatgta tctcaccaga atgctagttt gtagaggcta    26760
tgcgggatgc tgcggcggcg cgaccttccc tctccaccca gccccgtcaa acacacgcg     26820 actcgagcgg ttcgtatgaa aataaaaaaa cagcttttta tttacaggaa cggggaaaaa    26880
aaaggcacac ggtccgtggg agacgcgggt tcacgcgtcg tcaaaaagtt ggtggtccac    26940
tccgtaagga caggtaggct tatttagctt ccgcatgctc ctggttccgt aataaatgcc    27000
gttttcgtgg cagcgtgtca tgccgcgagt cacaaactcc atcaaactgt cggccacgat    27060
gcaaacgtgc tgattgttgg cagcaaagac gcgcatacag tcgtccacga agaggttgat    27120
cacgtcgtag gggctcacca accagcctaa aggttccacg tggttactgc cgaccatgac    27180
cctccagtcg ttaatctcgc tccagtcgta cagccgaatc gtggagacgc gaatgacgct    27240
gtaatcaccc atgaccatga gtcggccgcg atacgtagca cgccactgcg cgaacgcgtg    27300
gatgtgcatg cagccggcca gcgctctaag cgaggcggtg tgcggcagct cctctgggac    27360
ggtgatgaag ttgcagcgtc gcaaaccgat gttgagaaat tcagtgatgc tctcggccac    27420
aaaggtcaac gagtcagagt agatgtggtc ggtccacagg tacatggcgc ccgaggcgcc    27480
caggtacagt tcagacggca cgttgtgatc gcccttgtgt ttaagaaagt tgtaggtgca    27540
gatgctgccg acgaaacgca gcggctcggg gcagcagagg tagctggcca gacgctgtgc    27600
atcccgtcct tcgtcgcgca ccaagcgcca gcgacgccgg ataacgaggc agcggtcttt    27660
gggccagacc agggccacgc gttgcccggg tttccacggt cgcgacgtct taggaggcct    27720
ccagcggtcg agcagattga gaaaacagtc cttgattacc gacatcgcgg tcgcgcgtcg    27780
gtggacaaaa agaaatcggg ccgatccaga aaaaaaaaa acgacagcga aacaccgccg    27840
tgctcgagcg aagggtggcg gagggccaga agaggcggcc ttgacgacgt tggcagcgaa    27900
aaaattggca cgcgagtcaa acgggaagta gcgtcggtgt tttatgcccc aagcagcgtc    27960
gtcgtcactc gtggcgtcac agtcaacggt gctgacgtcc tttggggcag tcgggcacgc    28020
gatcgtagat gccgttgtgg ccgctgaaac gtcggttttc aaacagcagg ttaagtccca    28080
gacacatgaa cgtgttcaga ttatctccca cccggatgta gcggtcgtcg cgcacgtcgc    28140
aggcgtagac ggccccggta taggcgacga cgatggggat aaggtcgacg ggccagcgca    28200
ggtgaggaaa gggcgcgttc tcgcccttga ggctgacggt tcccaggccg agaacgcgca    28260
ttccgaaagc ggttttgatg ttgcgcagca agtgaccgcc ttccacgctg ttttcgaaac    28320
acctgaggtt gcatagacgc agttccgttc ccggcgggaa cgtcaatggc atgaactgcc    28380
cgtggtggcg gatgatgaat cgtgccatgg tatccaaacc gaggctccag gcgcgcaaca    28440
gcgggcgaaa gtagcgctta accaacgacg aggtcaggta gcgcatgcag tgcagggttt    28500
cgacggcgcg cagcccgacg cgcgcaaact ccatgaggtt gcgggccagg tagtagacgg    28560
cggtgtcctc gcgtacatag caaaagacat agccctcgtc cgagatgagg cacacggcgg    28620
tcttcttctg ctgatccggc gacaacacgg cctcgttcac gaagcgaccc acgaaggcca    28680
ggcgcgtctc gcagcacagg tagtgactcc aagctttcac gtcctccggt ttgaagtcct    28740
cgtccgtctc gatctcctgc agcactaggt tccagcccgg cggccagacc acgggcaaca    28800
```

```
cctggcctgc gttgatgcgc acgtaagctt ccagacagcc caggccgaac tcggccgtga   28860
gcgccaggct agccagatcg ctcatgtgac gcgccgagtc ggtgggcgag cccggggcc    28920 cgtcgcacac cacgctccgt cttcttgtcc tcaccgcggc cagcgtggcg aggacacttt   28980
ccgcgcccga ggctgtatct tcggtttgcc cgccggagcc ggccctcact atataacgtc   29040
ccgcccgggt ctcctccatg tatgcaggta agcaactgag ccgaacgcac ctcagcagac   29100
gagaggatgt cgtcgcggcg tcgcagctcg tcacgtcgct ctggcgaacc ctcgacggtg   29160
atttatatcc cctcgagcaa cgaggacacg ccggcggatg aggaggcgga ggacagcgtt   29220
ttcacgagca cgcgggcgcg cagcgccacg gaagatctgg atcgcatgga ggccggtttg   29280
tcgccctaca gcgtctcctc ggacgctccg tcgtccttcg agctcgtgcg cgagaccggc   29340
ggcaccggcg ccgccaagaa accgagcgaa aagaaacgat cgtcgtcacg tcggcaaccg   29400
cagatcgcag cgggcgcgcc tcgggctcg ccggcgacac ccaaggccgg caagtcgcct    29460
aaagtctcgc gaccgcctag tgtgccctcg ctgcccgaga acggcgccgg cggcggtggc   29520
gacgataaca gcagcagcgg cggtagcagc agtcgcacca ccagtaacag tagcagaagc   29580
accagtcccg tggcgccagg tgagccgtcc gctgccgagg gcgatgagtt ttccttctgt   29640
gacagcgaca tcgaagactt tgagcgcgaa tgttaccggg tcagcgtggc cgacaatctg   29700
ggcttcgagc ccagcgtggt cgcgccgcag cacgtcgagt atctcaaatt cgtgctgcaa   29760
gactttgacg tgcagcacct ccgccgcctc aacgaatgca tacccatgcc ggccttcgcg   29820
ctcaccagcc tcgtcgaccc cgtcttaaac aacgtagcgc ctggcgagcg cgatctcacg   29880
cgtcggataa tcacgcacgc ggtgatcatc aactattact acgtggcgca aaagaaagcg   29940
cgccacatgg tggaggccat acggaccacc gtgcgggacg acacggtacg ccgggtagcc   30000
gcgcaggtca acaaccagag ccgttcgggg cgtgcgccg cgctagcgct tcactttctc    30060
acgtcacgaa aaggagtgac ggacggtcag tacgccacgt ctctgcggcg gctggacgaa   30120
gagctgcgga tcgcggcac gcccgaatcg ccgcggctca ccgaggtcta ccagacgcta    30180
cgcgattaca acgtgctctt ctataccgcc cactacacct cgcgcggcgc gctctacctc   30240
tatcggcaaa acctgcagcg gctcaacgaa aaccaccggg gcatgctccg gctgcttcg    30300 gtcgaagaga tatgcgaaga gcacacgctc aacgatctgg cgttcctagt aggcgtcgag   30360
cttatgatca cgcactttca acgcaccatt cgcgtgctgc gctgctatct ccagcaccag   30420
ctgcagagca tctcggagct gtgttacctc atctatgtac aactgccgtc gctgcgcgaa   30480
gactacgcgc agcttagtga cgtgctctac tgggccgtca gtcaaaacta cgactacgcg   30540
ctctacgcga gcacgccggc gttgtttgac ttttacgcg tcgtgcgtca gcaggacgcc    30600
ttcatttgca ccgactacgt gtactgcgcc ctgcgtctgc tggcctgtcc cgacagacct   30660
attatcggtg acaccggcgg cagcagtagc tcccaacgcc tcgtaggcga gtttatggtg   30720
cgcgatccgc tgttgcgcga cccgcgcgcc acccacctgc gccagaaact catcacccgc   30780
gacatatgcg tggcgcggtt gcaagcgcag ccctcgagtc acacattcc ggtcgaacac    30840 acgggtgtct cctccgtcac cctgctcaag atctttagcc aggtccccc cgacgaacgc    30900 gaagaagaca cgttacgcga gatggctctt aaagcgttta tggaagcgaa cggtaatcac   30960
cccgaacaaa tctgccgatc cccaccaccc ccgctgccac cgcgcgacta tcctcaacgc   31020
gacgagcggg accgtcaccg tcgcgaccgc cgcgacagcg gggaatactg ttgctgatgg   31080
tgggacgaaa cagcagggcg gaacagttta tgatagaaag tcacaggaaa gtatgtgttg   31140
tttttttttt aatgtaccaa gaataaaaag tgcgtctacg accaaagcgg tgtgtggacg   31200
```

```
ctcgtcctct gtcttctccg gttttttttt atgtgtgtgt ttttcttttc cttcctattt    31260
tgttacggca acagcgctga tggcacgttg ccggcttcga acatcgcgtc ggtgatttct    31320
tgcttgcccg gcgtcacacg gtgacgcagc agcgcgcggc tcacgtagca ggccgactcg    31380
cggatgacct ggccgtcggc gtcgcgtcgc aggcccgagc ggttgccgtg acgcagtcgg    31440
ccctgcgcgg cgcgctccac gtcttcaaag tagctgtgta gcaggccgcg ctccagcagc    31500
tgcggcagcg agtcggcggc gcgcaccaca aagttctcac ggctgatctc gtagcacagc    31560
acgctgccgt cggctgccac gccggccacg ctgcggtccc aactgaagag gttggcgagt    31620
ccgatggtgc cgatgacgcg caactgaccc tgggtcacca ccagcagctt ccagtattct    31680
acgtcgcgcg gggtgaggat ggtctcctcc acgtcgcaga caaacaacgt gtagccgcgc    31740
ggatagggca gatccaggtg gcgaccgcgc tggcggcgta taaatcgtc taaattcaaa     31800 ccgccgtcgg gtgcgcgcct gctcgtcatc gccgcgcctc gtcggtcgat gaccccacgg    31860
tgcttataac gcgccgccgc ggcttcatgt ggcgtgacct ccgacctcgt gaggccgaaa    31920
acggcgtaca tgaagacgct caaacttttg aatgtgggcc cggtagcgca ccgagggccc    31980
cggggcggcg acgacggcgg gtccgagttc cagcggggcc ttgcggcggc agcggttggc    32040
gtggttgctc agctcggcgt ccgagagcgc cgagctgaac tgcggcagcc gcgtgcgatc    32100
ctgcggcgcg tccccgtgtc gcagcgagtg ccagagcagg cgctggacgc gcgccgtctc    32160
gggcgtcggc ggcgcgcgac agccccggcg cagcttgaaa acgtgcaggc acagcagctc    32220
gcgcttgatg cgcagcgaca cgctgcggta gtcgggaatc cgctgcacca gctcgagaaa    32280
gtcgcagaag gtctccacga acgtgtcctc ggtgaagcga atgcgcttca gatcgtggac    32340
gtgtttgcga aaccgcgaca gttctcgacg ttgcacgggg ttctgagcga gtcccttgcg    32400
cagcagcgca gcctcgcctt taaacagcct gatgagccgc tgcacgtccc cgctcaacat    32460
acgtatacac gccgtgtact cgtgacgtat actggcgcgc agcagccgaa tgatacgcag    32520
ggccagcacg gcgttggagg ccaggtacat ggcgtagccg cgacgcgggt tggcacaggc    32580
ccagcccgcg gggagcagaa agtagtcgtc gaccagcgtc tgcgaccagt cggcgaagcc    32640
caggtcacgt gatacgctgt cctggacgcg ggccacgtcg ccggctgtga ggtggcggat    32700
cgccggcagg tgaaacgcgc ccaggtgtcg attgcgctcc agcctcagct cggcgtgctc    32760
caaacgggaa tggtgggacg ccaccgcgga gggcgacaaa gaggagtggt cgccgccgcc    32820
gtagttaccg ttgtgattac cgccgtcgtc gcgcccgtcg ccgcactcgc aaaaggccgc    32880
gtagaggtcc ttcaacgccg cttcggctcg cgccataaac gtggcgtgga aaaaacggc     32940 ggcgcggtgc gtccggtact tgacgggcaa cccgcggcac agggccgccg gcaggcagcg    33000
gccgatgagt tcgcgctcct cgggctccag aaacaggcac agggtgccgt ccaggcgcag    33060
gtacagctcc tcggtcatcg agcatagctg ccgcaagtaa tgggtgcgcg tcccaaaggt    33120
cttgtaatcg agcaacgtgc acaccacgta ttgccccgtg gccacggcca gagcgatgcg    33180
tttggcggcg cgactgatct ctggcaagta ctgcgcctcg tgcaccagac ggcggaaagc    33240
gccggcgttg agccagcgaa aatgctgcgg atcgggcggc aagggcacgc ctcgaagcgc    33300
ggcccagaca gcgaggtccg actcgagcgt cagaccgcgg atgtcgtact tgccgtgcgc    33360
cgtagcgcag gctgaatgga ccagacagct gcggcgaatg tacaccatgg cgtgcttggg    33420
atgtttgggc gccggcgttt tcttttttctg accgccggcg gccgcagat cctcgggcgt     33480 gcgacacaac aggccggcgc gcacagcctc ctgtcgatta cgaatcggcg tcaggtaggc    33540
```

```
gcgcaggaac tggtgacaaa actcctcatc atcacgacag tcgtcgagat actcgtacgt    33600
ggtgagcgga tcgcgaaata ggcgctcgtc accgtcgtca tggtcttctt tagcctgctc    33660
ctccggctgc tggggttggcg gtggaggcgg cggctgatcc acggggttca tgactgagag    33720
gaagaagaag gtggcggcga agcgacgcgg agcgacggcg gtaaagccag acaccggcta    33780
tatagctagt catcacagtc tcctccttca cgacgccccc gtgccgctca cgctatccag    33840
cacgctacgg cccgaaaaca cgtactcgct gacgtcgtac gcgggcgatg tatggctgct    33900
caccggtttc gcggcgacgg ttgcgctcga gtccaacggc gagaagcaaa aacgccgtgg    33960
gcaacgaaac cagaaggagc cctgacggat aaaaccgcgc agcgtctcgg ccaacttaac    34020
cagcatcgta ccgtacagca gtacgtgaat gccgccgtgc gcgtccataa atacggcttt    34080
gtttacgggt tccatccatc cgatgactac aaagtgagcc tgttctagca cgccgatcac    34140
aaaattgttg gcctcgtcgg cctcggccac attccacgag ccgaaagtga agtacaagc    34200 gggcgagccg cccaggcgga ttttgctacc ggcgtggagc tgacatacgc gcagcagatt    34260
ggcgcggtcg tgcagtatct gggagagttc gtacatgccc gcgaaggtgt gcttaaacca    34320
cgcgccctct acgatttcat ccacgtaatc gcgctcaaag aagctataca cggcaaagag    34380
gccgttctca aaaaactcgc cgaacgagag ccccagcacg tacaccttgt cctcgccggg    34440
caggtacgca aaggcgtgcc cgtgcccgga gacccagatc tcgggcgccg tgtttgcgtc    34500
cggcacgcat tcgtacacac tgacgaggcc gataaagtac aagcggccag cctggcgcag    34560
gcacgagaag cgccggtagg tcttgtgatc gcgcaccacc ccaaagtact gagtgtcgcc    34620
cagcatgatg ccgtgcagcg gcggccagca cagcgggagc caacgacccg ccgtggcgcg    34680
cacgtagcgc tgcaggtgaa ccccgctcgc acgctcgcgc ggcttcgggc gcttgtgggt    34740
ccaggcatca cgcagaccgc gccagatgct gctgaacttg ggctgcccgc gcagatagag    34800
cgacgagagc gagtcaaagt agcccacgac gagcctgtcg ggagacacaa gagcgcgaaa    34860
atcaaaccta gagcgacgac ggtgaaaaaa ccgattataa gcgcgtgtct caaacacgct    34920
actttcggtt ataaaaacac cgtcgcccta tttctgggcg tgtgtacact gatgactcac    34980
ctacgctttt tgaacggcag tctcagctcg ggattggcct cgtacagcga gctgcggtcc    35040
acggggccga tgctctcgta gcgaaagtcg tcgatgagca gcgccagccc cacgcgcacg    35100
aagcccctga ggtcgcgcgc cagccgcacc aacttatcct gccccaccag cgccgcgtac    35160
acggtacccg tgtcgccgca gagaatccgc acgcggtgaa agaaggtctt gtcctcggcg    35220
ccctcgatct cgcccagcgg catgacgggc tcgcgcgtgt acaacgaacg ttgaaagcgg    35280
cgcagcatcg aggccgagag ccccagatcg cgcgccgtgc gcagcaccag ggaatgcttc    35340
tcgggccaga tgagggtcag ctgcgcctcg cgatgcgcct ctacgtaggc gcagcgagcg    35400
gcggtgtcct cgcaagccag caactcgcgg aaagccagca gcgaacgtag gtagcggccg    35460
cgagcggagg cgcgcgagcg gcggcacagc tcggcccgat gatcgggatg caccaagggc    35520
acgttgggtt gcagacgcgc gcagatggat tcgtgcaccg ggtcgcagcg gatcatgccc    35580
ttggcaaaaa atccggccag atccgaggcc aactcgtaca ggcagtcctc ttgcgcgtcg    35640
taggcgaaca cggcgccgta cgcgtccacg aacacctggt accggcaggt ggcgtgcgag    35700
accgtgccaa tgagatgcag agctcggaat tcgccgaaaa agtcgttctg gcagtgctcc    35760
agatcgatct cggtcagcga gtgcggcgaa tgctcgcccc cgaccacgta gatgcactgc    35820
gagggccagc ccagcgacac gcacgagccc tcgaagcgcc gcaagtaacg ccgcaggccc    35880
tcatagtcgc gtcgcacgca caggtcggcc aagtcgcgcg tgcaaaagac ctcgggtacc    35940
```

```
aagcagcgtt tgcgacgcgg ccgacgcgcg tgcccgggca gaggaggaag gcgcgacggc    36000
ggcgacgacg aggaggaaga cgccgtggcc gccgagcagc ccttgcgacg gccggacatg    36060
ccggcagtcc gcgacgatcc acaggagaca aaaaagcaga agcagcagta gcctcggcga    36120
cccgctccac cccgtcctcc acacgctcag ccgcgactga acgccgggc gcgccgctac     36180 ttgggttttt atagccatct gcccccgtc tcgggcaccc gggagcgatc tacggagacc     36240
tgacagcagt tgggcaacac aagataggga aatacaaaga cacttttaat aaaaaacgag    36300
actactttgt gtgtgtgctc cgtaaactgt ttattctccc cctccgcttc gctctggatg    36360
ggctccgggc ccgtcaacac gcgactcgcg cggcaaaagg cacgctgttg acggcgcgag    36420
agcccgtcgt gatagtccat catgccccgg agatcgtgca caaagcagct gtcgccgcgc    36480
agaaaccgac gcagcgtctc cacgtgctgc agctgccggc gcgtatcagg agccgtcatc    36540
gctgatgtcg tcatcgccct gacaggcgcg tagatggctc cgcgagatca cgcgcgtttt    36600
caaccgccgt gacacatcag gtccatcttg agctggcgcc gggcctcgcg caggtgtcgc    36660
acgcgttgtg agcgggaggc gagttcggct tcttgctcga actcctgctg ctcactgtcc    36720
gagagggtgc gataaaaggc ggcaaagtcc tccaagtcgg ctacatgcgc cctgggtctg    36780
acgctccaaa gcgtacgcag tctgatgaag cggacccatc gagcgtcacg gcacgccgtc    36840
ttgaacgcgg ggcccgggaa gaggttcttc tccccggcgc gctcgggccg gcgaggccga    36900
cgcggtttat ataccgtc tcggacggcg ggacgccgag cccgcgccgc ggccgctcat      36960
ccggagacgg cggaaaccgc ggcgccgag gaaacgggga ccggcaacga cggcggtggc     37020
ggcgaccaga ttatggggga aaaacccacg cttgtaaccc tgttgaccgt cgccgtgtcg    37080
tcgccgccac cgtcgtcgcc gctgccgctt gtcagcttca cggagctgct gttaccgccg    37140
ccgtccgtcg ccgccgccgc ggtggcggcg acagcgacga gcgaggtggg cgagaaaacc    37200
gcggagcaag aggtagcggc tgcgggtccg gagaccggga atgagagaag agaaaacagg    37260
gagaacgaag gaggggagac gaggacgaca gacaccaccg cggtcaaaag gtcgcacgac    37320
ggtatccctc gccaactagc agagcgcctg cggctgtgcc gccacatgga ccccgagcag    37380
gactatcgtc tgccggcgca ggacgtggtg acctcgtgga tcgaagcgct acgcgacgcg    37440
gaccgcgata actacggtcg ctgcgtgcgc cacgctaaga ttcaccgttc ggcctcgcac    37500
ctgacggcct acgaatcgta cttggtgtcc atcaccgagc agtacaacac ggcctcgaac    37560
gtgacggaga aagcttcgta cgtgcagggc tgcatctttc tctcgtttcc cgtcatttac    37620
aacaacacgc agggctgcgg ctacaagtac gactggtcca acgtggtgac gcccaaggcg    37680
gcgtacgccg agcttttctt tctgctctgc tccaccagcg agagctccgt ggtgctgcaa    37740
ccgctcatca ccaagggcgg gctctgctcg tccatggcgg tttacgacga ggaaaccatg    37800
cggcagtcgc aggcggtgca gatcggtttt ctgcacacac aactggtcat ggtgcccttc    37860
gtgccgcacg cctgcccgca ttacgccgtg ccttttcacga cgccgggaaa gccgggctgc    37920
ggcggtgctc cgagcggcgt tgcggggttg gaggaggcgg cgcccctttgg acgggtcagc   37980 gtcacgcggc atggcgcgac gctgctgtgt cgcgtggacc atctgacctg gatcagtaag    38040
cgcgtaacca cgtacggaca caaaaaaatt acgcgctacc tcgcgcagtt ccgcggcacg    38100
atggacgacg acgaggcggc gctacccggt gaggacgaag cgtggatcgc gtccaaaaac    38160
gtgcagtacg aattcatggg tctcattttc accgtcaacg tggattcact atgcgtggac    38220
gcggaacagc gccaactgct gggcaccgtg gccacctcct tctgtcaccg cgtctcggac    38280
```

```
aagatcacgg cgcgcaacat gccgcgcgcc ttttccttct acctgctgac gagcgcgcag    38340
cgcgggtacg acctgcgatt tagccgcaac ccgtcactct tttttagcgg cgacgcgctc    38400
aactgtccgc ttctcaatga gcccaacgtg ttttcgctca cggtgcacgc gccttacgat    38460
atccacttcg gggtgcaacc gcggcagacg gtggagttgg acttgcgcta cgtgcagatc    38520
acagaccggt gtttcttggt ggccaacttg ccacacgagg acgccttta cacggggctc    38580 agcgtgtggc gcggtggcga gccgctcaaa gtcacgctgt ggacgcgcac gcgttccatc    38640
gtgatcccgc agggcacccc catcgccacg ttgtatcaaa tcaccgaggg cgacggtaac    38700
gtgtactcgt acaaccacca cacggtgttt cggcagatgc acgccgccgg agcaaccacg    38760
ttctttctgg gcgacatgca attgcccgcg gacaactttc tcacgtctcc ccatccctga    38820
ccctccgtcc gtcctccttt cccgacacgt cactatccga tggtttcatt aaaaagtacg    38880
tctgcgtgtg tgtttcttaa ttattcctcc gtgttcttaa tcttctcgat cttttggagg    38940
atgttctgca cggcgtccga cggcgttttg gcgccccca tgccggcaga acccggttgc    39000
ggccccgtac cgctcttctg gggcgacgat aggtcgaaag ccaccgtttt catgcccgtc    39060
gtgctcttga cggggaacc tacggcggcg gttcccgtcg agcggcgtga ttgcaaagcc    39120
gcgctcgccc ccggtttcag gatggaggga gaggccacag gcggcgcatt cgatacgctg    39180
cttttggccg tagacgacgg tgggtaaacg gtggttaccg cgggatacgt cggcgtggtc    39240
gaggcggccc ggctggtgcc ggacaggcga cccggcgcgc taccgctcac ggggaccgag    39300
ggcggtcgac ctaccaccgc tttgccgccc aaagtaggtt tcaaggaagg aacaacaccg    39360
acacggccgc cccggccttt caccggagac ggggggcac tcttggccgg ggacggagag    39420
gctgacgaaa gcatggacag cggcgatgtg gcggggaca cgacatcatc ctccgtgggc    39480
gacaaaacgg acgccgaagc tgacggctgt cgagccgaag cggaagaggt tcccgcgcca    39540
gaagtcacgt tccttgatga cgtcgtttta cgaagccg gttgaggttg caacagcgtg    39600
gcgggtaccg tcgacggcgt gcccgacacc tgtttctcta gccttccctg aaccggtgtc    39660
gacgtcaccg tctgcgctcg gcggacgcg tgcggcgtcg cgactcgctt gcccagcacc    39720
ggtttctggc tcgtggatgt cgtcgtcatt ggagacgata acttagcttt acgtattctg    39780
gacggcgtcg actgctcggg cgtctgactg ggaggcgaaa tgacgtcgtt gtaatcggac    39840
gacggtgttg tgtgtcccag gctgacgacg gagccggtgt ccgaggagtc gtcgtcttcc    39900
tcctcgctgt cttcgaccgg tgactctgca gtttggtccc ttaaagccca aacctcatca    39960
gcggcgttct gagacgctgt ttgtgtcacc gcggcgcgtg gagtcgacgg cctccgaggg    40020
gtggtggaca cggtgttttg agaagccgtg gaagtcgtag gcatcctgaa gggattgtga    40080
gccaggtgag gattcttgag ggcccacgcg cgttcgcgcg gccagttggc ggggttcata    40140
tccccgggca acggcgccgt cggagcccag ggcgagttac cgttgaccgg gtttgggta    40200 cccgcgaagg taggtgtcgg ggccggagcg ggggccgtgg aaggattgac aggcgtcggc    40260
gtgaggatgg cagtgccggc gccagcaggg acgttaactc cggcgccgaa cgtcaacgtc    40320
ggttgctcga acttgtacgc ggtggtgacg ggcggtttgg cactcgtctc ggtatccgtg    40380
atgtccacca gcgtgtcggt gaaacgcgga tcttgacggt tgggggata gccatccgag    40440 ctgtcggaat cctcgtcgcc cgagaaaaga tcccctctgg tctccgtgag cggcctcacg    40500
tcccacgcgc tgtcccgacg gacccttccc gggctggcct tggtcacctg cggggagacg    40560
agactgaaag ccgcgtgacg ctgttgttgc tgcgggatgt tcaagggacc gctggtcggt    40620
ttctgactgc ccgaggataa caggccgctg aaaacgctgg aaacaccgcc accactagcg    40680
```

```
acgcccttgc cgctagttcc cggtttcttg atgggcgtaa agatgttttt ctcgtcatcg   40740
tcatcgtcgt cgtcctcatc ggcactggag ccaaagagcc tccgggaggc gctcggttta   40800
cgtgccgggg gcggtggttg ctgttgacgt tgctgcaggt tctgctgcct ctcctcccaa   40860
gccttcagct gctgtttctc acgctgcacc acctcgtcgt ccacccgttt ctgccgctcg   40920
cgacgctttt cctcttcgtc gtaatagccg acggccgccg aacgggcggc gtgggcgtcg   40980
gcggccggtc ccagagaacc atgggcctcg aagcggaacg gtttgtgtcc cttccaggga   41040
ctggcgatcc agctccagcc gtccagcggc tgcgtgggga catgtttctt gggtaccgac   41100
gagaaggcca accgccgcc gagcgagagg agattggcgt catcatcaaa ctccaacgac   41160
ggcgagcgcg cgcccaaaaa ggtgtgcgcc gactgcggga agctgtccac gtagatgtca   41220
aagtcctcga tgagcagctc cagcagcgtg tcggccgagt cgccgttttc cacggcgtgc   41280
ttgaggatat tgcgacagta gttggaatca aaggaaaggc acatacgcag ctccttgacc   41340
agcagcttgc agcgctcctg aatgcgcgcc agacatttgc gctccagctc ctcccaagac   41400
ctacgcacgt tcatgatgag acggcccgtg tacacgagct tgttgacggc gttgaccagc   41460
gccgtgttgg cgtgccggtc caggttaagg tcgagcggtt tcacacagaa catgttacgg   41520
cgcacaccct ccaggttttc ttcaatgcgc tgcacctccg tatccttgag gtgcacaaag   41580
gcgatgggtt ccgtctggcc gatggctgtg accagcgtct cgcgcaccga catcttggcc   41640
agaatgaccg cgcttacgag cgcgcgctcg acgatctcgg catcgtggcg cacgtccgta   41700
tcgaattcgg tatggtctag cacagccagg tgatcgcgcg ccttaccacg atcaccgaac   41760
gggtaagtgt agccgcgacg cgccacggcc gcgcaacgca cctcgaactc ctcgagcacc   41820
gaggagaggt cggggttgtg gaaacgcagc tcgcggtagt atcccaacca aagcatgagc   41880
tcgttgaaca gcaccgtacg ccggtgcagg cgttttcgc cacatttttt caggatcttg   41940
gggtgtgcct cgagatccac gtcgggcttt tgcgtgagat ggcgcagaaa gttgaccagg   42000
gctaccacat cgcgccgctg tagaccgata aactgcaaac tcatgctggc ttttctccag   42060
aacccggaag cgtcgtcgcc ccggactgcg cccgcggtct gctattcgcc cgcgatggac   42120
accatcatcc acaactcggt gagcgtccca cccaaaggga gggggggtag tttaatagcg   42180
gaggcggata cgcggttttc ttttaagcgc cgctgacttg tttcttctgt ttttcgccc   42240 cgtgtgctgt tccgcccaga cccgcaacaa cactcctccg cacatcaatg acacttgcaa   42300
catgacaggg ccgctattcg ccattcgaac caccgaagcc gtactcaaca cattcatcat   42360
cttcgtgggc ggtccactta acgccatagt gttgatcacg cagctgctca cgaatcgcgt   42420
gcttggctat tcgacgccca ccatttacat gaccaacctc tactctacta attttctcac   42480
gcttactgtg ctacccttta tcgtactcag caaccagtgg ctgttgccgg ccggcgtggc   42540
ctcgtgtaaa tttctatcgg tgatctacta ctcaagctgc acagtgggct ttgccaccgt   42600
agctttgatc gccgccgatc gttatcgcgt ccttcataaa cgaacatacg cacgccaatc   42660
ataccgttca acctatatga ttttgctatt gacatggctc gctggactaa ttttttccgt   42720
gcccgcagct gtttacacca cggtggtgat gcatcacgat gccaacgata ccaataatac   42780
taatgggcac gccacctgtg tactgtactt cgtagctgaa gaagtgcaca cagtgctgct   42840
ttcgtggaaa gtgctgctga cgctggtatg gggtgccgca cccgtgataa tgatgacgtg   42900
gttctacgca ttcttctact caaccgtaca gcgcacgtca cagaaacaaa ggagtcgtac   42960
cttaaccttt gttagcgtgc tactcatctc cttcgtggcg ctacagactc cctacgtctc   43020
```

```
tctcatgatc ttcaacagtt atgccacaac cgcctggccc atgcagtgtg aacacctcac    43080
actgcgacgc accattggca cgctggcgcg tgtggtgccc cacctacact gcctcattaa    43140
tcccatcctg tacgcactgc tgggtcatga ctttctgcag cgcatgcggc agtgtttccg    43200
cggccagttg ctggaccgcc gcgctttcct gagatcgcag cagaatcagc gagctacagc    43260
ggagacaaat ctagcggctg caacaattc acaatcagtg gctacgtcat tagaccccaa     43320
tagcaaaaac tgcaatcagc acgccaaacg cagcgtgtct tttaactttc ccagcggtac    43380
gtggaaaggc ggccagaaaa ccgcgtccaa cgacacatcc acaaaaatcc cccatcgact    43440
ctcacaatcg catcataacc tcagcggggt atgagctttc ctgttacttt attcagaaag    43500
caccagaacc cgtcgccatt tcccctcata tacggtacac gtcccsctga tctgtcatca    43560
cggtacacag atttcgcccg actgcggacg ccgacggcca atcgcgtggc gtaggagtgg    43620
cgccccggct tcattataac gccacgtcgg agccctgcg cgccacaacg ccgtccggcg     43680
caacttctgt ctcggcacgg tacgataaaa acgacgtccc ccgtcgacgt tgttttctcc    43740
gagcggtgat cgttcccgtc cctatcctcc ctccgcggcc cccacggcgg cggcctgctc    43800
gcacggacct atactattac cgccccaccg ccgtcgtcgt catgaacttc atcatcacca    43860
cccgagactt ctccaacgac gattcagtcc tgcgagccgc cgagatgcgt gacaacgtgg    43920
caggctcgat ttccaaagcg tacaagggca cggtacgcgc cgaaggcaag aagaagctgc    43980
tgctgaagca cttgcccgtg ccgccggcg gctgctcgcg ccgcaacagc aacctcttcg    44040
ttttctgcac cgaacgcgac taccgcaagt ccaccaggg catcgcacag ctcaagcgcg     44100
cgccggccga actggacccc cacgagatcc agcaagtcac ggccagtatc cgctgccgcc    44160
tgcagcccag tctccgcgag ccgcccacgc cggccgacga gctgcagacg gctgtgtcgc    44220
gcgtgtgcgc gctcttcaac cagctggttt tcacggccca gctgcgccac tactgcgagc    44280
accaggacaa ggtggtgagc tacgcgcgcg acgagttgac caaacgctgc ggcgaaaaat    44340
cggcgctggg cgtggaggtg catcaactgg tagccttgct gccacacgag cgccaccgcg    44400
aactgtgcca cgtcctcatc ggcttgttgc accagacgcc gcacatgtgg gcgcgctcca    44460
tccgtctcat cggacacctg cgccactacc tgcagaacag cttcctacac ctgttgatga    44520
actcaggttt ggatatcgcg caagtcttcg acggctgtta ccacagcgag gcctaccgca    44580
tgctcttcca gatcggtcat acggactcgg tgtcggcggc cctggaactc tcacacagcg    44640
cggcggccgg gctgcccgag gccgatgaga acaacgacga gggagaggag gacgacgacg    44700
agctccgtca cagcgacccg cgccgcttc acgagtccaa gaagccccgc aacgcccgtc    44760
gtccccgcac acgcatgccg cctcacgagc aaaagcccga agaaacgag gaggaagaag     44820 aggagctgtt tccctcctgc aaggcaaccg cagcattcct gcgggcagaa ccctccgtct    44880
ccaacgacga cggcaacggc ggcgaacgct gcgacacgct agcgaccgcc ctgcggcatt    44940
gcgccgacga agaagacgga cctctagcca gccagaccgc tgtgcgggtc gccgcgaccc    45000
cctcaccttc agtcaccca gcccttaccc ccgtcacgtc cccataacc ccgttgtgta      45060 tttaacgtca ctggagaaca ataaagcgtt gatttctcaa gttccgctct ggttttggtt    45120 tcgtttcaa agggagcccc atcatggccc aaggatcgcg agcccatcg ggcccgccac      45180 tgcccgttct ccccgtggac gactggctca actttcgggt tgacctgttt ggggacgagc    45240
accggcgcct gctgctcgaa atgttgaccc agggctgctc caactttgtg ggctgctca     45300 acttcggcgt gcccagcccc gtatacgcgc tggaggccct ggtggacttc caggtgcgca    45360
acgcttttat gaaggtaaag cccgtggccc aggagattat ccgtatctgc atcctcgcta    45420
```

```
accactaccg caacagccgc gacgtgttgc gggacctgcg cacgcagctc gacgtgctgt    45480
actcggagcc gcttaagacg cggctgctta gagggctcat ccggctctgc cgcgctcgcg    45540
aaaccggcgt caagcccgag gacatcagcg tgcacctggg cgccgacgat gtgacattcg    45600
gcgtgctaaa acgagcgctg gtccggctgc accgggtacg cgacgcgctg gggctgcgcg    45660
cgtctcccga ggccgaggcg cgctatccgc gcctcaccac ctacaacctg ctgttccacc    45720
caccgcccct taccacggtc gaggcggtgg atctgtgcgc cgagaacctg tccgacgtaa    45780
cacaacgtcg caaccgaccg ctgcgctgcc tcacctccat caaacgcccg ggctcacgca    45840
ccctggagga cgcactaaac gatatgtatc tgttgttgac gctgcgacac ttgcagctgc    45900
gacacgcgct ggagctacaa atgatgcagg actgggtagt ggaacgctgc aaccggcttt    45960
gcgacgcgct ttacttttgt tacacgcaag cccccgagac gcggcagact ttcgtcacgc    46020
tggtgcgtgg gctggaactt gcgcggcaac acagcagtcc ggccttccag ccgatgctgt    46080
acaatctgtt gcagctactg acgcaactgc acgaggccaa cgtgtacctc tgcccgggat    46140
atttacattt cagcgcgtac aagctgctga aaaagatcca atcggtctcg gacgcccgcg    46200
agcgcggcga gttcggggac gaggacgaag agcaggagaa cgacggcgag ccgcgcgagg    46260
cccagctcga tctcgaagcc gatcccacgg cgcgcgaggg cgagctttt ttcttctcca    46320 agaacctgta cggcaacggt gaggttttcc gcgtgccaga acagcccagc cgctacctgc    46380
gccgacgtat gttcgtggaa cggcccgaaa ccctgcagat cttctataac ttccacgaag    46440
gcaagatcac caccgagacg tatcacctcc agcgcatcta tagcatgatg atcgagggcg    46500
cctctcggca gacgggcctg acacccaagc gcttcatgga actcctcgac agagcgcctc    46560
tgggccagga gtcggaaccc gagatcacag aacatcgcga tttatttgcc gatgtttttc    46620
gccgtcctgt gaccgacgcg gcttcttcgt cgtccgcgtc ttcgtcgtcg tcctcagcat    46680
ctccgaattc tgtttcgctg ccgtctgcca ggtcgtcatc cacacgaacc accacgcccg    46740
cgtccacgta cacctcggcc gggacttctt ctaccacggg tctcttgctc tcctcttctt    46800
ccttgtcggg atcgcacggc attagctccg cggacctgga gcagccgccc cggcaacgac    46860
gccgcatggt cagcgtgacc ctcttttcgc cctactcggt agcctacagc caccaccgac    46920
gtcaccgaag acgacgcagc ccgccacccg caccccgagg gccggccac acacgcttcc    46980 agggacccga cagcatgccg agcactagct acggcagcga cgtcgaagac ccgcgggacg    47040
atctggccga aaacctacgg catctctgaa cgcggttttt cctcttttc tacgtgtctg    47100 tctcaggacg agacgtcgat atcaataaaa ataccgtcga cgtggttttt ttaacagtgt    47160
ggttttcttt attgactagc ggagtacaca gtttacgagt aaaaaagaca gggaaaggtt    47220
atataaaatg ctgtattata tacaaaaaca tgcacataaa cagacgggac caccgtgctc    47280
gtcatcctct cctcaatcag ttgttcatgt aggcgtgtgg cggggtgagg ggcggcatgc    47340
cgttggcggc gccgggaata atgtgccgtc gaccgacgtc gcacaccttg aaacgccgtc    47400
ggcgcacgca gcggtcgcag gacgggatat cccagaggaa gcccatgtag gtctcggggt    47460
cctcgtcgtg aaagcggtag gagagttcaa agtggtgcaa cgagcccgtc cgagctcgca    47520
gcttctggcg aacaccctcc acgtcatcgg tgcacaacga cagtgctggg ctctcacaca    47580
gggcctgaag ctcctgcggc cacaggtgcg tggccagggg cgagtccgtc gtcaccagtt    47640
tgacgcagtg catcaggttc tcggtgatgg cgtcgtacag gcgactctca gcctcctcgt    47700
gcgtcatcac gtttcgaggc agcgacagct cgtcgtcgtc atcctcgtca aacatgatca    47760
```

```
tggggtcagg ggttttttg ggatgttgac aggtgggtgt cttttccaga cgcacgatgg    47820
cctcacgccg gccgctgaaa cggtggtttc ggtgtccctt ctttcccatg acgcaggtga    47880
acataaccac gtcctcggcc aaacggtaga cggcgtccat ggcggggtcg tagccgtaga    47940
cgacgccgaa agtgtccacc aagacgtact ggcgtacgag gaactctttg cgttctggca    48000
cctcgtggcc cagcgcgccc aacaactggt ggtaacaggt gatgcgcggc acggtacgga    48060
tcatgagctc catggtctgg atgctgccgc ccgcgcggac gacgctgaag gatgtttcct    48120
tgaacttcat aacctctgtg ttgtgggtcc agaaggcgaa atgggtgtcg ggacactcat    48180
cgaaagggtc gtcgatggtg taggaagcgt agccccgctt ggtcacctcg gccgacaggc    48240
tctccacgtc accgcggtag agcatgacgg cgttccagta atcgtcgtac tgcaccatgg    48300
gccgctggta gtcgcgcata gtgtggaagt ggtcgcagtg acgaaagcca tgccgcagaa    48360
agtccttcat ggtggatgcc agctcgtaga cgcagtcgcg caggtcatcg tagcagtaga    48420
tgccgccgcg ctgcccgatg agcacgatga gttggtagcg cataaagccc ggaccctcga    48480
cgaagccaaa ggggtgcagg tattcctgac agcacacgta agcacctggt ggagaaataa    48540
gaaaaatcca cgcacgttga aaacacctgg aaagaacgtg cccgagcgaa cgtcctcttt    48600
ccaggtgtct tcaacgacgt ggggcttacc ttgcgaacag acggtgccca tcttgcccac    48660
gaagggcccc agggcgttgc gcgaacggag ctggatgaag cagcgttcgg gccaggccac    48720
gtgcagccgg gtgccgcatt cctgctccag aaagtcgttg agaccgttaa agtccccggc    48780
tcgaatggcg atgcagccgt aggccatcag cgtgtcccgt aggtcgtcca tgacggactc    48840
ctctaccttc gctcgccgac gctgcgcttc tccagccacc gctgcggtcg acagactcct    48900
tcgtccgcct tcggagaact acggcgcggc ggcacggcct ttatagacac tatcagcgtt    48960
gacgtcagac gatccgatga acgtcgtttt ttgtgctgga acttccctcg tcccgacaaa    49020
tgtagcggaa atcttcaagc aaatcgcgac gaagtccgat gaggaggatg caaaagaggc    49080
tgagcaacgc gatgctgccc gccgccacag tacatatgct caacaacgcc cagtgtccca    49140
acgcgcgact tttggctcgg agcagagccg aacggcggtt tctccacatg acagataacg    49200
tggtccagta cgtccatcct ttgcattccg gcgtccagac gggaagcgtt gtcatgttag    49260
ttcccgtaaa ggtcgtgttt tgtcttgttt tgtttctcat gagtttaaca gtccttttta    49320
gaaaccgcgg gcacatgtct tgtagaaaga tgtaatcact ctccgcgtat gtcgctaggg    49380
ttgacatcac agtggtagtg ttttccgaag aagtgacgtt gtcagtgata ttgtcagtga    49440
cgttaatttc ttcccagtgt acggataact cgaacggtgt cgtatgcgcc accgctctca    49500
acacgtaact acggccggtg aggttaagtg ttagttgtcc cacggtcaca ttggtgtcat    49560
ttgtaaaaca cgcgatttct ccgcgaactt ccgtgacgtt ggtttcacgg gtctcgttga    49620
gaacacgcag aggaaaccag ccttccagat gatactggaa accaaacgta agcatgacgc    49680
tatgccattg tctccgtggt tgccgaaacg ttacgttcag aggcagtttg gcttcggctc    49740
ctgcgcaagg cccgttatag atttgcgtgt cattgcgcgt acagtttaac cggcagttca    49800
tactcgtggt gttagaagtg atgttaacac ccgtgccgtg gtacgtgcat cggaccgaaa    49860
caccgtgtcc cgtgctccaa aacagcgtca acaacagcca cacagacacc tacgtggaga    49920
cgacacggga cttttattg acggagactc acgtttctac cctccccttt cccgtaggta    49980
aaacccacg tttatcacac acgttgtttt tacctgaaac ccgcgcagcc cgtggacgcg    50040
acaaaaaacc gcggcactag aaagaaaatg aaacaagtat gttttattaag cagcatgtgg    50100
ggctaatagg ggggataact gaggtatagc aactatgaaa aaatactaca aaaaaaaaag    50160
```

```
ctgaacatgg tcatctagca gcaaagttct ccttctagac cacgaccacc atctgtacca    50220
cgtcgccctc cccggtcgtg tacatcacat ccttcaccac gaccggtggc aacggcggcg    50280
acgaggacaa ctcgctctcg acggaggccg ggacgacaga ggacgggggg gtggtggcgg    50340
cggaggacgg aggggtggcg gcgacagcgg ggtcttcttc cgacacgggc gacggcaggc    50400
tcggcggcgc ggacagcacc cgttgcgccg gggcgtgaga aggctgagcc ccggtggcct    50460
ggatgtgggc caacgaattg gctcgcagcg agtcgcgatc cacgaaggtc ataggaattt    50520
tcccttcgcg gatccgccgc tcagattcca ggatggcgcg cacgtagctg ttcaccgact    50580
tggcaaaagt gcgcggccct tccgtattct tgtcgcgacg cgcttccagc acctgctttt    50640
cgtagtccag ctggtggaag accatcacca ggtcgtccat agtgtgcgcg tgctgacgga    50700
cgtgggagcg cacctccacc gggaacaaag cgttccaata ctccagcacg atggcaccgt    50760
gccagaactg cgccatgctg ggcgccagga aaaacaggat accggagtcg taggcgaaca    50820
cgtcccactt gggcgtcatg aacaacacca gctgacgcgt gggccgcacc gaagcttcct    50880
cccaggcctc gatgaccccg aacatgatga gctcctggtc caacgggggg cagtgtcgct    50940
ccagccaact gatcttgctc aggttcatct gcagaaactc gtaagagggg tcgcagatgc    51000
acacgtagag acccgagtcg tgccgcagcc tggctccgcg cttcatcagt ttcctcaccg    51060
cgtagcgaag cgccaccttg cccaacgccg acgcctggat cagtccccccc acgtccatct    51120 gcgtctgtcg ccactcggcc tcgtccagca ggctcgtgat agcggaagtg ctatgcgtgg    51180
tcgtagtcat cctttctatc cttctctatg aatagcagca atagcggtaa agtcccttct    51240
tatactatcc cggagtctgt ggttttttt gtttacccct gcttactggt gagactgctg    51300
ggggccgttg tgctgcagca gctgagctcg tcgccgccgt tgccacagga accggtgcct    51360
ccgcagggcc ttttttgaggg cctcgcaggc ttctcgcgca agtcctgaga ggccctcggc    51420
gtcgatgggg ttcacctcgg gcgtccgagc ctcgtttttct tcttcttcat cctcccttttc    51480 ctcctccgtg tcctcccgct ctgtgtcctc cgttacgctc tcctccccgg cctcggccaa    51540
gagcgcagcc accaagtcca cggaccgctc ggtctccgag ttctcaccgt caattacgcc    51600
atgttggcgg cgtaaccggt gccgagaacg ccgggtgagc gcacatgctt ttttctttct    51660
taaccaaggc gggagaggat cttcaaggcg ttttcgctgg atccagcggt agctaaagta    51720
ccaaaaggcc agcaggccca cgctacctaa cagattcacg tagactggag acataattaa    51780
agaaagaagt gaaacccgcg tgtgggtctc acgtcgtctt gaaacaccgt cttatataca    51840
tgaagatgcc ggacatgacg cgcccaagac acgtgggggtt tccccttag gggacccggt    51900 ttcttaagat gtttttcatc ttcgcacgcg atgtactaca tcaaagggtc ggctgaccga    51960
ccgcattgac gcacagtttc cgagtacgcg cgtctcggag cacctgacgg tgagccaccc    52020
agctcacgcg gataggggac aacactgacg tgaggggcga ttcacgtcac tgacggctga    52080
cgggaataag acgggtgagg gatttccacc tttttcttaa gtgtgactct ccttacggta    52140
aatcgcacct gtgacctctt aaccctcct ccctggtacc caataacagt gaaaaacaca    52200
caccacacgt cacgacaccg atcgattttc tttattctta gtgtgatgat aggtaagggc    52260
actcgtgagg atgtgcagtt atcattatca agccttcttc aaggcgtagt gatgatcgtt    52320
gggcagaacc cccaagctcc tagcgatctg ggaatagaag gaggagaacg accccagggc    52380
cagaatgccc acagtgtaca tggcccaggt ctccagaccg aacgtggcgg gtcgcagctt    52440
cagatggtag gccacccgct ccgagagttg tgaatgctcg ttcaggcaac aggactgcag    52500
```

-continued

```
gtgggtgagc ccaaaagcgc tttcgtttac gccgcgcacg tgcaccgtct gggccgggca   52560
atcctggtgt tgcgcgcgaa aatggtcctg acaggagatt ccgtctacgt ggcggcgcgt   52620
gttgttaccc acttcgatca gcaacgtgtt atcggcagga tgatgcgaga acgcgacgac   52680
ggtgttgctg gaggtctggc ggcagcagta cacgtcgagc gtcatgaggg ccatgtcgcc   52740
ttggtggtac acggcgtacg cccaaccctg gaacacgagc ggacatcgcg gaccgtgagc   52800
ggacatcgcg ccggcggttg ttaccgtcgt ctcggcagga gaacacaata aactcctgat   52860
cctcatacac aggagtccaa gcgtcagaat taaagtccgc ggagccataa ccgcgcaagt   52920
gaagccgata cgagtgttgc tgaatttgtt cattctgccg actgttgctc acgagcgttc   52980
ggaggcggtg ccacaggctg ttggccatta aaaagtcctg gcccgaatga cgacgagaca   53040
gagcccgagg cgaagaaaaa ggcgcccgtc atgaagacgt aggcagggga attcccatat   53100
ttttatggct tcttttaaaa gtctgtatcc gactccatcc ggcgcttttc ccaaaccgtg   53160
gtctcctcgt cgtccgactc ggtacccagg aggtggtaag tcttttgccg cacgtagaaa   53220
gctttcaacg tggagcaaaa aatgagaata aagaccccga aaacgaaaca aaccacgccg   53280
atcatgccga tgcagacgtt catgtcgacg tagccggcgg tgctgttggc ggtgcggcaa   53340
aagagtgtca tgtcgtgcgt gcacaaaaaa caacacacac cacaggccag gtcgtagcgt   53400
agttattatt ccgtagcagc aatgatggta cagtcaagca catgctctat ttcccgttac   53460
cccgatgatg atgatgatgt tgtccccgtt gcagtggaat tgtcccggtt aatcaccacg   53520
gtgaacacca cggccaagaa aatgatccct aatatagcga ccactaagag agcaaaagtc   53580
catttccagc cgttgtcaaa gtacgccccc gtggtgggat gcatggtggc gggcatttcc   53640
atcatatcca tgtcgaacgt gtgtcgcggc gacggcgaac taaccaggca gtacggggt   53700 cgatagggcg gtgggctgca gtcggtggt ggcggcggtg gcgtggaaac cgtcgtcggg   53760
cacagaccca tggcctgctc gtaggtgggg ggcgcgtcgt cgtgatcccg gtcgcggagc   53820
atcggcgtgg gctccatgtc ggtggcagtg acggcgacgg tggtaactgt ggtggagacg   53880
gtaccgacgg cgtccgcggc tcaccttcga gcaaagagcc ccttcttttt gcgcaaacga   53940
cggcaaaaca gttctctggg acagccggtg gcgcggtaag cgggtgccac gctttcaggg   54000
tgggtaaaac agtcgcgggc gaagcagtag ttgttgcaga accgcaaaaa cccgacgcga   54060
aagaagccca ggagtccgcg cgccagaaag tgcgcctgcc gcgtctcggg atgcacgccg   54120
aagacggcgc cgctctcgtt caccagtatg gagatgtcca ggcgctgctg cgactccacc   54180
ggcacggccc gcaccacaaa tacctgcagc acgttcagcg agcacgtctc ttttaaccag   54240
ttgccgtggg ccggatcctc gtaagtctgg ctcccgttca agacgaccgt cgtcagcgcc   54300
tcattaccgt ctcgccagct gaagatggaa ccctcgcgct tcatgcacag gcgccacagg   54360
gccagcaggt cgcgcgccaa catgaactcg cgacccacgt cgccgccggt ctcgaagcgg   54420
acatagccca gttcttcgcg cagcggcgcg tagttgcgca ggccctcctg cacgaagccg   54480
cggaaaccgg accgcgacac caggtacagc gattccacca cgggcgagta gacgtagacg   54540
cggccgccct cgccgatgag tacgggtagc ggtgggcggc cgatggcttc gcaacgactc   54600
acagtgccca ccggcagcag gaacttgtcg cagcacagga aggtcttctc caaacccttta   54660 atattgagat gtccaaagta gccgacgcgt aacaggtcgc agtaggtgaa aaaccaaccg   54720
ttcggccagc tgagacgcag caccgtgccg ctgacgcgac gaaccagctt ctgcaggtcc   54780
ttgcgggcgt cggcggtgac agagcagcgg aaggtctcgt tgaccagctc gacagccagc   54840
gcgtcctcca gcgtacgttc cttcatctcg tcgttgatgc tctggcggcg ccgccggatt   54900
```

```
tcgtcgaaac gagccgcgga ggcggcgacc gacgcggagg tcgtccgaac gccctctgtg   54960
acgctgtcgt ccggccagtc aagaaagcta aggctggcgc tgcgccgcct aaagtgtccg   55020
atccgcgcgg gacgtcgctg agggacggtg gctggtctgc tggggcgggt acggccgcgg   55080
gtgtccgcgg acacgttagt tatacacgga attgagtcac gtggcacgtt gccagctgaa   55140
accgccgtcg tctccgccgg cgttttctcc atcacgggac cgcgccgtgc gcgcgttccc   55200
aggcacgcgg cccacgctct acccgcactt ttgcttcttg gtgttaggga cgaactcgaa   55260
cgttacagaa tcctcgctgt cgctctcctc tttcgcgtcg ttaaagtaat tgccggagtt   55320
gcgatccaaa ccgccgcctc ctcctcctcc gccgccgccc gatccacctt tggacgtcag   55380
gtagctggtg atcttgtgct gctcgtattt ttccttggag gaaagaccgt ggtcgtgatc   55440
accgccgccg ccaccgctgc tcattttccg cgtaccggaa ccaccgccac caccgcggtc   55500
gtgcttcttg ccgccaccgc cgccacctcc tcccagaccg ccgagaccca tgggttcgtt   55560
catgagatcg ttatccagac ccgggccgtc gtcgtgcaga ccgccggcat tggccagcga   55620
agagaggctg ccgccaccac cgccgccgcc acgcgacttg ccgctgttcc cgacgtaatt   55680
tttatcgaag ggatcgccac gctggaaagg ttcctcggtg agaaaattct ccacggcgaa   55740
cagaccgttg cgactggcca cgtacaacag cgtgtcgtgc tccgtaacta tacgcaacgt   55800
gcacggcagt ttggtgacgg cgcaattgag cagcgtctgg tagaagttct tcagctgcac   55860
gttgatacgc atgttttta cgccgtggaa actgacgcgg ttattggccg tgaattccag   55920
ctcgctgccg ttggtcagga tgaatttgat ggccggcgga ccggcgtgca ccagaatctg   55980
cacggtgccc gtagggcagg gcgcttttt aacgttacgc ttgacgcggg tatgcggccc   56040
gatccactta agcaggtcgg ccaccacgcc gaaatctaga tccacgtgca cggccgaatt   56100
ctcgctttcg cgcacaatgt cttggccgtg cacgcaggcc gagctgaact ccatattgaa   56160
atcgggcgcg cacatggaga tcttggccga aaggtccgag atgtcctgca cgtagaactt   56220
ggtcaggtcc ttgctggaag tcaggtacat gaaattaccg agcagcggcg tggaattgtt   56280
aatggtcttg ggctgaaacg acttgtcagt gatgtagaga catgagctgt taaaagtgat   56340
ttttgacacg cagtgactgc gtaccgtttg caagataagc gacggcgtgg gcaagaaggt   56400
aaccgtggtg ttctccttga gcgcacggat cacagatcgc agctgctgga tagccgtctt   56460
gtacggcttc agccgcagcg ccagcgtcgg cggctccgag aggcgcgtct tgcgatccat   56520
cccggacagc gtgcaagtct cgactaagga gcgggcgcga gcgagcgaaa gttttataga   56580
gagcacacac gacgaccggg aacgctgcga agacgcccgg cgtctaataa tacagccgcg   56640
ccgagccagc gggcccccga ctaagaggca cagtacttat atactccgac cttaaagcgc   56700
cagtggtacc acttgagcat cctggccaga agcacgtcgg gcgtcatccc cgagtcatag   56760
tagaaaacca gggccacgca ctggtccaca aacacgctca ggttcacggc cgccatttcc   56820
acgtcgtttt ggatcgccgg cgccgcctgg aacagacact cgctcgcctt accctcctcc   56880
tggtgctgct ccaaccacgc gtaattcacc acgggcacgc gcagcggcct ccgcaccacg   56940
gtggggaagt aacactcacg gttgggcggg cacaatgacc acaccgtctc ctcctcgaac   57000
acggtgccgc gcgaagccca cactgacggc gtcacgcccc acagatgcgc cacctcgtcg   57060
tcgggaccca ccgccagaaa ctgacagttg cgcaatccga actcgagcat gtcggcgcgc   57120
agcgcttccc agcgcgcgct ggcgatagag agccgcggca accgatacaa ttcgaaaatg   57180
aatttgccct cttgatagat ggtgcgttcg aaccactcgc agcgcggcaa acccgacttg   57240
```

```
cacaaatcga cgctagcgcg caccgcggca aagtacatgt gctcaaagat gcgctcgatc    57300
aagtcccaag aggcaaagta cgtgaaccct aaccgcatga gcgccgtgtg caagccggcc    57360
acgccgatgt gcagcggacg cagttttttcc agcgcgctct ctacccacca ttcggacgct    57420
gacattagcg cgtccaggcg cgcgttgccc caaaccaccg cctcggtcac caactcgcgc    57480
agcacgctca aatcaaagta acgtcgcgtg ttccccaaaa ccacgtcggg tagatgcagc    57540
ttctgctcgt cgctacgcgc aaacacgcag cgagccacgt tcaccgtcag ccgctgcacc    57600
ggcatgtcac actcgccaaa gtggcacgac gccatatcgg gactcaagca cggcggcagg    57660
cacacgctgt cggccataat cgagtacttg actacgtgat ggacaaagac caccgaggca    57720
cggcccttga gcgcgcacag caacatcttt ttcagaaaat cgtccgtgtt cacgatcacc    57780
ttggggcacg attgctcgca gcgcgaatac tctttctcga aagccgactc ctgacccagg    57840
tccgagagcc gccgggagac aggccgcccg aacagcgagt agcgctgctc acgcgcacgg    57900
tatcgcttca ttaacacgct aggcacgttg aaagcgtagc aaaccccgt caactccgac    57960 gtgctttctt tgagaataaa gttaatcacg cggatagcgg ccacgtccca catgtccaca    58020
aacacacgta ccacgggtcg atgcacctcc ttctcgcgta tcaaatcgca gtatcccccc    58080
aggcaacgaa tcacgctgtt cacatcggcg ttaagtcgcg ttacgttcac cgacacagaa    58140
acgccgcaac tcaaggtgct catccatttg cacatagccg cccaactggc gtcacgcgaa    58200
aaagggtcgg ccgagatcag aaagtcgtac tgcggcacgc gatcgaaacc cacggtagac    58260
atggtgaagg tggacagcga cagctgccca tcgcgacagc gcttcaacac cgattccaac    58320
acctcgcctt cgaaacgcgc atccagatgg aaacgataga tgcgcgagtg cctactgttc    58380
tcgatagccg ccgtcaacgc cacggcgatg cgcaaaaaca cgccgcccgg actctcgtcc    58440
tgtccgtgca gttggcgaca caccttatcc aaacacaaaa tggccgcgta caagcccag    58500 caaccggcca attccacaaa acgcgccgtc cctcggcca gcttgggtag atcctccatg    58560
tgacgcagca caaaacggcg caccgactca tcgcacagct ccgaagcgta acacagtggc    58620
gtgcggcttt cacgcgccca gttggctttg aaataaaagc gacccaacag cagatcgcaa    58680
cgcggcgagt gacgaattag acagggaccg tggcgcatga taagctgaaa cagcctgaaa    58740
ctgcccaaac cggcactgtg ccgcgacacg gtgtccatct cgcgccacag cgcgttcctg    58800
tcggacggca gctcccgtgc cggctcctgt acgccgcaaa agcgaaactt gccccaatag    58860
ccgtgacaat gacactttt gcccatcaac atgcgcgtag cctgtatcgg cggcgatact    58920
ttgcagagcg aagccccgaa atcgtcctcc tcctcgacac tgtccagctc catcctggtc    58980
gcgccggtcg gattgaaggt gctcaaaccg ctactcacgc gtccaccgcg actgggcacg    59040
gcggaaccgc tgtcacgcgt caacgacagc acagacggcg tgccgtcagg agacggcgac    59100
tcgggacgcc aactgacgac gccgccacca ctcgtaaaac ccgctacaca cgctacgccg    59160
ctcgacatgt tagtatttc agcggatgct tccttgtcac ccccgggcag cggcccttcc    59220
tcgagctcgc tgtcatctcc cccggtagta tcagcgacgg cctctgccga cgattcctcc    59280
gtctcggttt ccgcgccgcg gctcggaatc ctacctggcc ggcaccgatg tgcgggcacc    59340
gaggacaccc gctgttcctc gtccgcgtca gccgagtca taagtttacg aggaaaagaa    59400
caaagaaatc aggtagattt caataaagtg agtctagatg gcgccgataa ctacggttta    59460
taaagtctgt gtgcgatgtg tttatttttt tcttctgtgt ctcctccccg tatgctgtca    59520
gcgccgctca gacgaattct cgaaagtctc ccaattcgac gctaaagttg tccaaacgga    59580
cgacggacag tttgagttct ttgtgtacca ggaacgaggt gtgaatgtcg tcagccaggc    59640
```

```
accagcccag cttttgtatg accccggtac acagagggat ctggcgtggg cgcgtgatgc    59700
gacggttgac aaagctacag cgctcgcggg cgaactttcc gcgtgcaacg tcgaccaggg    59760
tctgccagtg tgcgatgctg gaggtgagca cgtagatgcc gggacgtgtt tcgggcccgt    59820
catagtcata gacgatgatt aaatacacgt attgcagccg tccccgggtc tcttcccacg    59880
tcagatacat gtctttcggt atcatcaacg cgaacacctc cgttttgagc gtgttgtaaa    59940
ggtagccgcg catgacgcag gtgagcaacg aggtgatgcc cagcgagacg tcttgacgc     60000 agcccagcgt ctcgaggcgg cggtgcagca gatgcgggcc cagatccagc cactgcagcg    60060
cggcgcgcgc ggccgaggcc gtgtacacgc tttcgagcag gcagcgcgtg ctggccgaga    60120
cgttggaggc gcgaatgcct aacaggtaga ggctaatgta gaggtgtcgc ggcgagtcgc    60180
aacccgtctc catgcggatg agcagcgcgc ccggctgcgc ctcgaactct accaggccct    60240
cgggcacgaa gaaacgcgcc gtgagcgcct ggtgatcggc gtggtagagg tagcgcaccg    60300
atatagtatt tacctcgcgt ttggctttga gcgccgtcac tagttcattg tcctcgtcgg    60360
ccgggtcgcg cggccgtttg gccaccgcgc gcgcgtccat gatggcgagg cgcacggtag    60420
atttcaaaaa gttgatagag cagctgcggg cacgggccac ggacaaagcg gaggcgttaa    60480
ataccgtgag ccaattggag atcggcgcgg tggatgccca ggacgtgacc gcgagcgccg    60540
tgcgcgcctt cgtgggtgcg ttgccgagct cgggctacca ctttggcttc gtgcgtcaga    60600
acgtggtctt ttacctccta agccacgcca cggtacagac ggcgcgcgac ccgctgtacg    60660
ccgccgagca gttgcacgaa cagctggacc gcttcctgcg acaccagcac gacggcggcg    60720
gggacgagga ccggttgccg ttctaccaca acggggccac actgacggct ttccagaagc    60780
tgttgcagac cctgcgcgag atccagaccg taatagccga acagagcggc ggcaccgcgg    60840
cagcggcgga cttgatcgcc agtaacaacg cgtcgaccga gcgccgcggc aagaagggcg    60900
gttcgagttc cggggccag cagccgctgg tccgccgggt gatcacgcag ctggaaacgg      60960
ctgccacgga ggcgcggccc tacgtcaatt gtcgcgccgt ggccgaactc ctggacctga    61020
cctaccagcg gctcatctac tgggcctgca cgctcatgcc ctacgtgttg tttcggcgcg    61080
acaccgacac cgaactggac acggtgcttc tgatgcattt tttttacaca cactaccgtt    61140
cggttaacgg cgatttggcc gtggagtttc aaaactacgt caagaacagc gtgcggcaca    61200
tgagctcttt cgtcagttcc gatatcgacg gcgaccagaa gcccggtgcc gaacacatgc    61260
gtgacgtcag ctacaagctg ttcgtgggta atctgcaggc gcgtgacgcc agcggcctca    61320
tgtttcccat cattagcacg cgcatctcca ccgtgaacct ttacctgtcg cccgaacgta    61380 tgttttttcca cccgggtctg atctcgcgtc tgttgagtga ggaagtttcg ccacgcgcca    61440
acctagacgc ttacgcgcgc gtgtgcgatc gcgtgctgga agaccacttg catacgccgc    61500
gacgcgtgca gcggctactg gatctgacgc agatggtaac gcgactggtg gaactgggtt    61560
tcaatcacga tacctgcgcg gcctacgcac aaatggcgct gatccagccg ccagtcaga     61620 agagctcgct ctttgtcagc gagattcgcg agaaactcat acagatcatc tacaattttt    61680
acacgttttt catgtgcctc tatgtgtaca gccccacgtt cctgttcgac caccggcggc    61740
ggttgatttt ggagcagcat cgatccacgt tgatcggctc caaggaggaa ctacagcacg    61800
tctggagcaa cgtgatactg aacgtcaata cgcactttgc ggttcagtac acggaagaag    61860
actttgaggc acatacgaag ggtgccacgg aggcggagcg cgagtacctg tatcgggacc    61920
tgcacagcaa gtggggcgtg cacctgttta ccttgcgtcc gtctcgcggc gcggccggcg    61980
```

-continued

| | | | | |
|---|---|---|---|---|
| cggcctcgcc | tttgcctccg | cttgacggcg | tcacacgctc cgacatctta | cgcgaatgcg | 62040 |
| cgctcgttaa | tctgaacgaa | ggccgcgtca | actacgcctc cctgctagcc | ttcagtcatc | 62100 |
| atcccgagtt | ccccagcatc | ttcgcgcagt | tggtggtggt aactgaattt | tcggagatct | 62160 |
| ttggtatccc | gcagggcctg | tttcaagccg | tgggttcgcc gcgtcttttt | gcgctcattc | 62220 |
| agctgtgtcg | tgtattgttg | cccgagcagg | tgacgctgta ccagaacctg | gtctccatct | 62280 |
| acaacctgac | cacctttgtc | aagcacatcg | acgccgcggt ttttaagacg | gtacgcgatt | 62340 |
| gcgtcttcga | catcgccacg | accctcgagc | acctcagcgg tgtacccgtc | acgcccaatg | 62400 |
| tggacctgct | ggccgagctc | atggcgcgct | ccgtagcgca taacctgtac | accaccgtca | 62460 |
| acccgctgat | cgaggacgtg | atgcgcagca | gcgccggcag tctgagaaac | tatctgcgac | 62520 |
| acacgcgact | ctgtttcggt | ctggcgcgtg | ggcgggcgcg cctctcggag | gacggcgtga | 62580 |
| cggtgtacgt | ggaggtacag | ggtcagtacg | gactgcgcgt acctaccacg | cgtttcgtag | 62640 |
| aacagttgcg | cgagctggtt | cgccgcgatc | ggctgttggc cgagaatctg | cgcggcttga | 62700 |
| atgagcgcct | gctgagtgtt | cgcgtgcgcg | tacgtcagat cagcagcgac | acagaggaag | 62760 |
| taagccgaca | cgccaagggt | caccgcacgg | tggcccagat gagcaaggcg | ctcaaaaaga | 62820 |
| cggcctccaa | aatcaaagtg | ttggaaacac | gcgtgacatt ggcgctcgag | caggcgcaac | 62880 |
| gttccaatgg | cgccgtcgtt | accgcggtgc | aacgcgcgct agccgtcttt | gacgtactaa | 62940 |
| gtcgcgagaa | cttggaacgc | cgcggcgcac | agctctgtct gacggaagcg | acgagcctac | 63000 |
| tgcaccgaca | tcgcgcgcta | gcgccgatga | cctggcccgc gggcacgggc | gttgcggcgg | 63060 |
| cggccgaagc | ggatcgcgcc | ttacgcgagt | tcttggaggc gccctgggaa | tcggcgcccc | 63120 |
| aaccgccgcg | actccgcatg | acgcccgaca | ccgatcacga agaatcgacg | gcaggcgcga | 63180 |
| cgtccgtacc | ggaggtcctg | ggtgcgcgct | acgaacccgc acacctggcc | gcgagcgacc | 63240 |
| tattaaactg | gtacatcgtc | cccgtaagcc | aggcgcagca ggacatcttg | tcttcgatcg | 63300 |
| acccgcccgc | cggctcgaca | tcggtgtccc | tgccgccggc ctcgccatga | aagtcacgca | 63360 |
| ggccagctgc | caccagggcg | acatcgctcg | ctttggagcg cgagcgggca | atcaatgcgt | 63420 |
| ctgcaacgga | atcatgttcc | tacacgcctt | gcacctgggt ggaacgagcg | ccgtcctgca | 63480 |
| gaccgaggcg | ctggacgcca | ttatggaaga | gggcgcgcgt ctggacgcgc | ggctagagcg | 63540 |
| cgagttgcaa | aagaagctgc | ccgccggcgg | cggctgccg gtctaccgac | tgggcgacga | 63600 |
| agtgccgcgc | cgcctggagt | cgcggttcgg | ccggaccgtg cacgcgctct | cgcggccctt | 63660 |
| caacggcacc | accgagacgt | gcgacctgga | cggctacatg tgtccgggca | tcttcgactt | 63720 |
| tctgcggtac | gcgcacgcca | aaccgcggcc | cacctacgta ctcgtcaccg | tcaactcgtt | 63780 |
| ggcgcgcgcc | gtggtcttca | ccgaggacca | catgttggtc tttgatccgc | acagctccgc | 63840 |
| ggaatgtcac | aacgccgccg | tgtatcactg | cgagggtctc catcaggtgc | tgatggtgct | 63900 |
| cacgggcttc | ggcgtgcagc | tgtcgcccgc | tttctactat gaggccctt | ttctctacat | 63960 |
| gctggatgtg | gcgaccgtgc | cagaggctga | gatcgccgcg cgtttggtct | ccacctatcg | 64020 |
| cgaccgcgat | atcgacctca | ccggcgtcgt | ccgggaaagc gcggacacgg | cggcgacaac | 64080 |
| gaccaccgcc | gcaccttcct | tacctccgct | gcccgacccc atcgtcgacc | cgggctgccc | 64140 |
| tcctggcgtg | gcgcccagca | ttcccgtcta | cgatccctcg tcctcaccca | aaaaaacacc | 64200 |
| cgagaaacgc | cgcaaggacc | tcagcggtag | caaacacgga ggcaaaaaga | aaccccgtc | 64260 |
| cacgacgtcc | aaaacactgg | ccaccgcctc | ctcctcctcc tcagcgatag | cggcggcctc | 64320 |
| ttcttcgtcc | gcggtaccac | cgtcctacag | ctgcggcgaa ggggccctgc | cggccctggg | 64380 |

```
ccgctaccaa cagctggtcg acgaggtaga gcaggagttg aaggctctga cgctgccgcc   64440
gttgcctgcc aacaccagcg cctggacgtt gcacgcggcg ggtaccgaaa gcggcgctaa   64500
cgcggcaacg gccacggcgc cgtccttcga cgaagctttc ctcaccgatc gtctccagca   64560
gctcatcatc catgccgtca atcaacgctc gtgtctgcgt cgcccctgcg gcccgcaatc   64620
ggcggcgcag caggcggtac gcgcctatct gggcctatcc aagaaactgg atgcctttct   64680
gctcaattgg ctgcaccacg gcctggatct gcggcgcatg cacgactacc tgagccacaa   64740
gaccaccaaa ggcacgtact cgacgctgga tcgcgcactg ctggagaaga tgcaagtcgt   64800
cttcgatccc tacggacgtc agcacggccc ggcgctcatc gcctgggtgg aggagatgct   64860
gcgctacgtg gaaagcaagc ccactaacga actgtctcaa cgactgcaac gtttcgtaac   64920
caagcgaccg atgcccgtta gcgacagctt cgtctgcctg cgacccgtag actttcagcg   64980
tctgacgcag atcatcgaac agcgacgtcg ggtgttgcaa cgtcaacgcg aggaatacca   65040
cggcgtttac gagcacttgg ccggcctcat caccagcatc gacattcacg acctagacgc   65100
cagcgatctg aaccgacgcg aaattctgaa agcgctgcag ccgttggacg acaacgccaa   65160
gcaggaactc tttcgcctgg gcaacgccaa aatgctagag ttgcagatgg acctggaccg   65220
tctgagcacg cagctgctga cgcgcgtgca caatcacatc ctcaacggct ttttgccggt   65280
agaggaccta aagcagatgg aacgcgtcgt cgagcaggta ctgagactct tttacgacct   65340
gcgcgacctg aaactgtgtg acggcagcta cgaagaggga ttcgtcgtca tacgagaaca   65400
actgagctac ctcatgacgg gcactgtgcg cgacaacgta ccgctactgc aagagatcct   65460
gcagctgcga cacgcgtacc agcaagccac gcagcaaaac gagggtcgcc tcacgcagat   65520
ccacgacctg cttcatgtca tcgagacgct ggtgcgcgac ccgggcagcc gcggctcggc   65580
gctgacactg gccttggtac aggagcagct agctcaactg gaagcgctag gcggcctgca   65640
gctacccgaa gtgcagcagc gcctacgaaa cgcgcaactc gcgctaagcc gcctctacga   65700
agaggaagag gaaacgcagc gtttcctcga cggactctcg tacgacgatc cgcccaccga   65760
acagaccatc aagcgacacc cacaattacg cgagatgtta cgtcgcgacg aacagacgcg   65820
tctgcgactc atcaacgccg tactgagcat gttccacaca ttagtgatgc gactggcgcg   65880
cgacgagtcg ccgcgaccga cgttttttga cgccgtcagt ctgttgttgc agcaactgcc   65940
acccgactcg catgaacgtg aggatctgcg tgccgccaac gccacgtacg cgcagatggt   66000
caagaaactg gagcagatcg agaaagccgg taccggcgca tccgaaaaac gcttccaagc   66060
gttacgggaa ttggtttact ttttccgtaa ccatgaatat ttctttcaac atatggtcgg   66120
acgactgggc gtcggacctc aggtaacgga actctacgag cgatatcaac acgagatgga   66180
agaacagcac ctgaacggc tagaacgtga atggcaagaa gaggccggca agctcacggt   66240
aacttctgtg gaggacgtgc agcgtgtctt ggcccgggca ccgagccatc gtgtcatgca   66300
tcaaatgcaa caaacgttaa ccaccaagat gcaagacttt ttagacaagg agaaacgtaa   66360
acaggaagaa cagcaacggc agctactgga cggctaccaa aaaaaggtgc agcaggattt   66420
gcaacgcgtg gtggacgcca ttaagggcga gatgctctcc accatcccgc accaaccact   66480
ggaggccaca ctcgagctgc tcttgggcct agatcaacgc gcccaaccgt tactggacaa   66540
gttcaaccag gacttgctgt cggcgctaca gcagctgagc aaaaaactag acgggcgaat   66600
caacgagtgt ctgcacggcg tgctgacggg tgatgtagag cgacgctgtc acccgcaccg   66660
agaagcggct atgcaaaccc aagcctcgct aaaccacttg gaccaaattt tgggtccaca   66720
```

```
actcctgatc catgagacgc agcaggccct gcaacacgcc gtccatcaag cgcagttcat   66780
cgagaagtgt caacagggcg atccaactac agccatcacg ggcagcgagt tcgagggcga   66840 cttttgcacgc taccgcagca gtcaacagaa gatggaggga caattacaag agactagaca   66900
acagatgacc gaaactagcg agcggctgga tcgctcgctg cgccaggatc ccgggaacag   66960
ctccgtcacg cgtgtacccg aaaaacccttt caagggtcag gagctggcgg gtcgaatcac   67020
gccgccaccc gccgacttcc agcggcccgt cttcaaaacg ctgctagatc agcaggccga   67080
cgcggcccgg aaagcgctca gcgacgaggc cgatctgctg aatcagaaag tacagacgca   67140
gttgcgacaa cgcgacgagc agctgagcac ggcgcagaac ctgtggactg atctggtcac   67200
gcgccacaaa atgagcggcg gactggacgt gaccaccccc gacgccaagg cgctgatgga   67260
aaagccgctg gagacacttc gcgagctgtt gggcaaagcc acgcaacaac tgccgtacct   67320
gtcggcggag cgcacggtgc gctggatgct ggccttttctg gaggaagccc ttgcgcaaat   67380
caccgcggac cctacgcacc cgcatcacgg aagcaggacc cactaccgga acctacaaca   67440
gcaagccgtc gagagcgccg tgacgctagc gcatcaaatc gaacaaaacg cggcctgtga   67500
aaattttatt gcacagcatc aagagacgac tgccaacggc gcgtccacgc cgcgggtcga   67560
catggtccag gcggtggaag cggtctggca gcgactggaa cccggacgcg tagccggcgg   67620
cgccgcgcgt catcaaaaag tgcaggaact gttgcagcgc ttgggtcaga cgctaggcga   67680
cctagaactg caggaaacgt tggcgacgga atactttgcg ctgttacacg aatccagac   67740 cttcagctac gggctggact ttcggtcgca gttggaaaag atccgcgatc tgcggacccg   67800
ttttgcggaa ctggccaagc gacgcggtac gcgtctctcc aacgagggag ccctgcccaa   67860
cccccggaaa ccgcaggcga cgacttcgct gggcgccttt acacgcgggt tgaacgcgct   67920 ggaacgcac gtccagctgg gtcaccagta tctgctcaac aagctcaacg gctcatcgct   67980
agtctatagg ctggaagaca ttcctagcgt gcttccgcca acgcacgaga ccgatcccgc   68040
gctgataatg cgcgaccgcc tgcgtcgcct atgcttcgcg cgtcaccacg acaccttcct   68100
tgaagtggta gacgtcttcg gcatgcgaca aatcgtcacg caagccggcg aacccattca   68160
cctggtcacc gattacggca acgtagcctt taagtacttg gcgctgcgag acgatggccg   68220 gccctggca tggcggcgcc gctgtagcgg cggaggactc aagaacgtcg tcaccacacg   68280
ttataaagcc atcacggtag ccgtggccgt ctgtcagaca ttgcgcactt tctgccgcga   68340
gatctcgcag tacgacctac gaccctacct cacgcagcat cagagccaca cgcaccccac   68400
ggagactcac acgttacata accttaagct cttttgttat ctggtgagca ccgcctgca   68460 ccagcgcatc gacacgcagc aggagctgac ggccgccgat cgcgtaggaa gcggcgaggg   68520
tggtgacgta ggggaacaaa gaccgggccg cggtaccgtg ctgcgcctga gtctgcaaga   68580
gttttgtgta ctcatagcag ctctgtaccc cgagtacatc tacaccgtcc tcaagtaccc   68640
ggtgcaaatg tcactaccct ccctcacagc tcacctacat caggatgtga tacacgcggt   68700
agtcaataac acacacaaaa tgccccccga ccacctcccc gaacaggtca aggccttctg   68760
tatcaccccc acccaatggc ccgccatgca gctcaataaa ctgttttggg aaaataaact   68820
ggtacagcaa ctgtgccagg taggcccgca aaaagcaca ccaccctag gcaagctatg   68880 gctctacgcc atggccacgc tggtcttttcc acaagacatg ctgcaatgtc tgtggctaga   68940
actgaaaccc cagtacgccg agacctacgc ctcggtgtcc gaattggtac agacgttgtt   69000
tcagattttc acgcaacaat gcgagatggt gaccgagggg tacacgcaac cgcagctccc   69060
caccggagag ccggtgcttc agatgatccg cgtgcgacac caggacacaa ccaccacaga   69120
```

```
cacaaacacg accacagagc caggactttt agatgttttt attcaaacag aaaccgccct   69180
agactacgcg ttgggctcct ggcttttcgg catacccgtg tgtctcggcg tgcacgtagc   69240
cgacctgctg aaaggccaac gtgtactagt agcgcgccac ctcgaataca cgtcgcgaga   69300
ccgcgacttc ctccgcatcc aacgctcccg ggacctcaat ctcagtcaac tgctccagga   69360
cacgtggacc gaaacgccgc tggagcactg ctggctacaa gcccaaatca gacggctacg   69420
cgattacctg cgtttcccca cccgcttaga gtttattccc ctagtcattt acaacgcaca   69480
ggaccacacc gtcgtacgcg tgctgcgacc gccctccacg ttcgaacagg accacagtcg   69540
gctggtgttg gacgaggcct tccccacctt cccgctgtat gaccaagatg ataactcatc   69600
cgcggacaac gtcgctgcgt ctggcgccgc tccaacaccg ccggtacctt caaccgcgt    69660 gccagtcaat attcagtttc tgcgtgaaaa cccgccaccc atcgcgcgag ttcagcagcc   69720
gccgcgccga catcgtcatc gagcggccgc ggccgcagac gacgacggac agatagatca   69780
cgtacaagac gatacatcaa ggacagccga ctctgcatta gtctctaccg cctttggcgg   69840
gtccgtcttt caagaaaacc gactgggaga acaccacta tgccgagatg aacttgtggc    69900
cgtggcgccc ggcgccgcca gcaccagttt cgcctcgccg cctatcacgg tgctcacgca   69960
gaacgtcctc agtgctctag aaatactgcg gctagtgcga ttggacctgc gacaactggc   70020
gcaatctgtg caggacacta ttcaacacat gcggtttctc tatcttttgt aaccgacact   70080
gacagtagcg ggtaataaaa acaagaggat tgttatcgtt ttttttatgat aaaaaaacaa   70140 cgtgtcattt tcacggtgat ttattcttgc tattattttt ccccatgggc tgtcagcgtc   70200
gggtgcgcga cactgctacc atgcgcaaca ggtccagttt aaaggcgcac ttgtcgttaa   70260
acaggctgga catgcgtgta tatttgctca gcatggtggc cagcaccggg tgggtggcct   70320
ctgagatctc ggtcggcaac tccaaaacga cgttgacgac gtgacggtgt ttttcgtccc   70380
gcttgttggc caccgtgggt cccggcgcgg tgttagacat ggggcaggcc gtgggggag    70440 gacgaggagg aagtcgctgc taaaccgcca cgcgcctgct gcacaatgtg gccgccgacg   70500
tggcaggcgg tctgtttaac cagcgcgcag ccccgacaca gcgggcgcc gtcttcgctt    70560 tccaaacagc tgtcgcggta ctcgcccgtc tgacagcgcg cgcacagcag gccgtgcccg   70620
tgcgaagtga ggcgcaggag acgcgggacc gtcacgccgc gtaccaccac agtggagtcg   70680
caggtgcgtg ccgcgcaggg cagaatgacg tcgaaagcca ccggtgatc gtacacggcg    70740 caagccgcgt tgaggcccag cacggctttc cagcccacgc gtacgcagcg ctgtccaaag   70800
agcgtctcgg agacgagctc gtagacgcgc tgccgcacca cccgctgact gccgcagagc   70860
gagcagtgta cgagctcggc gtgcgtgttg aagatgacgc tcttttcttg acggtcccga   70920
taatagaaca tcgagttgag cggaaaattt tgctggcagt gtagcttttc cttacccagg   70980
ttgaggcagt gtccgcactg ccgacagacc acggccacca gcgagcgcgc gtccagatgg   71040
cgctcgcact tgagtcgaca cagacaccag agcggcaggt cgatgacgct gccgatgagg   71100
ccgccgcgca gcgcggcgct gagtgcaaag aggacgatct tggtgggctc tacgtgacgc   71160
gcctgctgtc cggcgcccgc gtgtcctacc gccgcagctg ccgccgtcga gcctcctccg   71220
cgcgtctcgt cgtgcagacc cagtgcccgc aacggcacca ggtatcgcgg acacgtgtcg   71280
caaaacgtct gcaccgcttg tcgggccagt acgtagagcg ggtttccgca gggtaccttc   71340
ccagcgtgcc ggcgcaaggc tgcgatgagg ccccgcagct gcggcgaccg cggctgccgt   71400
tggtgacacc actggttacg gtggtatacg gccaaatcag cgcgggcgtc gaagcgcttg   71460
```

```
gcgcgtagta gtgctaggca cggcgagctg gtggggtgaa gcacgggcag ccgaaggtcc   71520
accccgaaaa ggaaacggtg aaggtcacct agcagcgagg cggtgacacc gtccaacaac   71580
gcgtgcagcc gctcgggcgg gtagagccgc agacggcgca gcaggtagtc ggtgtcgtag   71640
cgttcgaaac gcagaaaggc catcgtgcgg acggccacgg tgtgcagaca gtccatgctg   71700
tagacgtaag cgagaaacac aaagtagggc ttggtcataa ccatacgctg aaagagcgcc   71760
gtcaccgcct cccgctcggc ctgccgacac accagccatt cgcgcaggaa gcgttggtag   71820
agacggtcgc ccagctcccg attcagaaag cgcttatccg tcacgaagag atgaaggacg   71880
caagaacgtg gcacgtgatg caccagctgc tgctggagga ccgccgacgt ctgcgccgca   71940
aactgcgccg gtggctgcga cgtttctacc gccgcttcct ccggctgcag cgcaccgcgg   72000
ccgatcacca gctgcacatg gaaatggtcc tcgtgaacgc agaggggcgc gaagagacgg   72060
cgcagagcct ggtggaactc atcagtcgcg gtgtgcggag cgtgtcggag acgacgactg   72120
gccatgaccg cgcccacagca gagccagcac cagcagaaga gccagcacca gcgggcccag   72180
agtcgcaaag cgcgcgggca gccacggccc agactgcggt cgcgatggcc cggagcgcgc   72240
tcgccaccac gatgacggtg cccaacgata accagtccgc tccaaggacg gcgcgcacgg   72300
cggagacggc ggatgacggt gatgggtcga caccctcgc cgacgactca cgtgctcctc   72360
cagaggccga cgcgcggacc ctccgacgtc ctggcccgcc gctgccgccg ccgccttccc   72420
ttctcccgcc agagccagca actcctcctc ctcttcatca gcgtctccct cgcttgcgca   72480
tccgcatcgt cccatacagg cctcacaacg acacagccgc cacgaccccg ccgccatggg   72540 tggcggcgg ggccgaggcc cggcagcggc gccgccagcg cgaccatgg tgggagagca   72600 actcggatga cgaggaggag gaggaggagg gggagatgcg gtccgagagg accgctttcc   72660
cgccgttcgc gtgagcgcgg ccgacatgcg ggcgcgccac agggacggac cgctgccgct   72720
gtgactgctt acggtgacgt ggttccggac cgccaacgac gtcgacgcgg ctttcttggc   72780
gtacagctcg cgcagcagat tctcgtactc gccctcgttt cgggtccga aggcgatgag   72840 ctcgatgttg aagaccgacg ccgaattgga tttgcgcacc acgcacttcg tcagcactcc   72900
gtaggccgag ggcttgatct cctcgatgtc cttgagcgtg acgatgagcg actcgttcac   72960
cttaagcaca ttgaactcac ctacgtggcg cgccggcgag acgagcttga cgggcgctcg   73020
cacaaaacag cagagggaga cggcgcagcc agtgttttta aagataaaac aaggcacgtg   73080
gtctgtgcgg ctctcccagt agctgagcag atactcgaca caatagaccg tgtctgtctt   73140
gagcatggcc tcgcacaccg agtaattggg attttacag ataaggccgg cgtcggtgac   73200
gcgcagctcg ctgggaccca acttgaggat acgccgcgtg gcctgcacca gatcctgatg   73260
gagaaccttg ttcatctcca tcgcaccgac gccaccgccg atttatttac ccggcgccgg   73320
ctcgtctttt ccctccagga ttccgttaat gtccatgagc ttgctgacga tcgccgttaa   73380
tagttgcgtc ttctcacgga ggatctctcc gtgactgcag gtcgcgcagt cgccgtgcac   73440
gtacttgagg aaggcggcgt acttctgacc cgcgttcacg aaatttaagc gcgcgtccag   73500
ggagggcagc aacagatcgt agacgcgcgg cagcatcggc tcgaactgta atagcagatc   73560
gtcgtcaaga tcgggtagcg cgtgcccgtc ttcaccgtcc tcgtcgtcac cacctccccc   73620
ctcgagccca ccgctcgtac cagccgcggg ctccgcgtcc tcgtcgatca ccagcggtcg   73680
cgtcggcacc ggagaatcca cgtcatcctg cacgtcgttt tcctcctctc cgtcgtcatc   73740
gtccagaaac ggcacccgct gcttagccca ggacattctt tctccgcgtc ctcaatcagc   73800
ggcgccgatc gccatgaatc cgagtaccca cgtgagcagt aacggcccaa cgactccccc   73860
```

```
ccacggggcc cacaccacgc ttcttccccc gaccagcccg gccccgtcca ccagctccgt    73920
cgccgccgct accttgtgca gtccgcaacg acaggccgtt tcgcgttaca gcggctggag    73980
caccgagtac acccagtggc actcggactt gacaactgag ctgctatggc acgcgcaccc    74040
gcgtcaagta cctatggacg aagcgctggc cgccgcggcg gccgcctcat accaggtgaa    74100
tcctcaacac cccgccaacc gttaccgtca ttacgaattc cagacgctca gcctcggcac    74160
ctcgggggta gacgaactgc tcaactgctg tgcggaagaa accacgtgcg gcggcacgca    74220
atccaccgta ctcaccaatg cgaccaacac caccaactgc ggcggagccg tcgccagcag    74280
tagcaacgca ggacctgccg gcgcttcggc cgcctgcgac ctagatgcgg aactggccgg    74340
cctcgaaacc tcggcggccg actttgaaca gctgcggcga ctgtgcgcgc cgctggccat    74400
cgacacgcgc tgtaacctat gcgccatcat cagcatctgc ctcaaacagg actgcgacca    74460
aagctggctc ctcgagtaca gcttactgtg cttcaagtgc agctacgcac cccgtgcggc    74520
gctcagcacg ctcatcatca tgtccgagtt tacgcatctg ctgcagcagc acttttccga    74580
cctgcgcatc gacgacctgt tccgacacca cgttctcacg gtcttcgatt tccacctgca    74640 cttttttcata aatcgttgct ttgaaaaaca agtgggcgac gcggttgata cgagaatgt    74700 caccctgaac catctggccg tggtgcgggc catggtcatg ggcgaagaca cggtgcctta    74760
caacaagcct cggcgccacc cgcaacagaa gcaaaaaaac aacccttatc acgtcgaagt    74820
gccgcaagaa ctgatcgaca actttctaga acacagctca cccagccgcg accgcttcgt    74880
gcagcttctt ttctatatgt gggccggcac cggcgtcatg agcaccacgc cactcacgga    74940
actcacgcac actaagttcg cgaggctaga cgcgttatcc acggcctcgg aaagagaaga    75000
cgcaaggatg acgatggaag aagaggagga tgaagaaggg gaagaaaaag gaggagacga    75060
tccgggccgt cacaacggca gtggcaccag cgggggggttc agcgagagca cgctaaagaa    75120
gaacgtgggt cccatttacc tatgtcccgt acccgccttt tttaccaaaa accaaaccag    75180
taccgtgtgt ctgctgtgcg aactcatggc ctgctcctat tacgataacg tcgtcctgcg    75240
cgagctgtac cgccgcgtcg tctcgtactg tcagaacaat gtgaagatgg tggaccgcat    75300
tcaactggta ttggccgatc tgttgcgcga atgcacgtcg ccgctcggcg cggcgcacga    75360
ggacgtggcg cgctgtggac tcgaagcacc cacctcgccc ggaggcgact cggactatca    75420
cggcctgagc ggcgtcgacg gcgcactggc gcgacccgac ccgtatttt gccacgtcct    75480 gcgtcaggcg ggcgttacgg gcatctacaa gcacttttc tgcgacccgc agtgcgccgg    75540
caacatccgc gtcaccaacg aggccgtgct cttcggacgc ctgcaccccc accacgtcca    75600
ggaggtgaaa ctggccatct gccacgacaa ttactatata agtcgacttc cgcgacgtgt    75660
gtggctctgc atcacactct tcaaggcctt tcagattaca aaacgcacct acaaaggcaa    75720
agtgcacctg gcggacttta tgcgcgattt cacgcagctg ttggagagtt gcgacatcaa    75780
gctggtggac cccacgtacg tgatagacaa gtatgtctag cgtgagcggc gtgcgcacgc    75840
cgcgcgaacg acgctcggcc ttgcgctccc tgctccgcaa gcgccgccaa cgcgagctgg    75900
ccagcaaagt ggcgtcaacg gtgaacggcg ctacgtcggc caacaaccac ggcgaatcgc    75960
cgtcaccggc cgacgcgcgc ccgcgcctca cgctgcacga cctgcacgac atcttccgcg    76020
agcaccccga actggagctc aagtatctca acatgatgaa gatggccatt acgggcaaag    76080
agtccatctg cttacccttc aatttccact cgcatcggca gcacacctgc ctcgacatct    76140
cgccgtacgg caacgagcag gtctcgcgca tcgcctgcac ctcgtgcgag gacaaccgca    76200
```

```
tcctgcccac cgcctccgac gccatggtgg ccttcatcaa tcagacgtcc aacatcatga  76260
aaaatagaaa cttttattac gggttctgta agagcagcga gctactcaag ctctccacca  76320
accagccgcc catcttccaa atttattacc tgctgcacgc cgctaaccac gacatcgtgc  76380
cctttatgca cgccgaggac ggccggttgc acatgcacgt catcttcgaa aactccgacg  76440
tgcacatccc ctgcgactgc atcacgcaga tgctcacggc ggcgcgcgaa gactacagcg  76500
tcacgctcaa catcgtgcgc gaccacgtcg ttatcagcgt gctgtgtcac gccgtctcgg  76560
ccagcagcgt caagatcgac gtgactattt tgcaacgcaa gattgacgag atggacattc  76620
ccaacgacgt gagcgagtcc tttgagcgct acaaagagct cattcaggag ctgtgtcagt  76680
ccagcggcaa caacctatac gaggaggcca cgtcatccta cgcgatacgg tctcccctaa  76740
ccgcgtcgcc gttgcacgta gtttccacca acggctgcgg cccctcctcc tcctcgtccc  76800
agtccacgcc gcctcatctc cacccgccgt cgcaggcgac gcagcccac cactactctc  76860 accaccagtc tcagtctcag cagcatcatc accgtcccca gtcaccaccg ccgccgctgt  76920
ttctcaacag cattcgtgcg ccttgacact gtacggcaga aaagccggct ccaagtgcaa  76980
gcgccgcggc agcaccatgt gcaaaaactt gtccttgcgc gcggtttcgc cgccgggaaa  77040
gacgggcgac agcacgttgg ttacagcctt gagaacctgc tcaaagtact tgtcggtgtg  77100
aatgggcacg ccgtgctcgc gcacgtagct cggatcttcg gctacctcgt agttgcacac  77160
ggccgacggt ggtttccgcg ccctcttctt tgccggctct cctcctctcc tgttgctctc  77220 ctctacccg ccgccgtcag cgtcgtcgtc cgtgccatca atcgcgtccg accgggaaac  77280
cacgccggcg gttacagaat caccgttgtc ggaggaaccc tgcggcgccg tccggacacc  77340
gggcgccgtc aggacgtaaa agacccgatc cccgaccgag ggtagctcct cagaacgggc  77400
cgccagtcgc ttaatgacgg caatgtgcgg caggttagat tgacggtaca acgagatgtc  77460
cttagaaagc accgacgaaa gcaccaggtc ctcgacacgc acacggtgca ggtacagatc  77520
gtcgcgggcc tgcaccaggc ggcgcaagat acgccagaaa ccgcgtggca cgccgtattt  77580
cttgacttca tcgagtgaga ggcgcgacag gcgcacggct gcttccgaga cctcgcgatc  77640
ctcaaagagc agcgagagga cgtcacgcgt gacgcccttg acgaactcgc aggccgtctt  77700
gcgcaccaga tccacgccct tcatgctcag acccgaggcg ccctccactt tgccgatgta  77760
acgtttcttg cagatcatca taagagagac gaagaccttt tcaaactcca gcttgacggg  77820
ctccacaaaa agacaggccg tcacgtagtg cgccaggctg ggcccacgcg ccaccagagc  77880
ctgcggcgtc aggccacgaa agcggacaaa cacgctgtcc gtgtcccgt agatgacccg  77940 cgcctccacc cgccgttcgt ccgagccccc tgacgatgtt tcgagcccct ccggtaacgt  78000
gctgctctcc tccgaatccc cctctcgcgt tctcactaca tagtcttcct gattaaaaaa  78060
attgtgcaaa aaacacggct ctgaaaaatt gtctttgatg aaccgcgccg tgcgctctag  78120
catgtcgcga ccgatgcgcg tgatgctggc ggcgatgggc agacacggca tcatgccgtt  78180
gaccacgccg gtaaaaccgt agaaagcgtt acacgttact ttgagtgcca tctgttcctt  78240
atcgagcagc atacggcgca cggggtcttg acactcgcgc atgcattcgc gcacggcacg  78300
gcgctgcgaa acccacttgt tgagcagttc cgaaagcacc gagacgcgca ccgaagcacg  78360
cacaaagcgg tgagtcacgc cgttctctag cgtgacgctg tatacgtcgg cggggtccac  78420
ggggtactcg ccacccggca ccagcagggt ggagtagcag aggttgtgag ccatgatgat  78480
ggaagggtag aggctggcaa agtcgaacac ggccacgggg tcgttgtaat aacccacctc  78540
gggctcaaac accgtggcac cctggtacga aaccgccgca gtaccgccgg cgccgtgact  78600
```

```
gtcgttggaa acgccgacgc tgccactact gccggagccg acgctgaaaa cgccgacgct    78660
gctactactg ttactgccag agccgggtaa aacgccgtcc tgactcgacg gcgcagattg    78720
caagggcggc gacatctgaa acatggccgc cacagaaccc gcgtcgccgg gcacggcagc    78780
ggtagagatg atagcggcgt taggtgacac ggcaacgcta ttcgtttcgg gcaccgtcgt    78840
acctttgctg tagtggttgg gcaggataaa atcgcggcag gcgcactcgt ccagcagcga    78900
ggtgtagata cggatctgct gtccgtcaaa gatgacacgc cgcaacggaa ttttagccag    78960
ccgcgcgatg gccccggcct cgtagtgaaa attaatggtg ttgaacagat cgcgcaccaa    79020
tacggcgtcc tgcagacagt aacggcctac ctgggcgcgg ccctcggcat tagccacgaa    79080
acaacgcggg atgtccttgt aggacaggtc atccttgcgt tgccgcaggt aaagctcggc    79140
catagtgttg agcttatagt tgggcgagtt agtcttggcc atgcatacgg ggtacatgtc    79200
gataaccacc gaacccgcaa tatacaccdt ggtggcggcc gtgctggccg gattgttgtg    79260
agaagccgag ggaaaggcgg cggcgtactg ccgcttaaaa cccacggcgg ggctgtgtaa    79320
aaagaaacgg ccgccctgcg ccgtgggcaa cttgcagaag cgctgcgagt ccaccttata    79380
caggtactcg aggcgcgtga ggatgtactt caagtcaaaa gagttgatgt tgtaaccggt    79440
cacaaaggcc ggcgcgtacc gttgaaagaa aagcataaag cccagcagca gctcgtattc    79500
ggaagggaac tcgtagacgt ccacgtctgg gcccacctgc ccgcaggtgc cgatcgtaaa    79560
gagatgaaga cccgagtgcc caaagatcac accctccgaa gtgcagcccc gaccatcgtt    79620
cccgtttggg atcccctgat ccacggcggt gtttccccc gtctcgtagc acacgcacga    79680
gatctgaatg acaatgtcat cggacttctc ggcgcaggga aaaccaccct cgccgctcat    79740
gcactcgata tcgaaggaca ggcatcgata gcgcggccac gagctgtcgt cgggcacggc    79800
caccaggtca gagacatcgc agtcgacctc gatatcacaa gtcgacgcgc gaccctgctg    79860
ccgccagtcg taacgattca cggagcacca gccgaacgtg gtgatccgcc gatcgatgac    79920
caaacgcgtc agcggatcca cacggacctc gtacacggga aaaccctgct ccagcagata    79980
ctcgccgatt tttctggcca tggtccagtt gctgatagac acacactgca aatcgggcac    80040
gggtcgcgtc ccgtacccgt agatggaggt cttggtggcc ggcgtgacag acacggcgta    80100
tggcgtccgc ggctcgggca ctagttcgcc cacgctggca atgacctcac gcagcctatc    80160
ggtgtcgctg tactcacagt aaaagtagct gcgctgcccg aaaacgttga cgcagatact    80220
gtagccgtgt tctgtggccc cgaagaaacg caacacgttc cccgaaggca ccagatgctg    80280
acgatagcgc ggcgacacgt tttcgggcga gtcgaagaag agcacggcgt ccgtctgatc    80340
gtaggtgtga aaacgaatag gtcccaccac gcgacccacc agggtctcgc gccaaggaca    80400
cggccaaacc atgtcatgac tcaacaaatg tttaatctct cgatagaaca tgagaggcag    80460
ccgtcccgtc ttatgcttga tcaaccccgt ctgaccgtcg aacatgacgc ctcgcggcac    80520
gatctgcaaa aactgtttct gtggcggccg cttcccgag ccctgcgcgg agccgggctg    80580
cgaacgctga cgccggccac ccgcgaccgc accgccggtc acgccgccgc tcagatacgg    80640
gttgaaaaac atagcggacc gtgagaggct gacagcttac gaagcacaat cacaaagaaa    80700
atacacatgc agcacctaga tatccagttt gaccccgtat atcacaagtc tctgtgtcac    80760 ttttttttgtc tgttttttttt ttcttctcct ggttcagacg ttctcttctt cgtcagagtc    80820
tttcaagtgt cggtagccgt ttttgcgatg tcgcagtcgg tctagcaggt tgggcttctg    80880
tcccttgtcc tgcgtgccag tctgtccgtc caaagaatct gtaccgttct gctgcgctcg    80940
```

```
ctgctctgcg tccagacgga ccagggccag aagcatctgg taagcctgct cgttggtgta   81000
aggcggagcc gccgtggatg catcagacga cggtggtccc gatcctttgc gaccagaatt   81060
ataaacactt tcctcgtagg aaggcggagc ctgtaacgac gtgtctttgg tgttgcccga   81120
cgtcacggtg gtcccgttgg cggacaccag atagggaaag aggttctgca gcggctgcat   81180
gcagagacgc cgctgtcgag tatagatcaa ataagtgata atgactacgg ctatggccac   81240
gaggatgatg gtgaaggctc cgaagggtt tttgaggaag gtggcaacgc cttcgaccac    81300
ggaggccacc gcgccaccca cggccccaat ggctacgcca acggcctttc ccgcggcgcc   81360
caggccgctc atgaggtcgt ccagacccct gaggtagggc ggtagcgggt cgactacctt   81420
gtcctccacg tactttaccc gctgcttgta cgagttgaat tcgcgcatga tctcttcgag   81480
gtcaaaaacg ttgctggaac gcagctcttt ctgcgagtaa agttccagta ccctgaagtc   81540 ggtatttttcc agcgggtcga tatccagggc gatcatgctg tcgacggtgg agatactgct  81600
gaggtcaatc atgcgtttga agaggtagtc cacgtactcg taggccgagt tcccggcgat   81660
gaagatcttg agactgggaa gctgacattc ctcagtgcgg tggttgccca acaggatttc   81720
gttgtcctcg cccagttgac cgtactgcac gtacgagctg ttggcgaaat taaagatgac   81780
cacgggtcgt gagtagcagc gtcctggcga atccttcacg ttcatatcac gcagcacctt   81840
gacgctggtt tggttgatgg tcacgcagct ggccaggccc aagacatcac ccatgaaacg   81900
cgcggcaatc ggtttgttgt agatggccga gagaatggct gacgggttga tcttgctgag   81960
ttccttgaag acctctaggc tgcgccgttg atccacacac caggcttctg cgatttgcgc   82020
cagcgcccgg ttgatgtaac cgcgcaatgt gtcataggtg aactgcagct gggcgtagac   82080
cagattgtgc accgattcca tgctggataa atgagttgca ttgttgccat ctgcacttct   82140
tttggttcta ctatgagtaa gattcagact ggagcggttg gccaaacgtt cgagttccac   82200
cagagatttt tgcttgatac cttgccagaa caccaccaaa ccaccagtgg tttcaaacac   82260
ggacacgttt ccatattttt catatgtttg attgtatgaa gtattgaaaa tctgctgtaa   82320
cttatttatg gcctcatcac gtacgcagtc cagcgcagag tcggacatgt tcacctcttg   82380
cttcttagat aagaaagtgg cggtcatttt ggcagaagaa aagtgatacg agtcctcggc   82440
ttcggaacga atggtgcgtt ccgaggcttc ccagaaagtg agttgacaag taacattctt   82500
ctcgtcctgt atatcccagg agatcactga gtccgcacgt tcaagaaaag ccaccaacct   82560
gtgggtctct aacgcagaat tcggtcttcc aaagtcggag acgatagtgt agttcggaaa   82620
aatgaaaaac ttgtcggcgt tttctccaaa atagctggca ttgcgattag ttccgttgta   82680
gaaaggagaa atgtcaacca catcacccgt ggaagttgcg aaaaaatgat agggatactt   82740
ggagcgcgca gtagtgatgg tcaccataca attcagatta caggtctcac gatagagcca   82800
ggtgctgccg cggctgtgcc attgatcctt gaccgtcacg taacgggtac tgtgggtgtt   82860
ggaataatcg tcgggcatta attgcatggt tttgttttca tagctgtccc tatgataagc   82920
cacgaaaacc gtgcctgcta taacgcggct gtaggaactg tagcactgac tgtggctgtt   82980
gatatgatga atctcccaca taggaggcgc cacgtattcc gtgttgctgc ccagcagata   83040
agtggtgtgg atgtaagcgt agctacgacg aaacgtcaaa accttctggt agactcgtac   83100
cttaaaggtg tgcgcgacga tgttgcgttt gtagaccacc atgatgccct cgtccaggtc   83160
ttcattgata ggcttcatcg aggtgcagac gatattacgt tcaaagcgaa taagatccgt   83220
accctgtgcc atagaacaca cgcgataggg gtacttggtg gtattgaccc ccaccacatc   83280
tccgtacttg agggtagtgt tgtagatggt ctcgttaaca ccatggctga ccgtttggga   83340
```

```
agaagttacg cgttgagaga ctgaaccgga tcgagagtga gcagcagacg tcgtatgaga    83400
ggaatggtga ctgtgagtag cagaagttcc acgagaagta aagatgagg aaaccgcagc     83460 acccagacag acgatacaca agttaacgca gactaccagg caccagatcc tggattccat    83520
gttcgtcgcg ggccaaatcc agcagcgatg aggcgcgtcg tggtctcttg cgtgttcgcg    83580
ggaccctccg ggaaacgccc gcggtcgagg aggagggta cggacttggc agccaaggtc     83640
ggtccggctc cctgaaggca cccgagacgg ccgcggcggc cgttagggtg gagggcttgg    83700
ccacgggagc tgttggcacg tcgccactct catccggtct ggacagatgc ctgtagagga    83760
ggagatatag atctttggac ttataaagac ttccttcgtg acgaagcagc agcggccact    83820
ctttgttata cgtgagaatc acatctctgt ccgggtgcag ttcgtcgcgc aggcacgcga    83880
tcgagagttg tttcccgaaa gtttcattat atagtgcgac ggagagcacg agctcccgca    83940
cgtgcatcca catctccttc tgcagcacgt ttaggtcctg acagtccgaa aaattgaaaa    84000
aacccatgta cttcaccacc atccactcac tgggatacac ggtaccttcc gcgcatttga    84060
ccaaatcgtc cttgacgtgg ggtagtacgc ccgcgttgtc gcaggcatag gccatgtcca    84120
cattgtgaga gaggggatag cgatcggtac agtgtgtgaa gaggggcccg ttacacaact    84180
cgtagatctg ctgacccagt agcgggaggg attccacagg cagactcttg tggatcaggt    84240
tattgaccac atacaggtgc tcatcgtacg tgaactgatc ccccacgtcc accacgtctt    84300
ggtcctggtg gtattggctg cggtatagaa acccattcat gagcttagag ataaagtcca    84360
gacacaaggg ccccactagg ttgacatcga tgagtttgct agtcagacgc tcctgcgttt    84420
tgatgcaacg gatcaccttg ccatagccca cctctgagac cttctgcagg taggcgcgtt    84480
tgcgcacgtt cacctcgcgg gtgacgttgt ggatgcggga acgcgcgtcc accaagtcga    84540
gagcctcgtg ttcgtcgcag ttgcgcaccc gtaagccgtt ctcgccgccg tcgccgtcct    84600
gcccattcgc ccctccccct accgctttct tgcctcctcc acgggccggg ccgccgccac    84660
cgttattcct ctgactgtga gtactgctgt tgctgctgtt gctggccgtc atcaaagtcg    84720
tacccgtccc cgacatcgcc tcccgtccac gcaggtgaat agcctcgccc tcggggccgt    84780
cgccccccgt gccatcgggc agcggacgtc gaatctcctc gagaatatgc ttgattttgg    84840
tgtacatctc gttgctttcg tggagcttgt tgaacaccgg gttgtcctcg aaagcttgaa    84900
tgctgaggga tgtgatgagg tcgatgatcc tgttgggggc ggcaaagacc gaccccacga    84960
acatgcgctc ctccccgtcc aacgccttt cccgagcac gaagatgtcc tccacgtcct      85020
ccccgtacag atggcgactg atgccgttca tgagcgcccg gcacagctgg tgatacacat    85080
ttagctgctg gatggtgatg cccacccgct tgacgataac ctccgaggta cgggaccagt    85140
aggtaaaatc cgacaaggaa tatattcgtt ccggtatatc cgtaaacagg ttgtactccc    85200
tcagcgcctc ctccgcctcc tggatgtagc tgtggtaggc cgatgaagaa gagaataggc    85260
ttttgagggc cgaaaggact ccagccaagt ggggatgcg cgttgtcagg tccagcaggt      85320
cctgctccac cgtctggata ttcacatcgg actggcttga cggacggtgg accgctatat    85380
ggttgcacag caagccctgc agccgcttgt tcagcgagcg gccctgattc gggatgatgg    85440
tcagctcctc gtagcattgg gcgcatgtcg tcccttcgac gtacacttcc tgacgcgcca    85500
ccggcgagat gccgcatagg cgacggagga gctccagcag ctgcgcgcag acctccaggc    85560
cggcctccgg cgccaggatc ccgtacacgt agttcatttt gcacaggaag cgctcgatgt    85620
cgttgagtgt ggccagactg acgctgaaac ggacgttgtc cgtaaactgg agctccacgg    85680
```

| | |
|---|---|
| tgtgatggcg atcgcagcga tccaaacgga ggacggtacg gtagaaggcc gcccggtccg | 85740 |
| gctggcgcga gtaggccatc agcgcccgat ccagcaaagc cgtatcctcg tgcagcgcct | 85800 |
| tcagcagcat ctccagatag agcgtcagca gcgaactctg cgtacgattc tgcgccacca | 85860 |
| cctccgggta gatcttccgg tacagataca ctatagccgc cgcgtttctc ttgaacggcg | 85920 |
| tggactccgc cagtaacacg ttcggatcgc agtactttag acactccagc tccatggcgt | 85980 |
| attcgttgca tttcgaacac actacgcata gtttctgtaa caaattcatc tccatgactc | 86040 |
| gactcgctca cgtacgagac gctgtcgtcc ggtctggcgc cggccagaga catggagtcg | 86100 |
| gtgcacaaat aactcgcggg ccgctcgcta tgccgactga cgttgacgtt aatatataac | 86160 |
| gacgtcgtcg acgacgcggg ttctgctccc gaagctgttg ccgccgcttg cggcgcaacc | 86220 |
| tcctccacca ccgccgccgc cggctcctcc gcctcgggcg acgggggctc ggagatgacc | 86280 |
| ggctgtgtct gacactcctc cccttcctca ggcggcccgg gcgccgacgc gaatgtcgga | 86340 |
| gtttgccagc gcggcggcgg tctctgtctc tggtgccgcg gcgctaacct tcgggctgt | 86400 |
| tgctgctgtt gatgatgcga cgccgtctgt cgccgctgtt gcggcggtag ctgatacggt | 86460 |
| gtcgcctggt gctgctgtgt cggtggctgc tgttgctgct gttgttgcgg tctgaaaagc | 86520 |
| ggccacgggg gctgcgactg ttgctgctgt tgttgcgatg ctcgtggctg cggcggccgt | 86580 |
| tgtcgcggcg tttgctggcg gttacaaccg gctgcgtttg gccggcaata acccgctgcc | 86640 |
| cccgccgccc ccgctgctcc cgccgacgcc gccagcctcg tcttcgccgg cgttcacgag | 86700 |
| aaagcagcca cctcccgtct cgccgggcac gccgaagcaa atggagttgc ccgcgacgga | 86760 |
| ctcgccgaga agaagaccgc cacccccgac gccgacgcc gcgccgacgc cactgggcgc | 86820 |
| gaagagcgcc gacaggtcgt gcacctcccc cccggcggcg tccgttaatc gctgggcgtc | 86880 |
| ggcgtccagc acgcgtcgca agttctccag cgaaaagtcc tccacgccct gctcctgcaa | 86940 |
| cgcggcaaac ttgtccatca gcgacgcggc cagcgcctcg cagccatcca cgaagaagag | 87000 |
| cacatcgtcg gacgcgggga tctcctcgcg cacgctcaga atctcgtaca cggccatcac | 87060 |
| ttcggggtcg caatccaagt tctcggcgtc cagcgccagc atgacgcggt tttttataag | 87120 |
| atccgcgtca aaaagcacgt tctcgcggcg cgagcgtttg atgagcacgt cggccagacg | 87180 |
| cgtagccaag aggtagcgct ggcgcatgaa acgataatct tggccgctca tagagctcac | 87240 |
| gttaaggctg cgttccacac cgttgcccga aaagtagccg atctgcccaa actgatagat | 87300 |
| ctccttgctg ttgttgatac ccgcatactt ttccacgctc acgggcacgg tcaccaagga | 87360 |
| acgatgctca aaaacgctcc gtaccaacga ttcacgcgcc acagtggcgg ccatgggcgc | 87420 |
| cggcacgcct gcggtcttca agcccttgac atgcaacgca aattcggcgg cgacgagaa | 87480 |
| acgcggacta gcacctaaca cgtgaggaaa ctgcgcgtgg ttctgcgtcg ttaagcgcgt | 87540 |
| cgtcaacccg tgcagcgagc caatgtagtc tttgaagccg tagtagcaga ggaatttgtt | 87600 |
| atggaaacgg ctttccacgt aactcagcac acagtctggc gccacatcca gcagatcgtg | 87660 |
| ctcctgatag tcagccgtca cagccaccag aaatttgacg aaagcattga actcgcccat | 87720 |
| gtcacctatg ggcacattct tgggcaacgc gttggaacag accttctgcc aaaactgtaa | 87780 |
| gcaggggaga ccacattcag gaaagagtcg ctcgtgatgt cgatacagca gaaatcccaa | 87840 |
| gcagccctta gccggattac gacgcggaac gtgatcgcgg cgaaaaaaca cgctacccgc | 87900 |
| gttgcccttg cccgcgcggt agatgggtcg gtttttcact cgcaccatga tcaacgtggg | 87960 |
| taccgacagc cgcgagagct tgatctccat gggcaccacg gcgtacgtgc cctgcgcgta | 88020 |
| cagcctaaag tccagcaggc ggtcgtgatc cgaattcttg gacgacttga tctgcttggt | 88080 |

```
gaagagaaag cccttgcgcg acgacgtggt ggagaacgcg ccgtgaatgg attgaaaatg    88140
ctgcgtcatc catttggata ccaagttggt ggtcaacgga ttgtccacaa tgtatgaggt    88200
agcggtaata agcgccacgt tctggatcac gtaaaagacg gatctgaaat aggcgtaggc    88260
cagcagcggc tggaaggcca cggcgtaggg attcagatcc aggttgaagg cctgcgtggc    88320
gcccgccacc tcgtcgcggc tgctcttgag gcgcacctcc gaaacgaaac ccagggcctc    88380
gtcgtccaca aacttgttga gcgccgaaaa gacggccaca aagtcgcttt tgccgtgcgc    88440
gctaaaggta tcctcgcccg tcacggggtc gatgagccgc atcttgcggc agtaatccaa    88500
gatgcgattg agccgatagg tacggtccac gctagcgccc agcatgcgac cgccgcgccc    88560
catcattccc ccggaatccc cgccacccCC accaccacga ccgccgccca gaccgtcgct    88620
cgggcccccg ctcacgtccc gtccaccacc cccgccagca ccgccgcccg gaaccccgtc    88680
gtcacctttg ccgtccaaac ccccgtcctt ggcgtcgacg ttgtaacgcc gaccgaagct    88740
gcccaaaata tccacgtcgt tgagaaaacg cgactcacg gtgatcacgc agggctcctt     88800
cttgggctgc ttgggcacca cgggcaagcg ggtgcgcacc cgcacgaagg ccgtctgata    88860
acacgtgtgg caacaagtac ccccacaggc ctcgcacagc cccgcggcgc agcccaccag    88920
gtgattcgtg agcgtcgacg aacccgacaa gcccgtgtta tacaccgaga cacgatttag    88980
ataccagacg aagcccgaaa ctagctgcgg acacgtgcca cacaccaacg ccaaatgctg    89040
cggcccatag cgttcgtcct tgagcggcgc gccttgaaat ttgagcacct tgcgcgcgtc    89100
gttgtagacg tcttcgcagg ccgccgacaa cccgttggtg aactgaatag ccttgagcaa    89160
cgtctcctga ctggccgtac cgccggcgct gggatgccgc gccgacgact ggagatacac    89220
cagcctgtgc tggtagagca ccgaattagc gctgaagacc aaggcggcca cgtgcgtcga    89280
gagatgcaac ttgagctcgg tcagcgcgcg gatcagatcg cggtgatcgg ttgcgttggt    89340
cactaaaggc cactcggaaa agagcataga ctcggcaggt tggtaggccg aatcgaaaaa    89400
taccgaggca aaactgaagg ccaactcgca aaccaccgcg tcactcagca tcagatgatc    89460 ctttccaga ctgctgagtc gctggctcat gtacccaag tagcgcttat gtggcgccag      89520
cttcaccgac tgctgactgt cgtgcacaaa ctgccgcaac gccgcctcga tcagcacacg    89580
cggctccgag aagcgcagcg attgacacca tgacgtgtac acgtagtaga aaagcgtctc    89640
gcttacggcc ggcacgtaga gccctcgcgc ctccacaaaa gcgctgcgcg catccagcga    89700
gacctcgtcg gcttcggcgt caagctgcag cgaattaaag agcgtaggcg ggtacaacgg    89760
cacgcgcacc gcctcgccgc cgtacagtcg caccgtggtc gcctcctcca cgcatggaat    89820
cagctgaccg gcaaagagaa actccttcaa gccgttgccc accaccacgt gcacagtcgt    89880
ctcggacgcc tgacagccca ccgccgcgca caacgccgac agatcggtag gcacgcgatc    89940
cgcctcgggc gtgtaggcct ccaacgcgta cttctggcgg gcgtcctcgc acaaccgatg    90000
cacgtctccg tgatcctcgg taaaagccac gatgccttgc gtatgatgaa agtagagcgc    90060
aaaaggacag aaggacgtga ctttcgtgag caccccgccg tcgtaacaaa gcacaggcgt    90120
gcgcacagag acgccgaaat ccgcctccac cgtcagcccc gccaacagag gagcgatcac    90180
cacgctcgag gaacggtcgc atagcgagag agtggccaga atctcctgcg tttctgcgtt    90240
caacctgctg aagtagagaa aagccgcggg ccccaccggc gctagcgcgg ttagttcctc    90300
gtggctcatg gtggatgaac ggaagacaat ggctacgccg ccactgagtg aatttttatac   90360 caaggaaaag ttcagcacgt catgtttgac gcacgacgtc tgatacacca ccgtggccac    90420
```

```
cactgcggtc tggctgcggt tgcggaccac caaaggcgac aaccgcaacg atcccagcaa    90480
ttcgtaagaa aagctaaccg ttacggtcgg gcagcctctc gcagccagac cgctagccga    90540
cgcacccgcc cgcgaaaata gcgtgatgtt cgggacggct tcgcgtcacc gcaaactaac    90600
gtcggtagtc gcgcacgtcg tttatcctca gcacaccgtc cgatcacaac ccgttttccc    90660
actcagtcgc acaagcagca cataaaaacc ccacacagtg cacgtgaaaa caacgtccct    90720
agaaaacggt gttttctgtc ctaccgtcac cgggccacac aggcaaatcc cgagcccgat    90780
ccccgaaaac accgtacggt gtttgtggcc tccaaaatca catcagataa caaaccgtga    90840
aaagtcacgt ttcacgaaca cggtgttttt aaatcacaaa gaaccacctg acggtttaca    90900
agcagaaaca ccgcaccacg gtggtacaag cgcggtggat ctggtctcgc aacctcaatc    90960
gccgctatca ccaccgactt tcgctgcgct ccgccgacaa aacgccgtat aagctacaca    91020
ccccaaaaac ccgcacgcct atgggcgcca aacgtgtgta ttatctcaac gtcacgacac    91080
gacacaaaca gcgtaacgtg gtttcccgaa cacgtacgcg gcacagaccc ccgacacgta    91140
ctcgaagacc ttacagttta cgagtcaata aaacaggaaa agatccgaac tttaaaattg    91200 tgtatttta tttcccatc cccctctttt taccaaaaaa cacatttttc gtcttgtaaa    91260
aagtaacttt cgcccattgc catgaaacac cgtgatgggg aacggtgttg tgtgtcgact    91320
gacgtcacta cggcgatcag tatcgacgtc gtgtatacat aacggtgccc ggtgttttta    91380
ttcggggcgt tgtcgcgtct tgatgtaatg taacctgaaa ccgccgtgtc caagaatgcg    91440
gaagccagcg tgtaatcata acggggtttt gggtacaatc tgacgacatc tggcggcgag    91500
cgtacaccat cgaatgtggc gatcgccggc tctacgtcac aatgacgcaa aaacacactg    91560
taaaacacgc gtagacagct ttcctggtca acgagcgcca tctggtgtcg gcataagaac    91620
aggcatcaac cccgtggccg gcgaggcggt gagcactttt gctggtcacg tgaccatcag    91680
cgcaggaagc gaggcccgta gaaccgccca agaggcggtg ccagatgcca acgtcataat    91740
cacaaggtga tttgttacgt cacgcgcgcg cacgcacgcg cgcgcggtag aatacagcga    91800
tccctagtga agccacaccc attacgtgta gccatatccg cttacgtata cagccacacc    91860
cctaggtacg ccaccttatc taccaatcat agaaacggat atacaatgac ccctccctag    91920
actccacccc ttgtacggaa atttcagata ggtggaaccc gttagggttc caccgtcctc    91980
ggtgtacgta caggcttctc cgtctaccgg aaatatacac ctgctgacgt agacgctact    92040
cccggatacg cgtcataagc tactggaccc tagggggggag tgtctacagg gctacgtgca    92100
cgccccctta cttagggtat ccgcccccctt cctctgtttt ggcctagtaa acttaacgcc    92160
gccgcttctc acgtgacccc tggcaagcct acgtcacact cgcgtgacca cacccactcc    92220
ggatatacgt catcctgtgg aattccggac atacggtgac gtagcgagcg tagcgagcta    92280
cgtcacgtat gcgtacgtca cctccggcgg aaatcatctc tgatgacgta gcgagcgaag    92340
cgagctacgt catcagtccg ttttacgtat accgggtgct aggcgacgcc ccgtaggggc    92400
ggagcctagc ttccacccct aggatgcata ccctatatag cataattctt ctaacgaaac    92460
gttctacgaa aacggactgg cggaacggga accaccgtaa cccccccccc tcaccccccc    92520
ccttctcctc cggaaccggg gggggcaaat ttttaccaaa tttgggcaac catgttttcc    92580
aatgggacgg cgtttccgtg cgcatgcgca gtcgggcgaa ttttttggtt gtcagggcgt    92640
tgccacgcgg attatgggat gggggctcga gtgcgcatgc gccggggatg ccgcatggaa    92700
agcctatata taaggagggg tgaaccaggg gccccggtgc gcatgcgcgg accaggcccc    92760
gcgggagggt cgccctgcgc atgcgccggt aaaattccac tgggtgtgtg tcgtgcgcat    92820
```

```
gcgccagtat ttttccactg gaggcggtca gtgcgcatgc gtcggtaaaa ttccactgga     92880
tgtgcaccgt gcgcatgcgc cggtatttt ccactgggcg gccgcaccta gggagcgcga     92940
gccccgtgcc gggcatgggc cgcggcggtg gaaaattacc gctccgccca cctaggcggg     93000
gcatcttaaa acctataaaa cccggcgtac ccgccgcccc ccggcgcagt ccgcggcagg     93060
gttccggccg tgctgcggtc cgcacgctgc gcccgctccc gcctgcctcc cgccctaccc     93120
cccaccctcc ccggccgagg cccggcgccg gtccgtccgc gggcccgtcc caccgccctg     93180
gagcaccatc cggggccgtg ggccgggcac cgggcgcggc ccgctccgga cctcggccgg     93240
gggtccctcc cctcccccg ctcgaccccc ccatccgacg gcccggccgg gctgggaccc     93300
ccgcaccggg gtcccggttc ccgtccgcgg cccgggggga cccgagcggg ggcttcccac     93360
ccccaccccg ctcctcccccg ggctccggcc cgggatccct cgctgctccc ggcgacctcc     93420
gccggcttcc cggtccaccc gccgcggaac ggacgggacc cggggtccgc gcccttcccc     93480
tcccccacg gggggctggg tcacggaccc cggttcctag gctcgttccg cggtgggcga     93540
ccggggatcc cccacccagc tccccttccc ggcccgcccc gctggctttt gggcccctcc     93600
gggcttttt tccggctggg ggtcgcgcg ctcggccgac gacgacggta ggtgggccgg     93660
gtggacggtg gtggggacgg gcgacgcccc ggctcgacgg cagtcggtcc cggaaggttg     93720
ggggctgggg gcccggtcag gagctccggg agcggggtcg accgcgacgg cttccgggtc     93780
tcgcggcggc tccctctcgg cggctccggt tgggctcccc tcccccctct cgagggtccg     93840
gccgccagtc gtgaccgggg gtccctcggc ctagccgccg gctctcggtc cgccttatcc     93900
tgggcgttgg ccggtccgt gacgctcccc tccccgctg ctccccaaaa aactccgccc     93960
gaaccgtcgc ggcttgctgg ccctgggcgt ggtcccccac tcccctcccc ccatcggccg     94020
cccagccggg gtcggcgcct cggacccac caggctgtgg cgtgtgtgct ggccgatgcg     94080
gcggcgaggt tgggtgtggc cggaagcgct cggggtcgac ggtgggccgt catgacacct     94140
caattgccgt cagtacgccc ctccacaatc accgtcccta cacgatgggc ccggcaggtc     94200
acccaacgtt ggttcaggcc cagtcgggtt ttttccccggc acaaacgcac gtccccgtgg     94260
gctccacgcg ttttccaccc tttcctggag gggtccggaa caccgtgaat ccgcggggag     94320
ggtctcggca cgggccgagg agaccacgac cgtcccaccc ggcgtgtcga cccgtccgag     94380
acccgggaag ggaacaggcc ccacccttt ttttccctttc tccgatttgc cgtggaaaac     94440
ccgtgaaccg atacgggtac agacggccga aaaaattcga gacgacaata cgacggcagg     94500
gcgtgatttt cttccccatc cgacaaaacc gtgtccctca aaattcccca cctttctctg     94560
ttcaaatggc cccgaaactg taaaacaccg ttcgaccgca ccccaaccgg cgccatcttg     94620
gtgaccttct cgacggttct ctcgctcgtc atgccgttct gagctccgac atggcggacg     94680
agagaaaatg gcgtcgagag cataggagcg ttttcgctcc aggcgggtaa aagaatagca     94740
cgataacttt tctgtgcttt ttttgagacg ttttagaaga gcttttttc tgctcagagc     94800
gaaaaaatga tagccctgaa aatctcgacg agtctggccg agcggcgcca tcttggagga     94860
ggggcgagtc gcgggcaccg cctcggtacc ccctggccga ggcgagtccg cggtcgccgc     94920
ctgttccgtg atgctaccta gagggcgccg tcgaggcgac tcttcctgtt ttcgccctga     94980
gggctaacgg tcgctgacgt caaaccatct cgtgctcgct gagtcacatc cggttgttga     95040
caagcgatga aggaccgcac ccaaagtgcg ccctctagtc atcgcgcctg accccttta     95100
taaactgctc gaagaaaaga acaccttatg tgaaaaaata cagaatgatg acaagttcat     95160
```

```
ccaacacaac cgctcaacaa cgccatatct atcagtgtcc aaaaactatc ttctatcctt    95220
tgaaactata aatgctgcct atatacatat ttagtatcca agactcttac cacgtagacg    95280
aaaagaagtg atacaatgat cttgacgtgt atcgtctata tcgtgctaga tatattcaga    95340
taagacgcgc aaaccataga tttctcatca gtatcatgaa agacctatag ctctatatac    95400
gaacctagtc attttaggac agccgccgga gaagccgacg agggatcggg cgggtgcagc    95460
cagaacctca cgcccgatcc cgcctccggt aggcgatttg catctgtttg gtaaaaagct    95520
cataagtctg tatgtgacct atatatatat tatacgctat gtacaccgaa ctgtcgctgt    95580
tgtataagaa gaaaaaactc tccatattta tatcgtctga atttttgctt gatagacacg    95640
tgtttggaac tctgtccccc cacgttttca ctgtgtataa caaaaatatg tgtttctcaa    95700
aagatcttga ggtgtttgaa aacgggggaa accgcgtttt gggtgcgcta agccccggac    95760
tgggacgtag ccggcgtccg gcacctatat ttttctattt tttttacaaa atatatgatg    95820
aaccaagaat aaaactctag ctctcgtcta tttttaatat gctctactta gaaccttttt    95880
aatgacagaa tgaactccat gttatacgct ctttatatag tttctctgca ctaacccttta    95940 aaatcgtatc cttccctgtt gtacaaatca tcttttgata cacaatgatg acctgatatc    96000
cctccatata tatgatcgga tattattccg ttagacttgt cctcctttt tttcctcatc    96060 tcctgtatct ggagatatat gttgaccacc accgccatga ccaccaaaaa gctagccgtc    96120
acgactagaa atgtgtagga ttcggacttt ccgttcgaga agaaagagac cgcgtctctg    96180
gacgctcttt ttgtcggtct gaatcgaccc gggatacgta agagagcggc cctacatcgg    96240
ggggcgctcg agaccgacga cgttccatct gaccagaaaa aaaaaaggca cccctcggta    96300
gcgacctctc accatcgttt gcccgtccgc ccgtccttcg tagccatcat catcatctca    96360
ggctctatcg gtaccatcgt tgtcatctga aaaaaaaaaa ctgcctcacc cacctgcgta    96420
aaaacaccat ctttccggag gtgcggtaag acgggcaaat acggtcgtgc cgaggcaaaa    96480
aaacgcacca tcgacaccac accctcatga gcaccacctg tcggtgttgg tcgtcctcca    96540
tcgttctcta cgaacatctc gacgcccggg tgacggacga cggcaagacg tcccggagaa    96600
gacggtgttc tctcgggcgg tacgctctct ggatctataa tatctatagt agctaaacga    96660
gactgtgagt acgacgaacc acatcatctt ttttttatgt tgctcccttta gaaaatgact    96720 tatgtcgacg acactcggca tcagccatct cgtgaaacac gctcgctttt cgtctctcca    96780
aggaacactg ggtccgctga aagggaccgt gtaccgacca aagcaaaaaa cacacacgta    96840
gtaacatgat caaccacgtc tgaatgacac gaaaacacaa tcgtataacg ctctattcat    96900
ggaacgaact tggaataaaa aaaccatcgc aggccagagg ctaagccgaa accgtccggg    96960
gaagcgggcg cgagttttcc gacttagtct ctggtgctcg ttgagcctct ttttttttcc    97020
tgattctctg aagaatcacc gtcacagccc tatgacgcga aatcaattgc tagaacataa    97080
acgttctcaa caggtatgaa atgaacaaac tagatgatgc tataacctta tattgtgtgt    97140
atatagatag gtgtgaaatt tgtaggataa aaagtgtcgt tgtatgatgc acaacgatcg    97200
tgaaactgga gactgtagct ctctaccgaa tgcaaataca caaatgacat cgattcccgt    97260
ccccacataa agaaatgtgc tttactgtga aagaatgaag aagattcttg ttcctcgtac    97320
gacggggccc tcgctcgtcg tacctcttcc cccctccggg agaggggacg tcggggccct    97380
ccgtcgcacc gggccgaagc cagtgaaatg tttactacac tgtcatcaga atatatgatg    97440
tatattattt cctccaaaact cctcaccata gccaccaatt cgcatcactt aagaaagtag    97500
tagcaaccgc ggcggcggcg accggccggt cgtcgtctcc tcgtcctcaa atgttgtaca    97560
```

```
tgtgcagaaa aatgtgtaaa tacgtgttat ttatcccatg cgtcttgtac atagatatat    97620
gtttttatat acgctattta tactttatat atccttttgc ataaccatag acagtcaagg    97680
attttaatga tttgctcatc cgcctttgag ccatcgctta ggagttagtt cctctatgtt    97740
ctcggcccac cttttcgact acagtagcaa acccttgtac taccaccccg ataaaaacca    97800
catcatcatc gtcaccacga cctggaaacg acacacgttc cccccaatc ttgggcatgt     97860 gtatatatat aaagaatggg agggagagga cgtggggctc gagaagaaat aaacgccaag    97920
ctcgattcga accaaaaaac cacatgtgta ttgtgctttt tttgttttta cggtggggaa    97980 aaggagggg ccgtcattaa cgaaaaccgt gtatggggtc cggacacgaa cagtacacag      98040
cttatgggga aaaagctca cagagagaaa aaaacaccaa gctcaggcac gcgtacatca      98100
ttatcatcat cggatatctc accacgagtc atagtagtac caaggagtgt gtaacaccat    98160
tttttctttt ttctttgtaa cgggataagg acagcaatc atcacgcaca acacccttca     98220
ctctcttttt agtcatccat atcatcgctg taacacagca tgtcctcgta atcgggcgtc    98280
tggcagcgca ttaccaccga gtcgtcttct tgcggtaccg gtggtggcgg cggcggcggc    98340
ggctgctgct gggttaccgt cgtactgtga ttaccgttgg cggactgcac cgggatgata    98400
ggctgcttgt ggggaacctg gggtggactg ccgccgtgag aaggcgacgg cgtcatcaag    98460
ttaagctcac cacggtgact ccggacaccg gcgaggggcc ccgggggact gggagggacc    98520
gcggtcgtct tgtagacgac ggtgtccccg tgtcgatccg tggctcgtac cagatcttga    98580
ctgctagcgt cgtcactgtc ttcgtcctct tccagctcgc cctcagagta gtgctgctgc    98640
ggttgcgacg gtggctgggc gggaggagcg gcggcgatca ttggagaggg atgtcgatga    98700
ctcccttctc tgtcctttttt atcgtaggct gtcagcgttg ctgggtccgt cctgcttttcc   98760 atatttgcgc attgctcatc ggtgggatga atttggtctc ctccccgctg ttgtccgccg    98820
gcagtggcgt ggttgctggc ggttgtcgtt gtcgtaccgg caaagacggt gagatccaat    98880
agtgactgct cgtcgaaggg acagtacgct atcatgaaac gatagggtgc caacgcgcgt    98940
tggatgcgca gttcgcacat ctcgttctga cactcgtggc actgcagggc gcctaggatc    99000
aggtccgaga cagcgccgca gcggtaggta cccatgcgt tgttagtatc gaactggtca     99060
aaaaattggg gcgtaccggt gacttgcaac gcgcgacggc gtagcgagac ggccacgcgc    99120
gagaaagagc acacgtaggc catggcgcgg tgcatgggtt gcgagaaggt ctcgggcgga    99180
cgcttctgca gatcgcagac gtcgtcgcgt agccaggcgc tcatttgacc tggcttttg     99240 actagccgtt tgagcgtgct gcaatggtcg ccccagccgt cctggtggtc caggatgcag    99300
cccaggtcca ggttgttgag tttgttgaag agcagctgac gcatgccgcc caccgtctcc    99360
agatagggat cgtgcgggtt gacgggtagc ccgtgcaggt ggtggtactt catgtagctg    99420
agcgtttcgt cgatgatggc cagcaacgtg tgcaagttgg gagcgttgta cacggcgaag    99480
atcttttcca ccaccagctt gcgcagcaac ggttcctcca gccaatcgaa ctgttgacgg    99540
atgtgcaaca ggtagtcggt gtgcatgagc tcgtcgtgtg acagcaggat gcgaccgcgc    99600
ggctgatgat cttgcgggaa ggcggtgggg accttgagat cggcggggta gggtgccaga    99660
cgtagactct cggccgtgta gcgctgaagg tcgtagacgg gcgaggtaga actcggtgag    99720
gtacccgacg aggcggcgcc gcgctgcaga cgcgctcttt tcttcttttc gatcaaacgg    99780
ctgagttgct gtagttcgtc ctcgtccatg gcgtccagtt cgtcgtcaat aagcgccagc    99840
atctgttgtt gttgcggtcc ggtggacgat ccgtgatgat tattggctga agaggggtga    99900
```

-continued

```
gaagaaccga aagtcgtagg acaactggga actcggcgac gaagatgcgt cgaatcgccg   99960
ccgtgatggt gcggttcgcc gtcatcgttg tcgtaagact taccgtagtg ggggttaagg  100020
ggcaccgagg cggacgcggc cacgcgtcgc ttgaaagagg aggacgccct atgtccgcca  100080
cggaagcccg cggtgcccat gatgatgtgt ccgccggtgc ccccgagtgc gtggcgggag  100140
gagggtggaa ggggaggagg atagtggtcc ggatcgcctt cggtatcatc gtctttgctg  100200
tagcggggtc gtcgtgcggg gacgcagggt cggtgatgat gcgaggcggc gccgacggta  100260
tcttccgcga gatggtattc gctggcggct gctccgttcc gtgtcgacgg cgaggttgga  100320
cttcgctcgc gtcggaactt ccgtggcacg ggttcgtaat ctagacagaa gcgccgtgcg  100380
cgacgggcgc ggcgttcgcg ctcgctcagg gaagataacg acggagcgtc gtgacggccg  100440
cgtgagtgca gctccatggc cgccgtcgct aggaaggtca cgttcgggca cgctgatgta  100500
tatatagatg agaccgctgc cgggggggcgg gtcaccggcg ccgtggaaag tgaggctcag  100560
acggcggtcg ccggcggcat gggcgcgtcg ggcggtctga ttttgatgga aatgtggacg  100620
tttttggcgt tggagtgaca cttttttggtg aaacagcggc tccagaggct ggcccagagc  100680
gcgtagctgt gctcggtgcg caggtcgatg aacacctgca cggtctcttg cgggttgcgg  100740
tgcgtgtagt tgagacagcg aaaatcccgc gtgcgcgcgc cgtcgcgccg cttgacggcc  100800
acgcagcagg cgccgtgggg ctgaaagagg aggacgtggg gtgcggtaaa ctgctcgctg  100860
acgtgcggct cgtagtgttg cgtgaggtgc tcgagcagcg cgggccacac gcgggtgacg  100920
acgagccgct gcaagtccgt gtcggaaatc gcagcggcag tggcgccgtc gccaccgtac  100980
aggtgatagg cgagcacctc ggtgagaccg cggcgtcgat aacgcgtcac gttaagcgag  101040
cgcgtctcga taaagttggc ttcggtcgag gggcagattt tgtcgcgcac gctgagaatg  101100
acgcgtggcg gcggcgacag gggcaacgcg ggcaggtcgt gcggcgggtg gtggtgaagc  101160
aggttacgca gatccagttg ggcgcgcaca aagcctagcg ggtgttcgcg gtaggcgtcg  101220
ggcacgatga acagcggcaa cagacggcga tgcatgaaat agccgtcgtc ttggtccatt  101280
ttatacatgt agggcagacg tacagagcgt ccatggtggt agatgcctgt gtctaggctg  101340
ctctcgggat gcgagatggg gtccagcagc gtgtgcagtt cggcgtcgag acagacggcg  101400
tgattgagca cctgcgccac ggcgcgtaaa acgctggggt gtacggctac ggtgcaggcg  101460
gggaacggcg tgatgatgcg cagccccagt ttgcccttgc agcggcagta aggggggtgac  101520 gtgtcaacgg aggacgttgg ttttttgaaaa acgccgttat cagggacgtt attttttgtcc  101580 tctttcccgt cttcgtcttc ctctgtgtcg cgctcgtccc ggtaatcgag atagtcgtcg  101640
tcatcgaaag gcgcgccggc cgcgtccacg ggcacgctgt tgggtgggca cgcgcttttg  101700
aagaaataga ccgggtgccg gtcggggtgc gtgtagccaa agaggctcgc ccatacggtc  101760
atccagacgc gtcgtagtcc gcgacataat tcaaagacgg tgtgtcgcgc cagaccggag  101820
acgccgtcgc gcagtcgtaa atcaaagtcg gccacaaaat tgaagacggg cagacgttcg  101880
ttgaagactt cgtgtcgcgt gtagtagaac tgtgtctcgg ggctggtgct ggccacgtcg  101940
tcgtcgtgta gccacacggt ctcggtcagg gcctcgtccg agaaacggct gtcgggtacg  102000
tgacggagca ggtcgcgcgg aaagaggctg cgatgccagg tttcggaggc cacggcgcag  102060
aagacgtgct ggtcattggg caggtgtacg cggtagacgg gcagcggtcg ctccagcagc  102120
ggtgccagcg cgggctcggg tagcaggtag cgacgttgcg agtaacgcgt tagcgtgccg  102180
gtggtgtagg tctgggctgt gcgcagcgag gcgcatagac gtaacaagcc ggacagggag  102240
cgttccagtg gcgagaagac agactcggaa agcgtgttga tgcgttcgag ctggcgcgcc  102300
```

```
agctgcgtgg aggtgccaaa gaagcccgcc aggtgcgtgc cgtcgatgcg gccgccgtag 102360
ccggccagcc ccaggccgtg cgggctggtc gccgagtggg gggattcgtc gagacccagt 102420
aggtgcgtct ccacgtagtc gtgcagaaag ttgtcgagcg agaagtattt ttgcatgacg 102480
tccagcagct cggtggaaag ccggcggccc agaaaacccg gttcgcgcgt gcactgcgct 102540
tcgggcgccg cgtcagcgtc gtaagccacc acgcgccggt actcgagcaa ccgcgcgcgt 102600
gccagcgccg tgcggtaggc caggtagacg tagtgcacgc agaccgtgtc gggcagacgg 102660
gcacgttcgc ggaacgcgtt gatctgcgtg tccacctgct ctagctcggt gtagtcgcgg 102720
cggttgcgcg ccacggcgta cgccacgaaa gcggacacgc gctgacgaaa gggcgagccc 102780
agtagcagac gcgcgaactc gcccatggag gcgtgcgtgg ggatgatggt gcccaggtcg 102840
cgcgtgcaga agctgcgcac gtactcctcc acggtggaga tggtgctgta ctggccctcg 102900
aataggtagt aggccatggt cagcagcacc tggccctcgg tgtgcccgaa gacgctgatg 102960
aaccacgagg gcgaggtggg gcagaggaag acctggttga gatgacgtag cacggccgcg 103020
tggtgaaagt acaccaggtg cttgaattcg cgcacctcgc cgccgtgttc gggcgagagc 103080
acgggcgtgc ggaagagatg ccggtagagc ggttgcgtct cggcctcgtc cagactggcg 103140
atgagcgccg agagggggat gggctggcgc gcggccaggt agcgcgagag ctgcagcgtt 103200
tcgttgttca cggcgaagac gggcgccacc cgccgcgagt ccgagcactt ttgcgtttgt 103260
aggcagaaat aaacacgtcg cgagacctgg tgtttgacca gcaggggaa gacgcagtgg 103320 tccgtcggtg tctgcgagag tacgttggcg actatatgag cagaatcata ctctgttgcg 103380
aacagaacga gcgtcatcgt cgcgccggca cgatgcagct ggcccagcgc ctgtgcgagc 103440
tgctgatgtg ccgtcgcaaa gccgcgcctg tggccgatta cgtgctgctg cagcctagcg 103500
aggacgtgga gctgcgcgag ctgcaggcgt ttctggacga gaactttaag cagctggaga 103560
tcaccccggc cgacctgcga acctttctc gcgacacgga cgtggtgaac cacctgctga 103620
agctgctgcc gctctatagg caatgccaga gcaagtgcgc gttcctcaag ggctatctct 103680
cggagggctg tttgcctcac acgcggccgg cggccgaggt ggagtgcaag aaatcgcagc 103740
gtatcctaga ggccctggac attctcatcc tcaaactggt ggtgggcgag tttgccatgt 103800
ccgaggccga cagcctggag atgttgctgg acaagttctc cacggatcag gcctcgctgg 103860
tggaggtgca gcgcgttatg ggcctggtgg acatggactg cgagaaaagc gcgtacatgc 103920
tcgaggccgg cgcggctgcg acggttgcac caccgacgcc accggcggtc gttcagggg 103980 aaagcggcgt ccgcgaggac ggggaaacgg tcgccgccgt gtcggccttt gcctgtccct 104040
cggtttcgga ctcgctgatc cccgaggaaa cggggtcac gcgtcctatg atgagtttgg 104100
ctcacattaa caccgtctcc tgtcccaccg ttatgaggtt cgaccagcgg ctgctggaag 104160
agggcgacga ggaggatgaa gtgaccgtga tgtcgccgtc acccgagccc gtgcaacagc 104220
agccgccggc cgagcccgtg cagcagcagc cccaggacg cgggtctcac cgtcggcgtt 104280
acaaggagtc ggcgccgcag gagacgctgc ctacgaatca cgaacgcgag attttggatc 104340
tcatgcgaca cagccccgac gtgcctcggg aggcggtgat gtcaccgacc atggtcacca 104400
tacctcctcc ccagataccc tttgtggggtt ccgcgcgtga actcagggc gtgaagaaaa 104460 agaaacccac ggcggcggcc ttgctgtcct ccgcgtgaac agcctggcac gttttggaaa 104520
acgtacgtga tcacggacac gacgagcacg gggtttctca tagacgtact ttattaggtc 104580
agggatgacg gggaggtttc gggccgacgt caaaaataac gtcactcgtg ttgacagggc 104640
```

```
tttctgcgtc ggagctcttt tcatcttctt ctgtctcgtc gacgtcatcg tctaccggcg   104700
agggtgtccg ttgcagcaac gcgtgctcgg gcgtgtgggt gaaaccgatg tcggggtgg    104760 gcggcacgat catctgtcct aggggtgac  tgcccaccgg cagataggta aagcggtggg   104820
tggtaaaaac cgctttggct acggtggtgt gtggggagat gcagacgtg  gtgtgcgaag   104880 tgttgaccac cgtcacgccg gccgcggtac ccgggagcca gatggtgggt cgaatgatga   104940
gatccgattg actaaactgg cgcacgccca ctatgagggc gcagataccg ggcgcgtgca   105000
cgtaggccgc gtcaaaatag acggtttgcg tgtgacccgg accgatcacc agcgtctgac   105060
gggtacgtaa tgaaaagaaa cggtgttcgt tgggcggcgg caagttcatg agctgccagg   105120
gttctggcac aaaacagggg aaaacgccga tatcgccttc gatggtgccc ggaaagatgg   105180
actgaaaagt gtcgttgagg ttgacgacat ccaactgcgg gacttgcagc ccggattcca   105240
gcagctcggg catgcaaacg aattgcgcgt ccaggcattt gtaaaaggta atgccaaaaa   105300
aaccttcggg gatatagagg ctgactccca gcgaggtggg cactttgcgc tcgcgtgata   105360
gccaaatgat gtgtttattg taaaaagcca gctgcgtgtg gcattgttta acgatgaaac   105420
tggaaggcat ccacttgtag ggaactttga gcggcgacgg taatggcgac gacgcttcat   105480
cctctcccgg atgctgctct ttgtcgtatt tctcctcggt cgattgggc  agcgtaaatg   105540 tggtttgaaa atcgctatcg ctagcgaaac gcacgcagta acgcatgttg acggatttct   105600
cggctaggat gatggagcct gatgacggtg cggactcttc cttcattatt aacgtagggg   105660
tctcccagaa tcgctgaaaa cgggagcgcg gcagccgcga cagtaccagt tgagagtcga   105720
ttctgtcggt caacattgta agcatcgtgg cggtggtgtg atggagtgga aaacagtgat   105780
actaggtgtt tttgttttat cggtggcagc ggggagttct ggtaacagct catccacgtc   105840
aacctccgca actacgttaa aatcgtccag ttctagcgtg tcaacaagca aattgacgac   105900
aactgcgaca actacgacaa ctacgatgag tacgacctca tcgacaacta ccactaaacc   105960
aagttccact actcacgacc ctaatgtgat gaaacgacat actcacgatg attttacaa    106020 ggcacattgt acatcgcata tgtatgagct ttcactgtcc agcttcgcgg cttggtggac   106080
tatgcttaac gctctcattc tcatgggagc ttttttgtatc gtattacgac attgctgttt   106140
ccagaacttt actgcaacca ccaccaaagg ctattaaggg tggacagatt tacagctcga   106200
cggtgttccg gcggggtaag gtttccataa gtgggtgact ggagactaaa gttacggatc   106260
tcatctagaa atagcagcga gtctagatag tcccacaggg gatctataaa cgttctctga   106320
aatcccgttg atggtgacgt aggtgtagtt tcggaagccg ttttgttttc cacgaacatg   106380
gtttcgttgt aatataagga gctcatatca agagtaccgt aaatagtgta cggtgtttca   106440
ttacggatta gtacatgcgt gttttttcata aattctgata cggcggttcg gttgcggctt   106500
gattcacaaa aagggttttg ccggtaacgt agagtggtat acacccacgt cgctaggtcc   106560
cttaattgcg tggtcataat ggacttcata aagctactat caggacgata agcaattgta   106620
gacgtggaaa cccgccttgc ggtggtagta acactataag ttgcgttagt agtgacgttc   106680
agagcggttg acgttgtata gggagaatat ggcgtagtag tactttgaga tttcttactc   106740 ttttttttctg attgttcttt gactggagct tgtttacgct tgagttttcg catagtgttt   106800
ttcaacttag taccgttaat atacttaggg acgcgaaata aatttcggct catggcgtta   106860
accaggtaga aactgtgcgt acagttgcgt tgcgcgtaac gtagaagcaa ggcggttagg   106920
cctaaaaagt agatcgtttg actatccacg tttactttct tggaacctac atataacttc   106980
gtgttccaac gtggcacatt gaaaacatg  gggttgaacg tggtgaaatt gccgcagcct    107040
```

```
tgttcgccag tatcattacg tttggaaacg tttagcattt cggaaagaca agtcatggaa  107100
ggcaccgtac cgcaagatgg gggtctgaat gttattgttt tagccgtatg attgtattct  107160
gagaaaacgt acttagccgg ttttcgaagc tgagtgctat aaaaatcgaa ccaaagatag  107220
gtaacactgt tattttgaat gggtcccgct aaaatgtaat accgtggaaa ctcggtcatg  107280
ttcatagtca gattttaat gtgttgtctg gtcatattaa agtattttgt atagatatcc  107340 tttctagtt gtttcaaaat ctctaatttg aacttgtcta gtctttgctt gcctatcgta  107400
gacagtactt tacctgacca gtaacgtcct acggataatc gtaccgcagc cctacagttt  107460
atgaaagaga atagcaggaa agttagcgac ataaggaaga ataaattaaa aacacctctc  107520
atctctcctt ttctccccat gacagaggag gagaccccgc accgtccgtc tgccttgtgg  107580
tttggcttgc ctgcgtgtac tcactgctga ttctggtcgt tttgctgctc atctaccgct  107640
gttgcatcgg cttccaagac gacctagttt cccgcacctt ggctgtgtac cgagcttgta  107700
tccagggacc gatatgtaac cagacccaca acagtacctc gtaaataaag acgcacacac  107760
ctcacgcata tagtaccatc acaccgtgtg gcgtgtactt tattacaacg agcaagagtg  107820 cccctaact attggggccc gtaccgtttt agaaggtttt gtgtgaatgt ctttaacttc  107880
tctgtccctt ttctcataaa ctgtcaggtc ctacagtcag catgtcttga gcatgcggta  107940
gagcagatag atgccgatga tggccgatag cgcgtagacg gacatcatga ggagacgact  108000
gtcggtggcg tccacgacaa cgtcagttac ttctaggacc gtaccgtttt tcaaaagcat  108060
gaggtagtga gttcgcggag atgagaccac cacttcgttg tagggatcca gggcgaaaag  108120
gacgtcgtcc gagtcgtgca tgtacatgat gttgatgacg ccttgcgtgt cgtcgtattc  108180
tagcagggcg cttggcaaa aggcgcagtt ttctagggaa atgttgagcg ccgctgtgat  108240
gctgtgtgtg gtatgcatgt tgcgcgtcag ttcgcattta gtttgactgt ccgtctgggt  108300
gatgatgagg ctttggccta cgacggtggt ggagacaggg taggagatac ctttgatcag  108360
gtactggttt gttacgacat aactgacgtg ttcggagacg gtcagcgcgg agaaggattc  108420
gcctagtggc agacaaaaca ggtcggggaa ggtttccaac gtgcttggtt gcatggtaga  108480
taggatggag agggcggcgg gaacggtagt ggggacggtg gcatcgggga agagacgtgt  108540
gaggcgttcg agcgagtgat cgcgtcgccc gctactggaa cagggtgtgt acaggtcgct  108600
gaggtattcg tggtgcggat gagctagcaa ctgcgtaaag tgtgatagct cggccaatga  108660
acagaggccc gtttctacga tgaagatttc gcgtctctcc gtcgtatgta ccagcatgga  108720
gtggacgagg ctgcccatga ggtagagttc ttgacgcgcg aaggctgaaa gaaagaggc  108780 caggtgcgtt ttgtgtagtt ttagggcaaa gtcggcgatc tgtcgtagtg cccactgggg  108840
gatgagatgt tgctgattct gtttagagag tatgtagacc aggcgtacga ggctggtgat  108900
gtcggtgatc tgattcggtg tccaaagggc tcgtttggcc aggtccacgg ccgtgggata  108960
cagtagcaac gtggtgcgtg gtggtgtttg tgagaggcag gtgatcataa attcttgtat  109020
ttgtaagagt gcggcctggc ggtctagggc ccgtgggacg gagacttggg cgccggcctc  109080
ttcttgtcgg gctgctgcga acagtgctaa tgcgtaggcg aaggccattt ctaccgtgcg  109140
gcggtccagc atctgacatc gaccgctctt gagtacatcc acggcgtaac ggtgaaagct  109200
gttacgtagt agtgcgctga ggtctaggta gttgaagtca agtgcggcgt caagaaagtc  109260
cgggtctttg agataagagt gacggttcag ttgatcttc ttaactagca ccaggagctc  109320 gtgttttca gtttgtcgta gtataaagtt gtcgcgttga tagggcgctt tgaaaagtac  109380
```

```
gcgtggaaga tggccgaaga taagcagcat gggtgtgtcg tcgtctatgg acaccgtaac   109440
tacgaagaag tcctcggtca gtgtgatttt aacgtaacgt agttcgtcga tgaggtaaaa   109500
gccttggtgc aaacaaggtg tgacggtgct gaatagtaga tcgtgtccat caaagaggat   109560
acaggtctgg ttaaagtgtg gtcggtgtag tcctgaggtg gtatgtgatt ctgtccagcc   109620
gtgtggagtg gtttgcggtg gcatccaaac gtgaggtatt gacaggtcaa tgggcggtgg   109680
cacagtggtg ggctgttcac ctaggctgtc ttgtgccttt agctgctgcg aaaaagatcg   109740
gtagctggcc aggtctttgg ataccagcgc gtaagtgtta agtctctgtt ggtatctttc   109800
cagggtttcg gtcagatcta cctggttcag aaactgctcc gccagaggac ccgcaaaaag   109860
acatcgaggc atatggaata catagtattg attatagctt tggaaaaagt tgaaactgat   109920
ggcgttttcc ctgacgaccg tgctgttacg gaggctgctg ttgtaggtgc actgggtggt   109980
gttttcacgc aggaagcgga tgggtctccc gtaggtgttg agtagtaggt gaaacgcgtg   110040
agggtccagc gcttcggatg cggcgtctgc gccatatcgt tgcgaaggta ggtgactgag   110100
gaggtagacg gcgaagacgg tgaggtagga ggggaggccg ggccgcatag cgcggccgcg   110160
ccgctgggtt cagcggcgtg atccaggtgg tggttggcgt tacacccgag agaaggagaa   110220
aaaggatccc aggaaggagc acccgggtgc ggcgctacgg gttacaaaag tcgcgtctcc   110280
gtctatttaa tacgatgtca ttggccgctg cgaagggaga agagggggaca cgcgaataag   110340 ccatgccgtc cgggcgtggg gacgacgctg atttgacggg gaacgctctg cggagattgc   110400
ctcacgtgcg taagcgaatc ggtaagcgca agcacctgga catctaccgt cgtctgctgc   110460
gggtcttttc ctcgtttgtg gcgctcaacc gcctgttggg aggccttttc ccacccgagt   110520
tgcaaaagta ccgtcgccgt cttttcatcg aagtacgatt aagtcggcgg attcccgact   110580
gcgtgttggt gtttttaccg ccggactctg ggtcgcgcgg catcgtgtat tgctacgtga   110640
ttgagttcaa aaccacgtac tcagacgccg acgatcagtc cgtgcggtgg cacgccaccc   110700
acagcctgca gtacgccgag ggcctgcgcc agctcaaggg cgcactggtg gactttgatt   110760
ttctgcgtct gccacgcggt ggcggtcaag tctggagcgt ggtgcccagt ctggtttttt   110820
ttcagcaaaa ggccgatcgc ccatcctttt atcgggcttt ccgctcaggc cgttttaacc   110880
tgtgtaccga ttctgtcctg gactatctag ggaggcgtca ggatgagtct gttgcacacc   110940
ttttggcggc tacccgtcgc cgtcttcttc gagccgcacg aggaaaacgt gctgcgctgc   111000
cccgagcgcg tgcttcggcg gttgctggag gacgcggcgg tggcaacgcg cggcggggc   111060 tggcgcgagg acgtgctcat ggaccgggtg cgcaaacggt atctgcgtca ggagctcagg   111120
gatctgggtc acagggtgca gacttactgc gaggatctcg aagggcgcgt gtccgaggcg   111180
gaggcgttgt tgaaccagca gtgcgagctc gacgaaggac cgtcgccgcg gacgctgcta   111240
caaccaccgt gtcgtccgcg ttcgtcgtcc ccagggaccg gcgtggcagg agcttccgcc   111300
gtcccacacg gtctttatag tcggcacgat gccatcacgg gacccgccgc cgccccgtct   111360
gacgcggcga ccgcgtcagc ggccgccggt gcttcttcta cctggctggc gcagtgcgcc   111420
gagcggccgt tgcccgggaa cgtacctagc tactttggaa tcacgcagaa cgatcccttt   111480
atccgctttc acaccgattt tcgtggcgag gtggttaaca ccatgttcga aaacgcctcc   111540
acttggactt tctcctttgg tatctggtac tatcggctca agcgggggtt gtacacgcaa   111600
ccacggtgga aacgagtgta ccatctggcg cagatgacca ctttccat ttcgcaggag   111660 ctgctgcttg gcgtggtcaa cgcttttgaa aacgtgacga tgtatccgac gtacgactgc   111720
gtactctccg atttggaagc cgccgcctgt ctgctggccg cctacggaca cgcgctttgg   111780
```

-continued

```
gagggccgcg atccgccgga ctccgtgacg gcggtgttga gtgagctacc tcagctgttg 111840
ccgcgtctgg ccgacgacgt gagtcgtgag attgccgctt gggaaggccc cgtcgccgtg 111900
ggtaacaact attacgcgta tcgcgactcg cccgatctac gctactacat gccccta agc 111960 ggtggtcgcc actatcaccc gggcactttt gatcgtcacg tgctggtgcg gcttttccac 112020
aaacgcggcg tcctccagca tttgccgggc tacgggacga taacggagga gctggtgcaa 112080
gagcgtctgt cgggccaggt gcgcgacgac gtgctttctc tctggagtcg acgtctgctg 112140
gtcggcaagc tgggtcgcga cgtgcccgtc tttgtgcacg aacagcaata tctgcgttcg 112200
ggcctgacct gcctggctgg cctgctgttg ttgtggaagg tgaccaacgc ggatagcgtc 112260
ttcgctccgc gcacgggcaa atttacgttg gccgacctgc tgggttcgga tgccgtagcc 112320
agcggcgggt tgcccggggg gcgcgcgggc ggcgaagagg agggctacgg gggacggcac 112380
gggcgggtac gtaactttga gtttctggtg cagtactaca tcgggccgtg gtacgcgcgc 112440
gaccccgcgg tcacgctgtc gcagctcttt cccggcctgg ctctgttggc cgtgaccgaa 112500
agcgtgcgca gcggctggga tccctcacgt cgcgaggaca gcgccggagg tggcgacggc 112560
ggcggcgccg tgctcatgca gctcagcaag agcaaccccg tggccgacta catgttcgcg 112620
cagagctcca aacagtacgg cgatttacgt cgcttggagg tacacgacgc tctgctcttt 112680
cactacgaac acgggctagg gcggctgttg tcagtgaccc tgccgcgtca tcgtgtgtcc 112740
actctgggct cgtccctctt taacgtcaac gatatttacg aactgttgta cttttt agtg 112800 ttgggttttc ttccgagcgt ggcggtgttg taatttccac cacgtgtcgc tgctgcata 112860 aagggcgagc gtccccggag agggtatatt cgtttggcga gagcgggcag cggtggtggg 112920
tatgtcccct tctgcggaga agactacctc agtcaccgat tccatcatgc tcgctatcgt 112980
gaatttcaaa tacatgggcc cgttcgaagg ctactctatg tcggccgatc gcgccgcctc 113040
ggatctactc atcggcatgt tcggctccgt tagcctggtc aacctgctga ctatcatcgg 113100
ttgcctctgg gtgttgcgtg ttacgcggcc gcccgtgtcc gtgatgattt ttacttggaa 113160
tctggtactt agtcagtttt tttccatcgt ggccaccatg ttgtccaagg gtatcatgct 113220
gcgtggcgct ctaaatctca gcctctgtcg cttagtgctc tttgttgacg acgtgggcct 113280
atattcgacg gcgttgtttt tcctctttct gatactggat cgtctgtcgg ccatctctta 113340
cggccgtgat ctctggcatc atgagacgcg cgaaaacgcc ggcgtggcgc tctacgcggt 113400
cgcctttgcc tgggttcttt ccatcgtagc cgctgtgccc accgccgcta cgggttcact 113460
ggactaccgt tggctaggct gtcagatccc tatacagtat gccgcggtgg acctcaccat 113520
caagatgtgg tttttgctgg gggcgcccat gatcgccgta ctggctaacg tggtagagtt 113580
ggcctacagc gatcggcgtg accacgtctg gtcctacgtg ggtcgtgtct gcaccttcta 113640
cgtgacgtgt ctcatgcttt ttgtgcctta ctactgcttc agagtcctac gcggtgtact 113700
gcagcccgct agcgcggccg gcaccggttt cggcattatg gattacgtgg aattggctac 113760
gcgtacccct ctcaccatgc gtcttggcat tctgccgctc tttatcattg cgttcttctc 113820
ccgcgagccc accaaggatc tggatgactc ctttgattat ctggtcgaga gatgtcagca 113880
aagctgccac ggtcatttcg tacgtcggtt ggtgcaggcg ttgaagcggg ctatgtatag 113940
cgtggagctg gccgcgtgtt acttttctac gtccgtccga gacgtcgccg aggcggtgaa 114000
aaagtcctcc agccgttgtt acgccgacgc gacgtcggcg accgttgtgg taacgacggc 114060
cacgtctgag aaagccacgt tggtggagca cgcggaaggt atggcttccg aaatgtgtcc 114120
```

-continued

```
tgggactacg atcgacgttt cggccgagag ttcctccgtc ctctgcaccg acggcgaaaa  114180
caccgtcgcg tcggacgcga cggtgacggc attatgagcg gcggcgctgt acgccagcgg  114240
ggagaaaagt ggcagataaa tcacgtcagg ttcacacgtc gttagccagc gtcggcatat  114300
gaagggcgcg ggcggccagt acggcctctg ggctgagaca ggacgaggca gggtgagaaa  114360
gaggaggatg gggggaccg gggtggtggt gctgctgctg ttgtgggtgt ggacggtgcg  114420
gatgccggga cagcgtgccg gcgaacgttc tgtaatcttc cataataaag gtaaaaatgc  114480
ccgtctcgtg tcgactccgc tggatctcga aggcgtcggg ggtaatgcgc atcttgccgg  114540
tgccgatgag ataaaagtac cacattttt gacagatgat gcgaatcaag ggttcgtacg  114600
cttcggcacc ccagtggcgc gtgaagaagg ccgccagacg aaacaagcgg tgtccgtaga  114660
gcgtgcctag ggagaagagg atgttgccgt tgcgcgccag gtcttcgggg aaaacgaccg  114720
gcaggccggt gtggcgctgc acaaagcgcg tcagcagtcc gccgctcaag cgcgggtgac  114780
acaggcgctg gctgagacgg gcggcgcgcg tttcatcgaa cacgccgcc tcaaagtcca  114840 gccccgggaa ggcctgacgc agttcgcggt acagatgagg ccagtagggt tgcggcgtct  114900
tgcgactaag cacggcgtgg tccgagacgc ccaggttgtt catggtttcg cgcagtagca  114960
gcgtttcgag accgcggtga agaggagga cgcagatgag gcgtacgatt ttgagttctt  115020
ccaaacgcag cgagctcagc ggctgtccgc gcgacatctt ctcgctaatc tgtaatatta  115080
gatgattggc gcaagtaaag gagaatttgc ccgtgcggac ccgcgggacg gcggggttct  115140
cttcgtcgcg ggccatcatc gttcgctcgg tgagcgggta gcgacggtga cgacaatgac  115200
gatggacgag cagcagtcgc aggctgtggc gccggtctac gtgggcggct ttctcgcccg  115260
ctacgaccag tctccggacg aggccgaatt gctgttgccg cgggacgtag tggagcactg  115320
gttgcacgcg cagggccagg acagccttc gttgtcggtc gcgctcccgc tcaatatcaa  115380
ccacgacgac acggccgttg taggacacgt tgcggcgatg cagagcgtcc gcgacggtct  115440
tttttgcctg ggctgcgtca cttcgcccag gtttctggag attgtacgcc gcgcttcgga  115500
aaagtccgag ctggtttcgc gcgggcccgt cagtccgctg cagccggaca aggtggtgga  115560
gtttctcagc ggcagttacg ccggcctctc gctctccagc cggcgctgcg acgacgtgga  115620
ggccgcgacg tcgctttcgg gctcggaaac cacgccgttc aaacacgtgg ctttgtgcag  115680
cgtgggtcgg cgtcgcggta cgttggccgt gtacgggcgc gatcccgagt gggtcactca  115740
gcggtttcca gacctcacgg cggccgaccg cgacgggcta cgtgcacagt ggcagcgctg  115800
cggcagcact gctgtcgacg cgtcgggcga tcccttcgc tcagacagct acggcctgtt  115860
gggcaacagc gtggacgcgc tctacatccg tgagcgactg cccaagctgc gctacgacaa  115920
gcaactagtc ggcgtgacgg agcgcgagtc gtacgtcaag gcgagcgttt cgcctgaggc  115980
ggcgtgcgat attaaagcgg cgcccgccga gcgttcgggc gacagccgca gtcgggccgc  116040
cacgccggcg gctggggcgc gcgttccctc ttcatccccg tcacctccag tcgaaccgcc  116100
atctcctgtt cagtcgcctg cgcttccagt gtcgccgtcc gttctccccg cggaatcacc  116160
gccgtcgctt tctccctcgg agtcggcaga ggcggcgtcc atgtcgcacc ctctgagtgc  116220
tgcggttacc gccgctacgg ctcctccagg tgctaccgtg gcaggtgcgt cgccggctgt  116280
gccgtctcta gcgtggcctc acgacggagt ttatttaccc aaagacgctt ttttctcgct  116340
acttggggcc agtcgctcgg cagcgcccgt catgtatccc ggcgccgtag cggcccctcc  116400
ttctgcttcg ccagcaccgc tgcctttgcc gtcttatccc gcgtcctacg gcgccccgt   116460 cgtgggttac gaccagttgg cggcacgtca ctttgcggac tacgtggatc cccattatcc  116520
```

```
cgggtggggt cggcgttacg agcccacgcc gcctttgcat tcgtcttatc ccgtgccgcc 116580
gccaccatca ccggcctatt accgtcggcg cgactctccg ggcggtatgg atgaaccacc 116640
gtccggatgg gagcgttacg acggtggtca ccgtggtcag tcgcagaagc agcaccgtca 116700
cgggggcagc ggcggacaca acaaacgccg taaggaagcc gcggcggcgt cgtcgtcgtc 116760
ctcggacgaa gacttgagtt tccccggcga ggccgagcac ggccgggcgc gaaagcgtct 116820
aaaaagtcac gtcaatagcg acggtggaag tggcgggcac gcgggttcca atcagcagca 116880
gcaacaacgt tacgatgaac tgcgggatgc cattcacgag ctgaaacgcg atctgtttgc 116940
cgcgcggcag agttctacgt tactttcggc ggctctcccc gctgcggcct cttcctcccc 117000
aactactact accgtgtgta ctcccaccgg cgagctgacg agcggcggag gagaaacacc 117060
gacggcactt ctatccggag gtgccaaggt agctgagcgc gctcaggccg gcgtggtgaa 117120
cgccagttgc cgcctcgcta ccgcgtcggg ttctgaggcg gcaacggccg ggccctcgat 117180
ggcaggttct tcttcctgcc cggctagtgt cgtgttagcc gccgctgctg ctcaagccgc 117240
cgcagcttcc cagagcccgc ccaaagacat ggtagatctg aatcggcgga ttttgtggc 117300 tgcgctcaat aagctcgagt aagagagacg ctatatttag ggtttccctc tctttttttt 117360
ttctacaccg tgataccctg ataaagcaca ctgcggttat tatcaacgtc tctgtgtttt 117420
tattatttag aaataaatac agggaatggg aaaacacgc gggggaaaaa caaagaagtc 117480
tctctctact ggctcagagg atcgttgccg aacagggact tcagggacac caggggggc 117540 acctgctctc tgtccttctg ctcctgcttg ggcaggctgg cgatgccctc gcccatgccg 117600
aacagctcgg cgggagggggc ggtgggctcg ggtctgctct gggggaaatt gccgggtctg 117660
cccttgctgc taggccaaat cttgcccagg aaattggcct gcctctcggt gcagtccttc 117720
atctggtgcc cttccttgcc acacttccag cagcccttct tcctgggggc tctgcagttt 117780
ctggccaggt ggccctcctt gccgcagttg aagcacttga tccgcttctg gcctctgaag 117840 ttgcccgct gcatcatgat gttggtctgc tgggcctggc tcatggcctc ggccagcact 117900
ctggccttgt ggccgggtcc gcccactccc tggcaggcgg tcatcatctc ctccagtgtg 117960
gcgccgctgc ccagggcctt caggatgctc ttgcagtcgg ggttggcgtt ctgcaccagc 118020
agggtctcgg tcatccagcc cttcacgtcc tgggtggcct gctcggctct cagggccttg 118080
aagaaccggt ccacgtagtc tctgaagggc tccttgggc cctgcttgat atccaggatg 118140 gacacgggc tgtacatccg cacaatcttg ttcaggccca ggatgatcca ccgcttgtag 118200
atgttgccca cagggatggg agggttgccg gtcatccact gcagctgttc ttgaggggtg 118260
gaggtggtgc cggcgatgtc gctgcctctg ggctctctga tctggccagg ggggatgggt 118320
ccggcctgca cggggtgcag tctgtcccac tcggcggcct cctcattgat ggtgtccttc 118380
agcatctgca tggcggcctg gtgtccgccc acaatgttca gcatcacgtt caggtcctgg 118440
ggggtggcgc cctcgctcag ggcgctgaac atagggatca cttcggggct gaaggccttt 118500
tcctcgatca ctttcaccca ggcattcagg gttctggggc tcaggttctg gtggatcatc 118560
tggccctggg cattctggat gatggggtag ttctggctca ctttgctgct gtcgccggtg 118620
tcggcagcgg cctgctgggt tttctgcttg ctcttgttct ggatctcctc gatcttgtcc 118680
agggcctcct tggtatcctt cacgtcgatc cgctggtgca cgcagtacag ggtggccacg 118740
gtgttgaaca ggctcttgat ctcctcggtg ccggttttca cggcgggctg cagctggttc 118800
atgatctgct ggcagccctc ggtggtctcc agcaggctag gattcagggc gaagcgatcc 118860
```

```
agctctctgc tggcccacac caggtgcttc agccggtact tcttcttgcc gccaggcctc  118920
agtctgatct tctcccaggc gtccagcttg cccccgctca ggatgctggc tctggcggcc  118980
atggtggctg cgaaggcggg atgggggagg ggtcagggga tgcgcaaagg tgaacgggtc  119040
ttcgtgggag gtcgggaagg gttccggcaa ctgtcgcaaa tatagcagcg gcgacaggtg  119100
tggcgcccaa aagtcgcgtg tctgagtgga cgtgggtttt tatagagtcg tcttaagcgc  119160
gtgcgcggcg ggtggctcaa cctcgatgct ttttgggcgt cgaggcgatg catgcccgg   119220
gcagggcttc ttgccggtgg cggcgacgtt tgggttgcgc agcgggctgc catacgcctt  119280
ccaattcggc gaagatgcgg tagatgtcgt tggcgtccca gaagaactcc tggtacttca  119340
gattctgacc ctgaaccgta gccaccatgg gcaccaggtt gcgggccagg atgccggcct  119400
gccaggcgg ccaggtgaac acggccggat tgtggatttc gttgtcggaa tcctcgtcgg   119460
tgtcctcttc gggcgcgacg gtggactcgg ccttaaggcg gccgcgtgtc ataacgcccg  119520
ccgtgcacgc cgtcgccgag gatgctgatt tgcgtttgcg gcccgcggaa gtggaggcgc  119580
ccgccatggc gccgccgccg gtaacgcggg gcgtcttgcg ctcggtggtt acgagttctt  119640
cgtcggagtc cgatccgctg gtccagacgt cgtcgtcgcc ctgggcggca ccctcgtcgt  119700
gccggtccca ggtgtgtcgg tactcaagct tgccctggat gcgatactgg ctggtgaagg  119760
tggggtgctc gctgtactga ggcccgcgct gcagcagcaa gtcgatatcg aaaaagaaga  119820
gcgcagccac gggatcgtac tgacgcagtt ccacggtctc gcgtatcgct tgtacctcca  119880
ggaagatctg ctgcccgttc atcaacaggt tacctgagat gctcaggccc gggatgctct  119940
tgggacacag cagcccaaaa tgctcgtgtg aggtaaaagc cacatccagc atgatgtgcg  120000
agatcttgcc cggtttgatt atcatatttt tgggacacaa caccgtaaag ccgttgcgct  120060
cgtgggggcg catgaagggt tgcgggttgc gggtcatcgt caggtcctct tccacgtcag  120120
agcccagcgt gacgtgcata aagagcttgc cggagggcac gtcctcgcag aaggactcca  120180
ggtacacctt gacgtactgg tcacctatca cctgcatctt ggttgcgcgc gtgttctcca  120240
tggagcaaac cagctcgtgc gcgcacacca cgtgccgcag tgccacgtcc ttggtgggaa  120300
acacgaacgc tgacgtgtag tagacgtcgg gctctttcca ctggttctgc tgacgcgtcc  120360
aggccagtcc cgagaccgtg agacgcgcct gccacatctg cttgcccgac gcgtgaatca  120420
cagcgtcagc tacgggcagg tgtcggtgtt tgcgctcggc cgccgacggg tagtggtgca  120480
cgttgatgct ggggatgttc agcatcttga gcggcagcgc gtacacatag atcgacatgg  120540
gctcctggct ggggcagatg cttcggcccg tggggttgtg cacgttgacc gacacgttct  120600
ccacctcgct gcccgtaaag tacgtgtgct gcacctgcag ctgattgtcg ccgcggtggc  120660
atggcgtcga gtcgggcgtg tactgcgaca ccaggatcag cgagggctgg ctcacgcgta  120720
cgtggatacc cgtctgcagg agtcgcgtct cgtgcggcag caccggcgtg tcgccgcgac  120780
taaacacggc tttcagcacg tgccccgaaa tgggacccag tacggatatc atttcgggac  120840
aacggcgacc gcgcgactcc atgctgcctg cgcgtacggg tgtaggcgac tgagcggcgc  120900
gccctttgcg gccgccgcct tacataggca ggcgaccaaa cgcggaaccc gaaataaaaa  120960
cgttctacac agagacaacc gcggattatt gagtgtcttt ttttattaca aaaaaaaga   121020
ggcaaagccc caccgtcacc acaccccatc acacaccacc accgattttt tttgttttaa  121080
ccccgtatcg cgcggacgcc tagtgtccgt ttcccatcac cagggtcctc tgtttagaga  121140
tcgccgcaga ccatggctaa agtgacagga ctcgttttct ctgtcgtatt ttccgtgagc  121200
ttacagtctt gcggttccgt ctccggggac gccagtcgca tgggcagcag gtcctccagc  121260
```

```
gcgatggaag cgcccagcac cgagagctgc tgttgcgacg gcgaatggga cgtggaccgc   121320
gagtgtagcg tggatttgac ttggtgcgtc attgctgaca ggcaaccgcg attcagcgta   121380
tgctttgacg agataaaata gaggcgtccc aggagcgcgt cccgtgggaa cgtggcgccg   121440
ttctcgtcgc tcaccagtac ggttaattcc aaccaggagc gcggtagcca gaccgtaacg   121500
ggcattttga gtccctgacg gttgtgtggt acaaaaacac ccagataagg cccgtaaaag   121560
cggcggtaga tacgtaacgt gtgcgagttt ttcagcgtca attcgtaagg gacgcgcacc   121620
tccagtccct cgtccgccgc accggagcgt ggcggtacaa agtaaggcag tggcgcgtcc   121680
gaaaagaagg gtcgtcgcac cgtttcgcgt cgcagccgca ggcgaaacgc cactgggtcg   121740
gctggcgcct cggtgcggtc gcaggtcacg ttgaaacgta acatgccgtc ttggtatagc   121800
gtgagtgacg acagcgtcag gtccggcggt gattcgttcg ggtctagctc caatcgtcca   121860
aagacggagg gtcccaatgt cttggcagtg gtttccgaga ggcgcgccga gatacggctg   121920
gtgagtccac gcggccccga gatgccgcct tccactcgat gccagcacag cgcgtgtcgt   121980
acgcgcaccg tcagcgtggg cgtcagatcc gcgtccgttg attccgcggt atcagcgacg   122040
gaagccgcgt tctccgttac gttgtttata tccagcgtcg gctcgaacgt gagttctggc   122100
agatgcagcg caagacagtc gtgtaacgcc gtgtgatgcg cggctttacg tcgtagcggt   122160
agccgtttca gcagcggcgt gatgatacgg agcgcgaaga gattgagtga taagcgcacg   122220
atggccatgc gcgtcagttg ctggtcgatt actgagcgca ggatatggca gcctgggcgt   122280
gcgggaaaga gagagaaggc cgggcgtacg tcagaatcct cgttagatac cacgcataga   122340
atgccgcgtt cacgatcgtc gttgcggtca tcctcgtcct cttcttttt cttctctttt   122400 tcctttttt tctcgggctc atgggaagcc gccgtttctt cttcttgcga cgtcgcggag   122460
tcggtttgag actcgccgtt cgcttccccc aattgcagcg gcgtagagag cagaatctgg   122520
aagggatccc gcaattcttc gggtcggagg tcgaggtgca actggatcag atggtaggtg   122580
ccgcggtgca cccgaggctg acggatgtcg tgtttatccg tcagtgtgag gatggtctgc   122640
ggcgagccgc tgtgcttgtc cagctcgtcc ggcgttttca ggaggaggct gtcgtcgtcg   122700
gtactggcga cgcccatcat ggtcgtggtg gtagtggtgg cgaggaaagt gagcggcggc   122760
gctgacagag ctcggcgttg gcggcggcat ttgccgctgt gtcggctgct attgctgcca   122820
acgccaccgc cgccgcctcg tctggctcgt ggccggcggg cccgattccg aaggttgggg   122880
tcgacgcgtg gcatgcttgg tgtctgcggg cgcgagaggg ctggctcagc ctttaaatat   122940
gcaggtcgcg gatttgttat cgggtgaaac gtcacacacc gtgaagacga cctgttcgcg   123000
gatgaggtca tccagctgtc gcagcatgac gaaaagcgcc gacagccgcg cgatctcgtc   123060
gtcgggcgac acgtgctgcg gccgcgcggg cgtgcgcggc tcgccgacgc tgcgctcgcg   123120
gtccagccgc atcagcagct cctggcactt gacgagcagc atggagctgt cctctagcgc   123180
caacttgcgc acgtaggtca tggtcagctc cgaggctagg ttggccacca tggacatgga   123240
gaggcaggcg gtcttcatgt cgatcagcag gtgctggtcg atgaccggat cggggatggt   123300
gaaggtggcg tcgcgaaaag taatggtctg cagctgctgc acggcagcct ttacctcctc   123360
gtacgaacgg tcgagcgaga agaggcccat gatgagtagt cgctggttga tttccagcgc   123420
cagtggcatg ggtacgatcc agggcagcac cagctcccac tggcccagcg tcagcaggtt   123480
ctcgcgcgcc agcggtccgt ggaagagcgg cggcagcacg catagcgcgt cgcccttctc   123540
ccaagtcacg ggtcccgtgt tgaggacggt gtagagcagt ccgtgcgtcg gtacgtgtag   123600
```

```
gaggatctgg ttgccttcta cgcgccgcat caacgtcagc gtcatattgc gcagcaggcc    123660
gcgcagtcgt acgtagccgc gggtgtgatc tacgaactgg tgtaggccca gctggtagtg    123720
tttgatgaga tgtagacgct gcggaatggg cacaacggcc gctactagct tggtcagttt    123780
gcctacgtcg gcgatgctga gcttgtggtc gaaagtgcag aagatgttgg cctccatggc    123840
cgccatagcg gcggtgaaat cctggccgcg acggaggaga agcagagacg aacaacgtct    123900
gcaccgggcg cggcgtcaga gcgagcgtgg cgcgtccggg cccgcgtttg cgtctaggtg    123960
attcgccgtt aacctgcggt cgtcgccgtc ctcctcaccg gacggcctca cgagttaaat    124020
aacatggatt gctgtagcgg gatgatttcg cctacgacgt agttaccaaa gtgcgtttcg    124080
gacgtggcaa aagccccggc gccacccttg agtttggtct ccatcagcgc cagcgtggtg    124140
gtgctgagga tcggtagcgc ttcctgcgtc agacggcacg ggttttcgat gagttgttcc    124200
gtgccttcga cgcagacgta ctgcgtgtcc gtgtcgccgc ggatgcagtc cttggcgcgt    124260
agcaggtact cgtcgatggt tttgaagagc gttttgttgg ccgcgataat ctcttccgtg    124320
ttaaagtact gcgcgcaggg gctgtagaat ttggagttgt agcctagacg ttcgcgatgt    124380
cgggtgttgt agagtacgtc gctcagacag ccggcttgcg aggcccaggg gttgtgtgtg    124440
gccgcgaaag tctgtgcgtc cgcttcgcga tggtcgtaga tggccttggt ggcggcctcc    124500
gtgtcgtacg gatcgacggc cagcatgcag gaggcacgcc cgcgcgggtt gttgggatc    124560 ttaaagtaat taacgtccat cgtcaccggc gtaaggatta gttcgcacgc ggccttttgt    124620
ccgtgcaccg tggcggcggc attgcgctcg gacatgctgc cgaacgtcag catggagatg    124680
gtctccgtgt ctaacagttg cggccgttct acgccggccg cgtgccggat ccagcggtcc    124740
acctcgtcgt gccggtacac gttcataggg aagacgcgaa agaggtcctg cacgcggacg    124800
cccatgtcgg ttcgcacgcg gtttacgtag gctacgcagg tatttgacgt gtaacccaga    124860
cccatgtcta cggtgttaat gttctgcgtg acgtggtacg tggtgctgat gtcgcgttcc    124920
tccttggtca cgatagggtt gttgatgata actgacgtgc acgatttgcc gctgtagagc    124980
agcatgtcca cctcgaaggt gtcggtgcgt acggcgtga gtgcgaatcc cgggtggatg    125040
tgcgccttgg tctgcagcac cagtgaaact ggtgagattt tgtataacat ggcggccagc    125100
gtcatgactg agtgcaacac gttgggacag gtggccgagt aacgcgaaaa gggcgagcgc    125160
agccagttgt ggtactcgtg tgcgaaggct gtgggtagcg ggaaaccacc gtcgtgacgg    125220
tgatagtgcg ggaactcggt cacgtagcgt ttaatgtcgt cgctcaacgc cgcgcagatg    125280
gtggggtttg agtagaaacg gtggaaaggt acgggtaggc tgtactcgat caacgtctta    125340
ggcgccgtca cgacgcagca gccgttgtaa agcacgtgct gacgtgagat aaagtccggc    125400
aggccctgac gttgcgcgtg gtccagaggc gcgcgcactt cgagcacctt gacgtgctcg    125460
cccacgaatt gcacggccaa aaacagttca cgacaggcct gcagcagcgg cgtgtgcgcg    125520
tcggtggcga cgtcctccac cagctcggtc agcatctcgc ctacggcttg acgttgcgcc    125580
gctatcgagt cttcggggggt gacgccgctt gtgctctctt tcgacgtcgt acctgacgtg    125640
gagaccgcgg tggcggccgg catcaggaga aacgccggtc ggtaaaagag gtctactagc    125700
agcgtcttga ggttgagtcc caggccgcag gcccggttgt tggtcatggc gggcatgagg    125760
cagagataaa agaccttttg taacgtccat tcgtcgtcgg tggcacggta atcgtccaca    125820
aacagcggct cgtcggcatc catggcgccc aaacgcggta cgtcagaaac gccgtggtgt    125880
cgcgcctcga tgttggccgg gttcaacggt tgccggtcgg ccactacctg tacgccttcc    125940
atgttacgcg gcaggtgcgt aacgaagggg ggccacagcc ggtggtcgtg cagcgcgttc    126000
```

```
acgtaagccg atagcggttc ctcagccagt tgaccgttgt taagtcccgg cagcgctgag    126060
atgcgcgtta ccagacgcag cacgcgacc  agattgcggt agtgaaagag caactgcggt    126120
ggtagggcgc catcagccag gtgttcggcg atcaacgtca ccagcgcgta gctgtgcgca    126180
aaaaccagca gctgacgtgt gtgaaacatg ttgacgatac aacgtgctac gaaagtgcgg    126240
attagcaaaa aagcgtcgac gttgccgtgt accagcacgt cgaccaggta gcagagctcg    126300
gggtaattgg ggcttgtcac ggtggttttg aaaagtcgca acgtctcttc gtagtcgggt    126360
ggtggccgca gtcgcatgtg ttccatgatc tcccaggtgc gcagttcgtg aaggggccc     126420
ggtgccagtc catctggcaa attaccgatg acgatacgcg gtgtacacag cgccaccgtt    126480
tcgctgtttt cctggcagtg cgtaaagtcg aagaaggggt gcagctcggt gtagagcgtg    126540
atgttgccca ccttgtagaa gtcggtgacc acaaagtcct gcttcatttc gttcaccgtg    126600
cgcgggacct cgcgtcgtac gcggtaaaaa tgcggtatgc ggcgcgccgc accgcccatg    126660
ggttcctgct gaaaacgaca ctcgagcagt cgttgcatgg cggttccga  gggcggtccg    126720
cgttccgtga aggtctgtag acagggcgcg ggctcgtgca gcaccgggtg gcacagcgtc    126780
ttgagcgcgt ccacaaagtc tatcttttgt acggcacggt cccggtttag caggtaggcc    126840
gtggtgggca acgcgttgcg aacggtgtcg ttaagcttaa ctttgctttc caccgtggtg    126900
taaccgcgat cctcgggcag atacagccct acggggaaga aaacgtcag  gtccacgtta    126960
cgttctagcg gatctttggt atcggtgttt ttgtagacgc gccgcaagtt ttccataatc    127020
accgtttttt cgcccagtcg gatcacgtcc atgctcagcg gcgttaagct gtgcgccccg    127080
gcctgcgaaa gcgagtcgtt gggcaaatgc ggttggcccg aagtcagatg agccttgtac    127140
gagttgaaat cggccaggat cgagtgatag gatatggcag tgacggcatt ttcgggactg    127200
agtacaaaat tgccgtaggt ggccggcgcc gagaccgttt ctttggtgat gtggcttgag    127260
agcagcgaca tgatgatctg cataacgttg gccgtgctta ccatcacgcc gctgatcttg    127320
gcccccgagc tcgtggtgta cgtcgtgggg ttgtctagga tgctatcggt ggccgcttcg    127380
gctagacgcg tgaggaactt gagcacatag tcgcgatcgc gcgtgcgatt cagcaaaaag    127440
agcgtggcca gcattttggc cttgaagctc tgcaagatgt tgcttcgctg gatgcggttc    127500
agcgcctgtc gcgccagcgt ggcgttctct accagcgtct gcactacaaa gtacggcggc    127560
gccttgcgta gcagtgtctg taaaaagctg tgaatcaagc cgcgttccat ggcgtcggcc    127620
gtgttttttga gcgcgcgcag caccgtgtgc atagcttcca cgttgaggat cttgtccagg    127680
atggtgcctt cgaacgtctc gcgcagatac gtgaggcagg ctgcgctgag ctcaaagggg    127740
atggtgatgg gggattttc  actgtatttg gtgaccataa tggtggtctg acgactggtg    127800
ggcaaaccgg cgccgctggc cacacgcggc acctgcacgt ggaacagcat tttcccgta    127860
gtcagtttat tgaggtcgtg gaacttgatg gcgtgcgccg ccgcggccaa gccgctggtc    127920
aaaaaataaa cccattccag gcgattgcag aaggtgccga agatggcttc gaagtgaata    127980
ttgtaacgct cggggtcgtc gccgtagtag atgcgtaagg cctcgaacat ctcctcgccg    128040
gcgctggtct tgacgtgcgt cagaaagtca gtgggaatgc ctactttagg caggagctcg    128100
agcgccgacc agttctccat cgcggcgcg  gcgtgagcgc gaggcgtcgg agctcgggga    128160
aagcagcgcg accgggagaa tggccggcgc tgcgccgcgc cgcctcggct gtgacgctct    128220
aatagtcgtc ggcggctccg ctacgccgcg ccggggtttta cacgtccccg tgcacgttcg    128280
cgcctgcaac ctcacccaag agctatcgac gggcgaggac gcccgcttct gtcgtccgcg    128340
```

```
acccgttaac gtcgaacggg tgcgcgctgt ttttgcggct ctctaccgtg cctgtccgat    128400
acacgtgagg accgagcccg agcgtgtcaa gctggtactg ggtcgtctgt tactgggacc    128460
cgtggccgta ccctgttttt gcgacggtga agtggagggc cacggtgaac atctggtacc    128520
tacgacgcag ttttgtcgcg ggccgctgct ctacgtgcac cgacgttgtt gttgcggatc    128580
cgtgaccgcc gggcgcgcgc tgtcctacca cgttctcgaa aaccacgtgg ccacgcatgt    128640
gctacgcgga ttgctctcgc tgacggaatg gaatcgagaa ttgccgagcc tcttttgcga    128700
ctgtcctggc ggcggtggcg cctcgggaac cgaggaacgc tacgccatgg cctgcctgcc    128760
gcgcgacctc agcctgcacc tggacgacta tccttacctg atggtggaaa tcggacgcgt    128820
actcagtgtc agcgaggtag acgactacgt aaccgccgtc tccggctacc tgggcgaggc    128880
cgcggcgccg cgcattcagg ttcactacaa gctgctcttt ggactcaacg tgcgtccgca    128940
agcgccgtgc gcgttggacg ctacacgcga cttttttctg ctggagctgc aaaagctttg    129000
gctgggcgtt gaatatcacc acgaagtgac gtcggagttt ttcggtcgcg tgctggccca    129060
gctgcatcgc gaccgcgccc gcgtcatgat ggcgcttcgc ttgcccgagc agacggtgtg    129120
ccacctgagc accttcgttc tcagtcgctt caagcgacag gtactgtact tcaagttaca    129180
ggtgagctac ggcaagtgcc ggactggcca cgctgacaga agtgggggag gggggaacgg    129240
tggaaatcag ggacaccaca acctactgtg ttatcgacgc cttagcgtca catttgccga    129300
cacagacacg gtgtggagaa accttttcta cgtttattac gaactagctc gggatctggg    129360
gtcccatggg acagagaacc gacccgtaaa ccgcggttac ggtgtttctt gcgctccgag    129420
gacgtcgcgg ctatcaccgt cagaatcgac ggtggtttcg gcgaacggac acgcgctgtc    129480
ttccaccgcg ctcccgacga cgagcgcggg tcacaagctg tcactgccgc gcgacccggc    129540
cgccgatcgc gttcgacgtt acgtgtgcat tatctcgcgt ctcatgtacg ctcggtacgg    129600
ggagagatgg cgtaaacacc gtcaacggcg gtcggagacg ggagaagagg aggaggaaga    129660
gacgctggaa tcgggggaga ctgacgccac gccgccattt gactttacgg ggcagcagct    129720
gcgccgggcc tatcaggaac accgacgtcg taaacatcta gccgtgcagc gttacgcgcc    129780
gtgccgtcgt aagctcatcg gcgggatgga gtttgccgag gtgacgggcg tgagtctgga    129840
ccgcatcgcc gtcaacgctt tcaacaccaa ccgcgttatc aatatgaagg ccgcgctctc    129900
gtccatcgcc gcgtcgggtc tcggcgtgcg cgcgccgcgg cttcccaaga acatgaccca    129960
cagttttgtg atgtacaagc acacctttaa ggagcccgct tgcaccgtca gcacctttgt    130020
ttccaacgac gccgtctaca tcaactcgct caacgtcaat attcgcggtt cctacccega    130080 gtttctgtac tcgctgggcg tgtaccggct gcacgttaat atcgatcact tttttctgcc    130140
ggccgtggtg tgcaatagca actcctcgct ggacgtgcat ggactggagg accaggcggt    130200
gatccgctcg gagcgcagca aggtgtactg gaccaccaac tttccgtgca tgatctcgca    130260
tactaacaac gtcaacgtgg gctggttcaa agcggctacg gccattgtgc cgcgcgtctc    130320
gggcgctgac ctggaagcca ttctgctcaa agaactctcg tgcatcaaga acatgcgcga    130380
cgtgtgcatc gattacggtc tgcaccgcgt tttcacgcaa ctagagctgc gcaattcgta    130440
ccagatcccc ttcctggcca agcagttagt gctgtttctg cgtgcttgcc tgctcaagct    130500
gcacggtcga gagaagcggc tgcagttgga ccgcctagta tttgaggcgg cacagcgggg    130560
tctctttgac tacagcaaga acctcacggc gcacaccaag atcaagcaca cttgtgcgct    130620
catcggcagt cgtctagcca acaacgtgcc caagatcctg gcccgaaaca aaaagtcaa    130680 attggatcac ctgggccgga acgccaacgt gctgacggtg tgtcggcacg tggaagccca    130740
```

```
caagatccct cgcacgcgcc tcaaagtgtt agtcgaggtg ctgggcgcgt tgcagagtat   130800
cagcggtacg ccgcacacgc gcgaagtgat ccaccagacg ttgtttcgat tgtgctcggc   130860
ggccgcagcc acatcgggcc tgtgttcatc ccctccccca ttgtgtgtgt cctcatcttc   130920
ctccgtcccc tctgtcccaa cctccgtcag cgttgacggc agttctgaac ccacgtcgcc   130980
gcgagcgcgg tttgcatcac gatgatggaa gccgcggccg ctgccgccgc ggcgtttcgt   131040
ccggaggagc gtccgacgcc gggttggcac gacgcggcgt tgttaatgga cgacggtacg   131100
gtgcgcgagc acgcgtttcg caacggaccg ctgtcgcaac tgattcgccg tgtgttaccg   131160
ccgccgcccg acgccgaaga cgacgtggtt tttgcatccg agctgtgttt ttattgcagc   131220
ggtcgtttta accgcaggtc gtccgtcttc tccatctatt ggcagaagca tagcgatctg   131280
gtgtacgcgc ttacgggcat tacccattgc gccaagttgg tggtggaatg cggtcagttg   131340
gggagtagta ggctacggtg gcgcgacggt gatgcgagtg gtgaggagcg ccggggagac   131400
gacgacagca gggacgagct gtacgacgtg ccgggcattt atatgattcg cgtcaacgac   131460
ggcggcagca ccggtcccag acacgttatt tggccgggta ccagcgtgct ttgggcgccg   131520
gacgttgtga tcactacggt gcagcgacga atctcggcgg cgcgcgccct ggtgaacacg   131580
ttccgccaat attttttttt gctggaacgg cgctcgcacg aggagctggt tctttgtccg   131640
cccgagatgg aggagcgtct agcgccgttg ttgcagagtg ccacgcgcgg tgattcggac   131700
atgtttgacg gtgtggtggc cagcgcttat caccgtttgc gaatgagtaa tattccgcgt   131760
tcatccgccc gtctgctgga gcactgcgtg gggctggcgg gtgctaagaa gctgctcttg   131820
ctcgacgtgc cgcgtctgga gaactatttt ctttgtcagg tctgtcttta cgagctggac   131880
gaggacgaga tgggcgagga gatgctgggc atgttggccg gaaagcccga ggatgccgcc   131940
gtctcgggcg caagcggcgg ttttctgcta catcgcaaga cgatgaagct ggccgcctgt   132000
ctgtgtttgt tgctcaattc gctgcatttg caccaggagg cgctggaggc cttggatcct   132060
ccgccgccgc gcgtcgagga gaacgacctt gtcaacgtgg tgctgcgccg ttattatcgc   132120
agtcacggcg gcgtgcaggc gcggacgctg cggcggcccc gggctttgtt agccgactac   132180
gctgaaacgt tttcgccttt ggggagtttt acgcgcctgg gttacgatcg tctcgtttct   132240
gccgatgccg gcgtcagtcg ccggcacctg gtggctctgc tgcgtgccta gctgaccctg   132300
aaacggatgg cgtgtatatc gtcacacagg taggtggcca tgatgacggc gatgataaga   132360
tcgtccgaga tacgattctg gcgcttggcc gagtagcgtg ccgtcgtgcc ttcggccagc   132420
gtgacgcggt gcaggttctg aatctgctcc agaagatact cgatgggtc gtggctcagc   132480 ttgatggtgt aggagacgag ctcttgcgag gctttgatgt agcccgagtt gaaacgcgag   132540
atgaactgtt ccacgccag cgccttgtcg cggcccatga ggtagaaggg ctgttcgatg   132600
tggttctggt cgggcgtgtg gtagaagagc acgcggatga gcgtgctgct ctgcacgctc   132660
tgtcggatga ggcaggcgat gcgcacggcc gccgcctggt tggtgttgcc ctccacggcg   132720
atacgcagtt cgtccaggta agggtgcagg ctcagcaccg agatgatcat gtgcgccgcg   132780
cactcggcga tggctacctc agaactctcg gagaggtcgc gcaaaaagaa atgctctagg   132840
ccgtaaatga gaaactggtg tcggtaggcg cctacgccg ccacgcccgt gcccgaggcc   132900
ttgcggttgg tggtgaaggc cgggtccaga tacacgtaaa gcgtcttgcc gaaataatcg   132960
taggcgttgg tgttgagcgt gctgtaacgc aaaatatcga actcttcgcg gctctggtcc   133020
gtgatgagca cggtgttctg cgagatttta ttggtaccgc cgatgatctc gtccatgaaa   133080
```

```
gcgcccggca taaacatgtt ggccgtcttg cgcacctgcg agttgaggct gatgaaggtg    133140
ggcttgtgca gtcggtagca aggacacgcc gtggcgtcgc ccttctccgt gaagctgtgc    133200
aggtgctctt cgcacacgta agagaccacg ttgagcatgt caaagggcgc attgttgagg    133260
cgcgtcaaga acacgtggc gtcactggta gtgttggtgg acgatatgaa gatgatcttg    133320
gtggtattct gggccaggaa ccccagaatg gtgttgaagg cctctttctt gatgaagtgc    133380
gcctcgtcca ccagcagcaa gtggaagttt tgtcctcgga tgctctgtgt agagaggaga    133440
cagaaaaggg actcttataa ttacgcacgc tcggctggaa gcctacagag tcggggtggg    133500
gccggacagg tgagccaggt gagccgccag gtgaggcggg atcaccgtgt gccaaccggg    133560
ctgcgacctg aaaaccggaa ccaatccgcc gacaccggcg ccgcgtgacg cgcgcccata    133620
aaaacgaaag tgtcgtcgtc gcgacccgcc acagccgcca tgaactcgtt gctggcggaa    133680
ctcaaccgac tgggggtcgc gcacgccact acggaggatg ttttatctt tgtcgaccgc    133740 ctctttcaac acttttcctt ccttttccag gccgaggagt caggcccgcg ccgcttggaa    133800
ctggtcgcgt ccgtgttcga gcacctgacg gtggagtgcg tcaacgacat cctggacgcc    133860
tgcagccatc cggacgtgaa cgtcgcggag acaagcaaca cctgtcgtcc ctgcccttct    133920
cctgccccct ccgcccccaa aactgtcagc gacgctcaga cgtcatgtgc gacgcctcgg    133980
gcgcctgtga catgaggcac gtccagaacg cgtttaccga ggagatccag ttacattcgc    134040
tctacgcgtg cacgcgctgc tttcgcacgc acctgtgtga tctgggcagc ggctgcgcgc    134100
tcgtctccac gctcgagggc tccgtctgcg tcaagacggg cctggtatac gaggctctct    134160
atccggtggc gcgtagccac ctgttggaac ccatggagga ggcctcactg gacgacgtca    134220
acatcatcag cgccgtgctc agcggcgtgt acagctacct catgacgcac gcaggccgtt    134280
acgccgacgt gatccaagag gtggtcgagc gcgaccgcct caaaaagcag gtggaggaca    134340
gtatttactt cacctttaat aaggttttcc gttctatgca taacgtcaac cgtatttcgg    134400
tgcccgtcat cagccaactt tttattcagc ttatcatcgg tatctactca aagcagacca    134460
agtacgacgc gtgtgtcatc aaggttagtc gtaagaagcg cgaggacgcg cttctgaaac    134520
agatgcgttc cgaatatgga aacgcacctg tattcggatc tggcgtttga agcgcggttc    134580
gctgacgatg agcaattgcc tctacatctg gtgctcgacc aggaggtgct gagtaacgag    134640
gaggccgaga cgctgcgcta cgtctactat cgtaatgtag acagcgctgg ccgatccgcg    134700
ggccgcgctc cgggcggaga tgaggacgac gcaccggcct ccgacgacgc cgaggacgcc    134760
gtgggcggca tcgcgctttt tgatcgcgag cggcggactt ggcagcgggc ctgttttcgt    134820
gtattaccgc gcccactgga gttgcttgat tacctacgtc aaagcggtct cactgtgacg    134880
ttagagaaag agcagcgcgt gcgcatgttc tatgccgtct tcactacgtt gggtctgcgc    134940
tgccccgata atcggctctc aggcgcgcag acgctacacc tgagactggt ctggcccgac    135000
ggcagctatc gtgactggga gttttttagcg cgtgacctgt tacgagaaga aatgaagcg    135060 aataagcgcg accggcagca ccagttggcc acgaccacga atcaccgtcg gcggggcgga    135120
ctgcgtaata acttagacaa tgggtcggat cgccgttttgc ccgaagcggc tgtggcttct    135180
ctggagacgg ccgtcagtac tccattttt gaaattccga acggagcagg aacctcctcc    135240
gcgaacggcg gcggcagatt cagtaacctg gagcagcggg tagcgcgttt gttgcgcggc    135300
gacgaggaat tcatctatca cgcgggtcca ttggagccgc cttccaagat acgcggtcat    135360
gagttggtgc agctgcgcct ggacgtaaat ccagacctca tgtacgccac cgatccgcac    135420
gaccgcgacg aggtcgcgcg tacggacgag tggaagggtg ccggtgtctc gcgtctccgc    135480
```

```
gaggtctggg atgtgcagca tcgcgtgcgc ctccgtgtgc tgtggtacgt caattccttt    135540
tggcgcagtc gcgagctgag ctacgatgac cacgaagtcg aactataccg ggcgttggac    135600
gcttatcggg cgcgcatcgc cgtcgagtac gtgctgattc gcgccgtgcg cgacgagatc    135660
tacgctgtac tacgacggga cagcggcgcg ttgccacagc gtttcgcctg ctacgtgcca    135720
cggaacatgt cctggcgcgt tgtttgggaa ctttgccgtc atgccttggc gctctggatg    135780
gatcgggcgg acgtgcgtag ctgtattatt aaggcgctaa cgcctcgtct gagccggggt    135840
gccgccgctg ccgctcagcg agctcgtcgc cagcgcgagc gctcggcgcc caaaccgcag    135900
gagctgcttt tcggaccgcg gaacgagagc ggtccgcccg ccgaacggac ttggtacgct    135960
gacgtggtgc gctgcgttcg cgcgcaagtg gatttgggcg tggaagtgcg cgcggcgcgt    136020
tgtcctcgca ccgggctttg gatcgtccgt gatcgtcgcg gacgcttgcg acgttggctc    136080
tcgcaggccg aggtgtgcgt gctctacgtc acgccagact tggacttttta ctgggtgctg    136140 ccgggcggct tgccgtctc ttcgcgcgtc actcttcatg gcttggcgca gcgggctttg    136200
cgagaccgat tccagaactt tgaagcagtt cttgcaagag gaatgcatgt ggaagctggt    136260
cggcaagagc cggaaacacc gcgagtatcg ggccgtcgct tgccgttcga cgatctttag    136320
tccggaggac gacggctcgt gtatcttgtg ccaattgctg ttgctctacc gcgacggcga    136380
atggatcctc tgtctttgct gcaacggccg ttatcaaggc cactatggcg tgggccacgt    136440
acatcggcgt cgtcgacgca tctgtcattt acctaccttg taccaactga gcttcggagg    136500
tcctttgggt ccagccagca ttgatttctt gccaagcttt agccaggtga ccagcagtat    136560
gacgtgcgat ggtattacgc ccgacgtgat ttacgaggtc tgcatgttgg tgccccagga    136620
tgaagccaag cgcatcctgg tcaagggtca cggtgccatg gacctgacct gtcagaaggc    136680
agtgacgcta ggcggcgccg gcgcctggtt gctgccgcgt cccgaaggct acacgctttt    136740
cttttacatt ctgtgctacg acctgtttac ctcatgcggc aatcggtgcg atatccctc    136800 catgacgcgg ctcatggcgg cggccacggc ctgcgggcag gcgggttgca gcttttgcac    136860
ggatcacgag ggacatgtag atcccactgg caattacgtg ggttgcaccc ccgatatggg    136920
ccgctgtctt tgttacgtgc cctgtgggcc catgacgcag tcgctcatcc acaacgatga    136980
acccgcgact tttttctgtg agagcgatga cgccaagtac ctatgcgccg taggttctaa    137040
gaccgcggcg caggtcacac tgggagacgg cctggattat cacatcggtg tcaaggattc    137100
tgagggccga tggctgcccg tcaagaccga tgtgtgggac ctggtcaagg tagaggaacc    137160
tgtgtcacgt atgatagtgt gttcctgtcc ggtgcttaag aacctagtgc actaacgggg    137220
tctgacagtt cacggggaga agaaacaaga aataacaaaa aaaaaaagag gacatggact    137280
cgccacggtt tgtggcaagg cgtatgttat catcatggag ctactcacgt tggtgttgta    137340
gcaactggca aaaagcgccg tgctcttggc gccgcggtgg tcgatgctga tcacgttgtc    137400
cttgttctcg accacgtagt cgcgcgcgaa ggtgtggcgg cagcggaact cgacctcttt    137460
gagcacaaac tgcgacacgt gcttttggtg cgccacgtag ccgatgctga tgccgatcat    137520
gtgcttaagc agaaacgaga taatggggat gatgaaccaa gtcttgccgt gacgtcgcgg    137580
caccaggaac acgtggctt tctgcttaaa gatgtcgatg gaggtctgcg agaggaagtc    137640
gatctggaag gcgtggatga ggtactgcag cacgcgattg gccagcacgg ggatcttggt    137700
cacggctata aaaagatga cgtgtatcaa taaattcttt tgaaacggtt cgagtcggat    137760
ggcttttgcg tcgccctcga cggcggtact gaagccgccg tcgagccact ttttaaagtc    137820
```

```
ggtcatgaag ttgttgatct gctgaaactg cggatcgcgg tagagctcgg tcaacgcgtc   137880
cagcttctgg taggaggcgc gctgctcctc ggagcacggg cgaaacgtca gttcatcgag   137940
cgcgctcttg aggcgctcgt gaaacagcag ctcgcgctgg ctttcctcgg gcgagttgta   138000
gtcgcggtgg cggccgcaga aggccatgag cggcaggaag gcctcgttgc acgagtgggc   138060
cagcccgagt tcggggtgca tcatctggta gcgcttgcgg cacagcgccg ccacattggt   138120
gaaggccgtg gagatgcagg aggtgggggtg gctcttgcgc ttctgcagct ccgcgtagcg   138180
ctcctggatc ttgcggccg  aatctccgcg caacatgatg gcggcggcgg tggtgcgagc   138240
ggaggttagg cggcagcggc gagaggagag gaaaaagatg gcgtccgcga ggacgacgga   138300
ggatccaccc gaaaaccacg ttgtcgcgga cgtggcttgt gggacgggcg ccgtcactcg   138360
ttcgtcttcg tcgtccttag tggtgtcgtc ctcctcggcg tcaggctcag acgaatcttc   138420
atccgcctct cctctcagtt tccccgtctc ctccccctca actgccgtca ggtctccggg   138480
gtccgccggg gtttcaacgt ccctgtgctc ggtggaacgg atggtcgagc tgtcggcgca   138540
gtctccggcc gccgatttct cggtctccga ggcttggcgc ttcgaggagg ccgtaaatat   138600
ggcgctggtg gcctgcgagg ccgtgtcacc ttacgatcgc tttcgcctaa ttgaaacgcc   138660
cgacgagaat ttcttgttgg tcactaacgt aattccgcgc gagtcggccg aggtgccggt   138720
gttggatagc agtagcagcg gtggcgatag cgggccggag gacaaaaaga aaaacgtcgg   138780
gaataaaacc gcggggaaa  agaacggcgg tgggtctcgg gccaaacgcc gtcgtagacg   138840
acgcgctccg aaaaacgacg ccgccacgcc gtcttttcta cgtcgacacg acgtgctgga   138900
gcgtttcgcg gccgcggctg agcctttgcc gtcgctttgt gtgcgtgatt atgtgttacg   138960
caatgctgac cgtgttacct acgacggcga attaatctac ggcagttacc tgttgtatcg   139020
caaggctcac gtggagctgt cactctccag caacaaggtg caacacgtgg aagccgtgct   139080
gcgacaggtg tacacgccgg gcttgttaga tcatcacaac gtgtgcgacg tggaggccct   139140
gctgtggctg ctgtactgtg gaccgcgaag cttttgcgcg cgtgacacct gtttcggtcg   139200
cgaaaagaac ggctgtcctt tccccgcgtt gttgcccaaa ctcttttacg aacccgtgcg   139260
ggactatatg acctacatga atctggctga gctgtacgtc tttgtttggt atcgcggcta   139320
cgaattccct gcgccgacgc cgcaggcgac gacggcgggt ggtggtggta gtggtggcgg   139380
cggcggggcc ggcgcttgtg cggtcgagac gagcgcgtca gcaggccggg tcgatgacgc   139440
cggcgacgag gtgcatttgc cttttaaagcc cgtctcgctg gaccgtctca gagaggtatt   139500
gcaggcggtg cgcggccgct ctcggggcg  cgaggtgccc gcctggccgg cctcgtcgcg   139560
cacctgtttg ttgtgcgcgc tctacagtca gaaccgtctc tgtttagatc tcgcgcgtga   139620
cgaggcgcgg accgtgagtt atagcccat  cgttatccaa gactgcgccg cggctgtcac   139680
cgacgtcact ttgagccaca tcttgcccgg ccagagcacc gtctcgcttt tccccgtcta   139740
ccacgtcggc aagttgctgg acgctctctc gctgaacgac gcgggtctca tcacgttgaa   139800
tctatgacgt cggtcaacaa acagctctta aaggacgtga tgcgcgtcga ccttgagcga   139860
cagcagcatc agtttctgcg gcgtacctac ggaccgcagc accggctcac cacgcagcag   139920
gctttgacgg tgatgcgtgt ggccgctcgg gaacagaccc gatacagtca gcgaacgacg   139980
cagtgcgtgg ccgcacacct gttggagcaa cgggcggccg tgcagcaaga gttgcaacgc   140040
gcccgacagc tgcaatccgg taacgtggac gacgcgctgg actctttaac cgagctgaag   140100
gacacggtag acgacgtgag agccaccttg gtggactcgg tttcggcgac gtgcgatttg   140160
gacctggagg tcgacgacgc cgtctaacag gtatagcaat ccccgtcacg cctctgttca   140220
```

```
tattttatta aaaaaaaaca caacataacg acagtgtcgg tgtggtagct agtgcagccc 140280
taggaacagg gaagactgtc gccactatgt cctccgcact tcggtctcgg gctcgctcgg 140340
cctcgctcgg aacgacgact cagggctggg atccgccgcc attgcgtcgt cccagcaggg 140400
cgcgccggcg ccagtggatg cgcgaagctg cgcaggccgc cgctcaagcc gcggtgcagg 140460
ccgcgcaggc cgccgccgct caggtcgccc aggctcacgt tgatgaaaac gaggtcgtgg 140520
atctgatggc cgacgaggcc ggcggcggcg tcaccacttt gaccaccctg agttccgtca 140580
gcacaaccac cgtgcttgga cacgcgactt tttccgcatg cgttcgaagt gacgtgatgc 140640
gtgacggaga aaaagaggac gcggcttcgg acaaggagaa cctgcgtcgg cccgtagtgc 140700
cgtccacgtc gtctcgcggc agcgccgcca gcggcgacgg ttaccacggc ttgcgctgcc 140760
gcgaaacttc ggccatgtgg tcgttcgagt acgatcgcga cggcgacgtg accagcgtac 140820
gccgcgctct cttcaccggc ggcagcgacc cctcggacag cgtgagcggc gtccgcggtg 140880
gacgcaaacg cccgttgcgt ccgccgttgg tgtcgctggc ccgcacccc ctgtgccgac 140940 gtcgtgtggg cggtgtggac gcggtgctcg aagaaaacga cgtggagctg cgcgcggaaa 141000
gtcaggacag cgccgtggca tcgggcccgg gccgcattcc gcagccgctc agcggtagtt 141060
ccggggagga atccgccacg gcggtggagg ccgactccac gtcacacgac gacgtgcatt 141120
gcacctgttc caacgaccag atcatcacca cgtccatccg cggccttacg tgcgacccgc 141180
gtatgttctt gcgccttacg catcccgagc tctgcgagct ctctatctcc tacctgctgg 141240
tctacgtgcc caaagaggac gatttttgcc acaagatttg ttatgccgtg gacatgagcg 141300
acgagagcta ccgcctgggc cagggctcct tcggcgaggt ctggccgctc gatcgctatc 141360
gcgtggtcaa ggtggcgcgt aagcacagcg agacggtgct cacggtctgg atgtcgggcc 141420
tgatccgcac gcgcgccgct ggcgagcaac agcagccgcc gtcgctggtg ggcacgggcg 141480
tgcaccgcgg tctgctcacg gccacgggct gctgtctgct gcacaacgtc acggtacatc 141540 gacgttttcca cacagacatg tttcatcacg accagtggaa gctggcgtgc atcgacagct 141600
accgacgtgc cttttgcacg ttggccgacg ctatcaaatt tctcaatcac cagtgtcgtg 141660
tatgccactt tgacattaca cccatgaacg tgctcatcga cgtgaacccg cacaaccca 141720 gcgagatcgt gcgcgccgcg ctgtgcgatt acagcctcag cgagccctat ccggattaca 141780
acgagcgctg tgtggccgtc tttcaggaga cgggtacggc gcgccgcatc cccaactgct 141840
cgcaccgtct gcgcgaatgt taccaccctg cttttccgacc catgccgctg cagaagctgc 141900
tcatctgcga cccgcacgcg cgttttccccg tagccggcct acggcgttat tgcatgtcgg 141960
agctgtcggc gctgggtaac gtgctgggct tttgcctcat gcggctgttg gaccggcgcg 142020
gtctggacga ggtgcgcatg ggcacggagg cgttgctctt taagcacgcc ggcgcggcct 142080
gccgcgcgtt ggagaacggt aagctcacgc actgctccga cgcctgtctg ctcattctgg 142140
cggcgcaaat gagctacggc gcctgtctcc tgggcgagca tggcgccgcg ctggtgtcgc 142200
acacgctgcg cttttgtggag gccaagatgt cctcgtgtcg cgtacgcgcc tttcgccgct 142260
tctaccacga atgctcgcag accatgctgc acgaatacgt cagaaagaac gtggagcgtc 142320
tgttggccac gagcgacggg ctgtatttat ataacgcctt tcggcgcacc accagcataa 142380
tctgcgagga ggaccttgac ggtgactgcc gccaactgtt ccccgagtaa ccgggacgcg 142440
gaacgtgacg gttgctgagg ggaaaggcaa cagagaaggt acaaacccac cggcggggaa 142500
aataccgagg cgccgccatc atcatgtggg gcgtctcgag tttggactac gacgacgatg 142560
```

```
aggagctcac ccggctgctg gcggtttggg acgatgagcc cctcagtctc tttctcatga   142620
acaccttttt gctgcaccag gagggcttcc gtaatctgcc ctttacggtg ctgcgtttgt   142680
cttacgccta ccgcatcttc gccaagatgc tgcgggccca cggtacgcca gtagccgagg   142740
actttatgac gcgcgtggcc gcgctggctc gcgacgaggg tctgcgcgac attttgggtc   142800
agcggcacgc cgccgaagcc tcgcgcgccg agatcgccga ggccctggag cgcgtggccg   142860
agcggtgcga cgaccggcac ggcggctcgg acgactacgt gtggcttagc cggttgctgg   142920
atttggcgcc caactatcgg caggtcgagc tcttccagtt gctggaaaag gaatcgcgcg   142980
gacagtcgcg caactcggtg tggcatctgt tgcgtatgga cacggtctcg gccaccaagt   143040
tctacgaggc cttcgtcagc ggctgtctgc ccggcgccgc ggcggcggac ggttcgggtg   143100
gcggcggctc gcactacacg ggctcgcgcg ccggcgtctc gccgggcatc cagttcggta   143160
tcaaacacga gggcttagtc aaaacgctgg tggaatgtta cgtgatgcac ggacgcgagc   143220
cggtgcgcga cggcctcggt ctgctcatcg accccacgtc ggggctgctg ggcgcttcca   143280
tggacctgtg cttcggcgtg ctcaagcagg gcagcggtcg caccttgctg gtggaaccgt   143340
gcgcgcgcgt ctacgagatc aagtgccgct acaaatattt gcgcaaaaag gaggacccct   143400
ttgtgcagaa cgtgctgcgg aggcacgacg cggcggccgt ggcctcgctg ttgcagtcac   143460
acccggtgcc gggcgtggag tttgcgggtg aacgcgagac cccgtcggca cgcgagtttc   143520
tgctttcgca cgacgcggcg ctcttcaggg ccacgctcaa gcgcgcgcgc ccgctcaagc   143580
cgcccgaacc gctgcgcgag tacctggccg atctgctgta tctcaataag gccgagtgtt   143640
cggaagtgat tgtgtttgac gccaagcacc tgaatgacga caacagcgac ggggacgcca   143700
cgaccactat taacgcgagt ctcgacctag ccgcgggcga cgccgctggc ggcggcgctg   143760
atcaccacct gcggggcagc ccgggcgatt cgccgccgcc gatacctttc gaggacgaaa   143820
acacgcccga gctgctgggc cggctcaacg tgtacgaggt agcgcgcttt tcactgccgg   143880
cttttgtcaa tccgcgtcac cagtattact ttcagatgct cattcagcag tacgtgctca   143940
gccaatacta tataaagaag catccggacc cggagcggat cgatttccgt gacctgccta   144000
ccgtctacct ggtctcggcc atcttccgcg agcgcgagga aagcgaactg ggctgcgagt   144060
tgctggccgg cggtcgcgtt ttccactgcg accacattcc gctcctgctc atcgtcacgc   144120
ccgtggtctt tgaccctcag tttacgcgcc atgccgtctc taccgtgcta gaccgttgga   144180
gtcgcgacct gtcccgcaag acgaacctac cgatatgggt gccgaactct gcaaacgaat   144240
atgttgtgag ttcggtacca cgcccggtga gcccctgaaa gatgctctgg gtcgccaggt   144300
gtctctacgc tcctacgaca acatccctcc gacttcctcc tcggacgaag gggaggacga   144360
tgacgacggg gaggatgacg ataacgagga gcggcaacag aagctgcggc tctgcggtag   144420
tggctgcggg ggaaacgaca gtagtagcgg cagccaccgc gaggccgccc acgacagctc   144480
caagaaaaac gcggtgcgct cgacgttttcg cgaggacaag gctccgaaac cgagcaagcg   144540
gtcaaaaaag aaaagaaaac cctcaaaaca tcaccaccat cagcaaagct ccattatgca   144600
ggagacggac gacctagacg aagaggacac ctcaatttac ctgtccccgc cccggtccc   144660 ccccgtccag gtggtggcta agcgactgcc gcggcccgac acacccagga ctccgcgcca   144720
aaagaagatt tcacaacgtc cacccacccc cgggacaaaa aagcccgccg cctccttgcc   144780
cttttaactc ataaactttc aggtctcgcg tacgattcgc gagtcgggaa tgggacaccc   144840
gtgggtgttt ctccgtgtgt atattatttt tttttgtgtg tgtgtgtgtt tgcgcccccg   144900
tgtgtctaat gtgctgtttg aaacacgtaa agtagctggt ggaagaacag ataaaccttt   144960
```

```
aataaaaaaa aagtatgtgc tcccgaccca cggtctgcgt gtctcttttt tatgtccatg   145020
tctccaagtc tggtgcgggt ggcggcgggg tcaagcgtcc tcgaagtctt catcatcgtc   145080
gtcgtcctct tgttcgcgga ggcgacggct ttccaagctg tcgtggtgac tgagcgcagc   145140
gacttcttcg ccggaggctg tggccagcgc ctggtacttg acactgccgc taccgcgtcc   145200
gcgaaagtag cggacggcgc gacacgtcgt aaacatggcc catatgaaaa agagcatgcc   145260
gaacgaccag ctgatgccgg tgcggtattc gttgctgagg aaggtatcgt actgcacgat   145320
ggggtagatg aggccgcaga gtccaaagaa ggcgcccagg tggtagccga attgcacctt   145380
gacgtattga aaaagacgg cctcgatcag taaaaagtag atgatggaga tgatagcgta   145440
gaccacgaag acggctaaca ccatgtggcc tgtacgcacg aaaaagttgt ttccgaagcc   145500
gtagcacagg gccatggcta ccacggtggt gttgaaacca agcgctacct ccaccaggtt   145560
gacgatgagc gtgcggaact gcaccgtacc tttgagcttg gggtgcagac gcgagaagaa   145620
aaagagtgag cgtttgtagc tgcggtactg cgtgaccatg ctcacgttga aaatggtcag   145680
gcagaaaaag tgcacggcgg ccatgaaggc gatcatgctg ggcagccgaa atgacatggt   145740
cagtgtgaat agttggaacg tgtccatgct gagaatgaag aggaaggctg tgaggctgtc   145800
gcccatgtac gaaatgtcgc gtgtcgactg gtttaggctc atgcctttgt ccttgcgcat   145860
gctgatcttg atccagcata ccaggtagta gatggtcacg gctaaaaaga cgagctgcat   145920
gaacacggcg tagcacacca actgcaccga gtctaagaaa agcataggcg tgtgcaggtg   145980
cattacgttg taggccgaca tgttgagcct ttcaaagtcc acgacgtgat agtgagacgca  146040 ggggtagccc aggtgcggaa aattgctcag cactagatgc acgctgacgt tgacaaaagt   146100
gagcaccatg aaaacgatag aagcgctcca tgtccgtgta ttcactttat ccacgtgcga   146160
gggggccatg gcgatagcgg cggcccgctc gctcgggagg cgatgggggc gcgccgatga   146220
cgacaggctc gcgggtcgtt aaatactacg atgggagccg ccgcggctca cgacgcggtt   146280
tgagcacgtc cgggcgatcg gtgaaaaaag accccgcggg ccttcgcgac tctcttctgt   146340
ccgaggatga ccgctcagcc gccgctgcac caccgccacc acccgtacac cctgttcggg   146400
accagctgtc atctcagctg gtacggcctt ctggaggcct cggtgcctat cgtacaatgt   146460 ctgttttttgg atctgggtgg cggccgtgcc gagccgcggc ttcacacgtt cgtggtgcgc   146520
ggtgaccgtc tgccgccggc tgaggtgcgt gctgtgcatc gtgccagcta cgccgcgctg   146580
gcctcggccg tgactacgga cgccgacgag cgccggcgcg gcctagagca gcgtagcgcc   146640
gtgttggcgc gcgtgttgct agaaggcagc gcgttaatcc gcgtgttggc gcgcaccttc   146700
acgccggtgc agattcagac ggacgctagc ggcgtggaga ttttggaggc cgcaccggca   146760
ctgggcgtgg aaaccgcagc gctatcgaac gcgcttagtc ttttccacgt agccaagcta   146820
gtggtcatcg gctcgtatcc cgaagtgcac gagccgcgtg tggtcacgca tgccgcggaa   146880
cgcgtctccg aagagtatgg cacccacgcg cacaaaaaat tgcgtcgcgg ttactacgcc   146940
tacgatttgg ccatgtcgtt tcgcgtcggc actcacaagt atgtgctgga gcgcgacgac   147000
gaggccgtcc tggcacgcct ctttgaggtg cgcgaggtgt gttttttgcg cacctgtctg   147060
cgtctggtca cgcctgtcgg tttcgtggcc gtggcagtga ccgacgagca gtgttgttta   147120
ttgctgcagt cggcctggac tcacctttac gacgtgcttt tccgtggttt cgctgggcag   147180
ccgccgttac gcgactacct ggggccggac cttttttgaga cgggcggcgc ccgttctttc   147240
tttttttccg gtttcccacc cgtgcccgtc tacgcggtcc acggtctgca cacgttaatg   147300
```

```
cgcgagacgg cgttggacgc ggcggctgag gtgctctcgt ggtgcggcct gcccgacatc  147360
gtgggctcgg ccggcaagct ggaggtggaa ccctgcgcgc tctcgctcgg cgtgcccgag  147420
gatgagtggc aggtcttcgg caccgaggcc ggcggcggcg ccgtgcgtct caatgccacg  147480
gcttttcgcg agcgaccggc cggcggcgat cgtcgctggc tgttgccgcc gctgccgcgt  147540
gacgacggcg acggtgaaaa caacgtcgtg gaagtcagca gcagcaccgg cggtgcgcac  147600
ccgccgagcg acgacgctac tttcaccgtg cacgttcgcg acgccacgct acatcgagtg  147660
ctcatcgtgg atttggtcga gcgcgtgctg gccaagtgtg tacgcgcgcg cgacttcaat  147720
ccctacgtgc gttatagtca tcgactccac acttatgcgg tttgtgaaaa gtttattgaa  147780
aatctgcgtt ttcgctcgcg acgcgccttc tggcagatcc agagtctgct gggctacatc  147840
tccgagcacg ttacgtcagc ctgcgcttcg gccggccttt tgtgggttct gtcgcgtgga  147900
caccgcgagt tttatgtcta cgacggctat tcgggtcacg acccgtctc ggccgaagtg  147960 tgcgtgcgga ctgtggtcga ctgttattgg cgcaaacttt ttggcggcga cgatccgggt  148020
cccacctgtc gtgttcaaga gagcgcgccc ggcgtgctgt tggtttgggg cgacgagcgg  148080
ttggtgggtc ccttcaactt cttctacggc aacggcggcg ccggtggtag tccgctccac  148140
ggggtggtgg gtggtttcgc ggcgggacat tgtggcggcg cttgttgcgc gggctgcgtc  148200
gtcactcacc gccattctag cggtggcggc ggcggtggtg gtggcgtggg cgacacggac  148260
cacgcgagtg gcggcggtct agatgccgct gccgggagtg gtcataacgg cggtagtgat  148320
cgggtttctc cctccacgcc gcccgcggcg ttaggtggct gttgctgcgc ggccggtggc  148380
gactggctct cggccgtggg tcatgttctg ggccggctgc cggcgctgtt acgggagcgc  148440
gtgagcgtgt ccgagctgga agccgtgtac cgcgagatcc tctttcgctt cgtggctcgc  148500
cgcaacgacg tggactttg gttactgcgc ttccagcccg gtgaaaacga agtaaggccg  148560
cacgccgggg tgattgactg cgcgcccttc cacggcgtgt gggccgagca gggccagatc  148620
atcgtacagt cacgcgatac ggcgttagcg gccgatatcg gctacggcgt ctatgtggac  148680
aaggcctttg ccatgctcac ggcttgcgtg gaggtctggg cgcgagagtt attgtcgtcc  148740
tccaccgctt ccaccaccgc ttgttcttct tcttccgttc tctcttccgc cttgccgtcc  148800
gtcacttcgt cctcttcggg cacggcgacg tgtgtcctc cgtcttgttc ttcttcgtcg  148860
gcgacttggc tcgaggagcg cgacgagtgg gtgcgttcgc tggcggttga cgcgcaacac  148920
gctgctaagc gggtggcttc cgagggcctg cggttttcc ggctcaacgc ttaacgagtc  148980
acgtagggga actacgtggg taagtgacgt ggatactagt aaaaaagtg cgtcaaagtt  149040 ctcagcgtgt gacgtggata ctagtaaaag ggacgtcaaa gctcactacg tgttgcgtgt  149100 ttttttttt tctatgatat gcgtgtctag ttcgcttctc actcttcctc tccccgttcc  149160
cagcgcggtg gcagcttggg gggtgagggc aaattggggt agttggcgtt gagcacgtct  149220
agcaggccca ggcccacggg ccaaccgtcc acggtcttac gctcggtcag cttgaggcta  149280
aacgagtgtg cctcgtcttg accggtaagg cggaaaaaga agcgtgctac cagctgcagg  149340
caggtatgcc gcgtctgctg gaagagcacg aaggtagcgg gcacgtactg cacaatgtgc  149400
ggttcttttt cctcaaagag taggtagagc gcgctgcaga tcagccgccg ggcgctgtgg  149460
tgcagcagcc ggccgaagct ttcgcgcacg ttcactgcgt ccaggtactg gagcaggtcg  149520
tgcaggcact tgcgcgttaa gttgcaattt tccacgcatg aaataacggt acagagcgcg  149580
aagtgcagca ggttgtcggc cttgacgatg ccgcagcggt gtttgagccg cagatccgag  149640
agcctcacct gcgtgacgac gtcttcggtc tcgagcaaaa acacggcgga gtagcccaga  149700
```

```
aaggccgagg tgcacagcaa ctcgctgcgg tactcggcca tggaaaccag cagcccgtgc   149760
tccgtgtgca gccacagctt gtcgccgcgc accgtaaagt cgagcacttg cggctccatg   149820
atcatcacat tctgtctagt gaaatccgta tggacctcca gcacgccgcg gatcatcagg   149880
gcctccattt cgaaatcggc cgacacgctc tgggccgcgc cgctcctcgt ctgccgtgat   149940
caagcggcgc ggcgcggacc tttcaagcgt tcctgggccg ccgctcgagg cagttcccct   150000
ttctggcact ccgcccgccg cttcgcggct catttggcgc cggcgcgcct tctcgcggct   150060
gcaaatcagc tccacgtatc ggcaaaactt gctgtcgtcg taggcggcgg ccacgatctc   150120
gccgaaggag agctgcaggt aggcttcggg tacggggtcc agcgtgccta gcgccaggat   150180
gtgacacaga tagggcaggg tcacgcgctc taccgtgtaa ttggagtaga cgatggcctc   150240
ttcggcccct tgatgcgtga ccagacgccg taggcgaaag gtgcggaaat actcgttttc   150300
ccacaactgc gtgaggaagc gttctagcga ctcggtgcca ggcacgaact gcgagaagaa   150360
gctgttggcc accaggcggt tgtcttccac cgccagcgga cggaagggcg ccgcgtcgcg   150420
cgccttgcgc acggcctcca acacgggcag gtggtagagt tcggcgtcgc gcgcgcccag   150480
gctcatggag tcctcgcgcc gcgaggcgta gcgcgtgagc aggtcgcgca gctcgcgcac   150540
gcgattctcc caggtctggt tgagcgtgcg caggtcctgg atctcgtcca cctgcgactg   150600
gatctgctcc tccaggcact tgatgacctg cttcttaaac aggtcgcgga tgtcccgctc   150660
gggcgccgcc gggccgggtg gcggcggcag cagcccgacg tggcccgcgg gtcctcccac   150720
cacggcgccg ccgggtccca ccacgccggg tccaccccgga ccacgcgcgg gtagtagacg   150780
gttttggtcc accagcgagg gggtcaggtc ctgcagaaag gactcgacgc tgtcctcgat   150840
gccgatgcgc gatttgctgt ccgagacgtt aagcaaaaac ttcataatgg acttttggc    150900 gtcgctgccc cggtcgtgct gctccatcat ctccaccagc ttcttgcagt tgagctcgtg   150960
gcggctggcg gtcaccactt tcacaggaaa ggtattgagc agctggcaga tcttttggtg   151020
gcggcagagc ccgtcgtagc gcagaatctc ctcgtgcagg tgtgccaccg gcgtggtgaa   151080
cagcagcttg tcgcgctcat aagccagcgg ttcggccgcc acgtacaagc ggatgtgctt   151140
gccgcgcagc tgcgcctcca gccgctccga gcgcaccttc ttgaagacgc gtacctcggg   151200
cgcgttggct acgcgcacgg cgcccaggcg ctcggccacc tgcagcagca gcgccaggtt   151260
agcctgcagc aggtcctgcg ccagcgggtg tgtctcggtg gcccgctgca cggccgcgcg   151320
tacaaattgc gcccgctcgg ccgcctcgct cggcttggtt ttcacgtcca gcagcggtac   151380
cagtcccacc gttacgcacc aatccacgta gagaccatag tcgtcgttat cggcgtactg   151440
atataaaatg tcgcggagcg cgcccagcac gcccgtttgc acgctctggc gcaacgaggc   151500
gctccacacc aacagatact gctccaggtc ctcttcgtcc agcgcgcggt agggaaacag   151560
cgccgcgtgt aacttccact cctcggccac gcgccgcacc gtgatggtgt caaagagcgt   151620
cttgcacact ccgtagagca gctgcttgcg cagcacgcac gggtcgcgca gcacctggtg   151680
catgctctgg ccgcgacacg tccccagaaa gccgtgcagc aaccgcagga agctcatcgt   151740
ctggcccgtg gggaaaatgt cgatgacggc ctcgtcatcc acgccgcggc ccacgcccaa   151800
gtacgacgac gccttgatcc tcaacctctc gtcggctgcc aagatcgaac ggatcgtcga   151860
caaggtcaag tctctctcgc gcgagcgctt tgcgcccgag gattttttcgt tccagtggtt   151920 tcgctccatc agtcgcgttg aacgaacgac agataacaac ccctctgccg caactaccgc   151980
cgcggcaacg acgaccgttc actcctccgc ctcctcttct gccgccgctg ccgcttcgtc   152040
```

```
cgaggccggc ggcacgcgcg taccctgcgt cgaccgttgg cccttctttc ccttccgcgc   152100
gctgctcgtc accggcacgg cgggcgccgg caagacttcc agcatccagg tgctggcggc   152160
caatctagat tgcgtgatca ccggtaccac ggtgatcgcc gcgcagaacc tcagcgcgat   152220
cctcaaccgc actcgctcgg cgcaggtcaa gaccatctac cgcgtcttcg gtttcgtcag   152280
caagcacgtg ccgctggctg atagcgccgt tagccacgag acgctggaac gctaccgcgt   152340
gtgcgagccg cacgaggaga ccaccatcca gcgcctgcag atcaacgatc tgctcgccta   152400
ctggccggtc atcgccgaca tcgtggacaa atgcttaaat atgtgggagc gcaaggccgc   152460
ttcggcctcc gccgcggccg cggccgccgc ctgcgaggac ctctcggagc tgtgcgagag   152520
caatatcatc gtcatcgacg agtgcggcct tatgctgcgc tacatgctgc aggtggtggt   152580 gttttttac tacttttaca acgccctggg cgacacgcga ctttaccgcg aacgccgcgt   152640
gccctgcatc atctgcgtcg gttcgcccac gcagaccgag gcgctggaga ccgctacga   152700 ccactacacg caaaacaaga gcgtgcgcaa gggcgttgac gtgctctcgg cgctgattca   152760
gaacgaggtg ctcatcaact actgcgacat cgccgacaac tgggtcatgt ttattcacaa   152820
caagcgttgc accgacctgg actttggcga cctgctcaag tacatggagt tcggtatccc   152880
gctcaaggag gagcacgtgg cctacgtgga ccgcttcgtg cggccgccca gctccatccg   152940 caaccctcg tacgccgccg agatgacgcg gcttttctc tcgcacgtcg aggtgcaggc   153000
ttacttcaag cggctgcacg agcagatccg cctgagcgag cgccaccgtc tcttcgatct   153060
gcccgtctac tgcgtggtca acaaccgcgc gtaccaggag ctctgcgagc tggccgaccc   153120
gctgggcgac tcgccgcagc ccgtcgagct ctggttccgc cagaacttgg cgcgcatcat   153180
taactactcg cagtttgtcg accacaacct ctccagcgag atcaccaagg aggcgctgcg   153240
ccccgcggcc gacgtcgttg ccaccaacaa ctcctccgtc caggctcacg gaggggagg   153300 atctgtcatc gggagcaccg gcggcaacga cgagacggcg tttttccagg acgatgatac   153360
caccaccgcg cccgatagcc gtgagacgct gctcaccttg cgcattacct acatcaaggg   153420
cagttcggtg ggagtcaact ctaaggtgcg ggcctgtgtt atcggatacc agggcacggt   153480
cgaacgtttc gtggacatct tgcaaaagga cacgttatc gaacgcacgc cctgcgagca   153540
ggcggcctac gcctactcgt tagtttcggg cctgctcttc tcggccatgt actacttcta   153600
cgtgtcgccc tacacgaccg aggagatgtt gcgtgagctg gcgcgcgttg agctgcccga   153660
cgtgagttcg ctctgcgccg ctgccgccgc cacggccgcc gctcccgctt ggagcgggg   153720 agagaatccg ataaataatc acgtcgacgc ggattcttct cagggcggcc agagcgtgcc   153780
ggtatctcaa cggatggaac atggccaaga ggaaacccac gacatcccct gcctgtccag   153840
ccaccatgac gactcggacg ccatcacgga cgccgaactc atggatcaca ccagtctgta   153900
cgcggatccc ttttttctca aatacgtcaa gccacctagc ctggcgctgc tttctttcga   153960
ggagacggtg cacatgtaca ctaccttccg cgacattttt ctcaagcgct accagctcat   154020
gcagcgtctc acgggcggtc gcttcgccac gttgccgctc gttacctaca atcgccgtaa   154080
cgtggtgttc aaggccaact gtcagatcag ctcgcaaacc ggctccttcg tgggcatgct   154140
ttcgcatgtg tcgccggcgc agacgtacac gctcgagggc tacaccagcg acaacgtgct   154200
cagtctgccc agtgaccgcc accgcatcca ccccgaggtg gtgcagcgcg tctttcgcg   154260 gctggtacta cgcgatgcgc tcgggttcct cttgtgctc gacgttaacg tctcgcgctt   154320
cgtcgagtcg gcgcagggca agagtctgca cgtgtgcacc accgtggact acggcctcac   154380
ttcgcgcacg gccatgacca tcgccaagag tcagggcctg tcgctcgaga aggtggccgt   154440
```

```
ggactttggg gaccatccca agaacctcaa gatgagccac atctacgtgg ccatgtcgcg   154500
agtcacggac cccgagcacc tcatgatgaa cgttaacccg ttgcgactgc cctatgagaa   154560
gaacaccgct atcaccccct atatctgtcg cgcgctcaaa gacaaacgca ccacgcttat   154620
tttttgacac aacaccgtgt aagcaaaacg tgactttatt gagcagggta aaaaccacgt   154680
acaagaacca cgttgtctat cccccaaaa aaaacacac cgtcagggaa cacatcgcct      154740
atagatagcg gcactttaca taaaaccacc gtacctgcat cacggtggct cgatacactg   154800
gaaattcaat aaaaccacc gtgtccacgt tacggtactt gccgggtcag cgtccttctc     154860
ttgagatttc tgttcgcaaa cttatccgtt tccccggtcc gcggtgtctc ctcgcgaggc   154920
tgacagtcta cgagtggtat ctacaagaga aagaaacccg ggtgggagcg acgccgtcgc   154980
tgggtatcaa ccccgcggct gaccgtcgtc cggtaaagga acaacccgtc gtcgcaagcc   155040
gggttcgacc aagagaaaaa aacccgggtg cggggggaga cgggtcgtcc tttggtcgtt   155100
cgcggacggc gtacatgccg cgtgggtcag tcgacggcgt cgctccgtgc ggtcggtcat   155160
cattctgctt cacatatatg ggttgtttgt gttttttta taatgaatac gcactcatcc     155220
tatccgtgac tgcgcgtgtg gcagagagga tgccttataa catgtatttt gaaaaattgc   155280
caacagctat aatttctctc atgtagcaga atagagacct tttgtcgtct ttttgtttgt   155340
cattacttgt tttccaggga attagagaga gggaaccgcg cctccggcgg cggtgcccgc   155400
ggaccccggc cccttctcgc gtgcgcggtg tgactggttg agcgaatgag cagctaggct   155460
tggtggtgct ccgcgtgcgg gggagaagac gattaacaac aaaaaataag tggaagtggc   155520
cggtgggtct ttgtccgcgt gcgcgcccat ccgtcgccgg gaccgagcag aaagtgatgt   155580
ggtggtacat tgattttttc cttgacagga agaaaaaaa agagttttgt tttcctatgt     155640
gagaggagaa aggtatgtga ggagatgttc gatgatcgta tgttacagtt atgctgtaag   155700
gaagctttta tcgtgcgtcc tgttttttcat ttgatgtata tgacacaatt gaaacctatc   155760
gataggcgta tatcgaggat tcatcaattc ttagaatcgt cgtctttttg gctaattgga   155820
ctttgcccat gttggttgtc attcgtggcc tgaggtcatc gtcgtccacg acgacgtgtc   155880
tatagcgtgc ggtgtgatca ttgtgtcgag ccagagaaag cgcgcctcgc acgacgtttg   155940
cggatcggct cgcgggtgtg tggaattcct aagaacataa tcagctggtc gtctttcttt   156000
gatgtgttgt tgtcgtcgag gtcttgcttc gttttctttt ttcttttttag tcgatggaac   156060 ttttcttcgg tacgggttct tgttatggaa gcttgtgttt tcgaacatga attcgaaaaa   156120
ataaaaaggc ctatcttcgt ttcaaaaaaa ggacagatat caatcttctt aacttatatc   156180
atggtaaatt cagaatccta tggtgtctta ttatctctaa agtagtcaac attatggtct   156240
aacttgtatt tccctgacga gatatatatg atccttataa cctggctact atcatgaaca   156300
acaatatcct tacttacagt catcttcgtg agttaatgaa gtataatatc ggtcatctat    156360
caacttatct gctatgtaac gtacccttt aggtattttg cgtttcttaa cgagtgtacc     156420
cgcctgtgtg aggcgaaact ctgagaagtc taccgagtcg agttacaagt cactaaaaca   156480
cttacacgag ttatctatac taaaatcact atctatgttg tttgcttacc taattattat    156540
cctacatgac gaagctacct cccaacgtaa ggtagggga gaggagacag aacaataaaa     156600
agtaactaat gtttcttaga acttacccgc taaggactta ccaaactata ttcaccaaaa   156660
aacaacagct acgtgtttca tttgttttaa tctaccgaag taaaaaaaaa aaagatgatt   156720
agctatccag aacctactta cttcttaatg ttttaactaa ggatgcctat gggattggaa   156780
```

```
aaaaaatcac agcaacttgc tactaatcag ttgacagcga agagactcat aacaaagatt   156840
tctgggtaat acggttataa taatgcttat ggactaaagg atacttggaa aaaagaacg    156900 ggctatgact atagagattc gtcgagatat taaacttcaa ataggcggct atcattcatg   156960
gttgtggtga ctatatcgtg gagaaaaaat gtgatcgtta gttagctagg tgagacttac   157020
agctatccat ccgtctagtt tttcgttgta atgatgatag tacgtctatg gtggtgatcg   157080
attttggtta acaatttgtt cgtttaaagg cttaatgtac ttatgctaca tgatgtatta   157140
ttctttgatt catcgttcct cctaagggg tgtatgtatg tatgtactag tcgtatagtg    157200
ttcctaacat catgattatt cagactatgg cttcatctat cgtgtctaaa gttcacttat   157260
tctactatta ctatatatat gcactactat gtaactagga tatggtccta aaggtgtct    157320 tctatcacgg tggcttgttt atcgcttggc ggttacgagc aagagttcat cacggaccag   157380
ccgtgaggca gggcacacgc gggtcggcgg cgatgatgtc ccccgcgaag gggacaacaa   157440
aaacaagaca agaggccgcc ggccgcggcc acggacgcgt agcggttaca caatgtttgg   157500
ttgagcgttt tgtttcatcg tcgtggtggt ggttttgttg ttctctgtat atatcgtgtg   157560
gtggctttat cgtcatcatt attatcatca ttcttgtttc catcatcacg atgagttttc   157620 tccgtttttcc tctcctccag tggtagtcgt gtatcatcat caatcatcgt agtgacgtcg   157680
ttgctgctgc tgctcttgcc ttcatggcgg tatttctctt cctccccct aaccccatat    157740 taactcgtga gtgtgatggt tagagtggct gcttgttttt ttttcttttc tctttggaac   157800
aacaaaagag gataaagatg gtcggtgaat gtattattat tattatcatc attatgatac   157860
ggtcgcggtc ttcttctccg atgacgaaac ctgcgcacat cgaagaaaag acgagcgcgc   157920
gaaccgatag ccgtccgtct gggacgaagg agaagatgat ggggagagga ggagagcccc   157980
agaagccaga gcgagaaggg agacgacaga catacgtcgt caccgtcctc tggaggaggc   158040
acggcggcgc tgtttgttgt ttggatgctt gattatatcc tgttctatgg ggtagattat    158100
tatcaatagg cttggttttc aaaggtcagc ctgtgtattg tcgtgtcttt ttttcgttc    158160 tcatgatcgc ggagaccaca cagacgtgcg cgtctcccaa tggctaggcg ttctttttag   158220
gtagtaattt tttgatcttt tttttttctt aacaagtctg gcttgatttc ttttatctat   158280
gatcgattct tctttttctc ggggggttgca tcttccgtga agtaaagtg acactactct    158340 aaatggtaac catattatct gttgattagg agaaaaaata atttttttcgc acgaaatcga   158400 tcctaagtga ggtgatttac ttgctatcac acgaaatgat tatcttttgc tgctaacgta   158460 ctgaatttttt taacagaatt gcttctccgt aactatttcc gcagattcag acagattgtc   158520
aaaaaaaaat acggcacaga aatagtgggt ctgtggcttt tggttcgtgt acattcgcgt   158580
ttgcgtgtcg agatttctac ggtatgttta ttcttcctgc gatgatgtag ggtccttggt    158640
gtaagtagga tttcgagtat ctctcttaga gcgaacaaaa taatcaaaaa acaacagcta   158700
ggaaatcgag ggttactcta cgataaagtg tctctacaaa gtgaagaatg ttacgttgtg   158760
gtggaataat aagactcgcg tgatcgatga gtgatcgaga gcggctcgaa ccttctttaa   158820
gagctttgtt tagtgcaact ttaaattaca aggagtagaa agctgaaatg aatctatgaa   158880
ggtgctattc tttgaatatc ttactttgta cgcttcacat tcgttatttg gatagagagt    158940
tgtctagaga aaatctgtga ttctctatga gtgttatttt tattatcctt tgggggacta   159000
cgatttttct tcttgttcta cataccacta ctactcgtaa tcacatacat ggacgaaaaa   159060
aaaattcgtc aggcagtaga taccagattc tccgacgtta cggcgtcttt ttttcttttg   159120
agagagtatc tgctgagatt gtccgtggtg tatctagtcg ctattttttgt tgttactagt    159180
```

```
agttttgcac acagtttatt cagtataatt tttcttcttg ccatgatcaa ttgagcccac   159240
cacctttttt ttttagagag gaggaatttc gtcttgatct ccagccggag acaacggcgg   159300
cggtggtggt ggcgggagag atttcaaggc aatgaaaaaa aaaatttcgt tttgccatca   159360
agtggtgacg ataacccgtc agattgataa ttggttccta cagaaactat tctaaccgcg   159420
gaagaaagaa attgaaaaaa aaaattgaca aaacatcat aacataaagg accacctacc   159480
tgggacgcgc agttgggcgg cggactgggg cggcatgctg cggcgatgct gtcggtgatg   159540
gtctcttcct ctctggtcct gatcgtcttt tttctaggcg cttccgagga ggcgaagccg   159600
gcgacgacga cgacgacgat aaagaataca agccgcggt gtcgtccgga ggattacgcg    159660
accagattgc aagatctccg cgtcacctt catcgagtaa aacctacgtt ggtaggtcac    159720
gtaggtacgg tttattgcga cggtctttct tttccgcgtg tcgggtgacg tagtttcct    159780
cttgtagcaa cgtgaggacg actactccgt gtggctcgac ggtacggtgg tcaaaggctg   159840
ttggggatgc agcgtcatgg actggttgtt gaggcggtat ctggagatcg tgttccccgc   159900
aggcgaccac gtctatcctg gacttaagac ggaattgcat agtatgcgct cgacgctaga   159960
atccatctac aaagacatgc ggcaatgcgt aagtgtctct gtggcggcgc tgtccgcgca   160020
gaggtaacaa cgtgttcata gcacggtgtt ttacttttgt cgggctccca gcctctgtta   160080
ggttgcggag ataagtccgt gattagtcgg ctgtctcagg aggcggaaag gaaatcggat   160140
aacggcacgc ggaaaggtct cagcgagttg gacacgttgt ttagccgtct cgaagagtat   160200
ctgcactcga gaaagtagcg ttgcgatttg cagtccgctc cggtgtcgtt cacccagtta   160260
cttttaataaa cgtactgttt aaccacgttg cgtcgtgacg ttgtttgtgg gtgttgctag   160320
gcgggctgga aagatgatgt ataaatagag tctgcgacgg ggttcggcgc tctgccggct   160380
gcggcggcac tcgctccacg gcctccgacg agcgttgcgc tcgcgctttg cgccgccgcg   160440
tcatggatct gcctactacc gtcgtgcgaa aatactggac ttttacgaat cctaaccgca   160500
tcctgcatca gagcgtcaat cagactttcg acgtgcgcca gttcgtcttt gacaacgccc   160560
gtctggtcaa ctgcgtggac ggcgatggca aggtgctgca ccttaacaag ggctggctct   160620
gcgctaccat tatgcagcac ggcgaggctt cggccgcgc caagacgcag cagggcttca   160680
tgtccattga cattacgggc gacggggaac ttcaggagca cctctttgta cgcggcggta   160740
tcgtctttaa caaatccgtc tcctcggtgg tgggctccag cggacccaat gagagcgcgc   160800
tgctcactat gatttccgag aacggtaatt gcaagtgac ttacgtgcgg cattacctga    160860
aaaaccacgg cgaatcctcc agcggaggcg gtggttgcgg tgccgcgtct accgcctccg   160920
ccgtctgcgt gtcctcgctg ggtggcagcg gcgggactcg cgacggccct tctgcggagg   160980
aacagcaacg gcgaaggcag gaacagcgtc acgaagaacg gcgcaaaaaa tcgtcctcgt   161040
ctgccggtgg tggtggaggc ggcggcactg gtggtggcgg tggcggcggc gggagcggcg   161100
gtcagcactc ctcggactcc gccaacggac tgctgcggga tccccggttg atgaaccggc   161160
agaaggagcg gcggccgcct ccctcctccg agaacgacgg tgagtccgg ccctcctcgc    161220
gtcacggtgc tttccgagtg gactcgtgag ccccccgtag cgcacgagcg agcaggcgag   161280
cggtgttggt gcgctggtgg ttgtgtggat gataaccatg tgcttttcg tgcgctatgt    161340
gtcgtcccgt ctgtaggctc tcctcccctc cgggaggcga agagacaaaa gaccaccgca   161400
cagcacgaag gccatggcgg cggcggcaag aacgagacgg agcagcagtc cggtggtgct   161460
ggcggtggtg gtggcggcgg cagcggccgc atgtcgctgc cgctggacac gtctgaagcg   161520
```

```
gtggcctttc tcaattactc gtcctcatcc tccgcggtct cttcttcctc caacaaccac   161580
caccaccatc atcaccacca taacgccgtg acggacgtgg ccgccggcac cgacggtgcg   161640
ttacttctac ccattgagcg cggagcggtg gtttcgtcgc cgtcgtcgac gtcgccgtcg   161700
tcacttcttt cgctccctcg acccagcagc gcccacagcg cgggcgagac ggtgcaggag   161760
tccgaggcgg cggcgacggc ggcggctgcg gggttaatga tgatgaggag gatgaggagg   161820
gctccggctg aggcggcgga ggcaccaccg cagtcggagg aggagaatga ttccaccact   161880
ccagtctcta actgccgtgt tcctccgaat tcgcaggaat ccgcggcgcc tcagcctcct   161940
cgcagtccgc gttttgatga cattatacag tcattgacca aaatgctcaa tgattgtaag   162000
gagaaaagat tgtgcgatct ccccctggtt tccagcagac tcttgccaga gacgtcgggc   162060
gggactgtcg tcgtcaacca cagcagcgtc gcgaggaccg ccgcagctgt ctccacagcc   162120
ggcgttggcc ccccagcagc cgcatgtccg ccactcgtca ccaccggtgt tgtaccctca   162180
ggttccgtcg ccggtgtcgc gcccgttgcc ccgcagtcg aaacaccagc tgctcctccc   162240
cggcccgtgt gtgaaatcaa gccctacgtg gtaaaccccg ttgtcgccac cgccgcggct   162300
gccagtaact cttcctcgtc ttcttcggct ccactgccgc cgccgccacc accgccgggc   162360
ggacgtcggg gtcgggcccg gaacaatacc cgaggaggcg gcggtggtgg cggtggtaga   162420
aacagccggc ggcaggccgc atcgtcgtcg tcctcctcct ctcggagatc gcgacggaga   162480
aacaaccgcc acgaggacga ggacaacgat cctctgctcc ggttgtcgca agtcgccggc   162540
agcggccgcc ggcgagggcc ctcgttcctc gaggacggac tcgaaattat cgatcccagc   162600
gaggaggctg cgatcgccgc cgcctcgatc gcggcgtttt tcgacgatta aaaaaccgag   162660
ccgagaccgg aaaaattatg aaacaggacg cgcttggaca tttgggtttc caccccttc   162720
ggtgtgtgtc tatatatatt gtggtcactg atttttttt tacaataaag agatagacat   162780
cacagttcac catcttgtct ccccggtgtg tctattatca tcaatcaccc acagagtcgc   162840
cagtccatgg tctctcggta atgcgtgtcc agatacgcgt tggccagtat aaagtggtcg   162900
ttgcccacga aggcgcgggt ggtgttgcgc ggcgacgggt ggcaggactt aagtaccaag   162960
tgccgccgtc ggtcgatcag gtactcgcag gtgtgcgcgt cggcgcccca cagcatgaac   163020
accagatgct cccggcgctc tgacagcctc cggatcacat ggttactcag cgtctgccag   163080
cctaagtgac ggtgagatcc aggctgtccg tgcaccacgg tgaacacggt gttgagcagc   163140
agcacgccgc gtcgcgccca ggcgtccagg caacccgagg ccggacgctg aaacccgtcc   163200
accgtacgcg ccagttcgcg aaacacgttg ttgagggagg gcggcggcgg tcggcccgcc   163260
agcgtgccga aggccaggcc gctggcgctg ccgtcgcagt acgggtcctg gcccacgatc   163320
accacgcgca cctgctcggg cggacacaga tagctccagc ggtgtacgtg ctcgggtgcc   163380
gggtacacca tctcgagttg ccgcgcgcct tccaccgccg ccaccgtgtc gcgcagcagc   163440
accgtgtcgt ggtcgggcaa gctgaggaag cggatccagt cggcgctcag acaaaacacg   163500
cgagcctgct cgtcggggt taacagagag cctttattat cagcaatgtt agcgagcatc   163560
cactgcttga gggccatagc gcgagtgagc cggcaggttg acgcgcgtct gcttcagctc   163620
gggcggcagt ccggcgtagt atttatctag gtggcgtagc agcggcgggt ccagctggtg   163680
acgcaggcag aattccttca ccgcgttgta caggccgtaa aagagcgtga tgccctcggg   163740
cgcggcagcg gtgctcacgg gcagacgcac ggcgcggttg gtacgcgtgg cttcgttgcg   163800
tatgccacc accacgttaa agagagacgg tggcaccagc tcgaagccta acacgtgttc   163860
cgtgaagatg ctgcgcccgt atgacagtcg cgtgaggtcg tagccgcggc acaggtcgtc   163920
```

```
cacgcacgtg tacacggccg gcgagccatc gccgcactcg ctgtagccgc gcattaccgt   163980
catccagcgc ggcgctgtgt ccgagcttaa cagcgtcagc agggcccgca attgatccgg   164040
attgttgtac agcagggcca gagtgtccag gaaagcatcg tccaacagca cggagttggc   164100
ggcctccggc gtaacgggac ggtaacggat aagttgcgat agcgggccat cgcgcccggt   164160
aacattcacc aacgggcgca gccaactttc atacttgtca ccctgaaaca cctcacccaa   164220
caggcatcgg cgcgttagtt cggggcactc cgcggggact ttctcggcgg cggtaggagc   164280
gacgctgacg gcggctgagg aaacaatgga cagcagaagg caacaccaca gcagtatcac   164340
cggtccaggt gagaaagaga agccgcaatc cgggcggcgg cacatcaagt ctgcggcacg   164400
atgagagtgt gacggtaagg agccagttgg cgccgaaagt tggcactcag gtcttcgatc   164460
cctaaaacgt tatatattgc atccagcagg tgagccaggc taaacggatt cacgtaccag   164520
gtttggttac ccgcgacgat gacggccaga ccgtgggcgc tacagttgga gaggttcctg   164580
ggtacgaagg taactgagtc gatgtcgcgc acgggggga atgagacaga cgactggcgc   164640
acgctgtaat cacaactgtg attgacgtat tgtagcgtgt aatttaggtt gcactcagcc   164700
tcgaagtaga gggggaacca cagttcgtcg tactcgtcgt cgtcctccag ttctggctct   164760
tcttcatcca ccgcaatgtc tacgctgctt tgagattcct cttcgtacag gatgattgac   164820
aggttatggc tacaaaggtc ctgggcggga ggacgcgtgg gagcgcgggt ggtggtaatg   164880
ttttccagat caaaagttgg agtgtagtcg gatgttacat ccccgttgtt ggaggtggta   164940
gaagttgcgg ccggtgtcgc ggtggtaagt atggatacag aaggggaggg ggaagtagcg   165000
ttcgtaccga tggttgtggt attattattc cctgtgtttc ttgttccaga aaccgttgac   165060
gttgagatgg gaatcgacgt ggtgctggac gtcagattgc tgaccgagga aaccgtggtg   165120
ggagtggtga cggtgttact cgtggttgaa gtgacgttag gggaggtagt agtggtaccg   165180
gtggtggcga cggtagtgtt tgtcgtggcg gcggcagcgg tggtaccggt aacggtggtc   165240
gcgttggttt ccaccgcttc acacagtaag caaaagcaca gagccaggaa aagcaaccag   165300
ccccgccatc gccgccgccg cttcatgagg tgggcaggcg aaagctggtg aattcgttgt   165360
acagcggcaa gtggggcgcc gcgatcgaag ggtacgtcaa caagctgacg ttgatattaa   165420
atacgtctgg ctgcttttct acgatggaag cgcacagggt tacggcgtca aacaggtctt   165480
tcttggtggc gcccgagacc cacatctggt atacacccgt ctcgtggtac gaagtagagc   165540
gcggcaccac cggacggatg cagtccagaa cgcggttggg atcttggtga aagaatttga   165600
acgtggctac ggcctgtggc gtgtgcggca tcgtctgcgt gatgagctgc tggcccgcta   165660
acacggtgac gttgtgcaac ttgagcaggg cactcttgag ggcctggaaa gcgttgccgc   165720
acgaggcgct gatctgcagc tgcacggccg tggagtcgtg cagccgcatg agacgtgaca   165780
cctcttcgaa gacgtactta tacttactgg caaagagtgg cgcgtatcga cagtcggccg   165840
gcaaaatgta ggtggcgttg ccgccgttgg tagccacggc gggcgcagcg gccgcggagg   165900
ccggcgtaaa cagcgtcagc ggccggtggt ggctggtaag gtcgatcatg ggcggcgtgg   165960
tgaccgtggc ggtggcgggc atgacggggt ttgcggcgac gggcactccg gccacagcgg   166020
cggccgcggc ggccacggcg gcgctggccg agccacacc cgccgcagt cctccgctac   166080 ccatgacgcc gccgggcaga gcgtcgccca gacagacttc cacagtggcg ggcgcgctct   166140
cggcggtcag tacggtttgc cgatcgacct cgcgacgaaa gctggtgagg aactcactat   166200
gatccatggc cgcagggccc gagatcccgg gattctgcgg gtgctgaccg agtgcgggcc   166260
```

```
gagttatatg gaagacgatt agcttggagc ggagttttgc gtccctagct gacctgcgga  166320
tcagcgacgt accataggga tagactgtga gcggcggccg caacggcggg gtcggccgcc  166380
gttcgtcgtc acgggcggc gcgagggagg aggaggtggt gggtacgatc ttgacgtggt   166440
tgacgtcctg cccgtccggg ggaatacgca aaaaaacccg tcgcgcgct accacgatgg    166500 tgcgatgggt ctttctcttg ttggccgggg ccagggactt gcagatgcgt gtggagccgt  166560
agacgatctg gacgtggtcc tgggagaaca tgaccatcgc cgccaacgct cagcgggggg  166620
acgtattggg aacacagagg atgagggaaa actccgtaga agtcagcgaa ataaagacaa   166680
cacagcagcc actcctctcg tctcgggccc taccactgct tgaagtaggg cacccgggtgt  166740 ttcttttcct caacgggctc ctccagtctc ttataggacc agtcccgccg gcgcgccagc   166800
atgtaggtca cgtacaaaag aataatcacc atgaacacca ggaaagccag cacgccgtag   166860
gccagcagcc ggtcctcgaa cagcgggtcg ctcttgataa acacgtaggt ggtggtaaaa  166920
cttcggcccg cgatctgaac gtggagacgc acgacagtat acgtgccgtt gaggtagaag   166980
acaaactcgc gtaaccgttg tccgttatac gtcacgttac taatattcca cggcggaatg   167040
agctggttgc cctgatgcag atgcacggtg ctgttggggt gatagaggct gctaccgttg   167100
agcaagcagt gttcgtgttc ctgaagcagc acgcggaccc gcatcgtggt agcgttcaag   167160
cgagtcccgt acacggcgta gatgggatag gtgaaaaggt cccaagtggc gttgtgatgg   167220 cggcccagc tgaagaaaga gcacgtgtac tcagtggtct cctgcggcct gagtcccgag    167280
ataagcagct cttgagcagt agcgttgtag gagagatgta gttttcctgt ggaaaaaatt   167340
aatgagttgt ttattttgtt agcaggttgg cgagggagga aggagaacaa aacagaaagg   167400
tacgtgttac ttacctttat cgttggaggg aaaagcgcta agataccca cctgagtgaa     167460 gggacccttg cagtctgtcc gtgcataaca agtaactgat aaaatgtctg gattttggt     167520 attattcaac aggattactt tgcaggtggc gtttagagac acttggtcgt agctgtagct   167580
ggcttcgcaa ttcacagtat acaggtgccc ctctttctgc gtcgtggcta tcacggaggt  167640
ggaggcggac gaggtagagg tttgtaccgt ggtggtgaca gcagaagtga cgttgttaga   167700
ggtacttatt gacgtagtag acgtgacggt ggtattacta ggggaagtga cggcgcttgt  167760
ggtgctactt ttcactctcg ggtgcatgtc gcccaagagc gcaactacga gcgcgatcgc    167820
cagcacggaa cacatgttgc cgtgtgacga gacggcgtgt ggacgagcta tatgtggcag   167880
gaggtcgcgt cacctcttgt gacgcctaaa cgtccagctc cagataaaag aggcgttaat   167940
aatgaagacc acaaaaacca cttgcgtcag tatgacaatc ataaaggctc ggtgattgct  168000
acgcctaaag tacgcgggat tatccaccag ttcatcctgc tgaacaaagt ggatgattga   168060
cgtgctggtg ttaccggccg tcgtattgat catggatttt actaagaaag ttttggcacc   168120
aaaagtcccg ttagagcccc agcaggtaac gctgccgttc ataggctc ccggtgcccc    168180 tgtcagcatg cgtttcagtt catgagtata atttttccta tcgttataca tatcatcact   168240
gtagttgact ttgctggtga gaaactgtgt gttctgtgga atactgatca tcatccccga   168300
ggccaaaaag ggcgaatcgc aagctgtagt gttacagaaa atagtcaggt tagtgtcatt   168360
atgctcatac atataagcca cgctaacctg gggctcatac cacccaatcg caaccgccag   168420
cacgtcccat ctcccgacat ttatcaccgc caccactaac aacgtcaccc ccgcacggta   168480
catagttacc ctctcgacgt cgccggctgt caatgacgtg cctgcgtcag tggctatgat   168540
ttatagcttt tggacacaac cgcaacggat ctgtcgtaat ctaccttcca cagggccgcc   168600
gcgacgatgc tgaacgacag gatcagacag acggcgtata ggagtcctag gtcggcgtcg   168660
```

```
acgcggcaag tgcggatgtc tcgcagggtg ggtagatggg cgatgcacaa ctctttctcc   168720
ccccgcacgt acatcccatc tcgtatcagc agccgtagcg tagcattaat ggtcagcggg   168780
gtaaccaaag aaatcacata gggatgtgta caggaagtac agtgacgggt atccgtgaga   168840
tgtaagtcat caccttctc actgttatca tgaaagacca ggactcgggt aagacgaccc    168900
gatgaatact ggatctccca ccacagtctt tggtccaaca ccgagagggc acaagagatt   168960
ctaagtctcc ctgggttggg ggagcagatg taagccccgt gtgtgcccct cgccatcaga   169020
accatacaca tgaggggaa aaggacaagt atccgggacc acccgcaccc ccacatcacg     169080
agaccagaga cggagatgta taaaaaaaag ctacttttat taaacagcat tctcaccaca   169140
cgttaatact gtcacgggga atcactatgt acaagagtcc atgtctcttt ccagtttttc   169200
acttactgag acttgttcct caggtcctgg atggctgcct cgatggctag gctcaggggtg  169260 tccaggtctt cggagggggt ctcggtgggc tgctcaaact gccccacgtc gtaggccttc   169320
gcggccgtct cgtagatagg cagcatgaac ccaccctggt tggtggagaa gatgcgcacc   169380
atgacctgtt tgggaaactt ttgcatcagg ggcaggcaca ggttgagagc gcccaacagg   169440
tccacggggg tggcagcgtg gatgatcatg ttgcggtaat cggaagaacg ggggcataat   169500
tggtgggtgt gcaattcttt gaggctccac gcggccttga cgccttcgtt acaagcatcg   169560
gccgtgcgct gcgccacttc gggtgggtgt gtcacaggca tggtgtgctc catgagaaag   169620
ggagtggaga gggccaggtt gcacatggtg cccaggcgac accgcaccgc atccacctca   169680
ctcttcacct catgattgcg ggtgtagatg atctggatgc ccttgttgtt cacctgcatg   169740
gttttgcaag ctttgatggc ctcatctaac acctggtgca tactgggaat catgaagggc   169800
aggttcttgt attcaagaga gcgattggtg ttgcggaaca tgcggctcac ctcgtcaatc   169860
ttgacgcgac cccgccgagt ctgcacgttg ggtgtgcaga aggggggtgtt cttatctttc  169920 atgatattgc gcaccttctc gttgtccaac tcggagatgc gttttgctctt cttcttgcgg   169980 ggtccggtgc tcgccccgcc gctgctctga tggccgcagc tcagcagaga ggaggaggcc   170040
gcgccaccaa aaccgccgcg cccatggtgg ctcgaggtca cggatgctcc tccgccactg   170100
ctgcatttca tctcctcgga ctcactctcc gagtccgaag ccgaactgca ggaggaggaa   170160
gacgaagagg aactatcttc atcgggccgg cccaagggat cgggaagagg agggtggttc   170220
atctgggaga gcgggtgcgt gggagaggtc actcgcggcg tgccgctgcc ggtggaaggg   170280
gaagacgcgg tagcaccgcg ggtttcgact tcttcaccct gttcttcctc gctatcagag   170340
atcacgatac agccggcggt atcgataatc ttgttgcggt actggatggt aaagtcggcc   170400
tcgggcttga tgtcttcctg tttgatgagg aggggcagca tgataggcgc gggaggcacg   170460
ggcggtttaa taatcaccctt gaaaggacgc gtggttttgc gcggtttctt acgcgggctg   170520
agctcgggag tagcggatgc cccgggggaga ggagtgttag taaccgcgac gctggtgggg  170580
gtcggcttgt taagaggggc gctgctaacg ctgcaagagt gggttgtcag cgtgtggccg   170640
gtgctactgg aatcgatacc ggcatgattg acagcctggg cgaggatgtc acctgatggt   170700
gataagaaga cacgggagac ttagtacggt ttcacaggcg taacacgttt attgagtagg   170760
attacagagt ataacataga gtataatata gagtatacaa tagtgacgtg ggatccataa   170820
cagtaactga tatatataca atagtttact ggtcagcctt gcttctagtc accataggt    170880 gggtgctctt gcctccagag gtggtgggtt cctcagcacc atcctcttct tcctctgagg   170940
caacttcccc tatctcagac actggctcag acttgacaga cacagtgtcc tcccgctcct   171000
```

```
cctgagcacc ctccccctgt tcctcatcac tctgctcact ttcttcctga tcactgttct   171060
cagccacaat cactgaggac agagggatag tggcgggtac aggggactct gggggtgaca   171120
ccagagaatc agaggagcta gcaccagcgg tggccaaagt gtaggctgca atagcatctt   171180
cctcatctga ctcctcagcg atggcccgta ggtcatccac actaggagag cagactctca   171240
gaggatcggc ccccagaatg tactgggcaa agaccttcat gcagatctcc tcaatgcggc   171300
gcttcatgac attgataacc tcaggcttgg ttatcagagg ccgcttggcc agcatcacac   171360
tagtctcctc taagatatag cagcacagca cccgacaaaa ctcacttaag agagagatgg   171420
acccgtacat ggtcatcatg caagcgtcac tggtgacctt gtactcatta cacatggttt   171480
ccacacatgt agtgaggata tccataaata tgtgatcaat gtgcgtgagc accttgtctc   171540
tctcctcatc caaaatctta aagattttct gggcataagc tataatctca tcaggggagc   171600
actgaggcaa gttctgcaat gccgccatgg cctgactgca gccattggtg gtcttaggga   171660
aggctgagtt cttggtaaag aactctatat tcctgtagca catataaatc attttttctct  171720 taagttcatc cttcttagca cgggcctag ccttcagtgc accccctaac ttgttagcgg    171780 cgccttggt cacatcatgc agctccttaa tacaagccat ccacatctcc cgcttatcct    171840
cgggtacaat gtagttctca tacatgctct gcatagttag cccaatacac ttcatctcct   171900
cgaaaggctc atgaacctta tctaagatat ctaaggcatt ctgcaaacat cccccatca    171960 tattaaaggc gccagtgaat ttctcttccg tctgggtata ttttttcagc atgtgctcct   172020
tgattctatg ccgcaccatg tccactcgaa ccttaatctg tttgactgta gaggaggata   172080
acaacacata taagtatccg tcctcctgac tcatttatcg ctatctcgat gccccgctca   172140
catgcaagag ttaatcttca ctctatctga catacacaag taaatccacg tcccatgcag   172200
gttagtatat atcacataca tgtcaacaga cttaccgagt tctgccagga catcttttc    172260 ggggttctcg ttgcaatcct cggtcacttg ttcaaaggtt ttgagagatt cttcggccaa   172320
ttctgggaac agcgggtctc ccaggctcag ctgactgtta acctccttcc ttaacatagt   172380
ctgcaggaac gtcgtggcct tggtcacggg tgtctcgggc ctaaacacat gataaacaaa   172440
gtcataagca catgggtcac atacaggaaa tatgtatata acattaaaga tataacttt    172500 tattaaaaaa aggggaacac aagtcccgac acgtaccgtg gcaccttgga ggaagggccc   172560
tcgtcaggat tatcagggtc catctttctc ttggcagagg actccatcgt gtcaaggacg   172620
gtgactgcag aaaagaccca tggaaaggaa cagtctgtta gtctgtcagc tattatgtct   172680
ggtggcgcgc gcggcagcaa cgagtactgc tcagactaca ctgccctcca ccgttaacag   172740
caccgcaaca ggagttacct ctgactctca acagaacaca actcagctgc ctgcttcttc   172800
tgctgctgct gccttaaatc ttccatctgc gtcagcggtg caagcccatt ccccgagctc   172860
attttcagac acatacccta ccgccacggc cttgtgcggc acactggtgg tggtgggcat   172920
cgtgctgtgc ctaagtctgg cctccactgt taggagcaag gagctgccga gcgaccatga   172980
gccgctggag gcatgggagc agggctcgga tgtagaagct ccaccgctac cggagaagag   173040
cccatgtccg gaacacgtac ccgagattcg cgtggagatc ccacgctatg tttaataaaa   173100
actgcgggca ctgggacgg tggtgttgta tatgtgaatt tgtaaataat aaatgagacc    173160
ccatcctgta aaaatacaga gtccgtgtca gtctctgaag gacagagtat tggcatatag   173220
ccaataaaga tagttgtggc aaagagccat gttatggatt agtaatggaa agtatcgtca   173280
ccaatagggg agtggtcaat aatggtcaat aacccacacc tataggctaa gctataccat   173340
cacctatagc ataaggaagc ggggtgtat agaccccaag ccaaaaacag tatagcatgc    173400
```

-continued

```
ataagaagcc aaggggggtgg gcctatagag tctataggcg gtacttacgt cactcttggc   173460
acggggaatc cgcgttccaa tgcaccgttc ccggccgcgg aggctggatc ggtcccggtg   173520
tcttctatgg aggtcaaaac agcgtggatg gcgtctccag gcgatctgac ggttcactaa   173580
acgagctctg cttatataga cctcccatcg tacacgccta ccgcccattt gcgtcaatgg   173640
ggcggagtta ttacgacatt ttggaaagtc ccgttgaatt tggtgccaaa acaaactccc   173700
attgacgtca atggggtgga gacttggaaa tccccgtgag tcaaaccgct atccacgccc   173760
attgatgtac tgccaaaacc gcatcaccat ggtaatagcg atgactaata cgtagatgta   173820
ctgccaagta ggaaagtccc gtaaggtcat gtactgggca taatgccagg cgggccattt   173880
accgtcattg acgtcaatag ggggcgtact tggcatatga tacacttgat gtactgccaa   173940
gtgggcagtt taccgtaaat actcctccca ttgacgtcaa tggaaagtcc ctattggcgt   174000
tactatggga acatacgtca ttattgacgt caatgggcgg gggtcgttgg gcggtcagcc   174060
aggcgggcca tttaccgtaa gttatgtaac gcggaactcc atatatgggc tatgaactaa   174120
tgaccccgta attgattact attaataact agtcaataat caatgtcacc atggcggtca   174180
tattggacat gagccaatat aaatgtacat attatgatat ggatacaacg tatgcaatgg   174240
ccattagcca atattgattt atgctatata accaatgact aatatggcta atggccaata   174300
ttgattcaat gtatatatcg atatggattg gccatgtgcc aacttgatgt cgcctctatc   174360
ggcgatatgg cctcatatcg tctgtcacct atatcgaaac tgcgatattt gcgacacaca   174420
gaatcgccca ggtcgccaaa gtcgtctatc gccatccccc gtaaacgata taagcgctat   174480
cgccagatat cgcgtatgcc caaaaatcac ttttggaaaa atggcgatat cagttacaca   174540
gagactcaca tcggcgacat tttcaatatg ccatattttc aaatatcgat ttttccaata   174600
tcgccatctc tatcggcgat aaacaccact atcgcgcgac atgaatttag tcggcgacag   174660
aaatctcaaa acgcgtattt cggacaaaca cacattttat tattcactgc agcatatagc   174720
ccattttagc gcggcacaca tccagccgtt tgtgtttctt aacgctctcc aggtactgat   174780
ccaggcccac gatccgggtt atcttgtcgt attccaggtt gatccatcga tagggaacgc   174840
tgccagcggc gcccagcagg tactgcgcct tgtcgttcac tttgccgcag cgtattcgcc   174900
cgtcagcttc gaggtataac ctacaacacg gaagggaagg ggggtacaaa acgtgaaatt   174960
agactttttt tttaatgatg tttgtccct ctctgtctta ctctcccata ggctgtaagg   175020
ccctcgagga agagacttac ggattgtagt tgcagctcgt cagtttgttg tgtacgacct   175080
ggcgtgtcaa tgaatgggtc atggtggtga tgatcccgcg aatctcagcc gttttctcgg   175140
gactgtagca gacttcgccg tccggacacc gcagcctgtg gattcatgaa aatctactct   175200
ggcattcccg aggatcgtcg atggaacatg gctatcagaa acgtcgagag acagatccag   175260
acgcaccaca gaacgcagac aatcatgaaa atacgtacgc gacggtgaag cgattgcaca   175320
ttttgaaatc gtaacagcgt tccggcgggt ggttgacgtt tatgaattcg caacattctt   175380
ctgcgcgtac ccgcggcacg cggctgtgac ccagtagcaa ccacaacgtc gtcaagaacg   175440
gcgtcaggtc tttgggactc atgacgcgcg gttttcaaaa ttccctgcgc gcgcgacggg   175500
ctcaaacgat gagattggga tgggtgcaga aggtgtaagt ctggttattg gcctcggtga   175560
acgtcaatcg cacctgaaaa gacacgctgt agtcccggaa gacgtgggcc cagctctcca   175620
gtttcatcac acacatctga taacgtgtgc catcgttgac gacgaagcgt agcagcttgg   175680
tctgcttggg caccatgtgc gctccaaaaa tcttggcgtc ttccacgctg atctgcacgt   175740
```

-continued

```
ttccgtcgct cggtttcgaa gccgttcggg gcatccgttg gaggatggtc tggttgcgac   175800
cgctcagata ccagatcacc tttttcaccc aggtggagct tttctccacc aaggtctggc   175860
cttcccggtt gtacagcaga tacagggtct cgttgcgaca ctcgggaccc gttgataccc   175920
gctggaaccc cgagaattgc gaggggggacc gtgggggcga gggatagaga aaaggacagt   175980
aaaacgtcgc cgcgtcatgc ggtttggaat acgtcagttt agaccatggc ggggacggat   176040
tctggttcgc cgttagcgtc gaccacgaag acgccagaca gggcgttgcc caaaccgcgc   176100
acagaagcag gcagtgaaag tagtgacgaa gcagaagccg cagcatatta tttcccgtga   176160
cgcaggctag ttggcaaaga gccgcacgct gaactcgagg ctccgggcgt gcggcgccag   176220
cgaaccggcg gcgttgaacg tggtccttt gttggtgccg ccgcgacggt tctgacgtct   176280
aaagtcgctg atgagcaacg acacctcggt cacgttgatt ctgcaagcac aggttccgaa   176340
cgtcatttca caccccatgc ggttacctac ccgttacccg ttcgcccta ccttcccgtt    176400 gtcatacacc tttagcgcgt accctcacct cttgagcacg tcaaagttgt ccaagccgtg   176460
gctcgcatcg tagtggtagt tcaacgtgag gtccacgagc tgttccacat acttgtaacg   176520
ggtttggtcg ggcagcgcgc gagagcacgc gtcccagtaa tgcggtactc ggtaataatc   176580
gttttttcct gcggtctccc gctggcactg acccagcacc acggcgcaca gacaaacaga   176640
cagccacacc cgatacagcc gcatgttgca gactgagaaa gagagcttta ttatgagaca   176700
tcatacacat agtataggcg aggtaatggg gcggggaaag agttggaacc gaaagacaaa   176760
aaaaaaagcc tagtcgtact cgggatctct gagcgagacg gattgcgtag caactttcat   176820
tagtttggga atctgccagc tggtgctgtt ggaaggttct tccatttccg aggcggtcag   176880
ttcatcgtac accgagacgt agtacctgat ggggtcctcc tcattgtccg agaggtgaga   176940
ttcgatggtc aaaggcgagc ctctcccata attgggattc acgaacgacg tgtccaagtt   177000
gccatccttt ctgaaataga tgacgttctc aggatcatgt ttcatgcgct cgcgggccgc   177060
ggacgcctcc tcctcctcgt cccagtcccg agtttccaac cgctgataag ggctcgagga   177120
acaaaatccg gcggggatct gagaacctcg tcgggaaccg ctgccaaacg ggctgctgcc   177180
gccactatcg tccgtgtcgt ccaacaggtt gacggcctct tcgtcggcga aacgaaagcg   177240
gcccgggtgc ttgcaacacg aggagtaaac taccgcgatg agtaccgcta tgaagctgaa   177300
aatggaggtg cctgtcacaa tgtagaagag gatagccagc actttcatga tttcgtcatt   177360
gcgcgcgtcg tgaacggaag attcgcgggc ggtggtcatg ttggtttcgg ttgtaggttc   177420
gctactcgta gtgctctcga cggtatttct gctgctggtg ctagtaggga cgtttgtgct   177480
gctggtcata tttgtagcgt cgctgaagtc catgtgaagc agcaacccga acgcgaccag   177540
gaccaggaat gttgcgcgaa ggagaccccg cggggccggc attcttgaga cgtgggcgacg   177600 tggatttctt gttatgtccg cgaacgacgt gtgacgagga cgtggtttcc gcaagcctct   177660
accgacgccg cgacaccagg taggttatga aaacgcgagc ccatatcgcc gccatcattg   177720
taatcagcaa tgtgttgagg tactgcacga tgaatctgtc tagtgacacc agccaaccct   177780
ctgcttttgc gggcaagcgc gctttcggtg acagggtgta tcgtacgtag ccgcgggtca   177840
ggcgcgcgtt gtagcggtac acgcagaaat ctatccacag gccaacgccc ggctgtagct   177900
tcggatggtg gataatagcg cggtgacgta cgccgcgggg ctttagaatc tccacctgta   177960
aggccatctc ctccaggtag tgggtctgac tgcgacgcag cgtccagttc atgtaaaagt   178020
cggtctcgcc gtgtccggcc acgaagaggc tgcttactaa atcgggcgcc agagctaggt   178080
caggcgtatc aaattccact gccaggcgac ctgattctaa cggttccacg atccgggaga   178140
```

```
gcgtttctag atatagagca aagcgtacca cgtctacctg cggtgtaaaa aactgttgtg  178200
ggcgttcacc gtcgttgacc acgtaggcca cgtagaggcc aacatttttcc accacgggtt  178260 ctagctgcag gcggcacgta aagcttagaa acgacggctg tacggtttgg ttcccgtgaa  178320
gctgaagcgt cacttccttg ccggggctca ccgtgctgta acgtcgcacc gagtcggtca  178380
tctgctccag atcggtagac cagaaaggcg tgcaatgcat actgtcccag tcgcgacaca  178440
cagcccagcc tagctcggtg aagggtcgac gcacacccga aaaagtgtgc ttgaagacca  178500
gggggtcgcc tcggtagctc agtagccgaa catgcacata gtcgcggcta gcgttgacag  178560
acggcccgtg gagggccagt aggacgagcg tgaacagcaa gcgcaacatg ctgcgcgggt  178620
taggaaatgc ggcgtgccgg ccaccgcccg actcataaac gctaccagca tgacgtctca  178680
gatcacacaa gtgacgagga gcgtaccgca aatcactagg gaaaaggcca gcagagcccg  178740
atagtcttgc tcttcgcgaa cgatctcgtc cggttcctcg cagtcttcgt ggtccacaga  178800
agatgaggag caggattctt cgttaatctc tgccaggata ctagtgctat accacaccag  178860
agcgctcagc gtgcccaggg ctaccgcacg gtaaaatagg gacatgatca ccagcgcagt  178920
ctaaagtagt ggtaattaag tttcttggcg tatttccaga gaaaggcttt gtaggccgta  178980
gggactggcc aggcaccgaa ctcaatattg gtagacacta cgtcgtaaat gcgttgttcc  179040
tcatctaaga ttaaccgaaa aaatagccgg ttgatgtgac ggcgcacggc ttgcgcgtta  179100
ggattgagac acttggtgcc cttgtccttt aaaatagcca gcacttcctg acgattgcag  179160
ctttcgctcg ctgcgattgg cttaagcagt tgagttccga ctggcagggt attcaacaga  179220
atttggttgt tgcaacggca gcgcctgtcg taatcttcta gttctaaaac atggacggct  179280
aggggacata tggtaagtaa catatatgcg attaatgaca ggtatcgtac cgataacaga  179340
ttgatatgcg agtttgaaac cggatggtgc aaccatgtta gtaccatatt aaacacatac  179400
tgtaatattt tgttttaacg aacttgtctg tttgaaaaca tacattaaat attatcctct  179460
aacacctatc aaggttatat ttattcgtct cggttctggt gatttcgtta tgttaacatt  179520
ataccaccta ttatcgttgc gtttgtctaa ccattttgag aagaggtgat cgggcgataa  179580
acatactcca tgtccaggcg gcttccttcc gtctggatac aataaatgtt cattttttatc  179640 gcatccgggc cctctgggat cgcgatgaag ccaataatta cccaatataa ttttattagg  179700
cggccatttt ctatgaagac atctgcagcg taattctgtt ccattcacct cataatgata  179760
cacatatgct aaaaaaataa tcaacgcacc aaaaattaat cgcattataa ttttattatc  179820
tacgtcacta ccagtaattc gtaatatccg gtattcccgg aaaatcactc aaaactgcgt  179880
ccatgacaca tcaattcccg ataagtaccc cccttttgaaa tcggatcccc ccacatacca  179940
atcaatcaca caacacacag gtttaaaaat cgatcacacg tcaattaggt ttcaaaatcg  180000
atactgttta ttatcaggaa tctagactaa ttctacaatg acagctctga atttctctct  180060
tgtctttctt gtcaggttct catcatcagt catcacttcc acccatcgag gagtcatcgt  180120
cgctccaaaa tcctttgggg tcgctagttg gaaaagtctc tgacacgatc caggcacccc  180180
gcacccagtc cgactgatct agcttgcgga gcatctcaac aggcatgagc tgcagggcca  180240
cggctgtcac ggcactgtat cgatgtaaca ctagggactt tctttgcgat gtagccatca  180300
acacggcgta tgccccatag ttcgcgtgat acgacgcatg atgggttaaa cgttcccatc  180360
cggcagtgcc gtctcgggtc cgtgcacaca acagctgcac agcgttatga tgcttaaaat  180420
taaccataac gctgggacta ctgatgaagg agtagtaatg agccaggacg ccgtacatcg  180480
```

```
aaggcaacaa gaaagagtga cagcacgata gcaccgggct cttatgtagg cgacagctta   180540
ttttccctga cgtcggcaaa aagtacctaa attccccaca gatattcaga cacggttccg   180600
taaagtgctt cttttttag tgcaggaatt ggaaaaaata ataaaaaata tgaacagctc    180660
atctgtaatt atctgtgtga cttcatcgta ccgtgatgta aaacaacaa caggaagctt    180720 acagggtgcg gtagaaaaat ttgccgattg tgcaacactg ttggcatctc tcactccgat   180780
aggcggctat aagatagaga attaaaagta tgatacccac aagaaagatg aagagggaca   180840
accaggctag agtatgacga ccgcttttcc tttgtttgac ggttacatgt gcggtatgat   180900
tttgctgtcg ttgcttgtga tgttggacac ctggagtgga aaacgacgta tgattcttag   180960
atgcgcatat ggtgttatta gtggaagtgc agttacgaac cgtgatctga gtgtcgttac   181020
attgagtaca attagtacag ttgtaaagcc ctgtgagata agtaccgttt gggcacagtg   181080
tacacgttat gccactattc tctgtacaca cttttgtaac ttttgtcct gatccgcatg    181140 gcggcaaca ttgattaccc agcttcacct catcgggctt acacatttta cttcccccaa    181200
gctgtagtaa aaacataccg aagcagatga gcatcaccag aggcttcatg cctcctaccg   181260
gaagaataaa aataactcat agggccgaac ggtgtcatcc tctccgcggt ttgtaatacg   181320
agattgcaaa cgtaaataaa tgacataact tcactaacac gcatactaca aagtccacct   181380
acgacgctga aagttcttcc aggacagaac aggatagtca gccatcttca cagtctacct   181440
cttaggccgt atccaggagc ataggtaatc agtttccagc cacagtacag cgagcccagg   181500
aaaccgcaca cggtccctgc cgggaacacg taccaccaca tcgattcgtc gtgccgtaga   181560
accgtagagt tttccgaact tttatacacg ccggtggcgt tagggccgtg tgtgctgctg   181620
tgattggagg ttttgtgagc taggtaacag ctgtgatttc acctgtcgcc aacactgaca   181680
gcgattaccc aggtggagca caatcacata gctgatggac gttggttgat ccgttgattc   181740
ccatggacat tttaacggcg acagtacagc tcccgttaaa cattagaata atagacgtta   181800
gtggataaca gcatgttatt cgcccaagtg tgatcgtggt tatacacttt cttgtttttt   181860
gctcatatgc tgtaaggtgt tcgaggatcg tggggagtat atgtgttgaa tcggaatcat   181920
gtttactgac cgcgccatac ttcgtatacg aacctaaccg gcgtaaagtg ttttccgata   181980
tataaactgg cgcctattgt ggctgtagcg cccataggta tggcgtatac ccacggtgat   182040
gttgtgttat tcgtttttg tgataaaacg tagcttatgt ttaacgtgtg ttccgtcacg    182100
ttatgtgtgt cgttaaaaga cggcgcctgt acagtatggc tttgagttgt atcttgaatt   182160
gttattgcat ctggaggtgt tgtgtacaga gtggttgttg cgtgttgagg tgttgttacg   182220
ttttgaggca cagttgcggt gtacacgggc tccaaggtgt agttacggag tctttctatg   182280
caggtagtgt tgagatattt ttgaatgctg gttatgttcg attctgtgag gttaaagtgt   182340
gtactattta tgacggtgta atttagacgg tcttgccatc ccgaggatat tagtgttagg   182400
taattcgtgt tgttcacgtt tgcttgatat gtataggtag gtgtactgtt tgtgaggtcg   182460
caagtgtgat tttcttgcag agattttatc catcttgtgt gaaaatattg agatacgcga   182520
tgaatgtttt cgctatctat attataaagc gtttcagtgt caccctagggg ttgtttgttg   182580 taacttttat tttggaccct gggtgtgaac catgattcca atgtttgtat agtaaggtgt   182640
cctactaata aagacgaact gattcctacc gtaatgttat accgcacacc cagggtgccg   182700
tttacaaaca cggaaatgtt tccgttacaa accacgttgg cagatgaatt agattccagg   182760
tggtaacgat aggataatga ccgttcgctc ccaacggatg acacaaagta tccgaataac   182820
caacacgccc attcaatccg catatttaa tcacactatt cacacctcac acactgcatt    182880
```

```
ttttaacatc ttattttttt attttatgcg tgttctcacc tcttcatctt tttaacaccg    182940
gggtaactat cgtaagtcgg taggcgtcga tagccctcac cacctcgtcg tccccttccc    183000
ggcgtggggc accagcgtcc acagcactgc aggtaacaca ggtagcatag gaaacatacg    183060
gtgaaaatac tccaaaatcc caaaaatgcc gcgattcccc gagtggccca gggagacatc    183120
ccggtgtcta tgtcggccgg cggtgctggc gtcaccggta aaaatttcgg cgggtgtggc    183180
tgcgaacggt agcagtcgcc ggggagccgg taacgctgta tcactgtcca acagcggtcg    183240
ggttcctcgt ccggacatgc gggtttccag caatcctcgg cgtcggcgcg tccgatatag    183300
aagtagttgc gctgaaaacc gcggtacatc ccgcagtcgt gattccgtag acgccagggc    183360
gtcggcgacc agatctggtc tcccagcgag tagcgaccta acgccggcgt gcagcaaggt    183420
tcgtcgggcc ggctgagcgt ctccagttgc gtgagaatta cgaagcgttg catgatgagg    183480
ccgtggctgt agttgcgcag cacgcattcg tacatgccgg ccgtgtccgt cgatacgttg    183540
aaagtcagcg agaatatttg gccgagatgc aattgcgaga aattccaagt ggcgtacggc    183600
aggcggtact ggagtccgtt catcagccga tggcctttga cggcgtccag gatgagctcg    183660
tcgctgccgt cgtgggaacg acagaaacgt gcgcgaatgg agaccatggg ccaggagtgt    183720
gtcatgaccg tgcaggggat ggtaacttgc tctccctcgg cgaccaacac cggcgccggc    183780
gacgtggtct cataattctc ggcccacatc ttttcggcaa tgtcagcggt ggcgaagggg    183840
aacgaagagg aagaatattc gaggagtcgc gggcagctca acagcaccca gaacagccac    183900
ggcagagttc ggagcgactc ccggcggcac atgatgattc tttccttccc tttttcgcag    183960
agacgctgcg cgcctgctcc tgctccgtgt gtcggccgct caaacgtcgg gccggcgtgg    184020
tggtgaccac cgtgcgacgc agcttctcgc ccgggatgcc cgcgactgag cgtccggttt    184080
ttttgcaggt cttttttgct gcctcctcct cgccgtcgcc gtcgcggccg acgtggtgga    184140
ccagcaccgc gcaggaactc tcgcgtcgcc ggcggtacgc gacctgtctc attgctacct    184200
cggatgttta agaaggaacg ttcatctgcg tcacagggtc tgatgaagct gccaagagtc    184260
gtggctgtgg cgcagcgcgt tctgtacggc gcgtttcacc gctttctgca tggccgctac    184320
cacgtcgggg gggagcggct ccggcggaag ctcgatgagc agttgctgcg agtctcggcg    184380
ctcggcgtcc gccgtttcgt cggacgtggc gtagaaaacc gaggtggtcg cccagtcgtc    184440
cacgctgtcg acggcctctg tcagtgccgg gttgtcaaaa ccgccatcgg acgcgggtga    184500
taaaagaacg tacgatgaca cgctgttagt acgattctcg tcgtcgctct gggaacgacg    184560
tgatggacga cggtagatga cctcgtcttg ccacgcgtcg aagcgatcgc agcagcgctg    184620
gatccaagcg cagcgaagca gcttacggaa cacgtcgttg ttccaaaagt agagcataaa    184680
gagaaagaaa agtagcgtaa cgatgaagcc gaaaacgacg agggtcggca gggcactacc    184740
gccgctgccg ttttttgtgt cgtgcgggtg cacggtggta gtggcgttag tctgagctgg    184800
ggtcatgaca agtctgaaga gatgagagcg tgggtgctca tcagggacag ttgaggtctc    184860
tccctaccga agccttagcc tctacggtgt tttatgatca acgtgtctac gaacgtcatt    184920
gtgaaagtga cgtctcaggc tttccgaaac cgcgtcagat tcaacgtggg tttcggttta    184980
gcctgcgtca ccgaggcgga ggtggaaatg agccgtcctg tggggagtg tacgaccctg    185040 tagtgcccat gggtaacgtc gcgtcggaag aagtgaatgc ggcattggtg tacgcgtggg    185100
ttgttttgct ctctgactcg gaggagttgc cgcagcagct gcagatttta cgtactagcc    185160
aaaagcagca aaagcagcag gtaaataaga gaaggagtcc agataatgtc cagccgctag    185220
```

```
cggcaaacag cgcaagttgc gcgactgtcc aattactacc accaaaactc tcaacacatt  185280
gaatcgacgc tgaggttggt gttgcagtgc tgttgctact agtggatgaa gacgaagtag  185340
attgactgga attagagctg gtacctgtag tggtttcact tgccgatgcg gcaagtgcaa  185400
ataaaactaa tatccacagc atgttcgtta ctatataatt gatatacgaa cccgtttgtc  185460
gtaacaatca gcgttatata cgctgtatcg gcatcgtttt accggaaagt ttatcgtaat  185520
gtaacccgcg ttgtgtacat tcgtactgaa agggaacccc cggtgatgtg cacattatac  185580
tctttcattc tggggtttcc caatgacgta aaaatttcca ctatacaata aaattacgga  185640
atcatgtgaa aagtgtgctt tttattaaca gagcagaggg tttacagtag atatatgttt  185700
gccagggcca ctgttttcta acaccgatca ccgccaccat taccacccgt tgaactccac  185760
acccgggagc cgcctgatcg ccagggactc ctcaccgtcc atcgtccgaa caagctcccg  185820
ccaccgatgc tgccaccatc accgagagaa agaaccgctt gctgcagata cgcttgggct  185880
cgcctccgtg cggacgccgt ttcgtgcaga cgctgagtag atcgagcaga gaatgtcaaa  185940
acgacattac cgcgatccgc tcccctcttt tttctttttc tcattcacgt gtattcttga  186000
tgataatgta ccatggctac ggtggtgaac tgcgtcgcgg atcccgtcac gggtttcaac  186060
agatcgacgt cggtcagcgg cgccgtcacc gccatgtccg gcggaggcac gctgtttctc  186120
tggttagcga cgtggaccga cgacgaagac gatgaacccg cgcggcggtc tgttatccgc  186180
gacgacgcgt agctgcactg ggaagacact tcctcccaac ggaccaagat ctcatcgggc  186240
cgttcggaga aacggtatcg tctgtccgac tcccgccgta cggcgccgag gcccagcgac  186300
gacaggtccg cgaaccggcg ctcgtattcc ccgtacagct cgcaacagcg gatcagccag  186360
cggtagctca aaaacatgcg caccagtttg aaggtgtcgt gccaatggta agctagatag  186420
cagagaatgg ccacgatcag cacgagcatc acgccgatga tgggtaaccc gacgttcagc  186480
ggcagatcgt ccatggtgac cgtcctctgt ccggatctac gtcccagtct ctctcttttg  186540
tacagcactc gcgcgggaac ggccccctca accctcttac gtagcgggag atacggcgtt  186600
ctcccgcggg ccacttactt gcacggtcgc ttgaacggcg gcttggactg ccacatgcac  186660
cgcatccatc catttcggca gcagcgcgtt cgacgatgtc gtacgagtcg cggatgatgt  186720
taccccgcca gcacctccgc cggcaaccgc gtcgtcgttg ctatcgtcgc cggtttcggg  186780
cgatgacagc gccggcggcg cgggtctcgt ctcgtccacc atttccaccg tgtcgaagcg  186840
acagccgctg ccgtagtaca tagctccgtt caacggccgg cgggccgggt cgccgagttc  186900
cgggtcgggc acatccatgg ctcgccgtct ccttcttttgc cgctcgtggt gccgacggca  186960
cttctcggga taatgacagc cgcaaaatag atcgtggagc atgtctcgcc aactgtcctg  187020
gtgataatat cttaagtacg cgatgagcgc gccgatggcc ataatcataa gcgtaagcaa  187080
aacggcacag ataacgtgaa acaccgcggt catccaagtc gggcggcgtc ggggacgcgg  187140
tgggtcggtt tctcttacgc cggcgtcact cagccaccac acccgtagcc gacattccca  187200
gaatcggtga atgcgactca aggcctttcg acgccgccat ttatttccaa cgtccaagtc  187260
ccacgtcatt tctggcatct ccacgcccttt gactgacata ctctctttct ctctcttagc  187320
tgcggtgaaa aagagggaag gcgtgtgctg ctatacaact gtacaacgga cgcgctcgct  187380
ctttcggtct caggtcatct gcatcgactc ggcgtccttc atgacgctct gcaccgcctt  187440
ttccaacagt tcctcgatgt ccgaccatcg aggaggcggg gctaactcgg aaaccgacac  187500
gataggcagc gtggtcggct ccgttggtgt gcggggtcgg ggacagggac acgagagtcc  187560
caccttcgag agattctcca gcccgacggt gcgcggcagt ctcggattcc gcggcggctt  187620
```

```
ttgcggcgtc ggcgttttcg ggaagggcct gggcgtcacc ggcggtgtcc agccgaccgg    187680
cttgggtttc gtgggcggcg gtgttttctt ggtgagcggc gtgctcaggt tcttacgcgg    187740
cgcgggtatc ggcgtcgggg gcctgtgcga cgacagccgc gtggtggggg cccggaccgg    187800
cggcgtaggc ggccgcttct tgcgcccggg cggcggaggt ggcttccagg atggtggcgg    187860
ctgatgcagc accgtgtcga cgctggtcga ggacgacaaa gagctcgacg aggaacaatg    187920
cgacggagat cggccgatgc tggttggcgt tcccggagtg gatacgtcgg ggatctcgaa    187980
ccgcgccgga ggaaactcgg gtttatctat cggcagacca tcctctccta tgtagagcga    188040
cgtacaccgc ggcacctgcg gcgtcggcgg gtgggtggcc accgcatga gccccagttc    188100 cagatccagc ggctcgacga cgtcttcttt cggattgcga tagcagcacg cgcaggcacc    188160
acgcttatca gaagcagcac ccgggagccg gcctcgcgac gaagtctcgt cggatcgctt    188220
gcggcctcgg cgctgggtaa ataaggaaat ggccaggacc agggaagcca gtccggtacc    188280
gccgaggagc ccgacgccga ccacagcca caccatgatc ttctctcctg cttggaatct    188340
caaactccgt gtcgggaagg gccggtgtac ggacatttat gccttggatt tctggaaacg    188400 tcatttttg gcaaggaatg tgtttattgt ccaaacactg aggaaggaga tgtgggccaa    188460
gtcggaaaat tccttatcac accggggcg ggttacgttc cggtctgatg ctgctgctgt    188520
tgttgtagag ccgcggccac ggccgtctgc acggcagctt gtaccgcctc ggccacgccg    188580
ggtggcatct gcggcatggc ggggggaggc gcgtcgggcg gaccgccggg catcgccgtc    188640
ggctgtgacg gtggttgtga actcaccgtc ggctcgcacg gaggtttgtt cttcggtcta    188700 ccctcggtt tgtctttcgc cctacctttc ttcggtttgg gttccgatgt cggtgttggc    188760
ggctgcggtg ggatgacggg ctggtgggac tcctccgacg gcgggggac gaacaccgtc    188820 ggcgccgaaa ccgggggact ctcgactatc tcgcagatca ccctgtcagg atcgtcgccg    188880
tgcccgggac gccgtcgatg accgtattgg accatgtcgt aaatcatcgt ctccttgtaa    188940
cacgctgaac agcagcggct gcaggggccc gagatgcatt tacagctgca cttacagctg    189000
cagctgcagt agcgcaccca tcggcaagtt aaaatgtcga ttatggaatc tttgaaaaat    189060
tcccggtagc ggatgaggta cgcgcagagg aaaatcatga aaacggaaca gacgaccaca    189120
gccgcgatgc caggtccaga aaaaatattc gctgatgaac ccgccaaaca ccaaattccc    189180
aaggccgcgc atatcatcca gatcacaatg atcgcgggga cgccccattg gcattggcac    189240
gaaggatctt gcacatcgca acccatcgct actgcgttct cccacaaacg ccatcgcact    189300
atttatccct acagcggctg ccgagtcacg tccgccggcg cccatcggcc gcggcgatct    189360
cctagtaaca ctcgtccgac acttccacca tctccagctc ggccggcggt tcggcatcct    189420
ccaccagcgg cgtcgtctca tctttgccgc agcagcggac gcacaccttc tccaggcaga    189480
acgccaccag ctgccgccga acgtaccaca ggtacacgtg cagacctgcg aacaggacta    189540
cggaggtcat gaccaccacg acgcacacgg gaatccaagg atcgagattg tcgctggaac    189600
tcatggctat cgccaccgac gtgcccgcgt ctgtctcacc gccgctcgcc cgatgtcgca    189660
cggcttgtta tacgctagcc cgtcgccgcc tcggggcacg gtgccctcct acccacgtaa    189720
cttcctccgt gacttaaagt cgcgtgtggt agatctcctg ctccgtggac gaaccgttcg    189780
gcaggatagc ggttaaggat tcggtgctaa ggccgtgtcg ccaacgtcga atgctacgtt    189840
gcaatagctt cgacggacgg ccatcctccc tctcatcgca ataataaaac accagcagcg    189900
cacacgacgc gatcacggtg accccatga ctagacccac gcagatagcc agcccgcta    189960
```

```
gcgtatccag cgccatcccg ttcgctcccg tcgtcgtctc ctgaacaaag caactccgca  190020
gtccccgttt tcaaccgttt tcaaccgttt ttgtttcctt ctccgcgact agatgttaac  190080
gcccgcggtc tttccggccg tgctctacct cctggcgctt gtcgtctggg ttgagatgtt  190140
ctgcctcgtc gccgtagccg tcgtcgagcg cgagatcgcc tgggcgctgc tgctgcggat  190200
gctggtcgtt ggcttgatgg tggaagtcgg cgccgccgcc gcttggacct tcgtgcgttg  190260
cctcgcctac cagcgctcct ttcccgtgct tacagccttc ccctgaaacc cgcgtcaatc  190320
gactgtcccg aaaacgccgg cgttaacaca ggaaaaaaaa accacgcagg aaccgcgtag  190380
gaaccacgcg gaacatggga cactatctgg aaatcctgtt gaacgtcatc gtcttcactc  190440
tgctgctcgg cgtcatggtc agcatcgccg cctggtactt cacgtgaacc accgtcgtcc  190500
cggtttaaaa accatcatcg acggccgtta taaagccacc cggacacgtg ccgcggcact  190560
tgcctacggc gctgctccag ggaaactcct cttccttctg ctcttcctcc ttcaccgcag  190620
ggaccgtctc cctcgaccag ggacccgccg aagcaaccgc cggaacaacc tggaggaggc  190680
gcggcatgac ggcacccaag tgtgttacga ccactactta tctggtcaag accaaggaac  190740
agccctggtg gcccgacaac gccatcagga gatggtggat cagcgttgcc atcgtcatct  190800
tcatcggagt ctgtctggtg gccctgatgt actttacgca gcagcaggca cgcaacggga  190860
gcggcagcgg ctagataagt ctctggcggc tacagctcca agcgccgtag ccggcccgcc  190920
tgccgatcgc gacgtcgtgg accatcgaac agagactcac gcgtacgaga ccccgaggta  190980
cgccacgcgg tgcctaacgc ggtataccac acccgtacgg tctgcagtgc ggcgtacaac  191040
gtgtggaaaa cgcgttgcgt cgcagagtca gccacgtccc cgtcttgtcg ctccccaatc  191100
ggctcccgca caccccccgc ggcacccaga gggcgggtga gccaagtatt cttaaggccg  191160
ttctctgttc catatcccat aaattgttta ttccggagct cgttggcgcg gaaatagccg  191220 gataaggga gcaacaaccg tcggcgaaag ccgtcccgct cattcagtcc gggtttcgcg  191280
tctagtcgga ggtgtgaccg ttggccaacg gaacggcgtt tcacgatcaa aatcgtatcg  191340
ggtagtgtag gagacgtcgg cggtgcagaa tgcgactcgc ggcgtagctc gccgtcgcta  191400
tgcggctcgt cgccgtgtgg cgcggcctgg ccggctgtct cgcgccagat ctgttggcct  191460
tttgggtcct ctggctgctg ctgcgtgtgt gctttggcag acgcggtggc aatttgcggt  191520
ctgcggtaag tgaggatatc gccgagcaag cgcatttgcg gcacgtgggc ggcacgcgtg  191580
ttattgttcg ttcgttgcca gatagcaagt gctgtcgaca gcagacgttg tgggcggttg  191640
gtgtattttt gcgggttgcg gtgaaagtcg gcagccggcg tcttgtgaag tatcttaacc  191700
atctgtgttg cttttttgcag cgtccagaaa agcgacgcga ctttggggat ggcctcgtgc  191760
tcaccttcgc ggagagcgcc gccggacctg ctcgtcagca gcgagctacg cagacggaat  191820
atctggagga gagttacgtg tgtcacaggg gagcgcgggt ctccggcggt aacgacggcg  191880
gtatcgtcga cacgtgtgcg gcctgctgtg ctctgcggaa aagcgccggt ctcggagacc  191940
gtggacgaaa aagagaacgc agcagctacc gctggcggcg gcgtcgttaa tgctgccgtt  192000
gatgatcgac gttgtgagta ctcggaaaca gcggtgaggc agaagctcgg ttctccaggg  192060
aacgaccgtc gatgcgtggt aggcgcagca ggtgaggttg gggcggacaa cgtgttgcgg  192120
atcgtggcga gaacgtcgtc ctccccttct tcaccgcccc acccaccctc ggttggtgtt  192180 tcttttttcct tgtgttctgc agatagttcc acggacagcg acggcaagtc cataagcacc  192240
ggtgtgcaag tggtggagca cgacgaagat atcaccgcgc cgcagagttt gtggtgcacg  192300
gcgttcaagg aagccctgtg ggatgtggcc ctgctggaag tgccgcgttg ggtgtggcag  192360
```

```
ggctggaaga ggtggcgcaa cagcgagtcc gggcgtcgat ggagtgctgg gtctgcgtcg    192420
gcttccagct tgtctgactt ggcgggcgag gccgtgggag aattggtggg ctcgctcgtc    192480
gcgtacgtca tcctcgaacg gctgtggttg gcggcccgag gctgggtgtg cgaaacgggt    192540
gtgcaagccg aggaggccat ggcgcgacgg cgacagcgca tgctgtggcg gatgttctct    192600
cgtggaggcg acggcgaatg cagcacacgg tgtgcgatgg agatggcgtg cgaggaagaa    192660
agcgccgtgt tgtgagccga cggcgcggga cgcgggccgg cgcagcgcgt gggccacgtg    192720
tggtggcagg cggcgtcgtc cgcttgcggc cgtcgccgcg ccgcacagac gcaaacacat    192780
gtcgccgtca agagaaacag tctgagcata gccgtctgca gcggtccgcg tgtagaagcg    192840
gggggagaac gacgttaata aagaatagcg gcggtgccga tagggcgacc gctgaagcga    192900
gctgcgtgtg cgtgcctgtt ttgttccccg tcgccgccga aaagctacgc gcggccccg    192960 tccctagcct tgagcgcgcc acagcacgcc gcaaactcgg cgtcgcgctt acgtcccgca    193020
aacccccctc agcctcgtcc cgccaaccaa taccgtggca cgcagtgcca tagcgccgcg    193080
cgtcaaggcg cttacacccc cctcagcccg gtcccgcacc ggcgtcggtc tgggtgtggc    193140
gggggtgcgg ctgggtgggt gtgtgccggg tgcggctggg tgtggcgggt gtgtcgcggg    193200
tgtgtcggct ggctgtgtgg cgggcgcgtg ccgggtgtgt cgcgggcgtg tgccgggtgt    193260
gtcgcgggtg tgtcaggggt gtgtcggcgg ggtgtgcgcg cggccagatg gaagcagtgt    193320
gccccggggc ccgcgatccc ccccccgcc ccggcgcggg cgcttcttct gcgtgtgtcc    193380
tcgacgcggg tctgtgcgcc tgcctgccgg tcccggcaga ctgggctgcg gcttcctcgt    193440
tttttttttc cgcctgtggc cgtccccggg gacttcctct tttccgcgtc cgatcttcgc    193500
gtccccaggg agtcgcgccg ccgtcccctc gggaccgctt cctcttttcc ccggggactc    193560
aaagacacgc aagacagacg cgcgactgaa agagacgcaa gacacgcgc cgtctgggtt    193620 tcgccgtgcg cgccgcacgg cgcttttatt cgccgtcgcc gtccccgcc accgccaact    193680 tcccaaattc ccacatttca ccccccccgat gaaaacaccc ccccgcccct cggggaccca    193740
gcacacggcc cggaatggag gtcaggcgtc cacctaggtg tgcgcgcgct cggcggcccg    193800
ttgttggtgg cttgtcgcgc atcttctttc ggttttttca cggccttcca gactgcgcgg    193860
cggcaaggcg gcgccagcaa gcgccgtgca cgtcgctgcc tataaaagcc aggtgcgtgt    193920
cgcccgcggc acacgggcga cggaggcgtc cgcgtgtgta acggcgtggg tcgctgacgc    193980
gggtttgctt cctatatata cagagtggac gtcggaggcg tccggcggcc atggcccagc    194040
gcaacggcat gtcgccgcgc ccccccgccc tcggtcgcgg ccgcggagcc ggagggcctt    194100 cggggggttgg ttcctctcgt tcttcttctt tggaagcgac gtcaacagcg gggactagta    194160
cgagtactgc gggtacggcg acgccggccc acgccgtcca ccgggtagaa ccccgcggc    194220 cgccgggcgc ccctccgggt agcggcaaca acagcacctt ttggcacggc ccggagcgct    194280
tgctgctgtc tcagattccg gtggagcgcc aggcgctgac ggagctggaa taccaggcca    194340
tgggcgccgt gtggcgcgcc gcgttttttgg ccaacagcac gggccgcgcc atgcgcaagt    194400
ggtcgcagcg cgacgcgggc acgctgctgc cgctcggacg gccgtacgga ttctacgcgc    194460
gagtgacgcc gcgcagccag atgaacgcg tgggcgccac ggacctgcgt cagctgtcgc    194520
cgcgggacgc gtggatcgtg ctggtggcga ccgtggtgca cgaggtggac cccgcgccg    194580 acccgacggt gggcgacaag gccggccatc ccgagggtct gtgcgcgcag gacgactgt    194640 acctggcgct gggcgccggg ttccgcgtgt tcgtgtacga cctggcgaac aacacgctga    194700
```

-continued

```
tcctggcggc gcgcgacgcg gacgagtggt tcggcacgg cgcgggcgag gtggtgcgcc   194760
tgtaccgctg caaccggctg ggcgtgggca ccccgcgcgc gacgctgctg cctcagccgg   194820
cgcttcgcca gacgttgctg cgcgccgagg aggcgacggc gctcggacgg gagctgcgcc   194880
ggcggtgggc cggcacgacg gtggcgctgc agacgccggg caggcgactg cagccgatgg   194940
tgctgctggg cgcgtggcag gagctggcgc agtacgagcc gttcgcgtcg cgccgcacc    195000
ccgcgtcgct gctgacggcc gtgcgtcggc acctgaacca gcgtctgtgc tgcggctggc   195060
tggcgctggg cgcggtgctg ccgtcgcggt ggctgcgctg cgcggcaggg ccggcgacag   195120
ggacgacggc ggggacgacg acgacgatga cggcggggac gacggcgatg gcgacgggga   195180
cgacgttgct gccgggggcg agcggcacgg agacggaggc cgccggcggg gacgcgccgt   195240
gcgcgatggc gggagccgtg gggtctgctg tgactttacc tccgcagccg tacgcgcccg   195300
ccggcgggag cgcgatttgc gtgccaaacg cggacgcgca cgcggtggtc ggaacggatg   195360
cggcagcggc agcagcggcg gcgccgacgg tgatggtggg tccgacggcg atggcgggtc   195420
cggcggcgtc ggggaccgtg ccgcgcgcca tgctggtggt ggtgctggac gagctgggcg   195480
ccgtgttcgg gtactgcccg ctggacgggc acgtgtaccc gctggcggcg gagctgtcgc   195540
actttctgcg cgcggggcgtg ttgggcgcgc tggcgctggg gcgcgagtcg gcgcccgccg   195600
ccgaggccgc gcggcggctg ctgcccgagc tggaccgcga gcagtgggag cggccgcgct   195660
gggacgcgct gcacctgcac ccgcgcgccg cgctgtgggc gcgcgagccg cacgggcagt   195720
gggagttcat gtttcgcgaa caacgcggtg accccataaa tgatcccgtc gcatttcgtc   195780
tttcggacgc tcgaactctc ggtctcgacc tcaccaccgt catgacagag cgtcaaagtc   195840
aattgcccga aaagtatatc ggtttctatc agattaggaa acctccttgg ctcatggaac   195900
aacctccacc cccatctcgc caaaccaaac cggacgctgc aactctgccc ccaccgctca   195960
gtgctcaggc aagcgtcagc cacgcactcc gatacgatga cgagttgtgg cgcccgctca   196020
gtacagttca cgaccacaaa gcctggttgg atctcgacga atcacactgg gtcctcgag   196080
acagccgacc cgacgatata aggcaacgca gactgctgaa ggccactcaa cgacgaggcg   196140
ccgaaatcga cagacccatg cctgtcgtgc ccgaagaatg ttacgaccaa cggttcacta   196200
ccgaaggcca ccaggtcatc ccgttgtgcg cgtccgaacc cgaggatgac gacgaagatc   196260
ctacctacga cgaattgccg tcgcgcccac cccagaaaca taagccgcca gacaaacctc   196320
cgcgcttatg caaaactggc cccggcccac ctccgctgcc gccaaagcaa cggcacggtt   196380
ccaccgacgg aaaagtttct gcgccccgac agtcggagca tcataaaaga cagacccgac   196440
cgccaaggcc gccaccgccc aaattcgggg atagaaccgc ggcccatctc tcgcaaaata   196500
tgcgagacat gtacctcgat atgtgtacat cttcggccca caggcacgg ccgccagcac    196560
ctccgcggcc gaaaaaatgt caaacacacg cccctcacca cgttcatcat tgaaagtctc   196620
tccagtccat atgttgtcag gacgtgctgt cgttctccgc ttgctgcgaa gcccgttctt   196680
ccgagtcgtg tcgctgcgtc cagcgtcgcg cccaagatgg gaatttgggt ctcttcacgc   196740
gtagcctcct ccaccacggc tgctgatcgc cgtcactaag gaccgacacg gaggatgacg   196800
aggagcttct ccccgactcc gcggtccgcg accggctacg tagcgcgtgt ccctgccagt   196860
ctccgcagtt acaccacacg tcgtgagcag cgtgcacctg ctgccgccac tgggcctcgg   196920
cgtgctcggg ccaccgccg gagcccggtc tgagctccga cgcaggatgc gcgtactcaa    196980
cgtgcgcctt ccagtccata cagcaacacc ataggtcgtg cgagtcgtcg gctacccgcc   197040
gccaggccag ttcccgcatg ggaaggctgg acacgccgac cgagaggtca ccgagcccgg   197100
```

```
acgccatctc ttcttcctct ccgtcgctgt cattaagcag ccaggtcacc tcctccgctc 197160
cgcggtccgc cggtctcgac ggaccgcgcc gccgtcggca acacggaaaa cagtacgcca 197220
gcccgagccg ctaaggccgc atgcccctgc cgcccaactg aacacgcata tcccgctcaa 197280
ctgcgttttg ccacccctgc cagtgctccc gctcgagcac caccccgcat ctcccaacct 197340
ttttccaata aacgaaaccg acatgacaca cgtaatgggt actcgtggct agatttattg 197400
aaataaaccg cgatcccggg cgtctcagca cacgaaaaac cgcatccaca tcatagacaa 197460
gttacagtcc acagtcacat acacgataaa caataccaac agggtaatgt ttatggagta 197520
aaacactatt gtccaggcca catgcgtgta tgacttccgc accatcccgt actgcatgtt 197580
ccacatgtac gcgctagacg tgtaatccac tcgcagttcg gggacgcaac gcagccagat 197640
cacatcccct tgcagtacca gacgcagggc tagcgtctcg aagatcggca tcacatctaa 197700
gttccgcacg ttccacttta acgactcccc gggaacgaac tccacgtcgt cggcgtgtac 197760
gtacaggttc tctcccacgc cgccataatc ggccttcgga tcgaagacga accgactcat 197820
gttgcccacg atgctccccc gagcaaacaa cttgccgttg tcaatgtagc accggttgtc 197880
ctcgatttga aaccagggat gcttggccgt ggacttccag ggccggagcg cgtcttcccc 197940
ggctttagtg attccatcgg gcaggcggat caagggaccc atggaggtcc aaagacccac 198000
ccaggctttc cagagattgt tcatggtgaa acagcgtgtg gactgtacgc tctttcccaa 198060
tttatatccc agagtagtga cgtgagccca gccacctccc agattcctga cgttttggtt 198120
gtctttcctg ccaattcctc ccgtaaactt atgattatcc tagcccattc ccgataaaaa 198180
tacacggaga cagtagatag agttacgaat aaaccggttt atttattcaa gtgtctcagg 198240
agattattga cgagcgtgg ataccacgcc gtcgtcagtt catggtggca ttgagcagcc 198300
atagcaccag agtcccggcg cccggtatca gacacgctga cctaccgggc gccttcgagt 198360
ccgtaccccg cggcctgggt gttagagtcc gtaccttgca gcccaggtag gtttcaggta 198420
ccagctggtt cgtacctgtt aaataaatcg cagacgggcg ctcacccta cggtcaggag 198480 cacaagaaca accagagaga acagatatac gagcagggtt ctgaacagca gaccccaatt 198540
gtcgtctctc atgcttcgct gaaggtacca gttgatggtc tgagagctat agtccatcct 198600
cacctgagga acacacgcgg catatttctt ggggtctccc cacctcgtag acaacgtgat 198660
gtccaccata tccacggtgt gcgtcaccgg gtgcccaccg atgttccact cgaaataggc 198720
tccgcgctca tcatggtggt actgctcacc ggacacctgc agtctgtcca tgtaagattg 198780
agagacgata cccacgttca caaagtgttt ctcggtgaag ttgcccgaca tcctccccctt 198840 gaagtacagc atgcccatat ggaaccagca ttggttctcc tccactcgaa agtgggccga 198900
tctgatctcc gataccacca catccagggg ccggggcacc gagtccgcga gtctcaggaa 198960
caagacggcc aggatcgcga gcaccaacac cggcttcatg gctccgaagg tccgctgctc 199020
ggctccgctc accgctccgg tctggctgca gcagtgcttc gctgagaagt agcgtgtgga 199080
ctgaacggtg ttttttgaata tatagcgttt cttggtgacg ttgtttcccc tacgtagtag 199140
gcaactacgt gccaaaagag gcgttacggt actttccgta ctgggatttc caaaccggga 199200
ctttccacac ggcggtttca acaccgggac ttttcacacg gtgatttcgg caccgggact 199260
ttccgcacgg cggtttcgcc accgctgacg ttctcatcgc cgcccacgtc aacggtggcg 199320
acaccgtact ttcccatgcg gtttataaac gtcaagagtc acgtcagtcg cccaccccca 199380
ttacacggcg atatcccgat agggcatgag gggacccggg tgtcgcgaca tgtcgacgac 199440
```

```
aggtgcggat tagtggtcgt gtcgcgacat ggacgtgcag ggggatgtct gtcgcgatag   199500
agttgatgtg acagcccgct acacctctct gtcgcgacat gcatacacaa cgggccggct   199560
tgtcggcgat tgtcgcgaca tatcgttatc agttagcgac cggagttgtc tatcgcgaca   199620
tatcgtcgac tatcgcgaca gaaaaaatac cgttcgtaga gaatgccgtg ttgaaggaac   199680
gcgcttttat tgagacgata aaacagcatc aggagccaca acgtcgaatc ccacgtccag   199740
tcgattcgta tgttatgctg cacagcaatg ctagaataac aaccagcagg gtaatcccgc   199800
aacataaata caaagtcaca gcgaagaatc cgtgtcgttc tatcaagcga aacgcgttcc   199860
aaacggcccc gtcacagacg cagttattca taagcgttaa caaccggtgg ctaggatgaa   199920
tatccaaatc acagggcagt agccgacgga ctcgttgaca ggtcagccta ccctcaaggt   199980
tcctatcgtt cggacgggat tgtgcgtttt taggcctctt tttcgccgcc tgcaagcatt   200040
ggtgcgcaaa gtcctcaccc agctgtttcc agctatcatc tgcatctgtg cagtcccctg   200100
tatcgttgta acaaacgggt ctgtgcgact tcgttctcgg aacacaagct tgttgtcgcg   200160
gagacagaga gagaagggtt ttcgggtcac gcgaagaccg ctcaccgggg gtcggcaacg   200220
cacacatcaa cagaaaaccg agacgaatca agagatccat agtgaaggag tgatatcgac   200280
gtgcttacga aacggcgatt atatatgttc tcaacaatac cgccctacgt tgtatgatgt   200340
aacgtgtgac gtgagtctga tccaacactg aacgctttcg tcgtgttttt catgcagctt   200400
ttacagacca tgacaagcct gacgagagcg ttcatcgggg catgaagtac gcattacaca   200460
aactccatat atttgttacg atagaatacg gaacggagga ggctttcgcc acacctatcc   200520
tgaaagcgtt gcattcttta tgataggtgt gacgatgtct ttaccattcc cacggctgct   200580
ttgcgtgatg atgacattca tcatgtattt ccattcacac atacctttttg tgcatacggt   200640 ttatatatga ccatccacgc ttataacgaa cctaacagtt tattagccct tgacaggata   200700
ggtcaaaaga ttatatgtag gttttccggt aaaccgaatt gtgatatttc tctgcaggaa   200760
atagaacagc ctggtaccta taaaacggac aatgcagtac tgtagcagcg taaccaagta   200820
ggtccacatg aacacgtaca aaattatggt aagccatcgt ttttcatacc acagcctgta   200880
gctgtcgtac atgaatgagg acggtcgagg aacccagggt agttgtaatt gggggcgaca   200940
ttcgtactgt ccagaagaca attgcacggg tttcagtgag atgagtactt tagcgatgtc   201000 ggcggggggcg ctacgtttca ccgtgacggt gagaacttga ccgtcgtttt gtatttcatg   201060
aggcacgtta tacaagccac tggtatcatg aaggatgacc tctgatgcga tgtgaggatt   201120
aaattgtccc tcaaaccgcc aaacgctggt catgttccca ccgtcaatta cgcagctgac   201180
ggtgtgagat accacgatgt tggacttagg tttgggggct aattgccttt ttacaaattc   201240
ccttctgtat tgcaggtcct gctgccactg cttttccgtg cggaaagtcg ccatgtcttc   201300
cacacgtgtg gcgacgatag acgccaccaa ggtagctacc agaagcagct ggatccgcat   201360
ggcattaccg tatgtcaatt agaaagttga gcggacacgg ttatcgttcc tggcggatat   201420
aagtatataa acgcgagtta gcctttcccg tccgttttgt acaccccgttc cccacacaaa   201480 tgacgaatac gaccttttttt tttataaaaa taaaccacgt gtattatata aaacatttta   201540
catagaaaag agacacactc tagattaatt aaggggccggc cgcatcagct tgatatcgaa   201600
ttcctgcaga tctgctagat aacttcgtat aatgtatgct atacgaagtt atgcggccac   201660
ggatgcatgt ttaaactcga cagcgacaca cttgcatcgg atgcagcccg gttaacgtgc   201720
cggcacggcc tgggtaacca ggtattttgt ccacataacc gtgcgcaaaa tgttgtggat   201780
aagcaggaca cagcagcaat ccacagcagg catacaaccg cacaccgagg ttactccgtt   201840
```

```
ctacaggtta cgacgacatg tcaatacttg cccttgacag gcattgatgg aatcgtagtc  201900
tcacgctgat agtctgatcg acaatacaag tgggaccgtg gtcccagacc gataatcaga  201960
ccgacaacac gagtgggatc gtggtcccag actaataatc agaccgacga tacgagtggg  202020
accgtggtcc cagactaata atcagaccga cgatacgagt gggaccgtgg ttccagacta  202080
ataatcagac cgacgatacg agtgggaccg tggtcccaga ctaataatca gaccgacgat  202140
acgagtggga ccatggtccc agactaataa tcagaccgac gatacgagtg ggaccgtggt  202200
cccagtctga ttatcagacc gacgatacga gtgggaccgt ggtcccagac taataatcag  202260
accgacgata cgagtgggac cgtggtccca gactaataat cagaccgacg atacgagtgg  202320
gaccgtggtc ccagtctgat tatcagaccg acgatacaag tggaacagtg gcccagaga   202380
gaatattcag gccagttatg ctttctggcc tgtaacaaag gacattaagt aaagacagat  202440
aaacgtagac taaacgtggt cgcatcaggg tgctggcttt tcaagttcct taagaatgg   202500
cctcaatttt ctctatacac tcagttggaa cacgagacct gtccaggtta agcacccatt  202560
tatcgccctt atacaatact gtcgctccag gagcaaactg atgtcgtgag cttaaactag  202620
ttcttgatgc agatgacgtt ttaagcacag aagttaaaag agtgataact tcttcagctt  202680
caaatatcac cccagctttt ttctgctcat gaaggttaga tgcctgctgc ttaagtaatt  202740
cctctttatc tgtaaaggct ttttgaagtg catcacctga ccgggcagat agttcaccgg  202800
ggtgagaaaa aagagcaaca actgatttag gcaatttggc ggtgttgata cagcgggtaa  202860
taatcttacg tgaaatattt tccgcatcag ccagcgcaga aatatttcca gcaaattcat  202920
tctgcaatcg gcttgcataa cgctgaccac gttcataagc acttgttggg cgataatcgt  202980
tacccaatct ggataatgca gccatctgct catcatccag ctcgccaacc agaacacgat  203040
aatcactttc ggtaagtgca gcagctttac gacggcgact cccatcggca atttctatga  203100
caccagatac tcttcgaccg aacgccggtg tctgttgacc agtcagtaga aaagaaggga  203160
tgagatcatc cagtgcgtcc tcagtaagca gctcctggtc acgttcatta cctgaccata  203220
cccgagaggt cttctcaaca ctatcacccc ggagcacttc aagagtaaac ttcacatccc  203280
gaccacatac aggcaaagta atggcattac cgcgagccat tactcctacg cgcgcaatta  203340
acgaatccac catcggggca gctggtgtcg ataacgaagt atcttcaacc ggttgagtat  203400
tgagcgtatg ttttggaata acaggcgcac gcttcattat ctaatctccc agcgtggttt  203460
aatcagacga tcgaaaattt cattgcagac aggttcccaa atagaaagag catttctcca  203520
ggcaccagtt gaagagcgtt gatcaatggc ctgttcaaaa acagttctca tccggatctg  203580
acctttacca acttcatccg tttcacgtac aacatttttt agaaccatgc ttccccaggc  203640
atcccgaatt tgctcctcca tccacgggga ctgagagcca ttactattgc tgtatttggt  203700
aagcaaaata cgtacatcag gctcgaaccc tttaagatca cgttcttga  gcagatcacg  203760
aagcatatcg aaaaactgca gtgcggaggt gtagtcaaac aactcagcag gcgtgggaac  203820
aatcagcaca tcagcagcac atacgacatt aatcgtgccg atacccaggt taggcgcgct  203880
gtcaataact atgacatcat agtcatgagc aacagtttca atggccagtc ggagcatcag  203940
gtgtggatcg gtgggcagtt taccttcatc aaatttgccc attaactcag tttcaatacg  204000
gtgcagagcc agacaggaag gaataatgtc aagccccggc cagcaagtgg gctttattgc  204060
ataagtgaca tcgtcctttt ccccaagata gaaaggcagg agagtgtctt ctgcatgaat  204120
atgaagatct ggtacccatc cgtgatacat tgaggctgtt ccctgggggt cgttaccttc  204180
```

-continued

```
cacgagcaaa acacgtagcc ccttcagagc cagatcctga gcaagatgaa cagaaactga 204240
ggttttgtaa acgccacctt tatgggcagc aaccccgatc accggtggaa atacgtcttc 204300
agcacgtcgc aatcgcgtac caaacacatc acgcatatga ttaatttgtt caattgtata 204360
accaacacgt tgctcaaccc gtcctcgaat ttccatatcc gggtgcggta gtcgccctgc 204420
tttctcggca tctctgatag cctgagaaga aaccccaact aaatccgctg cttcacctat 204480
tctccagcgc cgggttattt tcctcgcttc cgggctgtca tcattaaact gtgcaatggc 204540
gatagccttc gtcatttcat gaccagcgtt tatgcactgg ttaagtgttt ccatgagttt 204600
cattctgaac atcctttaat cattgctttg cgttttttta ttaaatcttg caatttactg 204660
caaagcaaca acaaaatcgc aaagtcatca aaaaaccgca aagttgttta aataagagc 204720 aacactacaa aaggagataa gaagagcaca tacctcagtc acttattatc actagcgctc 204780
gccgcagccg tgtaaccgag catagcgagc gaactggcga ggaagcaaag aagaactgtt 204840
ctgtcagata gctcttacgc tcagcgcaag aagaaatatc caccgtggga aaaactccag 204900
gtagaggtac acacgcggat agccaattca gagtaataaa ctgtgataat caaccctcat 204960
caatgatgac gaactaaccc ccgatatcag gtcacatgac gaagggaaag agaaggaaat 205020
caactgtgac aaactgccct caaatttggc ttccttaaaa attacagttc aaaaagtatg 205080
agaaaatcca tgcaggctga aggaaacagc aaaactgtga caaattaccc tcagtaggtc 205140
agaacaaatg tgacgaacca ccctcaaatc tgtgacagat aaccctcaga ctatcctgtc 205200
gtcatggaag tgatatcgcg gaaggaaaat acgatatgag tcgtctggcg gcctttcttt 205260
ttctcaatgt atgagaggcg cattggagtt ctgctgttga tctcattaac acagacctgc 205320
aggaagcggc ggcggaagtc aggcatacgc tggtaacttt gaggcagctg gtaacgctct 205380
atgatccagt cgattttcag agagacgatg cctgagccat ccggcttacg atactgcac 205440 agggattcgt ataaacgcat gggcatacgg attggtgatt tctttttgtt tcactaagcc 205500
gaaactgcgt aaaccggttc tgtaaccccg ataaagaagg gaaatgagat atgggttgat 205560
atgtacactg taaagccctc tggatggact gtgcgcacgt ttgataaacc aaggaaaaga 205620
ttcatagcct ttttcatcgc cggcatcctc ttcagggcga taaaaaacca cttccttccc 205680
cgcgaaactc ttcaatgcct gccgtatatc cttactggct tccgcagagg tcaatccgaa 205740
tatttcagca tatttagcaa catggatctc gcagataccg tcatgttcct gtagggtgcc 205800
atcagatttt ctgatctggt caacgaacag atacagcata cgttttgat cccgggagag 205860 actatatgcc gcctcagtga ggtcgttgga ctggacgatt cgcgggctat ttttacgttt 205920
cttgtgattg ataaccgctg tttccgccat gacagatcca tgtgaagtgt gacaagtttt 205980
tagattgtca cactaaataa aaagagtca ataagcaggg ataactttgt gaaaaaacag 206040
cttcttctga gggcaatttg tcacagggtt aagggcaatt tgtcacagac aggactgtca 206100
tttgagggtg atttgtcaca ctgaaagggc aatttgtcac aacaccttct ctagaaccag 206160
catggataaa ggcctacaag gcgctctaaa aagaagatc taaaaactat aaaaaaata 206220 attataaaaa tatccccgtg gataagtgga taaccccaag ggaagttttt tcaggcatcg 206280
tgtgtaagca gaatatataa gtgctgttcc ctggtgcttc ctcgctcact cgagggcttc 206340
gccctgtcgc tcgactgcgg cgagcactac tggctgtaaa aggacagacc acatcatggt 206400
tctgtgttca ttaggttgtt ctgtccattg ctgacataat ccgctccact tcaacgtaac 206460
accgcacgaa gatttctatt gttcctgaag gcatattcaa atcgttttcg ttaccgcttg 206520
caggcatcat gacagaacac tacttcctat aaacgctaca caggctcctg agattaataa 206580
```

```
tgcggatctc tacgataatg ggagattttc ccgactgttt cgttcgcttc tcagtggata  206640
acagccagct tctctgttta acagacaaaa acagcatatc cactcagttc cacatttcca  206700
tataaaggcc aaggcattta ttctcaggat aattgtttca gcatcgcaac cgcatcagac  206760
tccggcatcg caaactgcac ccggtgccgg gcagccacat ccagcgcaaa aaccttcgtg  206820
tagacttccg ttgaactgat ggacttatgt cccatcaggc tttgcagaac tttcagcggt  206880
ataccggcat acagcatgtg catcgcatag gaatggcgga acgtatgtgg tgtgaccgga  206940
acagagaacg tcacaccgtc agcagcagcg gcggcaaccg cctccccaat ccaggtcctg  207000
accgttctgt ccgtcacttc ccagatccgc gctttctctg tccttcctgt gcgacggtta  207060
cgccgctcca tgagcttatc gcgaataaat acctgtgacg gaagatcact tcgcagaata  207120
aataaatcct ggtgtccctg ttgataccgg gaagccctgg gccaactttt ggcgaaaatg  207180
agacgttgat cggcacgtaa gaggttccaa ctttcaccat aatgaaataa gatcactacc  207240
gggcgtattt tttgagttat cgagattttc aggagctaag gaagctaaaa tggagaaaaa  207300
aatcactgga tataccaccg ttgatatatc ccaatggcat cgtaaagaac attttgaggc  207360
atttcagtca gttgctcaat gtacctataa ccagaccgtt cagctggata ttacggcctt  207420
tttaaagacc gtaaagaaaa ataagcacaa gttttatccg gcctttattc acattcttgc  207480
ccgcctgatg aatgctcatc cggaattccg tatggcaatg aaagacggtg agctggtgat  207540
atgggatagt gttcacccct tgttacaccgt tttccatgag caaactgaaa cgttttcatc  207600
gctctggagt gaataccacg acgatttccg gcagtttcta cacatatatt cgcaagatgt  207660
ggcgtgttac ggtgaaaacc tggcctattt ccctaaaggg tttattgaga atatgttttt  207720
cgtctcagcc aatccctggg tgagtttcac cagttttgat ttaaacgtgg ccaatatgga  207780
caacttcttc gcccccgttt tcaccatggg caaatattat acgcaaggcg acaaggtgct  207840
gatgccgctg gcgattcagg ttcatcatgc cgtttgtgat ggcttccatg tcggcagaat  207900
gcttaatgaa ttacaacagt actgcgatga gtggcagggc ggggcgtaat tttttaagg  207960 cagttattgg tgcccttaaa cgcctggttg ctacgcctga ataagtgata ataagcggat  208020
gaatggcaga aattcgatga taagctgtca aacatgagaa ttggtcgacg gcccgggtcg  208080
acagttaggg tgtggaaagt ccccaggctc cccagcaggc agaagtatgc aaagcatgca  208140
tctcaattag tcagcaacca ggtgtggaaa gtccccaggc tccccagcag gcagaagtat  208200
gcaaagcatg catctcaatt agtcagcaac catagtcccg cccctaactc cgcccatccc  208260
gcccctaact ccgcccagtt ccgcccattc tccgccccat ggctgactaa ttttttttat  208320
ttatgcagag gccgaggccg cctcggcctc tgagctattc cagaagtagt gaggatcgat  208380
ccaccggtct cgaggaagat gtccaattta ctgaccgtac accaaaattt gcctgcatta  208440
ccggtcgatg caacgagtga tgaggttcgc aagaacctga tggacatgtt cagggatcgc  208500
caggcgtttt ctgagcatac ctggaaaatg cttctgtccg tttgccggtc gtgggcggca  208560
tggtgcaagt tgaataaccg gaaatggttt cccgcagaac ctgaagatgt tcgcgattat  208620
cttctatatc ttcaggcgcg cggtctggca gtaaaaacta tccagcaaca tttgggccag  208680
ctaaacatgc ttcatcgtcg gtccgggctg ccacgaccaa gtgacagcaa tgctgtttca  208740
ctggttatgc ggcggatccg aaaagaaaac gttgatgccg gtgaacgtgc aaaacaggct  208800
ctagcgttcg aacgcactga tttcgaccag gttcgttcac tcatgaaaaa tagcgatcgc  208860
tgccaggata tacgtaatct ggcatttctg gggattgctt ataacaccct gttacgtata  208920
```

```
gccgaaattg ccaggatcag ggttaaagat gtaagtatca aggttacaag acaggtttaa    208980
ggagaccaat agaaactggg cttgtcgaga cagagaagac tcttgcgttt ctgataggca    209040
cctattggtc ttactgacat ccactttgcc tttctctcca cagatctcac gtactgacgg    209100
tgggagaatg ttaatccata ttggcagaac gaaaacgctg gttagcaccg caggtgtaga    209160
gaaggcactt agcctggggg taactaaact ggtcgagcga tggatttccg tctctggtgt    209220
agctgatgat ccgaataact acctgttttg ccgggtcaga aaaatggtg ttgccgcgcc    209280 atctgccacc agccagctat caactcgcgc cctggaaggg attttttgaag caactcatcg    209340 attgatttac ggcgctaagg atgactctgg tcagagatac ctggcctggt ctggacacag    209400
tgcccgtgtc ggagccgcgc gagatatggc ccgcgctgga gtttcaatac cggagatcat    209460
gcaagctggt ggctggacca atgtaaatat tgtcatgaac tatatccgta acctggatag    209520
tgaaacaggg gcaatggtgc gcctgctgga agatggcgat tagcggccgc gactctagat    209580
cataatcagc cataccacat ttgtagaggt tttacttgct ttaaaaaacc tcccacacct    209640 cccccctgaac ctgaaacata aaatgaatgc aattgttgtt gttaacttgt ttattgcagc    209700
ttataatggt tacaaataaa gcaatagcat cacaaatttc acaaataaag cattttttc    209760 actgcattct agttgtggtt tgtccaaact catcaatgta tcttaagctt ataacttcgt    209820
ataatgtatg ctatacgaag ttatggatca acataaggac ttttcacact tttgggtac    209880 acaggcgtgc caccgcagat aataagcgct ggatacacgg tacacagtcc tggccagcac    209940
gtatcccaac agcagcacca tcgccatctg tatggcgatc acgaccccga gctctaagtg    210000
tctgtattca tagtgtagtc gtcgcaggtt atccactgaa ttcccgtagc tgaaataacg    210060
tatatggtac cgaggctggc accacatggg tttgcatttg gagcacggca ccaaatgcag    210120
agtgagatgg tccaagtccg tgggcaccca ctggcgcaaa cggaatacgg cttcggtggt    210180
ctccacgagg cactccgggg cttgcagacg gccccacttt cgtccgtgac ggcccgacca    210240
gccgacccga gccactatcc cttctcggg atagaacgta ccctgtacac gccatacagc    210300
gtccaacacg ccgtctttga cgacgcagct ggcctgatag ctggacacgt tgttaagcgg    210360
cggaaagcga aactgacgtg ccggcggagc cacatagttc ggttcaccgt gttgtcgcgg    210420
ttcgtcctcc ctatagtaat agtagtcgtc gtcctcatag gggttgccgg cgtgagccag    210480
cgttacccaa cagcagccca ggccgacgag gaggcgcagc caccgcctca tggcggcttc    210540
gccagtcaat cgtctttagc ctcttcttcc cgtgaggtcc ttccggtggc gcggtgccga    210600
cctcggaccc agggacgtat ccacctcagg tacacacagt aggctacctg gacaccgaag    210660
ctgaacaagg ctacatgttt cacaaactgc accagtacca catagaggaa tgtcaggtag    210720
cgtctctccg caaacagccg ttccaagtct gagggcgtta cccgcagcgg caaccagggc    210780
agcctggacg ccggccggca atggagcacg ctccggttac aggcactgca ggggtaaacg    210840
gttaacatca cgtaagagag tcgagcgtcc acctgtggga gctcagtttc gtaacgtaga    210900
gccccgtcat tttccagctg gggtgcgccg accttgaaat gggtcgcgct ccgttcgtta    210960
ccccaggtgc cgtaggctct cggggccgta tcggagaagt tgccgtgcac aagccaggcg    211020
gccacgagta ccccgtgctg gacgtaacat tcggacacgg aactggagac acggtagccg    211080
gacacgtccc caaacccgcg agggtactgg ggcagacgga cggacttgct atttgacaac    211140
ggacagatac gagacgacga ggacgcagac gactcgtcgc tggaccacga caaccggagc    211200
gactccttgg agcggctcga gagtacactt actgcgatca gacaccagtg ccagaagaag    211260
gaacaggtgg acggggacca caggatcata gccgccggca ccgcggccgg ccgcaggaag    211320
```

```
ccgcccggcg cgtcgtctgt gtgcgggagc cgaaacaccg tgcctcttta tatcgtcccg   211380
acgtgacgcg agtattacgt gtcagggaa acccccgtca tgacgaacgt gattcgtaag   211440
tgacgcgggg tgctgacggg gttcggctcg agaagtgacg gagcgcctca cgtcagtatg   211500
atgtccgatc cgcgtcagcc ccgacgtggt tatggtcacc gaaacccacg tttatatgga   211560
cgttgagaac agcgcctgac cacatgattc atcataccat ttctcggaat cgggcccatg   211620
ccgggaaagc acattccttt tcagtaaaca acaatgacat cataacaaat catttattc    211680 gcgaggtgga taataaccgc atatcaggag gagggatcgg gtgatgacgc aggccccgca   211740
aaacagtccg aaataaattt ttagtatcgc cccgtagtcg cctagatacc agaggtacgt   211800
caagttcatc aaaacgccca tcggcgtccc ggaatcgtat accgggcaca cgaagcgttc   211860
ataacaatcc cggaggcga gtgttagggt agcagaatag tttcggggtc ggtttccttc    211920
cggcgacgac agctccgtgg gcagcagaat gtagagcgcc tcggtagccg tcgcggtgcc   211980
ttccacgagg atgggctgcc ggtgcctttc gtgattttct ccgtcgtgta gccaagccga   212040
ggcccgcaaa gtcttaggcg aggggaattg tccatagact ttcaccgcac ccttcagtac   212100
atggttctga ataacacagc cgcacgtgaa gtaggtcggt tctctcgtct cctccgtggc   212160
tgccgccacc actcccagcc accacaacag gcaggtcgcg agagggttcc ggaggcttcc   212220
ccggcgtagc atggtttcgg gttaaagcaa aaagtctggt gagtcgtttc cgagcgactc   212280
gagatgcact ccgcttcagt ctatatatca ccactggtcc gaaaacatcc agggaaaatg   212340
tcggtgcagc caacctttca catacagccc ccaaaacact tgaatcactg ccaccatcat   212400
cagcgtatac tgcgccgact taatcgtgag cgcgtagtac gccattagac ggcgatcttc   212460
gaacaatagt cgttcgatgt cctctaacga gctccacaga ggaacccaag gcacgaggca   212520
ccggggttcg cactctacat aataagtttg gcattggtgg caggggggaaa agtagaacaa  212580 cacgagtttt gtgcgttggg gaacacgata gtcccggagc cagtagcgtt ttgcgacgag   212640
gctttcggag acgtcctcca ccggcgtcgg cactcgatcc gcgtagccct ccagcgtctg   212700
gtagtacacc cggggtgtcg gcgtgggcac ggacaggttc ccgcgcaggg tccacagagc   212760
ctccagtcga ccgcccgatc ggagcacgca gcgcgcctcg gaatactcta ctcggtactc   212820
cgaaacatcg ggcagaggcg gtaacggctc cgtctccacc aagggcggag gttcatcgaa   212880
aagagtcaag gataattcag gcatactacc tgcgaccggg gcccagaggg ctaggataag   212940
cattacaaga ttcattctgt cttacaaggg aaggctgttc ccctgtctag actcaaaagc   213000
tgtaaggctg tcttatagca tgtagtcttg cacgtcacgg ggaacagggt ggtgatctag   213060
tgacgtcggg agaacacggt gttttagggt gcggggggaca aaggacagta cgacagatta   213120
ggtgatagaa acgtttttt ttatttatga aaaagccagt gtgccgtgcg gcctagggcc    213180
ccggcgtagt ttggatacca gatgggggcc gtcagggggta ctaccacgag cagaaacata  213240
ataacttggt ccatgtatag cagcatagcg gtgcgtagca ggtcgccgtc cgtgtagcaa   213300
tttgacggtg agcgataaag caccgttaat gtgtcgcgga taagcacgat cttgaggccg   213360
tagatgaagc tcacagtcag tgctaaaatg atgcgttggt atggttccca ggactgcacg   213420
gcgatgaaga gccagagtat gggaagcatg aagcttagca aacagaggat ggctaaccgt   213480
cgttgcatgt tccaggccat gagccaggct aggcccgtac accagacgca gagcatggat   213540
gacaggacat aggcctggat taccacggtg cgatcgaaac acagcccgat ggtggacacg   213600
gatatcgtag tgagggtggt atataccatg accagcatca gggtcccggg taggcgccga   213660
```

```
cgttccagcc agtacgcgtg gcaacgcaga gcgcagggta gcagtgtgct ccagaagggc    213720
agtgtatcgc gcaggtaggg ggtcgtcacg cgccacggta tgagcatgaa aaggatggta    213780
gtggctatgg tggcgctggt ctggaacacg acggtgccgt agagacgtac catccagaga    213840
aagtgttgaa cgctccgcag ggtgtcttca tctttggtga ttacggtgac tcgacggatc    213900
ggcggtggtg acggcggcga cacgggtggg ggtttctctt tcttatggcc gagtggctcg    213960
ccttggtgaa actggatctg taccatgacg ggtgctcgac gaacagtcgt cggggcttta    214020
ggtacccggc aagttttata gagaaagggg gacgatgggt ggtggctacg agccaccgcc    214080
accttcgcaa tacgaggatc tgaaggcggc aaagacggtc gtccaggca ggtgccagag     214140 gttgggactg agcacgatca gcgtgatttt aaacatggtc accagtccta cgtagatcag    214200
cagcgagcca cgtaacgtct gagcagccgg cagttcgtcg cggatgtaac gcgtgccgta    214260
gaaagtcacg gtcatcataa ggaagacgat ggcgccgtag ccgtagagta gaatacgctg    214320
atgatggaac acggtctggt cgccgataac ccagagcgtg atgaaaaaaa cgctggtgag    214380 caccccgtgtg catatgagct cccaacgctt agcgcgaaag ctgtccccaa ccatgacagc    214440
gccggtgcaa gctatccaca cgtgaggac cagtgtgtag tcgatgagga tggcgggcag    214500
gtcggagcac caggtgtaga aaaccgtggt aacgagagg aggcctacgt agcccatggt     214560
caataccacg tcgtcggggt gcctttcgcc ctgtatcaag accaaacacc agagaaggga    214620
gggggcaaaa accagcagca gaggggaaga ttcatgttga catatgttgt gggaatcggg    214680
gatgcccagc caaatcattc gcagaaagc cgtactgatg gcgatgtgaa agaccactag      214740
ggcgtagacc cggacgagga cagcaaaacg gcgcagccac ataaggccgt ggtgcagctg    214800
caggagagaa gcccattgcg gcgaatgtag cgacggcagc ggcgggtcca tgaggcgggt    214860
gatgcacccg agtgaacggg tgagcgtctc ggtggagtct tcttataaac cagcggagct    214920
caggcagtct tgctctggag cgtcgcagtg gtggtgttga ggatgacgct gagcgtgccg    214980
ttgtcaatcc ggtaatgatg ataggtgcca agcttggcca ggtagctgaa catttggtcc    215040
cagcgtgccg accacaccac gggcgtgagc atcaggagtg tggtgtgata aatgagtgtt    215100
tcggtggcgt aaagtatcag cgagctgcgg atgatgtggc tcacgggcat tttggtggcg    215160
atgtagcgca cgtcttggaa aagaacggcc aggatgcagc ccacgaacac ggtatagaga    215220
cacagcagag tcttatgcaa ccaggtgtaa gtagaagcca ggacgctgac catcaccgtc    215280
aaaagtgtgg aggtaaaaag cgcgtcacgc cacacggagc tgagacggtg ctcccaagcc    215340
acgccgttgc aggccacgaa caacgtccac gttaagatga ggctgaaaac gccaatgggc    215400
gctgtggcgc acaggttgag cccggcggtg gtgaacgaca gaagcgccac atacagcgca    215460
aacaccaggc cgttgctggg gtgtctatga tcggtaagct ccagcgcgcc cagaaccaac    215520
accggtgtgc agctaagcaa taacggcgaa ggatcgtcgc ggcactcgta gcccagcgag    215580
gggtaaccca gccaaaccag cgcgctaatg agcacgctaa aagcggtttc cagcgtcagc    215640
aatccgtaga cacgcatgac gatcgcggtc cgccgtagcc aacacaccgc atcttcggaa    215700
gctgtggacg ctgtttccga ataccgggag gagatcgtgc ttccctcttc caaggatcgg    215760
aaagtagcgt ccgtcgtttc cgcagacgcg gcttccctgg tacgctccgt ttccgacgac    215820
gcggtttccc gctgcgtgga aactgtctcc atgtcgggac cgcagcgccc ggcggcgtat    215880
ccgcaaggtc tcgaagctac agcttgtcag aggaaaagta ggtttgcaaa aaggtgcgca    215940
gggtcatgat tctcagcacc atcagcagag tgaaaaccag gctgagaaac accttgacgg    216000
ccgccaaaag cgcgcgttcc agcggcgtct cgtagcgtac agccagggcc gcttcgtgga    216060
```

```
aatgcgagac ggctagacag gtaatgagca cgctgaagga caagacgatc ttaaagcacc  216120
aggaccaacc acgcctcaag atgaccacca cgattgccgt gaaggtcaac gtgatcaaag  216180
catggatgac cacgatctga cggcggacgg tacgttcggg agccaacaac gctacgccgg  216240
tgcagctgag aaaggccagt aaggtgaaca acgcggccga gatgaccaac gtaccgtcca  216300
ggcagagaca tatcacgatc aacggcggca cgtgaagcag cgtgtaaaag agcagaacgc  216360
cgatattgct gggatgcgat gtttcgtaac agtgaatgaa gatcaccgac gtgacgggta  216420
tgataaagac gaggctgggc gaggactccg tgagacacag acgggaatgg tgaaaccacg  216480
tcgcgggcgc cgcgtagcag aaggcgctca acaacgcggt caagccggcc agctgccaac  216540
ccacggcgcc ataggtgtgc agcgccacgc ggcaacagtc gacccaagcc agactgcggg  216600
tcgccagccg ggtctcttgg atcccggggg gcacgtagat gaccgtgcca tcggtgggta  216660
cctgaaaccc tttttctctt ctcatggtgc gctgcgttct ctggaaacgg ctgctctgtc  216720
cgaaaaccag ttccgaacga aaatctaggg cgagaggggtg acaacggcg tcgacgacga  216780 agcatgggac aggtcgttcg gcgttaacgt catcgcgtcg gacgacggta gttctaagag  216840
acgtagatcg ctcagcaggt cctgacagtt gcggattcgc aagatcagaa aaaaagggga  216900
aatgaacgta ataaagagct gtagcgacgt atgcgctaca tcgcgtggca taagaacgtg  216960
acggacgaaa aggacctgct gcgaaaagtg gccggcaaag ataaggccca ccgtgctgta  217020
gaagcccaaa agcagccgca ggggccaagt ccagggccgc gtaaagacga tgagaacgtt  217080
aaccagaaag accacgaccc agacgccgtt gatgagggta aattgatcgg acagggtgca  217140
gttgtcgcga cagatgaaga ctacttccgc gcagagcaag gtgatgacca atgtgagcac  217200
aaacgacgtc aacacctcgc ggggctcctg gcaggcacac gtgacaccta gcgccgggat  217260
gtgcgccagg aggccggcga gtaatagcac cagctgtcgg aacggacgac ggcagcgcgg  217320
gtgccggttt cgctgagcga gaaccggtcg ctcataacgg aaatacacga agagcgcgga  217380
ggccacaggc accaggagga gcacctcggg cgcccagacg acgtgacaag gaaagcctgg  217440
acgcgactta agagtcgctg tagggaagac cagagagaag ctacccaaga cggccaccgc  217500
cgcggagatt tggaagagga gcaagccggc gattcggacg acaacctcga agcgatgcac  217560
ccagcccagc acggccacca cggccgcttc atcatagtcg tcgttgttgc cgctgtcgaa  217620
cagccgccga aacacgatct gtcgctgggt cgcggtggga agcgcagac ccatgacagc  217680 cggaggctat atgaccgcgc gtctaaggcg cgagatccgt gggggggactt ttagatgttt  217740 gggcggcccg cggttctaac aggcttgatt ggtggagacg gccggcgcgg cgggtggggg  217800
aaacgacgag tttttccgtt acgccatggt tcgcgtgagg tttctctgta cctcccgcaa  217860
aaggtcacag cccgaaatgg aggccgcgtt ggtggcccg gtggcgcgtg acgataacca  217920
ggtcatccaa gtgatgagtt tgtctaatga gtcctcggtg gtgaagagga taagaatgag  217980
caggtacaag tacaccaggt tctcatagag acacaaggtg agcaggtcgg cctcggacca  218040
cgcgatctca acaggcgtg tggtgtcaaa gaccgtaacg accagcatga agctgagcgc  218100
catggcgtaa tagcccaaaa aaagtttgtg ccccaacggt acgggctgca ggtaaagtgc  218160
gatcaagaac gcgataacgc cgatcacaaa cagcgtgacg atgacctgcc atcgacgcg  218220 attatggccg gctagacccg tgacgcagct gcagaggcta aaaagcacgc aagccaagag  218280
gcccgagaag gtcaccagcg tagaggagga gcaggcgctg gccacgatca ccgaaagcgt  218340
cgtgagcacg ctataaatgg tgagcaggcc cgggctcggc ggcgacgtaa acgatccttc  218400
```

```
atcgcgtttg ccatgcagca gggccaaaca gatggtgggc accatcaaac tcaagggcgg   218460
cataaagccg gtgcaacaga gaaagacggt gcctttaaga tgcggaaaag ccagcaccag   218520
gcccagacag agcaagaagg tgcaggtgcc ctgcacggcc acggtgctgt agacccgcat   218580
acaaagtaaa aagcgacgta cgtcgttcgt cgagacggag gaaatcataa tgactccgcg   218640
cgagggtcgc gggggtgggg gcgcccaggc cgtcccggtg gcctctgagt tcggagacat   218700
gacggcggtg gctatcaaaa ggcgcgtatg agaaaccgtt tatagagtgt aatagaatca   218760
ccgtcattcc cacacggcgt tcccccataa agtcacgtca cactcgagta agcgtgaaaa   218820
agctttatta ttgaataaaa aacacgagta caacaccgag ttgcggtgtc ctgtctactg   218880
ggtgggggag gtttatcgtc tgtctctaga gggaaggtgg ggaacgtcta agcgagcggg   218940
agcgtgtcat ctcccccatc tttttacaac aagctgagga gactcacgcc gtcgatgcgt   219000
ccgccgtgtt tctcggcgta ctgctgcacc cagacgtggc cgctaaagat ggcgacgctc   219060
atgtttagga gactcatgac gatggtgtac aacacgacgc tgacacagac gctgttttta   219120
gacagcgttc cacgctggta gatgagatcc agggtctcgt aaataagcac ggccgaagcg   219180
gcggtcacca ccaggacgta gagtccgctg tagatcttgc tgaccacag cacgggcgaa   219240 aagtaaagca ataggtaaaa gacgatgacg gaccagccgt agccaatccc gatgactttc   219300
cagcgcgtgg gattgttgcc ggccaggtag gtgagaccgc tgcagagaac gaaaagacc   219360 atcaccaggg caaacgacag accgatgacg cgccttttctc cgcaaaagcc cgtgcacacg   219420
gtgatgccgg tgttgatcag caggcatgcc accgtgagat gagcaaaatt ggtggtgtgt   219480
gggcgaaact cggcgaaacc gcgtagcatg gccagcgtgg acacgggcac gatggaggac   219540
agggctggca ctatgccgtt ggcgcactgt ccctgcacat cggggaaggc gagccaagcc   219600
agcaggcaga ccgtgagggt acaagccagc tgccacacga gcccgtgata gacctccatg   219660
agcagcttga agcgtttcaa ccactggaag agctgctgtt cggccaccag cgcgtggctg   219720
cgatggagcg gcacgatggt gaccgtcggc gactcatggt gttcggaaac cgaggcggtg   219780
tcgcccatgc tgccgcttac gaccgctgtc ggtctaaggt aggcgtcgat gaaacagtcc   219840
gtcttatcag caccccggtta ccgcggattt gattgacgtc acgagtgtgg tcaaaccgtg   219900
gcggcaccct gtatccgacc cgtcgtcatg gcctccacaa ccagagcctc agaagatggt   219960
acatgccgat gaataaagcc acattttcga catagaggcg tagcgagggc tgaaaactct   220020
ccgggaaaga actctgacag gtgatcaggg acagatcgtg aattagcatc agcgtcaccg   220080
tcaacagcgt cgtcgcgtgt aaaccgagaa agaacggggt cgcggcccgc agcagccaaa   220140
gtcccagcgc cgtagcgcag agcagagaca ggaccgacgg tagccacagc cgccggagag   220200
acgcgccagg atcgcaaccc aaaagcgagg cccccaggca gccgagatct accgccaggg   220260
cgagaagagc cgcgccgaga aaggcctgcg gcgacggctg gcacatcagc aaggtcagaa   220320
aggctagcgc gtgcggcagg cagtaagcca acaggagtgg gagtttgcgg ggacaacggt   220380
cgatagacgg accgcgtagc agcaggaaca ggcagccgac gggcacgacg aggctgagat   220440
gagaaagcgg cggtgggtcg tcgtcccgtc cccgctcgca tagctcggcc accggtggcg   220500
gcatgagcca ccagctgagc acgctgaggg cgacggtggc ggtaagctgg aaggcgacga   220560
ggacggaggc gcgcagccat accgccagcc tctctaagta ggggactacc tcctcgacgg   220620
tccattctag cgggacgaca tgaagcatgg cgacaagcgc ggctgctgtg aaaatgagcg   220680
cggttttata ggcattagga cttcccgatc gtactggcgg ctgtcaaagt cccgttgtcc   220740
aaagacgcgc cgtccgaaag actaatccaa cggggacccg agagcatgag caacaacgtg   220800
```

```
agaaagatgg ccatgctgtc caggtagaga cagacggcat gacggatgca ctggttaggt    220860
gggcagaaaa agatgaccat gagactgtcg taggccagaa tacccaaaaa gaagctgatg    220920
gagaaggcgc acaacgtcac cactatcttc tgcagccagt cggcgtcgct tagcagagcg    220980
agcgtgagga acgaaagcag catcaccacg tagacgcagc tgatgcattt ccaacgacgt    221040
cggtcacggc cacctagaaa cgccagcccc gtaaaggaga taaacaacgc cagggtcatc    221100
acgtaggaac ctactagtac gcggctttca gagcacattt ggaagatggc cgccgtcagg    221160
ctgttggcca acagatagat gaaaagcacc gtggcgttac tagggtgctc gttgcccaaa    221220
gtgtacgtga tgaacatgca gacgatgggc acgagcacgg tgagaaagaa gctgtagttc    221280
tcgacgcaaa agttgcggtt ttgtgggaac cccaaccaaa aaacgcttcc caagccgaag    221340
ctgaaagcca actgaaagat gaagatggcg tacacacgca gccatacggt gaactttttg    221400
aaccactcga gagcctccat gcgggagagc agcagcgcgt tagcctcctg cgcctgcatg    221460
gtggcgacgg tctcggcaca aagccgctgc ggcgcaccta cccttctctt atacacaagc    221520
gagcgagtgg ggcacggtga cgtggtcacg ccgcggacac gtcgattagg agacgaactg    221580
gggcgacgcc gctgctgtgg cagcgaccgt cgtagcgacc gtcgtctgag cagtgtgggc    221640
gctgccgggc tcggagggca tgaagtagag cacggagaca aagaggtaca tgaggtccat    221700
gtacaagcag agcgcgcccg ggatataact ctcatactcg atgtcgtgca ggatgtcctg    221760
cgtatcgcac accaccgagg tcacgatgac ggccaaaccg gctatcatca ccaggatctc    221820
acttaccgcc tcgggaaaaa gagaaaatac ggcgaacagt aagagaatca gcgtggatgc    221880
gcccgtcaat agggaacgct gtaattccac gtcgcgggca aacagatacg tagcgagcgt    221940
aaggaaacaa aatagcgtta ctgtggccac catggcataa atgactgaac gatgactaaa    222000
atggaagcct gacgccgtga cagccacgct ggtaagcaac gtgtacgtca gtaagatcca    222060 tacgttttg ggaaagttgg gctcggccca acgcaacaga cctaggcaca cgatggagat    222120
cattaagcaa gacagcgtca gacgcacgct ggaaaagagc tgctccagcc ggtgcggcaa    222180
caccagccag caaaaggcgc agacgctcat aaggatgagg cattgcaccc agataaggat    222240
gtagatgcgc agcaggaaga ccgaccgggc tatctggacc tgaccgcgga gcgacatggc    222300
ggcaacgccg gcggttatcg ccgagattcg tctaaataca cgaagcgaac tagaaaacgc    222360
acacacgtta tttgcaaaaa gaaagcagct gccggcttat tattttatta aaaatttatc    222420
tgtgcagaat cataagttta tgatgaataa aaacgggaa agggaatctg cttttaggga    222480
cccgggtctg gtccgtcgtc tcccatctgg tcgggttcgg ggatggggac ctgtttcagc    222540
gtgtgtccgc gggcgtgcat ggcttttgct cgccggccgc gctgtaacca ggcctctttc    222600
tctgtggtcg gcgagtcttc cgacgggtag ggagtctggg agtccatcgc ttcaggccca    222660
ccgctcgttc cctcgaccgt cgtgtcgtcc tcgttttcgc tattacacgg ggtttctgga    222720
gtatcgccta tacggttggc gattctccgg gggtggccgc tctcgtcctc gtcgctgcta    222780
tcgccgcccg gtaattcgac gccgcattcg ttgtacggag cgcggcacat gggcggcgga    222840
aagaacttgg gcatgcgaaa gcagcgttgt ccatccacgg tctgcgtggt ttcatcatta    222900
tcctcccata atccccctg tagcgccggc agcgtttcga cgctgtgaga ggggaaggcc    222960
cagttctggt tgtcttgcag cgcgcccgtg ggcagtaggt ccgtgcggcc ccaggcgctg    223020
ctgttgttgg gtaccttgtc agtgccgcga gtaggtcgca gaaaccagtc cagagcgctc    223080
tctagctgcg agcgtgtgat ggtgcccagt gcgccgtgcc agcgcagcac gtctcttttc    223140
```

```
agcgtgtggt gacagacggg cagctcctcc aaccgacact cgccgcgcaa tccgcggtcg   223200
aagcggcaga gaccacgcaa tttaagcaga ccgcacttga gaaacatgtg aaaattatcg   223260
gcaatgcgat acaggtctga gtcctcgatc ttgtgtaggt agaccacgcc aaacttgtcg   223320
agcagcacca ggccgctggg cacaaaaggc ccgtaggcca ggtaatagcc cacgaggccg   223380
acgacgtacc actcgcagca caagcgttga cgaataaagt tcagaagatc gcgaaagtcc   223440
gcggccggca tgtggtcaaa aggccggcag gcgcgcaggc cctcgatgga gcccagcatg   223500
agcaacggct ccacctcggt gcgacccggc gtgcggatga ccaggttgag accgctcatt   223560
tcgcgggccg tcttggccac ggccgcagcg tcagtgtgggt cggtgcagag gaattttttgc   223620 acatgatagc gcggttcggt ggtggcgaac ggcgtttgtg ggtgccgata cacatattcg   223680
caccagagta ggccgttctt ggaaaaggct ttgatatcac tggccacctc gtagagcccg   223740
tcggtctccc agtcgtagac gtagacggtg ccgtaatgac ttagcatgag cacgcagggc   223800
agttcctgcg cctgcttggt gtttcgtgtt agatcgctgt cgggtggacg cacggctagt   223860
acaccgacgg cttccagggt gtcatcgcag cagagatagt cggcggccag agaacgtgcg   223920
taaatctgcg ggatggcggc ctgttcgcgc atcactagga accagttggc ggggttgcgc   223980
agtgctacgg tggttccttg gtggcgctgc acgtaggttc tcagcgccgg aggatcgtac   224040
tggcgcagat agaggccttg cagcatcgat aacgtctttt gaaagacggt gtttctaaat   224100
tggaaaacgc cgtagtcgca gcggatagca tcttcgcagc gctcgtcgcg ctgtcggaga   224160
taggtgcccc aggcttcggc ggcggctttg gtgagtaggg acatgccggc ggagccgtct   224220
cgacagcgag tcggataaag cgcgctgcgc gaaagcttaa tataggagca gcgtcagacg   224280
aatcgcggct ggtggcccgg ggggtgggac gcgccgccta cacaaaatgc tcccgaaaat   224340
cgaaactctt gacccactcc ggagacaaat ccgtattcag attgatgcgt cgcgcttcca   224400
cttcggcttc cgaaacctcg gcctccgtcc ggtaggcgtt aacaatacgc tgacccaggt   224460
gccaacgctc tttctctgcc aaacgccgtt gctcaaacca ctcgtctacg tccttgaggt   224520
caaagacagt gtcctcctca aggtcaaagc ctaggtcttc ccactcgtcg tcatcgctct   224580 cgtgccggc ggccatacgc gcggcaaccg cgtcttcccc tcctcttctt tcaacgttgg   224640
gtaccacgtt gttttcttcg ggttccatgg gttctgcgcc actatcgtca tcgtcctctc   224700
cctgctcctc atcgtccgcc aaggcgtcgt ggatcacctc caggttctga ttgtcgggta   224760
cgacgtggtt atcttcgtcg tcgtcgcgtg gcatgggcgg cggccgacgg cggacgaccg   224820
gcatggcgcg gccgtcgttt ccttcgtctt cctcttcacc gtctcccaag gaacgcggtc   224880
gacgacgttc cgcgaagtcg ccgcggacca cgcgcgcctg ccaaatggta aacgcgtccc   224940
aaccgtccca gttattgagc atttcggcgc gaaaacggtc gcctcgacag agccagcgaa   225000
actgccgcgc gtagtcgcgg tctacgccgc tgtcgaacat ggtaaagtgc agacgcgccg   225060
cctcgcccat gtgtacgcag cctccattgc gttccagcct ggccgcgcgc gcagaccgt   225120 gttcgtagcg gcgacgcacg tacaccttca tgaggccggc gcgaaaaagt tcctctaggc   225180
tgtcggccag acggtagatt tcaccggcta gacgctgcag gggcggcgag cggtccagat   225240
gcgacttgac aatcaccacg taaaaacgac agaaacggtc gaagatgatg aggaaggacg   225300
tgtcaaagaa accaccggcg cggtaggagc ccacggcgcc tagcaggtac cagcggcaac   225360
gcagttgcag cgtgacgtac atttcgcact cggccaagcg ggcggctggc gctacctcga   225420
agggccagca atccgtcaag cagccgaaac tggtcaggag tttcaacgtt ttggcatggc   225480
gcccaggtgt gtgaaagttc acgtcgcgtc cgtggtgttc gccaacgcag gcggccaacg   225540
```

```
cgtcggcgtc atgagcgtga cgcagcagca tcgctaccac gtcgtgcggt acccgcgtag   225600
caaacggcgt ctgtggctga cggtatacgg cttcggtgta catcataccg taacgtgcca   225660
gctcgtccag atgacgcgcg cacagcagca gaatctcttg cgagggttcg tagatgtaga   225720
ggcgcgtacc gccccccatg cagagcacca gctccgtctc ttcgtagtga tcttccacca   225780
tgatcacgca cttgcctagc acgataaggc gttcggggca acaaatcacg tcgtccagca   225840
gttggtcgcg cagctccggc atggtgctgc caggccgcac ctgcaggaac cagttgtgcg   225900
gaatgccgag cgacaacacc tggtcgacgt ggttacggac ccagtcgcga agcacgtcgg   225960
cgctgtactg gcactcaaag atgccctgaa agtcgctcat gacccgcaga aaagtttcgt   226020
agcgcgtgtg gcaatagagg aattcatcgt ttcgcgtgaa cgtgggagct ccgtcttccc   226080
aacgtgtacg ccacatgtca aaagaggccg ccagctagac accccagaaa agaagcagag   226140
aaagagagtt ctttgtgcga cacgttttat tccgcgtcct ccgctcgacg ctcaaatctg   226200
gatgtactcg cgcacacccg tcaggctctt taagggaaaa gggtccgagt acgtcactaa   226260
ccgcgactga tgcaccaggg cggtaatcac ccgctctgcg ccctcgcgcg tcgacgaacg   226320
cgtcgtcacc aggcagtgca gccgcgggcc cgtatcgtcc tgatgaccag cggcctcgcg   226380
ctcggctgct tccacaccga caatgtcggg atccaacacg tagctctgcg agttggtgtc   226440
gtagcggtgt aacaccaacg tgttggggtc cagacgctcc cacgcgccct cgtgcgggtc   226500
aaaacgctcc gttaaacaga gccagtcata ctgctgctgc agaatacgcc gctcgcgctc   226560
gcgtcgctca tcgggcaacg cagcgtcttc gttgaagaga atgtcccgct tgtggtctac   226620
ggcacgctcg tggtggtgcg ggcacagatg acggtgttcc atacgcgtct gacgctgacg   226680
ctcgcgttcg aagcgccggt gtcgaaagac cattttcagc aacccatgc ggaaaaactc    226740 cgtgatggtg ttggcaacgc gccgcacata gtggttgggg tcgtccatct ggatggcgta   226800
cacggcaccg aaccagtcca gcagtaccag cacttcggcc acaaagttgc gtcccggtcg   226860
cggacgtccc gtcacgccta gcacatacca cggcgtggcc agattagcac ggacagccca   226920
ccaccaacga cggctctcca cctcggtgag cgcacagaag ggccaaatgc ggtgtaactg   226980
ctgcaccgtt ttcatcagcc gcataatcac cgtaccgtaa cccggtgtat gcaacttcac   227040
gtcgcaaccc aggattcgtt cggccgtggc gtacgagccc tcgggcgtgg tgtcattgag   227100
aaacaaaaca tgcatggtac gcgcgccctt agggtatcgt cgcggaacag gtaccgtcat   227160
tctccgcaga gtggtgtgaa tcacgtcgcg atacgcaatc tccgaacgcg acacaccgta   227220
acgtgccagt tcatccaagt tgtgcgatac taacaccatg tacttttcac gagtgtcgta   227280
ggcgtagacg cgagaaaagc gacccataaa accacgtac ggggtagcca ccatgccatc    227340
atggtgatcg cgacgtggct cgggcaacaa aataacagcg tatcccaacg gcgtcagcgg   227400
ctcgcggcaa cagatgagct ttgacgccgc ctgtctggcg gcggtaatga tcccgtcctc   227460
cgtacgtaac atcacatgcc agcccttggg gggacccaag gacagacaac gtccctcgtt   227520
acgatgaacg taacgcgtga tttccattgg ctccaggcaa agaacagtt ccttaaaatc    227580 ccgcaacact tgtcggtata acgccatggg atcctcggcc gccacaggca gcgcggggag   227640
ctccggcggc acaactgcag cgccgtcagg gccagaaccc gcagccggat ccatcattac   227700
gcgacactct cagccggaca accggcgtca ctgacagaag ccgagccaaa tacagagaaa   227760
gcaacgctac accgtcaccc cgctcccaag cgccgcggaa agtgctccga tttttcaccg   227820
tcgttcgcga cgttgatttg cctcggtctg agaaccgacc tagcgttcgg accggtgcgc   227880
```

```
agaaacagcc ggcggtccga gccactgagc ggttcacagc cccggccgcc gatagttacc   227940
ggagagacgt tcgagctgca ggtacatcgg cgctccccgc ttcgccaccc cgcgcccgcc   228000
ccagtttata ctctccgacg ccccgtccaa cgcgcctgtg gagggccaat cggaccgcgg   228060
gagctctcca agtggatgac aggcacagcc gggtgcccga ccgtgaagag ccctcatcca   228120
cctgaacaga ccgctaaccg aaggaccccg agtcgcgtcc gtcggtcccg acgtccgtcg   228180
ccatctggct ccctgctgtt ggctacctct cggatttcaa aaagagcac gtgccgatga    228240
cggtgcacag gaaagagcca agtgtcacg gcgtcttttt ttatttgtat tccttcctg     228300
ttttgtactc gtaaactgtt gacgttgttt ttacatccaa aagggcaagt aagaaacagg   228360
atgaggcatg gtaggtttgg gcgtggggcg gccctccagc acgcggccc gggccgcccg    228420
gcgggtgagc acccggcgtt gcgccgtatc tatcttgtgt ttcttctgtg tcttttttcct  228480
atcttgttcc gcgacggcct cttttcatcac gttcagcatg cgttcctcga cgccctccag  228540
ggatcctggg gaggagggag tcctagtgag gcttccaatg ttgttttgtg gattttcggt   228600
ttcctcttct tggtcgtcat cgtcggacgt gtcgtcttcc tcttgatcct cttcttcgtc   228660
cgagtagtag acgcatagtc cctggttcat caggctggga ttcatcaggt tctgacgggg   228720
aatccgctgt tgtagacgtt taaccgcccg ttccaggcga gagctcatgc cgcaccgac    228780
gctgtaacgc cgcacgggcc cgtagcgggc tgtttgttcg cgtacatgat cgttgagctc   228840
ttgccaatat tgtttggcac actccagatc ggaggtttgt ggatagtcgg gtcggatccg   228900
cggatcccaa ctgacatcgg cggtgccaga gacttcgtcc agactgttac gcatagagca   228960
ccagtcgggt cggacgataa acctgtcctt gcggattaac catttataac gtagttcgtg   229020
atggcgtgta gaggcccgta cacgctccac ggtcccaaag cggtcccaga agggaaagtt   229080
ttcgtggggg cagcgacccg gcacttccaa acgttcggcg tcgtccacgg cgtagtggaa   229140
acgccggccg gcctggtaaa ttttgagcag acccacggtt aacaacatat ccacgctgtc   229200
agccaaccgc cagatctcgc gccgagatac gtcaaaatag aaaaattcgc aggctcggtc   229260
gaccaggatc acgaaatcgg cgtgaaaaac gccggagggt agcgactcgc ccaccacacc   229320
cattatcatg gtttcacagc ataagcggtc cacaaagaac ttcaacaggt cgttgaattg   229380
ctccgtctcc atacagatga agggccagac gcctttgagg ttctcggcct ggccgcagag   229440
cagcaacgga cgcgtcatct cgcctggagt gcgcagaggc acgcattcgc cgcgataacg   229500
acaggtcaca cgctgcagtt cgctgatgct gttgtcgtgc aggcgaaggt cgcagataat   229560
atgatccggt tgcgtggtta gcagcggcgt gcgcatttgc tcgccgtaga tggcctcgca   229620
gtgcaatagc ccgtgtcgtg caaaatcgtc cagactgtgc gccaggtagt aaagcacccc   229680
gcgatcgcgg tctagacacc acacggtttc gtaacgtcct agcagaagca ccagacgggc   229740
ctggctaggt ggctcaattt cctctacata cacgaaaaag tcgtcatcgt ccgagtcctc   229800
gtcctcagaa gaggaccgcg gcccgtgtac tctgggcaac acggtggtag agaactgcag   229860
gacgcccaga gactcgagcg actcttcgca gcagatgagc tgaccccagg gcgtttctgg   229920
cccgtcggtg acagccgcgc tgccaaagat gtcctcaaac tctacaaaat ctagacgcca   229980
tccgggtggc gctgaaacgg gaaggctaat gttcatatca gcatagctac gaactaagtg   230040
gcggatgtcc tgccgcaagt cttggcagag aatgagcttt cgtaaaccct tgagggtcct   230100
ccgaacaacg gccccagacg cgtagcgata ggactggcgc atggtgccgc ggcgtggagc   230160
ggcacttggc agcctatttt atggagtttc ttcagtgacg tggcttgttc acgtcgttcg   230220
tgggctgcgg ttggcagctc cggtctgtaa accacccgaa aagactgaca tcgacgtcaa   230280
```

```
agacccacgt aatttggaac atgtgcgacc gcaaagtgcg tcagaataac acgtggcttt   230340
aggacataaa aagtaccgtg aggtccagac gtggtttttg tgattgacac ttacaccagg   230400
taagccaagg gacggtgaaa ctgtatgtga ggaacctggg tgcttagacg actaacgtgt   230460
aatgcttttt acaggactgt tcgacaggtg atagtacctg taaggtgatg accacctcta   230520
caaataatca aaccttaaca caggtgagca acatgacaaa ccacacctta aacagcaccg   230580
aaatttatca gttgttcgag tacactcggc tcggagtatg gttgatgtgc atcgtgggca   230640
cgtttctgaa cgtgctggtg attaccacca tcctgtacta ccgtcgtaag aaaaaatctc   230700
cgagcgatac ttacatctgc aacctggctg tagccgatct gttgattgtc gtcggcctgc   230760
cgttttttct agaatatgcc aagcatcacc ccaaactcag ccgagaggtg gtttgttcgg   230820
gactcaatgc ttgtttctac atctgtcttt ttgccggcgt ttgttttctc atcaacctgt   230880
cgatggatcg ctactgcgtc atcgtctggg gtgtagaatt gaaccgcgtc cgaaataaca   230940
agcgggctac ctgttgggtg gtgattttt ggatactagc cgtgcttatg gggatgccac   231000
attacctgat gtacagccat accaacaacg agtgtgttgg tgaattcgct aacgagactt   231060
cgggttggtt ccccgtgttt ttgaatacca aagttaacat ttgcggctac ctggcgccca   231120
ttgcgctgat ggcgtacacg tacaaccgta tggtgcggtt tatcattaac tacgttggta   231180
aatggcacat gcagacgctc cacgttcttt tggttgtggt tgtgtctttt gccagtttt   231240 ggtttccttt caacctggcg ctattttag aatccatccg tcttctggcg ggagtgtaca   231300 atgcacact tcaaaacgtt attatcttct gtctatacgt cggtcagttt ttggcctacg   231360
ttcgcgcttg tctgaatcct gggatctaca tcctagtagg cactcaaatg aggaaggaca   231420
tgtggacaac cctaagggta ttcgcctgtt gctgcgtgaa gcaggagata ccttaccagg   231480
acattgatat tgagctacaa aaggacatac aaagaagggc caaaaacacc aaacgtaccc   231540
attatgacag aaaacatgca cctatggagt ccggggagga ggaatttctg ttgtaattcg   231600
atcctctctc acgcgtccgc cgcacatcta tttttgctaa ttgcacgttt cttcgtggtc   231660
acgtcggctc gaagaggttg gtgtgaaaac gtcatctcgc cgacgtggtg aaccgctcat   231720
atagaccaaa ccgacgctg cctcagtctc tcggtgcgtg gaccagacgg cgtccatgca   231780
ccgagggcag aactggtgct accatgacgc cgacgacgac gaccgcggaa ctcacgacgg   231840
agtttgacta cgatgaagcc gcgactcctt gtgttttcac cgacgtgctt aatcagtcaa   231900
agccggtcac gttgtttctg tacggcgttg tctttatctt cggttccatc ggcaacttt   231960 tggtgatctt caccatcacc tggcgacgtc ggattcaatg ctccggcgat gtttacttta   232020
tcaacctcgc ggccgccgat ttgcttttcg tttgtacact acctctgtgg atgcaatacc   232080
tcctagatca caactcccta gccagcgtgc cgtgtacgtt actcactgcc tgtttctacg   232140
tggctatgtt tgccagtttg tgttttatta cggagattgc actcgatcgc tactacgcta   232200
ttgtttacat gagatatcgg cctgtaaaac aggcctgcct tttcagtatt ttttggtgga   232260
tctttgccgt gatcatcgcc attccacact ttatggtggt gaccaaaaaa aacaatcaat   232320
gtatgaccga ctacgactac ttagaggtca gttacccgat catcctcaac gtagaactca   232380
tgctcggtgc tttcgtgatc ccgctcagtg tcatcagcta ctgctactac cgcatttcca   232440
gaatcgttgc ggtgtctcag tcacgccaca aggtcgcat tgtacgggta cttatagcgg   232500
tcgtgcttgt ctttatcatc tttttggctgc cgtaccacct gacgctgttt gtggacacgt   232560
tgaaactgct caaatggatc tccagcagct gcgagttcga aaaatcactc aagcgcgcgc   232620
```

```
tcatcttgac cgagtcactc gccttttgtc actgttgtct caatccgctg ctgtacgtct   232680
tcgtgggcac caagtttcgg caagaactgc actgtctgct ggccgagttt cgccagcgac   232740
tcttttcccg cgatgtatcc tggtaccaca gcatgagctt ttcgcgtcgg agctcgccga   232800
gccgaagaga gacgtcttcc gacacgctgt ccgacgaggt gtgtcgcgtc tcacaaatta   232860
taccgtaata aaaagcgct acctcggcct tttcatacaa accccgtgtc cgccccttt    232920 ttccccgtgc ccgatataca cgatattaaa cccacgacca tttccgttcg attagcgaac   232980
cggaaaagtt tatggggaaa aagacgtagg aaaggatcat gtagaaaaaa catgcggtgt   233040
ttccgatggt ggctctacag tgggtggtgg tggctcacgt ttggatgtgc tcggaccgtg   233100
acggtgggtt tcgtcgcgcc cacggtccgg gcacaatcaa ccgtggtccg ctctgagccg   233160
gctccgccgt cggaaacccg acgagacaac aatgacacgt cttacttcag cggcacctct   233220
ttccattctt ccgtgtcccc tgccacctca gtggaccgtc aatttcgacg gaccacgtac   233280
gaccgttggg acggtcgacg ttggctgcgc acccgctacg ggaacgccag cgcctgcgtg   233340
acgggcaccc aatggagcac caactttttt ttctctcagt gtgagcacta ccctagtttc   233400
gtgaaactca acggggtgca gcgctggaca cctgttcgga gacctatggg cgaggttgcc   233460
tactacgggg gttgttgtat ggtgggcggg ggtaatcgtg cgtatgtgat actcgtgagc   233520
ggttacggga ccgccagcta cggcaacgct ttacgcgtgg atttttgggcg cggcaactgc   233580 acggcgccga aacgcaccta ccctcggcgc ctggaactgc acgatggccg cacagaccct   233640
agccgttgcg atccctacca agtgtatttc tacggtctgc agtgtcctga gcaactggtt   233700
atcaccgccc acgcggcgt gggtatgcgc cgctgtccta ccggctctcg tcccaccccg   233760
tcccggcccc accggcatga cttggagaac gagctacatg gtctgtgtgt ggatcttctg   233820
gtgtgcgtcc tttattagc tctgctgctg ttggagctcg ttcccatgga agccgtgcgt   233880
cacccgctgc ttttctggcg acgcgtggcg ttatcgtcgt ccacttccaa ggtggaccgc   233940
gccgtcaagc tgtgtcttcg gcgcatgctg ggtctgccgc cgccaccgtc agtcgcacca   234000
cctggggaaa agaaggagct accggctcag gcggccttgt cgccgccact gaccacctgg   234060
tcactaccgc cgtttccgtc cacgcggata cctgacagtc cgccgccacc gtaccagctt   234120
cgtcacgcca cgtcactagt gacggtaccc acgttgctgt tatatacgtc atccgacatc   234180
ggtgacacag cttcagaaac aacgtgtgtg gcgcacgcta cttatgggga accccggag    234240 cccgctcgat cgacggctac ggttcaggaa tgtaccgttc ttaccgctcc aaattgcggc   234300
atcgtcaaca acgacggcgc ggtctctgaa ggccaagacc atggagatgc ggttcaccat   234360
agcctggatg tggtttccca gtgtgctgct gatactgggg ttgttgacgc ctccgagtaa   234420
cggctgcact gttgatgtcg gacgaaacat gtccattcga gaacagtgcc gccttcgaaa   234480
cggtgcgacg ttctccaagg gagacatcga aggtaacttc agtgggcccg tcgtcgtgga   234540
gttggactac gaagacatcg atattactgg cgaacggcag cgacttcggt tccacctcag   234600
cggactcggg tgtcctacaa gggagaaaat aagaaaagat aatgaaagcg acgtcaacgg   234660
tggaattcgc tgggctctat atatacaaac cggcgacgcc aagtacggta ttcgtaatca   234720
gcatttgagt atacgttaa tgtatcctgg ggaaaaaaat acacaacagc tgttgggttc    234780
tgatttcagt tgcgaacgtc accggagacc gtccacgccg ttgggaaaga acgccgaagt   234840
gcctcccgcg acccgcacgt cttctacata cagcgtcctc agcgcttttg tagtgtggat   234900
cggatccggc ctcaatatca tctggtggac cggcatcgtg cttctggcgg tggacgtctc   234960
cggacttggc gagcgttggc tgaggttagc actgtcccac cgggacaaac atcacgcatc   235020
```

```
gcgaaccgcg gcgctccagt gtcaacgcga catgttactt cggcaacgtc gacgggctcg   235080
gcggctgcat gccgtttctg aaggcaaact gcaggaagag aagaaacgac agtctgtctct  235140 ggtctggaac gttgaggcgc gacccttcc gtccacacat cagctgattg tgctgccccc    235200
tcctgtagcg tcagctcctc ctgcagttcc ctcgcagccc cccgagtatt cgtctgtgtt   235260
tccgcctgta taaaataaa gagacgggag gctgatcgcg gccttcagcg tctcatttgt    235320
ctttactctc gagtgcggtc ggtgtctcgt cggtgagacg aggccgccgc ccgacaagtt   235380
cgatctcatg tcgctcttgg agcgcgaaga gagttggcgt cgcgtagtcg actactcgca   235440
caacctgtgg tgtacgtgcg gtaactggca gagccacgtt gagattcagg acgaagagcc   235500
caactgcgag cagccggagc ccgcacactg gctggaatac gtggcggtcc agtggcaggc   235560
ccgggttcgc gattctcacg atcgctggtg tctctgcaac gcctggcgtg atcacgcttt   235620
gcgcggccgt tggggtacgg cgtattcctc gggttcctcg gcctcttcct ccggtttcgt   235680
cgcggagagc aagttcacct ggtggaaacg actgcgccac agtacccggc gctggttgtt   235740
tcgccgccgg cgagctcgat acactccatc taactgtggg gaaagtagca ctagcagcgg   235800
ccagagtagc ggtgacgaga gtaactgcag tctacgcacc cacggcgtgt acacacgggg   235860
tgaacaacac taatcgataa gtcgcgtgta ggcgactggc tacatcaacc ggatatctgc   235920
ggggatttaa aaagacgacc cgttgtcatc cggcttagag caaaccgtcc ttttatcatc   235980
ttccgtcgcc atggctatgt acacatccga atccgaacgc gactggcgtc gtgtaatcca   236040
cgactcgcac ggcctgtggt gcgactgcgg cgactggcga gagcacctct attgtgtgta   236100
cgacagccat tttcagcgac gacccacgac ccgagccgaa cggagggccg ccaattggcg   236160
gcgacagatg cggcggttac accgtctgtg gtgtttttgt caggactgga agtgtcacgc   236220
gttatacgcc gagtgggacg gcaaagaatc cgacgacgag tcgtcggcgt cttcctcggg   236280
cgaagcgcca gagcaacagg tccccgcttg gaagaccgtg cgggccttct cgcgggccta   236340
ccaccaccgc attaaccggg gtctgcgggg cacgccccca ccgcgcaact gccgggata    236400 cgagcacgcc tccgagggct ggcggttttg cagtcgacgg gaacggcgag aggacgatct   236460
tcgcacgcgg gctgagccgg accgcgtggt gttccagtta gggggagtac ctcctcgtcg   236520
tcaccgagaa acttacgtgt aagaacacgg cgtgacaata aacaacatag cgtaaatccc   236580
cgtgtgatgt gtgtgattga cgttcggaa acatgtcccc atcatcagcg tcacaactga    236640
cgtgggttgg tcactgacgt gcaggatgtt gcgcgagtca gagaatcgca taagaacggg   236700
gtggtgagcg ggttcccaca ggagtctctg gcgcaaaagc accatgagcc tcaggttccc   236760
cgagagggcg ggttacgaga aactgggata ccgcccgcat gccaaacgcg tgcgggtgca   236820
tgacccgttg ggattgacgc ggtttatcat gaggcaactc atgatgtacc cgctggtgtt   236880
gccgttcacc tttccgtttt acgtgccgcg gtcctagcac gtcagtggtg atgctgataa   236940
ttgcaacatg gccatgacg aaccgcttg gacgaacgt caataccacg tcaaaccacc     237000
gtgacttggc tgaacgttga aacataaagc caaagcgccg tcggcacttg gcttcagagc   237060
agcgcctcgg ggcgatgcga cggcgatgaa cttagagcaa ctcatcaacg tccttggtct   237120
gctcgtctgg attgccgctc gtgctgtcag ccgcgttggt ccgcatggct ccggactcgt   237180
ttatcgtgag cttcatgatt tctacgggta tctgcagctg gaccttctgg gaccagtggt   237240
ggcggggaat cgctcagtcc ggacctgaa agagcaggcg gaccgagcca gaggacctt     237300 cgttcggcgt tcaggcctta atactagcta catcttacct gtcggcggcc tgtctggggg   237360
```

```
ctccggtacc ttacccgtcg gcctgtatcg tcccgaagaa gaggtgttcc tcctcttgaa 237420
ccgctgccat gggccactgt caacgccgaa aaatgcttgt ctggctgagg tcggtgtcgc 237480
taatgccact tttttgtctc gcttcaatgt cggtgatttt cacggagcgt catgggaaaa 237540
cggtaccgct cccgatggag agcccggggt atgctgaaat tcctcttaag attccgtaaa 237600
cgacgttgtc cagtcgttgt gccgcgattc gtacggttca tcgtctacgt cgttttgttc 237660
accgtcgctg tgcaacgcgt gaaacaagag cgtgatgcgc accttcggcg gtatgaagaa 237720
cggttacgga aaaccgcgc acggcgtcgg cagtcttttc cgtgacttgg ggcgatgggt 237780
ccgagctgcg gtatgggtca cggcggcgtg tgttttattg acgaagatgc cgatgtgtga 237840
ctaaaaacgt cccagcccta gagcgatgtg tttcaataaa aattatgtcg tatcatagta 237900
tgcgtgtcct ggttttttcat tttttggatgt atttgtgaca taaaaggcga tagaatgtgg 237960
ggacgaaaca tatccagata cacagttttg ttattcgaac aaaacccgtg tgatgcagaa 238020
aacagtactg caggatgaaa gtcccatggg gggggggggg cagacagtag tcgtttttgc 238080
cgctgggcgt acgctatgct tgtatttatg actataatat gtgcactcgt gtgtcgatgt 238140
tcctattggg aagggtgtca atgtaggagg tataaagaat ggtgggatgc ggagaggcat 238200
cgctagacac aggttgatcg ctgtgctagc cccacctgat cagcgtcatg ggtaaagcgg 238260
tgattaagcg tgaaaacacc gtaaggggg gggggcagac aggaagcttg gtggcagtgg 238320
ccgttagatg cattacgtgt ctgtattggt acatttgcaa accgtcgggt gtggcggtat 238380
agtttagcga tgattatatt atgtatgtgc cgtatagaat ggcctaaaac attgtaacac 238440
gaaacgttac aatgatggga agatgccga taaaaaacac ataaaaggca tatacacgaa 238500
ttactagtta cacgtttgtc tatgtgcgag tttaaggacg cttgtataat gcgtatgacg 238560
gcaaacggcc gcggaaacga tggggggggg gggtagtaac tgtattaatt atacgtcttg 238620
cagtacacgg tattgtgtgc tggtgcgcgt attacgacac gaacggcata gcgctataac 238680
cgggtgtatg gtatttatat gtgcgtctag catccttgcg agattctgaa agtcttcttg 238740
taagcgtaat taaaacggtg tatgttctgc gtaaagtgca ttcaaacaac gtaacagtat 238800
gggatgaatg ccaataaata acatataaaa gcgagaagta tacatataag ggttgctaga 238860
cacaggtttg tttctgtgct agcccaatgg cacttgtaca atccatgcaa gcaaaaaaag 238920
gatgcgaaac caacatcgtg gggtgggggg ggggtaaaag caatgttaat cattggtctc 238980
gcggtgcaag ttgctgcgtt ttacgtgtat tgttacacgg gttgcgtatc ggtataatcg 239040
gatgtgtgtt actcattcgt ggcgttgtta tagtattgtg aaaagaatt ctcgtaagca 239100 tgttgacaac tgcaaaataa aaccatttta ttgagcattg taatggtagt gtgtcgctac 239160
attagaaaac gtgacgcgtc gcatgtcgcg gcacaatctg gcagcggggt cggggtaggg 239220
tacggtggga ggcatgtaca cagatggaac aaaagcagaa gtaacgtgag acggagcata 239280
tagtccagta tccagcggtt cctgagtagc accacccatc aactgaatgc cctcatgagt 239340
aaaagtctgc gggcggcagc ccttggggac cgttggcatg gacgatcga tctccaaacc 239400 acagcgtaac acggtttct tccaacgtcg ttgatacacg tcgtttttac ggttactccc 239460
cagaacccag aaagtctcgt ccaagtcgta ccaggagtct tccccaggga gacgtggcgg 239520
tttccaatcc tcatcgtccc gtcgcaaagc acgtcccaaa ctggcttggg gagtcaacgg 239580
tggttctgtg ggtcgggtgt agcgcgagtg ttttccgttc atgagcgatt cgtcctcctt 239640
gcctttaggc ttttttggcct ttttgtgtat catctgggcg ccggcctcca taaccaccgt 239700
ggccaagtcc agtcccagag cttgagcgtc ggcgcggcgt cgggcgtctt gcaggtagtc 239760
```

```
ttccacattt gcacagatgg ccgggtgttt ggtggctagg gtgaggacct cagcctcgcc   239820
gcggcccgga cgtagcaaaa aagctaactg cccgtgcggc tcgcgcgccc acagcgcggc   239880
gcgcgggtgc aggtgcagcg cgtcccagcg cggccgctcc cactgctcgc ggtccagctc   239940
gggcagcagc cgccgcgcgg cctcggcggc gggcgccgac tcgcgcccca cgcgcagcgc   240000
gcccaacacg cccgcgcgca gaaagtgcga cagctccgcc gccagcgggt acacgtgccc   240060
gtccagcggg cagtacccga acacggcgcc cagctcgtcc agcaccacca ccagcatggc   240120
gcgcggcacg gtccccgacg ccgccggacc cgccatcgcc gtcggaccca ccatcaccgt   240180
cggcgccgcc gctgctgccg ctgccgcatc cgttccgacc accgcgtgcg cgtccgcgtt   240240
tggcacgcaa atcgcgctcc cgccggcggc gccgtacggc tgcggaggta aagtcacagc   240300 agacccacg gctcccgcca tcgcgcacgg cgcgtcccg ccggcggcct ccgtctccgt   240360
gccgctcgcc cccggcagca acgtcgtccc cgtcgccatc gccgtcgtcc ccgccgtcat   240420
cgtcgtcgtc gtccccgccg tcgtccctgt cgccggccct gccgcgcagc gcagccaccg   240480
cgacggcagc accgcgccca gcgccagcca gccgcagcac agacgctggt tcaggtgccg   240540
acgcacggcc gtcagcagcg acgcggggtg cggcgccgac gcgaacggct cgtactgcgc   240600
cagctcctgc cacgcgccca gcagcaccat cggctgcagt cgcctgcccg gcgtctgcag   240660
cgccaccgtc gtgccggccc accgccggcg cagctcccgt ccgagcgccg tcgcctcctc   240720
ggcgcgcagc aacgtctggc gaagcgccgg ctgaggcagc agcgtcgcgc gcggggtgcc   240780
cacgcccagc cggttgcagc ggtacaggcg caccacctcg cccgcgccgt gccgaaacca   240840
ctcgtccgcg tcgcgcgccg ccaggatcag cgtgttgttc gccaggtcgt acacgaacac   240900
gcggaacccg gcgcccagcg ccaggtacag tccgtcctgc gcgcacagac cctcgggatg   240960
gccggccttg tcgcccaccg tcgggtcggc cgcggggtcc acctcgtgca ccacggtcgc   241020
caccagcacg atccacgcgt cccgcggcga cagctgacgc aggtccgtgg cgcccacgcc   241080
gttcatctgg ctgcgcggcg tcactcgcgc gtagaatccg tacggccgtc cgagcggcag   241140
cagcgtgccc gcgtcgcgct gcgaccactt gcgcatggcg cggccgtgc tgttggccaa   241200 aaacgcggcg cgccacacgg cgcccatggc ctggtattcc agctccgtca cgcctggcg   241260 ctccaccgga atctgagaca gcagcaagcg ctccgggccg tgccaaaagg tgctgttgtt   241320
gccgctaccc ggaggggcgc ccggcggccc gcggggttct acccggtgga cggcgtgggc   241380
cggcgtcgcc gtacccgcag tactcgtact agtccccgct gttgacgtcg cttccaaaga   241440
agaagaacga gaggaaccaa cccccgaagg ccctccggct ccgcggccgc gaccgagggg   241500
cggggggcgc ggcgacatgc cgttgcgctg ggccatggcc gccggacgcc tccgacgtcc   241560
actctgtata tataggaagc aaacccgcgt cagcgaccac gccgtttaca cacgcggacg   241620
cctccgtcgc ccgtgtgccg cgggcgacac gcacctggct tttataggca gcgacgtgca   241680
cggcgcttgc tggcgccgcc ttgccgccgc gcagtctgga aggccgtgaa aaaaccgaaa   241740
gaagatgcgc gacaagccac caacaacggg ccgccgagcg cgcgcacacc taggtggacg   241800
cctgacctcc attccgggcc gtgtgctggg tccccgaggg gcgggggggt gttttcatcg   241860
ggggggtgaa atgtgggaat ttgggaagtt ggcggtggcg gggacggcg acggcgaata   241920 aaagcgccgt gcggcgcgca cggcgaaacc cagacgcgcg tgtgtcttgc gtctctttca   241980
gtcgcgcgtc tgtcttgcgt gtcttttgagt ccccggggaa aagaggaagc ggtcccgagg   242040
ggacggcggc gcgactccct ggggacgcga agatcggacg cggaaaagag gaagtccccg   242100
```

```
gggacggcca caggcggaaa aaaaaaacga ggaagccgca gcccagtctg ccgggaccgg   242160
caggcaggcg cacagacccg cgtcgaggac acacgcagaa gaagcgcccg cgccggggcg   242220 gggggggggga tcgcgggccc cggggcacac tgcttccatc tggccgcgcg cacacccgc   242280 cgacacaccc ctgacacacc cgcgacacac ccggcacacg cccgcgacac acccggcacg   242340
cgcccgccac acagccagcc gacacacccg cgacacaccc gccacaccca gccgcacccg   242400
gcacacaccc acccagccgc accccgcca cacccagacc gacgccggtg cgggaccggg    242460
ctccattccg ggccgtgtgc tgggtccccg aggggcgggg gggtgttttc atcgggggggg  242520 tgaaatgtgg gaatttggga agttggcggt ggcgggggac ggcgacggcg aataaaagcg   242580
ccgtgcggcg cgcacggcga aacccagacg cgcgtgtgtc ttgcgtctct ttcagtcgcg   242640
cgtctgtctt gcgtgtcttt gagtccccgg ggaaaagagg aagcggtccc gaggggacgg   242700
cggcgcgact ccctggggac gcgaagatcg gacgcggaaa agaggaagtc cccggggacg   242760
gccacaggcg gaaaaaaaaa acgaggaagc cgcagcccag tctgccggga ccggcaggca   242820
ggcgcacaga cccgcgtcga ggacacacgc agaagaagcg cccgcgccgg ggcgggggggg 242880 gggatcgcgg gccccggggc acactgcttc catctggccg cgcgcacacc ccgccgacac   242940 accctgaca cacccgcgac acacccggca cacgcccgcg acacacccgg cacgcgcccg    243000
ccacacagcc agccgacaca cccgcgcacac cccgccaca cccagccgca cccggcacac   243060 acccaccccag ccgcaccccc gccacaccca gaccgacgcc ggtgcgggac cgggctccat  243120
tccgggccgt gtgctgggtc cccgaggggc gggggggtgt tttcatcggg ggggtgaaat   243180
gtgggaattt gggaagttgg cggtggcggg ggacggcgac ggcgaataaa agcgccgtgc   243240
ggcgcgcacg gcgaaaccca gacgcgcgtg tgtcttgcgt ctctttcagt cgcgcgtctg   243300
tcttgcgtgt ctttgagtcc ccggggaaaa gaggaagcgg tcccgagggg acggcggcgc   243360
gactccctgg ggacgcgaag atcggacgcg gaaaagagga agtccccggg gacggccaca   243420
ggcggaaaaa aaaacgagg aagccgcagc ccagtctgcc gggaccggca ggcaggcgca    243480
cagacccgcg tcgaggacac acgcagaaga gcgcccgcg ccggggcggg ggggggatc    243540 gcgggccccg gggcacactg cttccatctg gccgcgcgca caccccgccg acacacccct   243600
gacacacccg cgacacaccc ggcacacgcc cgcgacacac ccggcacgcg cccgccacac   243660
agccagccga cacacccgcg acacacccgc cacacccagc cgcacccggc acacacccac   243720
ccagccgcac cccgccaca cccagaccga cgccggtgcg ggaccgggct gagggggtg    243780 taagcgcctt gacgcgcggc gctatggcac tgcgtgccac ggtattggtt ggcgggacga   243840
ggctgagggg ggtttgcggg acgtaagcgc gacgccgagt ttgcggcgtg ctgtggcgcg   243900
ctcaaggcta gggacggggg ccgcgcgtag cttttcggcg gcgacgggga acaaaacagg   243960
cacgcacacg cagctcgctt cagcggtcgc cctatcggca ccgccgctat tctttattaa   244020
cgtcgttctc ccccgcttc tacacgcgga ccgctgcaga cggctatgct cagactgttt    244080
ctcttgacgg cgacatgtgt ttgcgtctgt gcggcgcggc gacggccgca agcggacgac   244140
gccgcctgcc accacacgtg gcccacgcgc tgcgccggcc cgcgtcccgc gccgtcggct   244200
cacaacacgg cgctttcttc ctcgcacgcc atctccatcg cacaccgtgt gctgcattcg   244260
ccgtcgcctc cacgagagaa catccgccac agcatgcgct gtcgccgtcg cgccatggcc   244320
tcctcggctt gcacacccgt ttcgcacacc cagcctcggg ccgccaacca cagccgttcg   244380
aggatgacgt acgcgacgag cgagcccacc aattctccca cggcctcgcc cgccaagtca   244440
gac                                                                244443
```

<210> SEQ ID NO 2
<211> LENGTH: 21
<212> TYPE: RNA
<213> ORGANISM: Artificial Sequence
<220> FEATURE:
<223> OTHER INFORMATION: siRNA

<400> SEQUENCE: 2
gcuacaagcu ggagaaugau u                                    21

<210> SEQ ID NO 3
<211> LENGTH: 21
<212> TYPE: RNA
<213> ORGANISM: Artificial Sequence
<220> FEATURE:
<223> OTHER INFORMATION: siRNA

<400> SEQUENCE: 3
ucauucucca gcuuguagcu u                                    21

<210> SEQ ID NO 4
<211> LENGTH: 498
<212> TYPE: PRT
<213> ORGANISM: Artificial Sequence
<220> FEATURE:
<223> OTHER INFORMATION: HIVgag

<400> SEQUENCE: 4

```
Met Ala Ala Arg Ala Ser Ile Leu Ser Gly Gly Lys Leu Asp Ala Trp
1               5                   10                  15

Glu Lys Ile Arg Leu Arg Pro Gly Gly Lys Lys Tyr Thr Leu Lys
            20                  25                  30

His Leu Val Trp Ala Ser Arg Glu Leu Asp Arg Phe Ala Leu Asn Pro
        35                  40                  45

Ser Leu Leu Glu Thr Thr Glu Gly Cys Gln Gln Ile Met Asn Gln Leu
    50                  55                  60

Gln Pro Ala Val Lys Thr Gly Thr Glu Glu Ile Lys Ser Leu Phe Asn
65                  70                  75                  80

Thr Val Ala Thr Leu Tyr Cys Val His Gln Arg Ile Asp Val Lys Asp
                85                  90                  95

Thr Lys Glu Ala Leu Asp Lys Ile Glu Glu Ile Gln Asn Lys Ser Lys
            100                 105                 110

Gln Lys Thr Gln Gln Ala Ala Ala Asp Thr Gly Asp Ser Ser Lys Val
        115                 120                 125

Ser Gln Asn Tyr Pro Ile Ile Gln Asn Ala Gln Gly Gln Met Ile His
    130                 135                 140

Gln Asn Leu Ser Pro Arg Thr Leu Asn Ala Trp Val Lys Val Ile Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Val Met Leu Asn Ile Val Gly
            180                 185                 190

Gly His Gln Ala Ala Met Gln Met Leu Lys Asp Thr Ile Asn Glu Glu
        195                 200                 205

Ala Ala Glu Trp Asp Arg Leu His Pro Val Gln Ala Gly Pro Ile Pro
    210                 215                 220

Pro Gly Gln Ile Arg Glu Pro Arg Gly Ser Asp Ile Ala Gly Thr Thr
225                 230                 235                 240
```

```
Ser Thr Pro Gln Glu Gln Leu Gln Trp Met Thr Gly Asn Pro Pro Ile
                245                 250                 255

Pro Val Gly Asn Ile Tyr Lys Arg Trp Ile Ile Leu Gly Leu Asn Lys
            260                 265                 270

Ile Val Arg Met Tyr Ser Pro Val Ser Ile Leu Asp Ile Lys Gln Gly
        275                 280                 285

Pro Lys Glu Pro Phe Arg Asp Tyr Val Asp Arg Phe Phe Lys Ala Leu
    290                 295                 300

Arg Ala Glu Gln Ala Thr Gln Asp Val Lys Gly Trp Met Thr Glu Thr
305                 310                 315                 320

Leu Leu Val Gln Asn Ala Asn Pro Asp Cys Lys Ser Ile Leu Lys Ala
                325                 330                 335

Leu Gly Ser Gly Ala Thr Leu Glu Glu Met Met Thr Ala Cys Gln Gly
            340                 345                 350

Val Gly Gly Pro Gly His Lys Ala Arg Val Leu Ala Glu Ala Met Ser
        355                 360                 365

Gln Ala Gln Gln Thr Asn Ile Met Met Gln Arg Gly Asn Phe Arg Gly
    370                 375                 380

Gln Lys Arg Ile Lys Cys Phe Asn Cys Gly Lys Glu Gly His Leu Ala
385                 390                 395                 400

Arg Asn Cys Arg Ala Pro Arg Lys Lys Gly Cys Trp Lys Cys Gly Lys
                405                 410                 415

Glu Gly His Gln Met Lys Asp Cys Thr Glu Arg Gln Ala Asn Phe Leu
            420                 425                 430

Gly Lys Ile Trp Pro Ser Ser Lys Gly Arg Pro Gly Asn Phe Pro Gln
        435                 440                 445

Ser Arg Pro Glu Pro Thr Ala Pro Pro Ala Glu Leu Phe Gly Met Gly
    450                 455                 460

Glu Gly Ile Ala Ser Leu Pro Lys Gln Glu Gln Lys Asp Arg Glu Gln
465                 470                 475                 480

Val Pro Pro Leu Val Ser Leu Lys Ser Leu Phe Gly Asn Asp Pro Leu
                485                 490                 495

Ser Gln

<210> SEQ ID NO 5
<211> LENGTH: 498
<212> TYPE: PRT
<213> ORGANISM: Artificial Sequence
<220> FEATURE:
<223> OTHER INFORMATION: #3D6 p4

<400> SEQUENCE: 5

Met Ala Ala Arg Ala Ser Ile Leu Ser Gly Gly Lys Leu Asp Ala Trp
1               5                   10                  15

Glu Lys Ile Arg Leu Arg Pro Gly Gly Lys Lys Lys Tyr Arg Leu Lys
            20                  25                  30

His Leu Val Trp Ala Ser Arg Glu Leu Asp Arg Phe Ala Leu Asn Pro
        35                  40                  45

Ser Leu Leu Glu Thr Thr Glu Gly Cys Gln Gln Ile Met Asn Gln Leu
    50                  55                  60

Gln Pro Ala Val Lys Thr Gly Thr Glu Glu Ile Lys Ser Leu Phe Asn
65                  70                  75                  80

Thr Val Ala Thr Leu Tyr Cys Val His Gln Arg Ile Asp Val Lys Asp
                85                  90                  95
```

Thr Lys Glu Ala Leu Asp Lys Ile Glu Ile Gln Asn Lys Ser Lys
            100                 105                 110

Gln Lys Thr Gln Gln Ala Ala Asp Thr Gly Asp Ser Ser Lys Val
        115                 120                 125

Ser Gln Asn Tyr Pro Ile Ile Gln Asn Ala Gln Gly Gln Met Ile His
    130                 135                 140

Gln Asn Leu Ser Pro Arg Thr Leu Asn Ala Trp Val Lys Val Ile Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Val Met Leu Asn Ile Val Gly
            180                 185                 190

Gly His Gln Ala Ala Met Gln Met Leu Lys Asp Thr Ile Asn Glu Glu
    195                 200                 205

Ala Ala Glu Trp Asp Arg Leu His Pro Val Gln Ala Gly Pro Ile Pro
210                 215                 220

Pro Gly Gln Ile Arg Glu Pro Arg Gly Ser Asp Ile Ala Gly Thr Thr
225                 230                 235                 240

Ser Thr Pro Gln Glu Gln Leu Gln Trp Met Thr Gly Asn Pro Pro Ile
                245                 250                 255

Pro Val Gly Asn Ile Tyr Lys Arg Trp Ile Ile Leu Gly Leu Asn Lys
            260                 265                 270

Ile Val Arg Met Tyr Ser Pro Val Ser Ile Leu Asp Ile Lys Gln Gly
    275                 280                 285

Pro Lys Glu Pro Phe Arg Asp Tyr Val Asp Arg Phe Phe Lys Ala Leu
290                 295                 300

Arg Ala Glu Gln Ala Thr Gln Asp Val Lys Gly Trp Met Thr Glu Thr
305                 310                 315                 320

Leu Leu Val Gln Asn Ala Asn Pro Asp Cys Lys Ser Ile Leu Lys Ala
                325                 330                 335

Leu Gly Ser Gly Ala Thr Leu Glu Glu Met Met Thr Ala Cys Gln Gly
            340                 345                 350

Val Gly Gly Pro Gly His Lys Ala Arg Val Leu Ala Glu Ala Met Ser
    355                 360                 365

Gln Ala Gln Gln Thr Asn Ile Met Met Gln Arg Gly Asn Phe Arg Gly
370                 375                 380

Gln Lys Arg Ile Lys Cys Phe Asn Cys Gly Lys Glu Gly His Leu Ala
385                 390                 395                 400

Arg Asn Cys Arg Ala Pro Arg Lys Lys Gly Cys Trp Lys Cys Gly Lys
                405                 410                 415

Glu Gly His Gln Met Lys Asp Cys Thr Glu Arg Gln Ala Asn Phe Leu
            420                 425                 430

Gly Lys Ile Trp Pro Ser Ser Lys Gly Arg Pro Gly Asn Phe Pro Gln
    435                 440                 445

Ser Arg Pro Glu Pro Thr Ala Pro Pro Ala Glu Leu Phe Gly Met Gly
450                 455                 460

Glu Gly Ile Ala Ser Leu Pro Lys Gln Glu Gln Lys Asp Arg Glu Gln
465                 470                 475                 480

Val Pro Pro Leu Val Ser Leu Lys Ser Leu Phe Gly Asn Asp Pro Leu
                485                 490                 495

Ser Gln

<210> SEQ ID NO 6

<211> LENGTH: 498
<212> TYPE: PRT
<213> ORGANISM: Artificial Sequence
<220> FEATURE:
<223> OTHER INFORMATION: #3D6 p5

<400> SEQUENCE: 6

```
Met Ala Arg Ala Ser Ile Leu Ser Gly Gly Lys Leu Asp Ala Trp
1               5                   10                  15

Glu Lys Ile Arg Leu Arg Pro Gly Gly Lys Lys Lys Tyr Arg Leu Lys
                20                  25                  30

His Leu Val Trp Ala Ser Arg Glu Leu Asp Arg Phe Ala Leu Asn Pro
            35                  40                  45

Ser Leu Leu Glu Thr Thr Glu Gly Cys Gln Gln Ile Met Asn Gln Leu
    50                  55                  60

Gln Pro Ala Val Lys Thr Gly Thr Glu Glu Ile Lys Ser Leu Phe Asn
65                  70                  75                  80

Thr Val Ala Thr Leu Tyr Cys Val His Gln Arg Ile Asp Val Lys Asp
                85                  90                  95

Thr Lys Glu Ala Leu Asp Lys Ile Glu Glu Ile Gln Asn Lys Ser Lys
            100                 105                 110

Gln Lys Thr Gln Gln Ala Ala Ala Asp Thr Gly Asp Ser Ser Lys Val
        115                 120                 125

Ser Gln Asn Tyr Pro Ile Ile Gln Asn Ala Gln Gly Gln Met Ile His
    130                 135                 140

Gln Asn Leu Ser Pro Arg Thr Leu Asn Ala Trp Val Lys Val Ile Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Val Met Leu Asn Ile Val Gly
            180                 185                 190

Gly His Gln Ala Ala Met Gln Met Leu Lys Asp Thr Ile Asn Glu Glu
        195                 200                 205

Ala Ala Glu Trp Asp Arg Leu His Pro Val Gln Ala Gly Pro Ile Pro
    210                 215                 220

Pro Gly Gln Ile Arg Glu Pro Arg Gly Ser Asp Ile Ala Gly Thr Thr
225                 230                 235                 240

Ser Thr Pro Gln Glu Gln Leu Gln Trp Met Thr Gly Asn Pro Pro Ile
                245                 250                 255

Pro Val Gly Asn Ile Tyr Lys Arg Trp Ile Ile Leu Gly Leu Asn Lys
            260                 265                 270

Ile Val Arg Met Tyr Ser Pro Val Ser Ile Leu Asp Ile Lys Gln Gly
        275                 280                 285

Pro Lys Glu Pro Phe Arg Asp Tyr Val Asp Arg Phe Phe Lys Ala Leu
    290                 295                 300

Arg Ala Glu Gln Ala Thr Gln Asp Val Lys Gly Trp Met Thr Glu Thr
305                 310                 315                 320

Leu Leu Val Gln Asn Ala Asn Pro Asp Cys Lys Ser Ile Leu Lys Ala
                325                 330                 335

Leu Gly Ser Gly Ala Thr Leu Glu Glu Met Met Thr Ala Cys Gln Gly
            340                 345                 350

Val Gly Gly Pro Gly His Lys Ala Arg Val Leu Ala Glu Ala Met Ser
        355                 360                 365

Gln Ala Gln Gln Thr Asn Ile Met Met Gln Arg Gly Asn Phe Arg Gly
    370                 375                 380
```

Gln Lys Arg Ile Lys Cys Phe Asn Cys Gly Lys Glu Gly His Leu Ala
385                 390                 395                 400

Arg Asn Cys Arg Ala Pro Arg Lys Lys Gly Cys Trp Lys Cys Gly Lys
                405                 410                 415

Glu Gly His Gln Met Lys Asp Cys Thr Glu Arg Gln Ala Asn Phe Leu
            420                 425                 430

Gly Lys Ile Trp Pro Ser Ser Lys Gly Arg Pro Gly Asn Phe Pro Gln
        435                 440                 445

Ser Arg Pro Glu Pro Thr Ala Pro Ala Glu Leu Phe Gly Met Gly
    450                 455                 460

Glu Gly Ile Ala Ser Leu Pro Lys Gln Glu Gln Lys Asp Arg Glu Gln
465                 470                 475                 480

Val Pro Pro Leu Val Ser Leu Lys Ser Leu Phe Gly Asn Asp Pro Leu
                485                 490                 495

Ser Gln

<210> SEQ ID NO 7
<211> LENGTH: 498
<212> TYPE: PRT
<213> ORGANISM: Artificial Sequence
<220> FEATURE:
<223> OTHER INFORMATION: #3D6 p6

<400> SEQUENCE: 7

Met Ala Ala Arg Ala Ser Ile Leu Ser Gly Gly Lys Leu Asp Ala Trp
1               5                   10                  15

Glu Lys Ile Arg Leu Arg Pro Gly Gly Lys Lys Lys Tyr Arg Leu Lys
            20                  25                  30

His Leu Val Trp Ala Ser Arg Glu Leu Asp Arg Phe Ala Leu Asn Pro
        35                  40                  45

Ser Leu Leu Glu Thr Thr Glu Gly Cys Gln Gln Ile Met Asn Gln Leu
    50                  55                  60

Gln Pro Ala Val Lys Thr Gly Thr Glu Glu Ile Lys Ser Leu Phe Asn
65                  70                  75                  80

Thr Val Ala Thr Leu Tyr Cys Val His Gln Arg Ile Asp Val Lys Asp
                85                  90                  95

Thr Lys Glu Ala Leu Asp Lys Ile Glu Glu Ile Gln Asn Lys Ser Lys
            100                 105                 110

Gln Lys Thr Gln Gln Ala Ala Ala Asp Thr Gly Asp Ser Ser Lys Val
        115                 120                 125

Ser Gln Asn Tyr Pro Ile Ile Gln Asn Ala Gln Gly Gln Met Ile His
    130                 135                 140

Gln Asn Leu Ser Pro Arg Thr Leu Asn Ala Trp Val Lys Val Ile Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Val Met Leu Asn Ile Val Gly
            180                 185                 190

Gly His Gln Ala Ala Met Gln Met Leu Lys Asp Thr Ile Asn Glu Glu
        195                 200                 205

Ala Ala Glu Trp Asp Arg Leu His Pro Val Gln Ala Gly Pro Ile Pro
    210                 215                 220

Pro Gly Gln Ile Arg Glu Pro Arg Gly Ser Asp Ile Ala Gly Thr Thr
225                 230                 235                 240

-continued

```
Ser Thr Pro Gln Glu Gln Leu Gln Trp Met Thr Gly Asn Pro Pro Ile
            245                 250                 255

Pro Val Gly Asn Ile Tyr Lys Arg Trp Ile Ile Leu Gly Leu Asn Lys
            260                 265                 270

Ile Val Arg Met Tyr Ser Pro Val Ser Ile Leu Asp Ile Lys Gln Gly
            275                 280             285

Pro Lys Glu Pro Phe Arg Asp Tyr Val Asp Arg Phe Phe Lys Ala Leu
            290             295             300

Arg Ala Glu Gln Ala Thr Gln Asp Val Lys Gly Trp Met Thr Glu Thr
305             310                 315                 320

Leu Leu Val Gln Asn Ala Asn Pro Asp Cys Lys Ser Ile Leu Lys Ala
                325                 330                 335

Leu Gly Ser Gly Ala Thr Leu Glu Glu Met Met Thr Ala Cys Gln Gly
            340                 345                 350

Val Gly Gly Pro Gly His Lys Ala Arg Val Leu Ala Glu Ala Met Ser
            355                 360             365

Gln Ala Gln Gln Thr Asn Ile Met Met Gln Arg Gly Asn Phe Arg Gly
            370                 375             380

Gln Lys Arg Ile Lys Cys Phe Asn Cys Gly Lys Glu Gly His Leu Ala
385             390                 395                 400

Arg Asn Cys Arg Ala Pro Arg Lys Lys Gly Cys Trp Lys Cys Gly Lys
                405                 410                 415

Glu Gly His Gln Met Lys Asp Cys Thr Glu Arg Gln Ala Asn Phe Leu
            420                 425             430

Gly Lys Ile Trp Pro Ser Ser Lys Gly Arg Pro Gly Asn Phe Pro Gln
            435                 440                 445

Ser Arg Pro Glu Pro Thr Ala Pro Pro Ala Glu Leu Phe Gly Met Gly
    450                 455                 460

Glu Gly Ile Ala Ser Leu Pro Lys Gln Glu Gln Lys Asp Arg Glu Gln
465                 470                 475                 480

Val Pro Pro Leu Val Ser Leu Lys Ser Leu Phe Gly Asn Asp Pro Leu
                485                 490                 495

Ser Gln
```

HUMAN CYTOMEGALOVIRUS COMPRISING EXOGENOUS ANTIGENS

CROSS REFERENCE TO RELATED APPLICATION

The present application is a continuation of U.S. application Ser. No. 15/326,444, filed May 16, 2017 which claims the priority benefit of International Application No. PCT/US2015/40807, filed Jul. 16, 2015, and U.S. Provisional Application No. 62/025,348, filed Jul. 16, 2014, entitled HUMAN CYTOMEGALOVIRUS COMPRISING EXOGENOUS ANTIGENS, the disclosure of which is hereby incorporated by reference in its entirety.

REFERENCE TO SEQUENCE LISTING SUBMITTED ELECTRONICALLY

The content of the electronically submitted sequence listing, (file name: 4153_0060002_Seqlising_st25.txt; size: 336,024 bytes; and date of creation: Aug. 21, 2019), filed herewith, is incorporated herein by reference in its entirety.

FIELD

Generally, the field involves vaccine platforms. More specifically, the field involves recombinant human cytomegalovirus vectors expressing exogenous antigen.

BACKGROUND

Animal experiments have demonstrated that cytomegalovirus (CMV)-vectored vaccines are unique in that they: a) induce and maintain high frequencies of extralymphoid T cell responses (so called effector memory T cells); b) superinfect CMV-positive hosts; and c) maintain immunogenicity even when rendered deficient in host-to-host spread. Furthermore, experiments in animal models have shown that vaccine vectors derived from animal CMVs induce a protective immune response against infectious diseases and cancer (US 20080199493; US 20100142823; US 20130136768; and US 20140141038; all of which are incorporated by reference herein). Particularly striking is the finding that a rhesus CMV (RhCMV)-vectored simian immunodeficiency virus (SIV)-vaccine was able to not only prevent AIDS in non-human primates, but ultimately cure these animals from SIV (Hansen S G et al., Nature 502, 100-104 (2013); incorporated by reference herein).

It is important to use an attenuated strain in the development of a cytomegalovirus vaccine because an unattenuated strain could spread from host to host and potentially be pathologic at least in immunocompromised individuals. Previously, attenuated human CMV (HCMV) strains have failed to a) establish latent infection (Plotkin S A and Huang E S, *J Infect Dis* 152, 395-397 (1985); incorporated by reference herein); b) induce long-lasting immunity (Jacobson M A et al., *J Clin Virol* 35, 332-337 (2006); incorporated by reference herein); c) reinfect the significant proportion of the population that has been previously naturally infected with CMV (Heineman T C et al., *J Infect Dis* 193, 1350-1360 (2006); incorporated by reference herein); or d) produce persistent infections (WO2013/036465; incorporated by reference herein.) Furthermore, clinical strains of HCMV genomes are highly unstable in vitro when grown in fibroblasts, resulting in fibroblast adaptations such as deletion of UL131A.

The impact of such adaptations to tissue culture for the ability to perform vector functions in vivo is mostly unknown. In addition to the need for attenuations to be stable in vitro and in vivo, it is important that these vectors can be manufactured with reproducible results. The most stable attenuation strategy is gene deletion. However, this generally requires the generation of complementing cell lines which is difficult to achieve for primary cells used to grow cytomegalovirus.

SUMMARY

Disclosed herein are severely attenuated, spread-deficient (i.e., deficient in cell to cell spread) vectors derived from HCMV-TR3, which is a genetically modified version of the HCMV TR strain. The disclosed vectors establish and maintain persistent infections, induce and maintain effector memory T cells against heterologous antigens, and re-infect CMV-seropositive hosts. Said vectors comprise heterologous antigens such as non-CMV pathogen specific antigens or tumor antigens.

Specifically, TR3 was engineered to be ganciclovir-sensitive. In one example, this is due to the addition of an active UL97 gene (which was mutated in the original clinical isolate of TR3). TR3 was further engineered to include active US2, US3, US6, and US7 genes which were removed during BAC cloning of the original clinical isolate of TR3. Additional versions of TR3 include a deleterious (i.e., inactivating) mutation in the pp71-encoding UL82 gene—which can be termed TR3Δpp71 or, alternatively TR3ΔUL82 herein.

In further examples of the vectors, the expression of a gene encoding a heterologous antigen can be driven by the UL82 promoter or another viral promoter such as the UL7, UL38, UL45, or US13 promoter. In still further examples, multiple genes encoding heterologous antigens can be inserted in place of UL82 and another viral gene such as UL7, UL38, UL45, or US13 such that the viral gene promoter drives expression of the heterologous antigen gene.

Also disclosed herein is a method of producing an HCMV lacking a functional pp71 protein (encoded by the UL82 gene). The method involves infecting a cell with the HCMV lacking a functional pp71 protein, wherein the cell contains an siRNA that silences the DAXX gene. In other embodiments, the method involves infecting a cell with the HCMV lacking a functional pp71 protein, wherein expression of the DAXX gene in the cell is downregulated at the protein or RNA level by other techniques known in the art, for example by RNA interference (e.g., microRNA targeting and short hairpin RNA (shRNA) targeting), ribozyme cleavage, regulated expression by a conditional or inducible promoter, expression of DAXX binding proteins, or targeting DAXX or DAXX protein complexes for ubiquitination and degradation. Using these methods, the HCMV is produced efficiently without complementation. The cell can be any cell, including a human fibroblast.

BRIEF DESCRIPTION OF THE SEVERAL VIEWS OF THE DRAWINGS

Some of the drawings herein are better understood when presented in color, which is not available in patent application publications. However, Applicants consider the color drawings to be part of the original disclosure and reserve the right to present color versions of the drawings herein in later proceedings.

FIG. 1A is a map of the genome organization of the HCMV clones used in FIG. 1B. HCMV genomes are flanked by terminal repeats (TRL and TRS as indicated) and internal repeats (IRS) that separate the unique long (UL) and unique short (US) regions. The location of the BAC cassette in each construct is indicated by the region indicated as B. The US region of HCMV TR lacks US2-7 due to insertion of the BAC-cassette. TRA4 lacks the genes UL128-UL150 in addition to lacking US2-7. The UL131A gene is deficient in AD169 but repaired in AD169 BAD UL131A (Wang and Schenk, 2005 infra). Toledo has an inversion of the UL133-128 region with a deletion in UL128 (Murphy et al., 2003 infra). FIG. 1B is a plot summarizing the results of NOD/SCID/IL2Rγ-null (NSG) mice engrafted with human CD34+ stem cells and inoculated intraperitoneally with human fibroblasts infected with the indicated HCMV strains. Four weeks after infection, human hematopoietic stem cells were mobilized by granulocyte colony-stimulating factor (G-CSF) treatment, and the viral load was measured in the liver by quantitative PCR.

FIG. 4A is an image of a gel showing the following: HCMV-TR3 BAC was reconstituted on MRC-5 cells and then passaged 20 times in vitro on primary human fibroblasts. At passage 1, 5, 10, 15, and 20, viral DNA was extracted from infected cells and subjected to restriction digestion analysis and PCR sequencing of the UL128-131 region, a region that is frequently mutated as a result of multiple passaging (Dargan et al., 2010, infra). FIG. 4B is a plot showing the infectivity of TR3 in human umbilical vein endothelial cells (HUVECs) after multiple passages on MRC-5 cells. A purified stock of virus was made at passage 10 and used to infect HUVECs at MOI=0.5. At the same time, HUVECs were also infected with the HCMV lab adapted strain AD169 as control. Supernatants and cells were harvested at 5, 10, 15, and 20 days post infection (pi) and titrated by plaque assay on MRC-5 cells. The increase in titers over time indicates that HCMV TR3 was able to grow on HUVECs, consistent with an intact UL131A-128 region, whereas HCMV AD169 does not grow.

FIG. 17a depicts a composite Western blot confirming the absence of pp71 protein expression in the ΔUL82(pp71) constructs and the presence of HIVgag(p24) expression. A positive control for HCMV expression (pp28) and a loading control to beta-Actin are included. FIG. 17b shows the sequence of the gag inserts (SEQ ID NO:4, SEQ ID NO:5, SEQ ID NO:6, and SEQ ID NO:7) are stable through these early passages with no polymorphisms detected by Sanger sequencing.

FIG. 18 is a plot showing an example of how alternative insertion sites and promoters can affect insert stability. In this example, the EF1a promoter driving the SIVgag insert has been placed into the UL36 locus. This construct shows the emergence of polymorphisms above the background level. In this case, the emergence of a G>T substitution generates a stop codon, thereby truncating the vectored antigen.

SEQUENCE LISTING

Figure 1A:
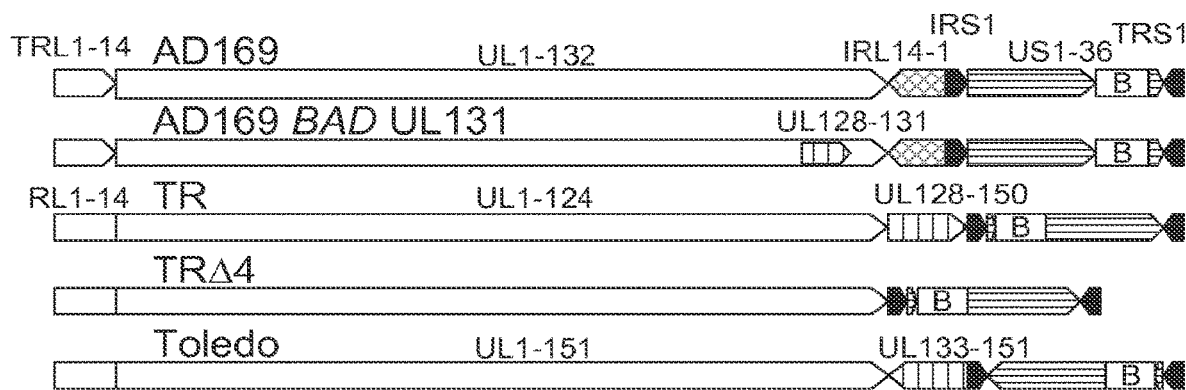
FIGS. 1A and 1B collectively show that HCMV TR is superior in establishing latency and in reactivating from latency (+G-CSF) compared to other HCMV strains.

SEQ ID NO: 1 is the nucleic acid sequence of HCMV TR3ΔUL82 BAC

SEQ ID NO: 2 is the nucleic acid sequence of the sense strand of an siRNA that silences DAXX.

SEQ ID NO: 3 is the nucleic acid sequence of the antisense strand of an siRNA that silences DAXX.

SEQ ID NO: 4 is the amino acid sequence of the HIVgag insert.

SEQ ID NO: 5 is the amino acid sequence of the HIVgag insert from #3D6 at passage 4.

SEQ ID NO: 6 is the amino acid sequence of the HIVgag insert from #3D6 at passage 5.

SEQ ID NO: 7 is the amino acid sequence of the HIVgag insert from #3D6 at passage 6.

*Homo sapiens* DAXX mRNA includes a number of splice variants. Examples of the splice variants include the following GenBank entries: AB015051; CR457085; AF006041; NM_001254717.1; NM_001350; NM_001141969; NM_001141970; HQ436529; HQ436528; all of which are incorporated by reference herein.

DETAILED DESCRIPTION

Terms:

As used herein, the term "antigen" refers to a substance, typically a protein, which is capable of inducing an immune response in a subject. The term also refers to proteins that are immunologically active in the sense that once administered to a subject (either directly or by administering to the subject a nucleotide sequence or vector that encodes the protein) is able to evoke an immune response of the humoral and/or cellular type directed against that protein.

As used herein, the terms "nucleotide sequences" and "nucleic acid sequences" refer to deoxyribonucleic acid (DNA) or ribonucleic acid (RNA) sequences, including, without limitation, messenger RNA (mRNA), DNA/RNA hybrids, or synthetic nucleic acids. The nucleic acid can be single-stranded, or partially or completely double-stranded (duplex). Duplex nucleic acids can be homoduplex or heteroduplex.

As used herein, the term "small interfering RNA" ("siRNA") (also referred to in the art as "short interfering RNAs") refers to an RNA agent, preferably a double-stranded agent, of about 10-50 nucleotides in length (the term "nucleotides" including nucleotide analogs), preferably between about 15-25 nucleotides in length, e.g., about 20-24 or 21-23 nucleotides in length, more preferably about 15, 16, 17, 18, 19, 20, 21, 22, 23, 24, or 25 nucleotides in length, the strands optionally having overhanging ends comprising, for example 1, 2 or 3 overhanging nucleotides (or nucleotide analogs), which is capable of directing or mediating RNA interference. Naturally-occurring siRNAs are generated from longer dsRNA molecules (e.g., >25 nucleotides in length) by a cell's RNAi machinery (e.g., Dicer or a homolog thereof).

The terms "protein", "peptide", "polypeptide", and "amino acid sequence" are used interchangeably herein to refer to polymers of amino acid residues of any length. The polymer can be linear or branched, it may comprise modified amino acids or amino acid analogs, and it can be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

As used herein the term "recombinant" means a nucleotide or protein molecule that has been generated through the use of recombinant DNA technology, resulting in a nucleotide or protein molecule that does not occur in nature. One example or a recombinant nucleic acid is a nucleic acid encoding an HCMV vector that expresses a heterologous (non-CMV) antigen.

As used herein, the term "vector" encompasses any biological molecule that allows or facilitates the transfer of nucleic acid molecules from one environment to another, including a virus such as a CMV virus.

It should be understood that the proteins and the nucleic acids encoding them may differ from the exact sequences illustrated and described herein. Thus, the invention contemplates deletions, additions, truncations, and substitutions to the sequences shown, so long as the differing HCMV vectors are still capable of generating immune responses to the heterologous antigen while, a) inducing and maintaining high frequencies of extralymphoid effector memory T cell responses (so called effector memory T cells); b) reinfecting CMV-positive individuals; and c) maintaining immunogenicity while remaining spread-deficient (i.e., deficient in spread from one subject or host to another subject or host).

In this regard, substitutions may be conservative in nature, i.e., those substitutions that take place within a family of amino acids. For example, amino acids are generally divided into four families: (1) acidic-aspartate and glutamate; (2) basic-lysine, arginine, histidine; (3) non-polar-alanine, valine, leucine, isoleucine, proline, phenylalanine, methionine, tryptophan; and (4) uncharged polar-glycine, asparagine, glutamine, cysteine, serine threonine, tyrosine. Phenylalanine, tryptophan, and tyrosine are sometimes classified as aromatic amino acids. It is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the sequences illustrated and described but possessing minor amino acid substitutions that do not substantially affect the activity of the vector are therefore, within the scope of the invention.

Alternatively, homologs can be expressed in terms of the percent homology relative to a described protein or nucleic acid sequence. Homologs can have at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% homology or identity to the HCMV vectors and/or heterologous antigens described herein.

Sequence identity or homology can be determined by comparing the sequences when aligned so as to maximize overlap and identity while minimizing sequence gaps. In particular, sequence identity may be determined using any of a number of mathematical algorithms. A nonlimiting example of a mathematical algorithm used for comparison of two sequences is the algorithm of Karlin & Altschul, *Proc. Natl. Acad. Sci. USA* 87, 2264-2268 (1990), modified as in Karlin & Altschul, *Proc. Natl. Acad. Sci. USA* 90, 5873-5877 (1993).

Another example of a mathematical algorithm used for comparison of sequences is the algorithm of Myers & Miller, *CABIOS* 4, 11-17 (1988). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, *Proc. Natl. Acad. Sci. USA* 85, 2444-2448 (1988).

Other examples of methods used to compare biological sequences, including those using the BLAST algorithms are readily available at the US National Center for Biotechnology Information website.

HCMV Vectors

Disclosed herein are human cytomegalovirus (HCMV) vectors. The vectors are engineered to prevent viral spread from subject to subject (i.e., cell to cellspread), yet still persistently infect subjects who have previously been infected naturally with HCMV. The vectors generate a persistent immune response to the heterologous antigen and are sensitive to the drug, ganciclovir.

In specific examples, the vectors are derived from the HCMV TR strain and have been engineered to include an active UL97 gene (not present in the original TR clinical isolate) as well as an active US2, US3, US6, and US7 gene (removed from the original TR-BAC during cloning). One example of a vector of the TR strain with these changes is referred to as TR3 herein. TR3 comprises UL97 as well as US2, US3, US6, and US7 genes from the AD169 strain. In some embodiments, the vectors derived from the HCMV TR strain further comprise an active UL131A gene. TR3 comprises an intact UL131A gene.

Additional TR3 variants have deleterious or inactivating mutations in one or more other viral genes including UL82 (which encodes the pp71 protein), UL7, UL45, UL78, and/or US13. The deleterious or inactivating mutation can be any mutation that results in a lack of function of the protein encoded by the gene, including a mutation that involves a partial or entire deletion of the coding sequence and/or the promoter of the gene. Deleterious or inactivating mutations also include point mutations and frameshift mutations of the coding sequence and/or the promoter of the gene that result in a lack of function of the protein encoded by the gene.

TR3 variants can also express heterologous antigens such as pathogen specific antigens or tumor antigens. These heterologous antigens can be expressed by any promoter including an endogenous HCMV promoter, including the UL82, UL7, UL45, UL78, and/or US13 promoters or the HCMV immediate-early promoter. In related TR3 variants, the heterologous antigen replaces the viral UL82, UL7, UL45, UL78, and/or US13 genes. In still other related TR3 variants, a first heterologous antigen replaces the UL82 gene and a second heterologous antigen replaces the viral UL7, UL45, UL78, or US13 gene.

In other examples of TR3 variants, the heterologous antigens are provided with a promoter from a CMV other than HCMV (such as MCMV-IE or RhCMV-IE), with a promoter from a herpesvirus other than CMV, from a virus other than herpesvirus, or with a non-viral promoter such as EF1α.

In some embodiments, the promoter comprises an association of DNA sequences corresponding to the minimal promoter and upstream regulatory sequences. A minimal promoter includes a CAP site plus a TATA box. These are the minimum sequences for basic, unregulated of transcription. Upstream regulatory sequences include upstream elements such as enhancer sequences. A truncated promoter is a promoter from which some portion of the full-length promoter has been removed.

Also disclosed herein are nucleic acids encoding any of the HCMV vectors described herein. While exemplary nucleic acid sequences are provided, one of skill in the art can understand that due to degeneracy in the genetic code, many different nucleic acid sequences can encode identical protein sequences. Also disclosed are cells comprising the HCMV vectors and/or nucleic acid sequences encoding the HCMV vectors. Such cells can be mammalian or human cells, such as human fetal fibroblasts and other cells. In some examples, the cells can be engineered to express an siRNA that silences the expression of a particular gene such as the DAXX gene.

Additionally disclosed herein are methods of producing an attenuated HCMV vector in a cell (e.g., an isolated cell). The methods involve infecting a cell with the attenuated HCMV vector. The cell is transfected with or expresses an siRNA that silences a gene that would otherwise prevent the attenuated HCMV vector from growing in the cell. In one example, the HCMV vector comprises a deleterious or inactivating mutation such as a deletion in pp71, and the siRNA silences expression of the DAXX gene. Also disclosed is a method of producing an attenuated HCMV vector lacking a functional pp71 protein in a cell (e.g., an isolated cell), wherein expression of the DAXX gene in the cell is downregulated at the protein or RNA level by other techniques known in the art, for example by RNA interference (e.g., microRNA targeting and short hairpin RNA (shRNA) targeting), ribozyme cleavage, regulated expression by a conditional or inducible promoter, expression of DAXX binding proteins, or targeting DAXX or DAXX protein complexes for ubiquitination and degradation.

Site-directed mutations of the type described here can be introduced using synthetic oligonucleotides. These oligonucleotides contain nucleotide sequences flanking the desired mutation sites. A suitable method is disclosed in Morinaga et al., Biotechnology 2, 646-649 (1984). Another method of introducing mutations into enzyme-encoding nucleotide sequences is described in Nelson and Long, Analytical Biochemistry 180, 147-151 (1989). Site directed mutagenesis methods for BACs are described in Chadburn A et al., *Histopathology* 53, 513-524 (2008); Lee E et al., *Genomics* 73, 56-65 (2001); and Yu D et al., *Proc Natl Acad Sci USA* 97, 5978-5983 (2000); all of which are incorporated by reference herein.

RNA interference (RNAi) is a method of post transcriptional gene silencing induced by the direct introduction of double-stranded RNA (dsRNA) and has emerged as a useful tool to knock out expression of specific genes in a variety of organisms. RNAi is described by Fire et al., *Nature* 391, 806-811 (1998) (incorporated by reference herein). One such method involves the introduction of siRNA (small interfering RNA) into cells by transfection. Other systems, such as specific plasmid vector systems result in stable siRNA expression in a cell (for example, the pSUPER system—Brummelkamp T R et al., Science 296, 550-553 (2002); incorporated by reference herein). Methods of designing siRNAs that can efficiently silence any gene are known in the art.

Heterologous Antigens

A heterologous antigen can be derived from any protein that is not natively expressed in HCMV and includes pathogen specific antigens, tumor antigens, markers (such as fluorescent proteins or enzymes), growth factors, fusion proteins, or any other protein or fragment thereof to which an immune response can be generated (such as an MHC class I or class II restricted peptide).

The heterologous antigens in the HCMV vectors described herein can be pathogen specific antigens. For example, a protein from a viral pathogen can be used. Viral pathogens include, but are not limited to Adenovirus, coxsackievirus, hepatitis A virus, poliovirus, rhinovirus, Herpes simplex, type 1, Herpes simplex, type 2, Varicella-zoster virus, Epstein-Barr virus, Kaposi's sarcoma herpesvirus, Hepatitis B virus, Hepatitis C virus, yellow fever virus, dengue virus, West Nile virus, Human immunodeficiency virus (HIV), Influenza virus, Measles virus, Mumps virus, Parainfluenza virus, Respiratory syncytial virus, Human metapneumovirus, Human papillomavirus, Rabies virus, Rubella virus, Human bocavirus, and Parvovirus B19. In some embodiments, the heterologous antigens in the HCMV vectors can be HIV antigens, including gag, pol, env, rev, tat, and nef. Advantageously, the HIV antigens include but are not limited to the HIV antigens discussed in U.S. Pub. Nos. 2008/0199493 A1 and 2013/0136768 A1, both of which are incorporated by reference herein.

Alternatively, the heterologous antigen can be a protein from a bacterial pathogen. Bacterial pathogens include: *Bordetella pertussis, Borrelia burgdorferi, Brucella abortus, Brucella canis, Brucella melitensis, Brucella suis, Campylobacter jejuni, Chlamydia pneumoniae, Chlamydia trachomatis, Chlamydophila psittaci, Clostridium botulinum, Clostridium difficile, Clostridium perfringens, Clostridium tetani, Corynebacterium diphtheriae, Enterococcus faecalis, Enterococcus faecium, Escherichia coli, Francisella tularensis, Haemophilus influenzae, Helicobacter pylori, Legionella pneumophila, Leptospira interrogans, Listeria monocytogenes, Mycobacterium leprae, Mycobacterium tuberculosis, Mycobacterium ulcerans, Mycoplasma pneumoniae, Neisseria gonorrhoeae, Neisseria meningitidis, Pseudomonas aeruginosa, Rickettsia rickettsii, Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyogenes, Treponema pallidum, Vibrio cholera*, and *Yersinia pestis*.

Alternatively, the heterologous antigen can be a protein from a parasitic organism. Parasitic organisms include but are not limited to protozoans that cause diseases such as Acanthamoeba, Babesiosis, Balantidiasis, Blastocystosis, Coccidioides, Dientamoebiasis, Amoebiasis, Giardia, Isosporiasis, Leishmaniasis, Primary amoebic meningoencephalitis (PAM), Malaria, Rhinosporidiosis, Toxoplasmosis, Parasitic pneumonia, Trichomoniasis, Sleeping sickness, and Chagas disease.

Alternatively, the heterologous antigen can be a protein from a helminth organism. Helminth organisms include but are not limited to: hookworms, roundworms, tapeworms, guinea worms, liver flukes, intestinal flukes, lung flukes, Schistosomosa, and whipworms.

Alternatively, the heterologous antigen can be a protein derived from a tumor.

Heterologous antigens can be codon optimized. Many viruses, including HIV and other lentiviruses, use a large number of rare codons and, by altering these codons to correspond to codons commonly used in the desired subject (for example, humans), enhanced expression of the antigens can be achieved. For example, rare codons used in HIV proteins can be mutated into those that appear frequently in highly expressed human genes (Andre et al., J. Virol 72, 1497-1503, (1998). Additionally antigens can be consensus sequences or mosaic antigens containing sequence fragments from different strains of pathogens.

Immunogenic Compositions:

Disclosed herein are immunogenic compositions containing the disclosed recombinant HCMV vectors, and a pharmaceutically acceptable carrier or diluent. An immunogenic composition containing the recombinant HCMV vector elicits an immunological response. The response can, but need not be, protective. A vaccine composition elicits protective response, generally involving the development of immunological memory.

Methods of inducing an immunological response in a subject are also disclosed. Such methods involve administering to the subject an immunogenic or vaccine composition comprising the disclosed recombinant HCMV vectors and a pharmaceutically acceptable carrier or diluent. For purposes of this specification, the term "subject" includes all animals and humans.

The immunogenic or vaccine compositions can be administered via a parenteral route (intradermal, intramuscular, or subcutaneous). Other administration can be via a mucosal route, e.g., oral, nasal, genital, etc.

The immunogenic or vaccine compositions can be formulated and administered in accordance with standard techniques well known to those skilled in the pharmaceutical arts. The compositions can be administered alone, or can be co-administered or sequentially administered with other HCMV vectors or with other immunogenic, vaccine, or therapeutic compositions.

Examples of such compositions include liquid preparations such as preparations for injectable administration—for example, parenteral, subcutaneous, intradermal, intramuscular or intravenous administration—such as sterile suspensions or emulsions. In such compositions the HCMV vector is in admixture with a suitable carrier, diluent, or excipient such as sterile water, physiological saline, glucose or the like.

Immunogenic or vaccine compositions can contain an adjuvant. Alum (aluminum phosphate or aluminum hydroxide) is a typical adjuvant. Saponin and its purified component Quil A, Freund's complete adjuvant, Freund's incomplete adjuvant and other adjuvants are often used in research and veterinary applications.

The composition can be packaged in a single dosage form for injectable administration or other administration with the effective dosage and route of administration determined by the nature of the composition, by the nature of the expression product and other factors. The dosage of the disclosed HCMV vectors can be expressed in plaque forming units (pfu) including a dosage of more than $10^2$ pfu, more than $10^3$ pfu, more than $10^4$ pfu, more than $10^5$ pfu, more than $10^6$ pfu, or more than $10^2$ pfu.

EXAMPLES

The following examples are illustrative of disclosed methods. In light of this disclosure, those of skill in the art will recognize that variations of these examples and other examples of the disclosed method would be possible without undue experimentation.

Example 1—The HCMV-TR3 Vector Platform

Clinical use of effector memory T cell-inducing CMV vectors requires vectors that are genetically stable and maintain a persistent infection, but lack the ability to spread to immunocompromised subjects in which HCMV can be pathogenic. Previous attenuation strategies for HCMV variants that entered clinical trials relied on serial passaging of virus in fibroblasts (Plotkin S A et al., J Infect Dis 134, 470-475 (1976); incorporated by reference herein), recombination of attenuated with non-attenuated HCMV strains (Heineman J et al. 2006 supra) or generation of replication-deficient recombinant vectors (WO2013/036465; incorporated by reference herein). However, the resulting viruses either retained pathogenicity or lost beneficial features such as the ability to establish latent infections or secondary infections in subjects previously infected naturally with CMV.

Disclosed herein is an HCMV vector platform—HCMV-TR3—that overcomes these limitations. HCMV TR3 is a modified version of the molecular clone HCMV-TR (Murphy E et al., *Proc Natl Acad Sci USA* 100 14976-14981 (2003); incorporated by reference herein). HCMV TR is superior to other HCMV strains in establishing latency and persistence in vivo. HCMV-TR is also superior to other clinical isolates of HCMV in vitro since it does not display the HCMV-typical fibroblast-adaptations upon multiple passages. TR3 was altered in order to make it ganciclovir-sensitive, to make it able to reinfect previously infected subjects, and to facilitate the recovery of CMV vector from the bacterial artificial chromosome (BAC) system.

Specifically, deletion of the UL82 gene (which encodes the pp71 protein) from TR3 results in the generation of a spread-deficient (i.e., defective in cell to cell spread) vector. However, previously viruses that lack pp71 expression were shown to require complementation for growth in vitro (Bresnahan, W. A., and T. E. Shenk. *Proc Natl Acad Sci USA* 97:14506-11 (2000); incorporated by reference herein). UL82 virion protein activates expression of immediate early viral genes in human cytomegalovirus-infected cells, which in turn results in the risk that the virus will revert to a wild type with active pp71. As a result, a new method of growing HCMV vectors lacking pp71 was developed and described in detail below.

A non-human primate model further demonstrates that pp71-deleted HCMV-TR3 maintains the ability to induce and maintain effector memory T cell responses while tropism-deficient versions of HCMV-TR3 that recapitulate viral adaptations that commonly result from passage through fibroblasts do not.

Additionally, pp71-deleted HCMV-TR3 vectors maintain latent infections but lack the ability to reactivate in humanized mice.

Further, internal expression sites that can be used to insert and express heterologous antigens are disclosed. These can be used to produce HCMV vectors that include multiple heterologous antigens.

Figure 1B:
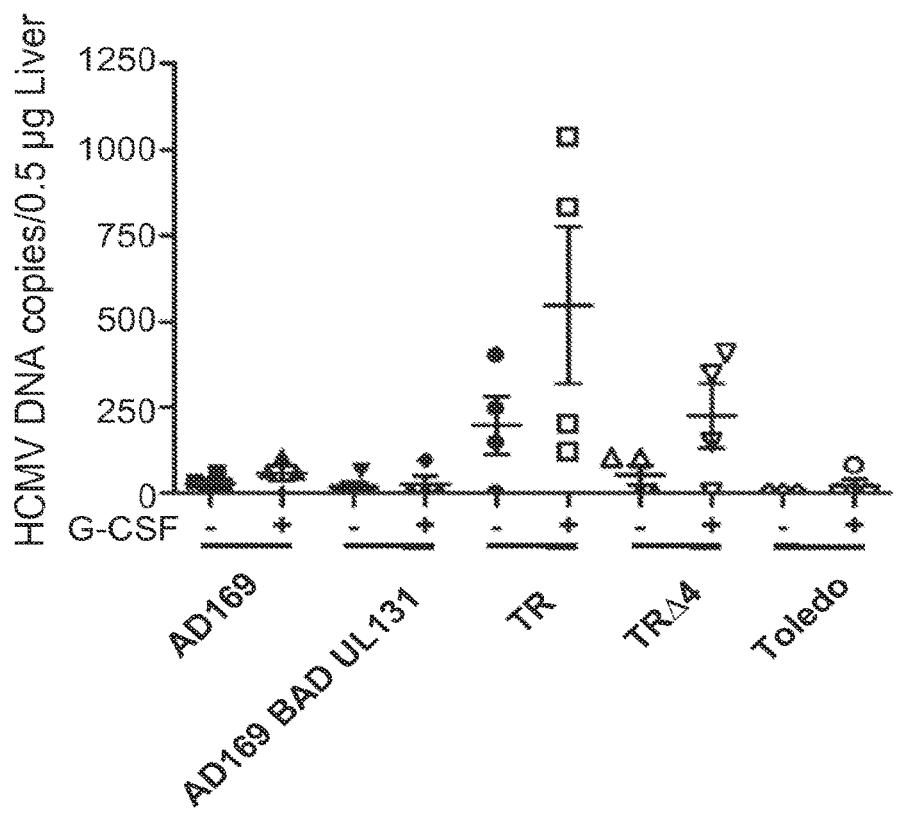

Example 2—HCMV-TR is Superior to Other HCMV Strains in Establishment of Latent Infection A humanized mouse model that permits studying HCMV latency and reactivation is described in Smith M S et al., *Cell Host Microbe* 8, 284-291 (2010) (incorporated by reference herein). This model was used to demonstrate that HCMV-TR is superior to other HCMV strains (AD169, Toledo) in establishing persistent infection. Persistent infection is important for the induction of effector memory T cells. The ability to generate a persistent infection is independent of the UL128-150 region, which is mutated in many HCMV strains including all strains previously used in clinical trials of HCMV vaccine (AD169, Towne and Toledo). The repair of UL131A in the AD169 strain does not restore the ability to establish latency, but the HCMV-TRΔ4 strain that lacks UL128-150 maintains the ability to establish latency (FIG. 1B). Note that these previous clinical trials did not involve HCMV comprising heterologous antigens. Genetic maps of these strains are shown in FIG. 1A.

Figure 3:
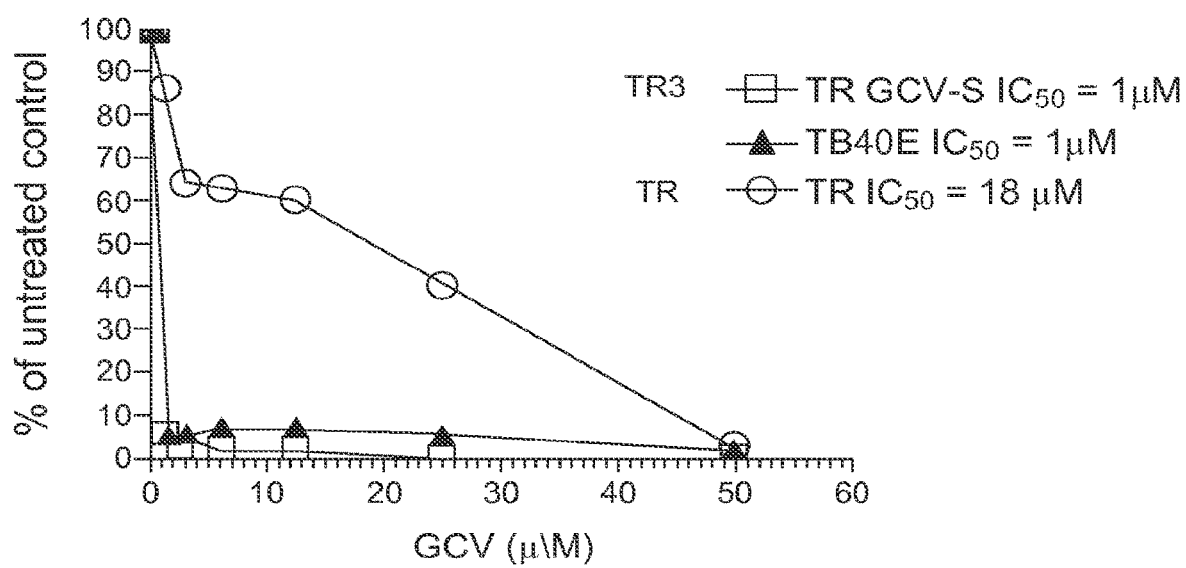
FIG. 3 is a plot showing that HCMV-TR3, but not HCMV-TR, is sensitive to ganciclovir (GCV). Growth-arrested human fetal fibroblast MRC-5 cells were infected with HCMV TR3, HCMV TB40E, and original HCMV TR (MOI of 1 PFU/cell) or mock infected. Where indicated, cells were treated with increasing concentrations of GCV 90 min after infection until an extensive viral cytopathic effect was observed in the untreated control (4 days post-infection). Supernatants of cell cultures were then assayed for infectivity by standard plaque reduction assay on MRC-5 cells. The number of plaques was plotted as a function of drug concentration, and the $IC_{50}$ was determined. Values are the means of two independent determinations.

Example 3—HCMV-TR3 is Sensitive to Ganciclovir and Includes the US2-7 Region Whereas the Original HCMV-TR Does Not HCMV TR was cloned by BAC recombineering from a viral isolate that is resistant to the antiviral drug ganciclovir (Smith I L et al., *J Infect Dis* 176, 69-77 (1997); incorporated by reference herein). ganciclovir resistance is not a desirable trait in a HCMV vector because treatment with ganciclovir would be important in the event of CMV-associated disease caused by HCMV-based vectors. Confirmation of ganciclovir resistance is shown in FIG. 3.

Figure 2:
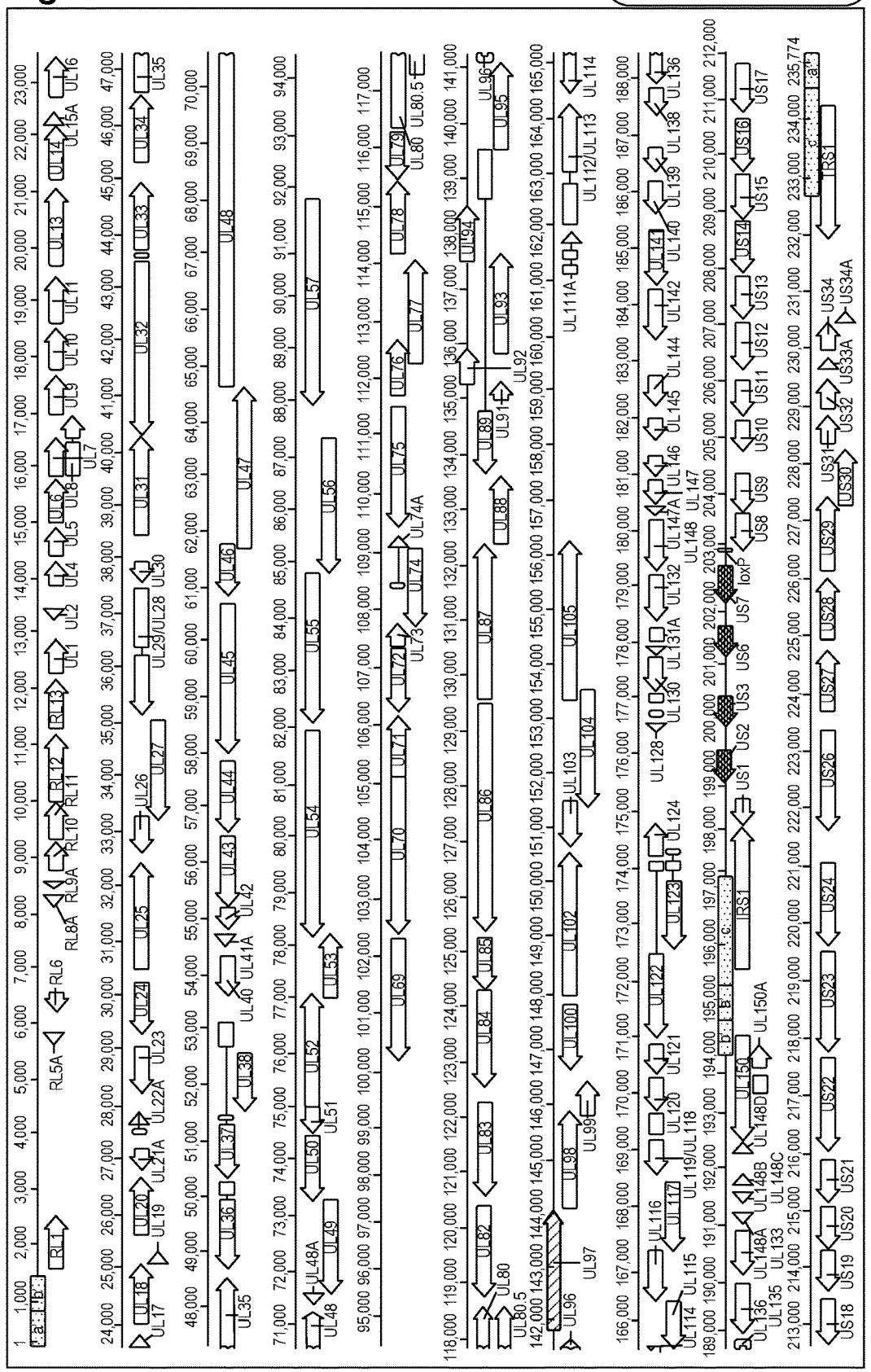
FIG. 2 is a graphical representation of the HCMV-TR3 genome showing alterations to the open reading frames (ORFs) present in the original HCMV TR strain. To confer ganciclovir sensitivity, UL97 of HCMV TR was replaced with that of HCMV AD169. The BAC cassette is flanked by loxP sites, and, after cre-mediated self-excision, a single loxP site remains in the genome. Since the HCMV-TR BAC lacks US2-7, the corresponding genes from HCMV AD169 were inserted. The terminal (ab and c'a) repeats and internal repeats (b'a'c) are shown.

An intact UL97 gene was inserted into HCMV TR (FIG. 2) to generate a ganciclovir-sensitive vector. The molecular clone of HCMV-TR was further modified. Insertion of a BAC cassette during the original cloning of HCMV TR resulted in a deletion of the US2-7 region (Murphy et al. 2003 supra). US2-7 was later determined to be a region that is essential for the reinfection of CMV-positive individuals (Hansen S G et al., *Science* 328, 102-106 (2010); incorporated by reference herein). A modified version of HCMV-TR was generated in which the US2-7 region of HCMV strain AD169 was inserted to modify the BAC cassette. This modification was made because in the original HCMV TR clone that BAC cassette could not be removed when virus is reconstituted by transfection of fibroblasts (Lauron E et al., *J Virol* 88, 403-416 (2014); incorporated by reference herein). HCMV-TR3, therefore also includes the US2-7 region of AD169 and a loxP site between US7 and US8 upon viral reconstitution as shown by full genome sequencing (FIG. 2).

Figure 4A:
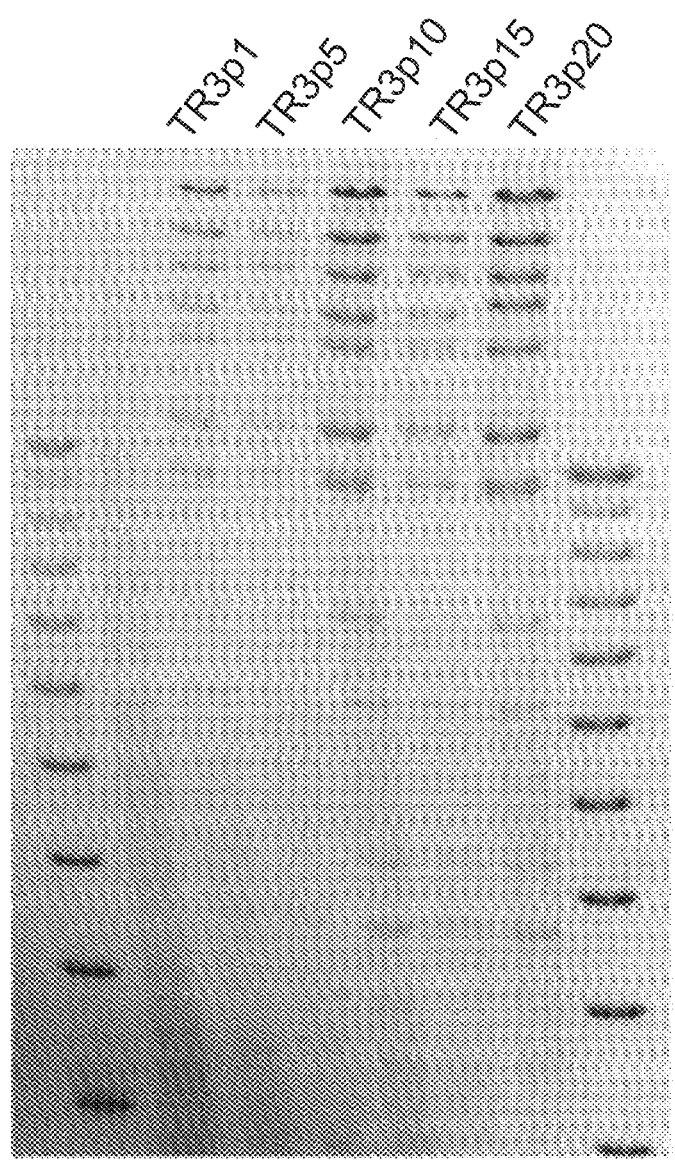
FIGS. 4A and 4B show that HCMV-TR3 surprisingly maintains the ability to infect endothelial cells and maintains genome stability after multiple passaging.
Figure 4B:
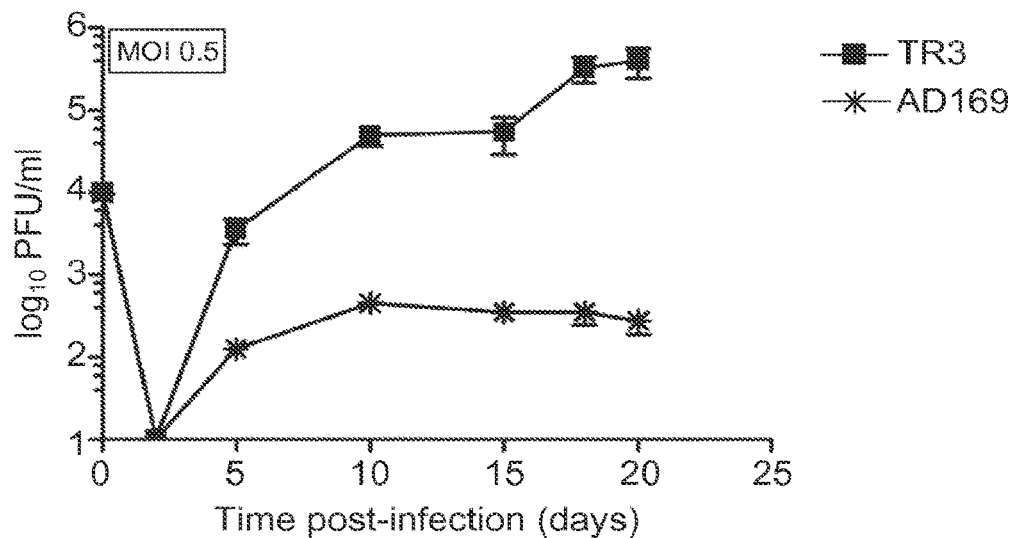

Example 4—HCMV-TR3 Displays Superior Genome Stability Upon Multiple Passages Through Fibroblasts Passaging of HCMV in fibroblasts results in the preferential selection of vectors with deleterious (i.e., inactivating) mutations in the UL128-131A region (Dargan D J et al., *J Gen Virol* 91, 1535-1546 (2010); incorporated by reference herein) and the RL13 gene (Stanton R J et al. *J Clin Invest* 120, 3191-208; (2010); incorporated by reference herein). However, passaging through fibroblasts results in the highest viral yields when producing vaccine. FIG. 4A shows that, surprisingly, the genome of HCMV-TR3 remains stable even after 20 passages in fibroblasts.

Figure 5:
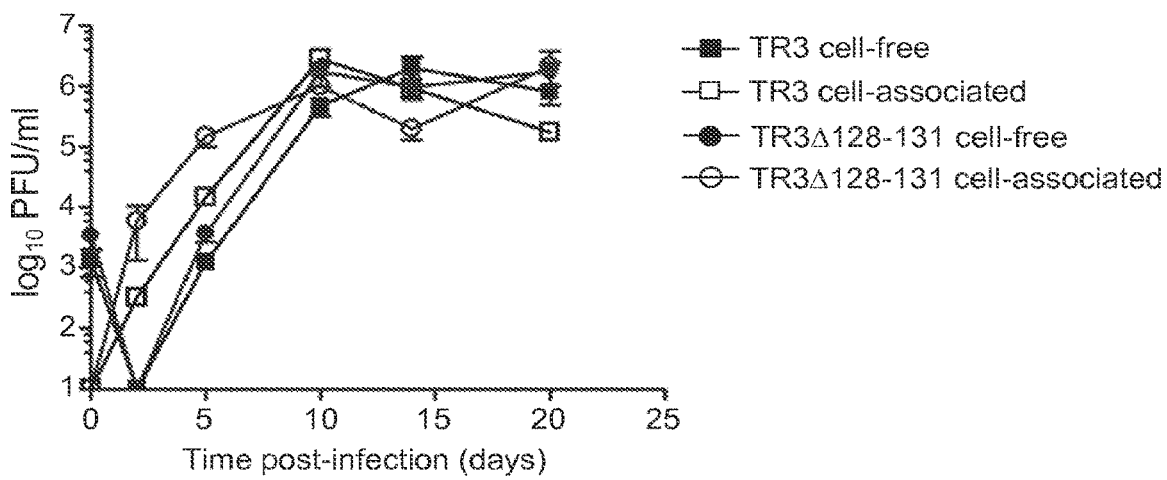
FIG. 5 is a plot showing that the presence of UL128-131 does not reduce the yield of cell-free HCMV-TR3. A multiple-step growth curve analysis was conducted using MRC-5 cells infected at MOI 0.01 with HCMV-TR3 and a strain identical to TR3 but with the UL128-131 deleted (HCMVΔUL128-131). Titers of infected cells and supernatants were measured at 2, 5, 10, 15 and 20 days post infection by standard plaque assay on MRC-5 cells.

Example 5—The Presence of UL128-131A Does Not Reduce the Yield of Cell Free HCMV-TR3 Unlike Other Strains of HCMV For vaccine manufacturing, cell supernatants, rather than cell pellets, are preferred to isolate vaccine vectors. In most HCMV strains, the yield of cell free virus from fibroblasts is drastically reduced when the genes UL131A, UL130 and UL128 are intact (Wang D and Shenk T, *J Virol* 79, 10330-10338 (2005); incorporated by reference herein). Surprisingly, removal of UL131A-128 does not affect the ratio of cell-free versus cell associated virus for HCMV-TR3 (FIG. 5).

Figure 6A:
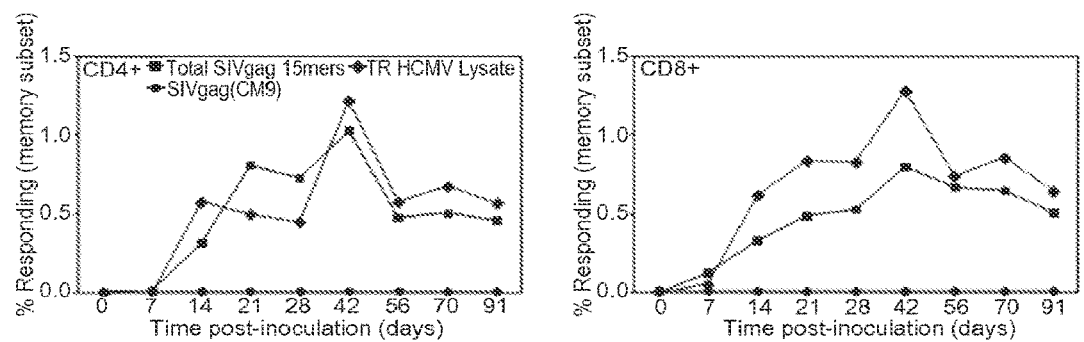
FIG. 6A is a set of two plots showing the results when SIVgag under control of the EF1α promoter was inserted into the HCMV-TR3 genome using BAC mutagenesis as described in Hansen S G et al., Nat Med 15, 293-299 (2009) (incorporated by reference herein). Rhesus macaques (RM) sero-positive for CMV were inoculated with $10^5$ plaque-forming units (PFU) of HCMV-TR expressing SIVgag. Shown is the % memory T cells in peripheral blood mononuclear cells (PMBC) responding to HCMV lysate (diamonds) or over-lapping SIVgag (squares) peptides. Note the absence of T cells to the canonical CM9 peptide (circles), indicating that the T cell response induced by HCMV is different from that of other vectors as described for RhCMV (Hansen et al., Science 2013 infra). The plot on the left shows $CD4^+$ T cell responses. The plot on the right shows $CD8^+$ T cell responses.
Figure 6B:
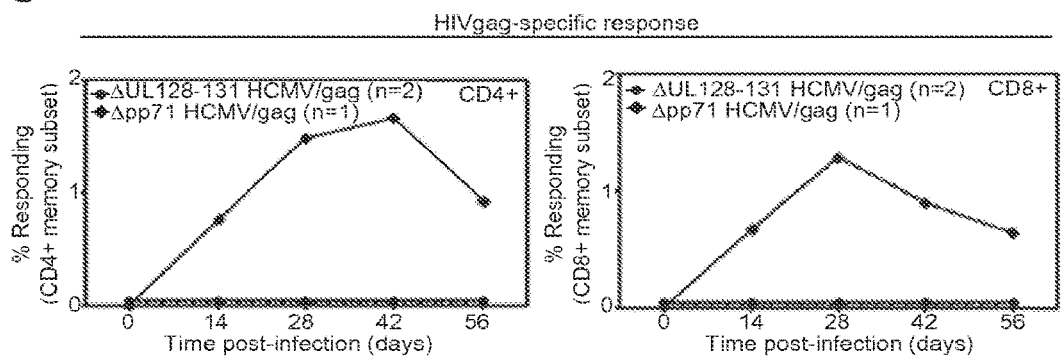
FIG. 6B is a set of two plots showing the HIVgag-specific T cell responses in RM inoculated with HCMV expressing HIVgag under control of the UL78 promoter with UL128-131 deleted (ΔUL128-131 HCMVgag) or HCMV expressing HIVgag under control of the UL82 promoter with UL128-131 intact (Δpp71 HCMVgag). When $10^6$ PFU of the ΔUL128-131 vector were inoculated into RM, no $CD4^+$ or $CD8^+$ T cell response to HIVgag was observed. In contrast, HIVgag-specific T cell responses were observed with Δpp71 HCMVgag vectors. The plot on the left show $CD4^+$ T cell responses, the plot on the right shows $CD8^+$ T cell responses.
Figure 11:
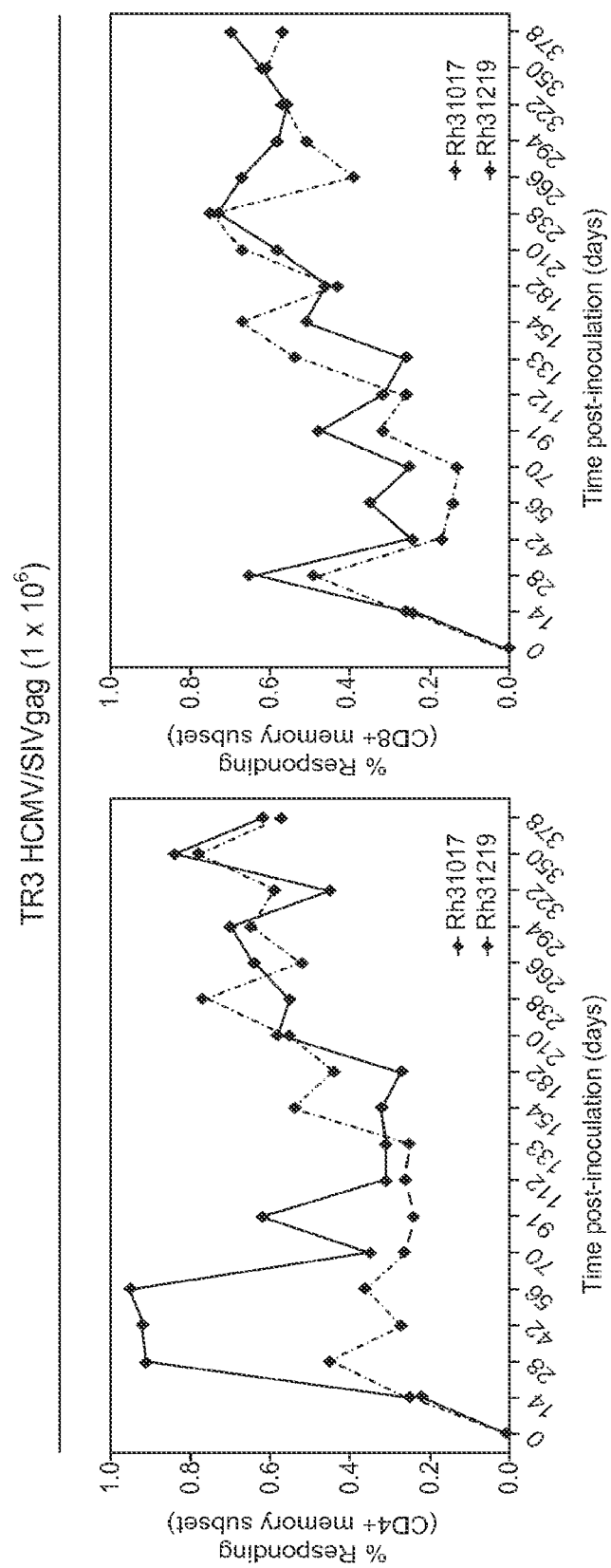
FIG. 11 is a set of two plots showing results with SIVgag under control of the EF1α promoter. SIVgag was inserted into the HCMV-TR3 genome using BAC mutagenesis as described in Hansen S G et al., Nat Med 15, 293-299 (2009) (incorporated by reference herein). Rhesus macaques (RM) sero-positive for CMV were inoculated with $10^5$ plaque-forming units (PFU) of HCMV-TR3 expressing SIVgag. Shown is the % CD4+ (left panel) and % CD8+ (right panel) T cells in peripheral blood mononuclear cells (PMBC) responding to over-lapping SIVgag peptides. Note that the plot shows a stable immune response for two rhesus monkeys (Rh31017, Rh31219) beyond 378 days post inoculation.
Figure 12:
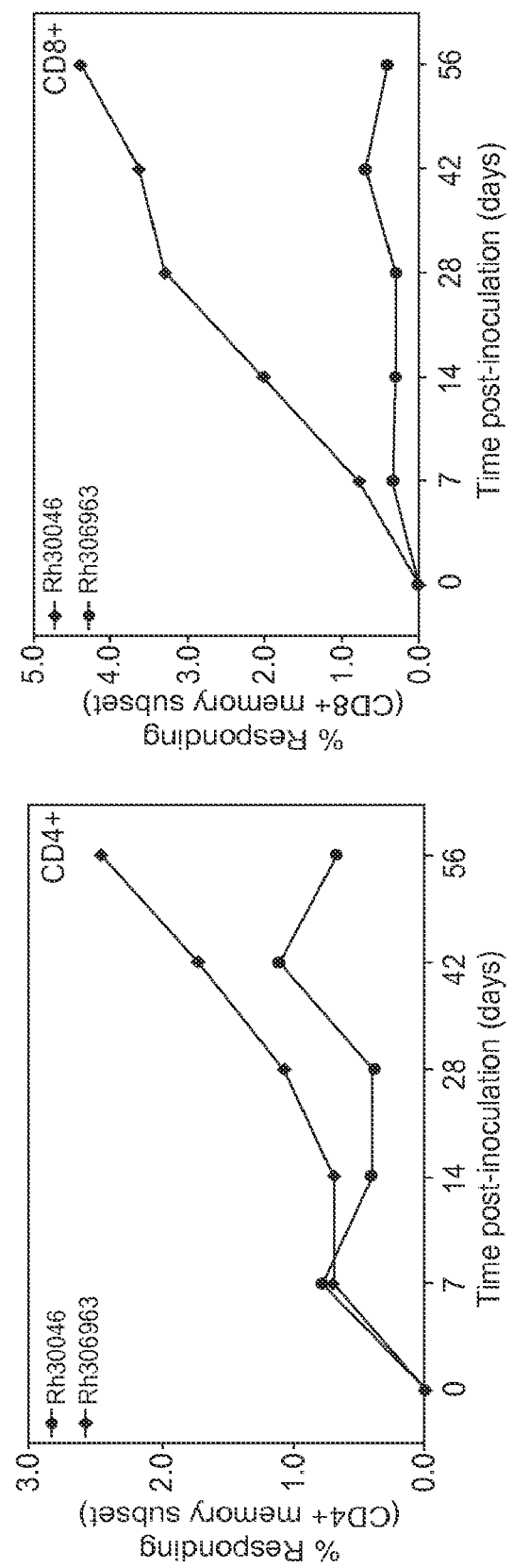
FIG. 12 plots the T cell immune response of two RM inoculated with the TR3ΔL78 HCMV/HIVgag ΔUL128-130. Unlike constructs that included deletion of UL131A, limiting the deletion to UL128-130 results in sustained CD4+ and CD8+ T cell responses.

Example 6—HCMV-TR3 Induces Effector Memory T Cells in Monkeys Whereas HCMV Mutants Lacking the UL128-131 Region are Unable To Do So HCMV-TR3 expressing the Gag-antigen of SIV is capable of inducing an effector memory T cell response against Gag in non-human primates (NHP; FIG. 6A). Importantly, this effector memory T cell response is maintained over time (FIG. 11). In contrast, HCMV-TR3 lacking the genes UL128-131, a gene region that is frequently mutated in HCMV strains attenuated by serial passaging in vitro, is unable to do so (FIG. 6B). This is also the first known demonstration of an HCMV vector inducing an immune response to a heterologous antigen in a non-human primate model. Further deletions in this genomic region demonstrated that viruses that lack UL128 and UL130 are able to elicit immune responses to heterologous antigens in vivo similar to the parental vectors (FIG. 12). Therefore, we conclude that UL131A is essential for infection by HCMV.

Example 7—Generation of Uncomplemented pp71-Deleted HCMV-TR3 Using DAXX siRNA. A Method to Grow Attenuated Virus without Complementation or FKBP-Fusion A major limitation for the manufacturing of HCMV lacking essential genes, or genes that are required for optimal replication in vitro, is the need for complementation—that is, the exogenous expression of the deleted gene in a producer cell line. Producer cell lines are well known to be difficult to make and maintain, particularly in the context of GMP vaccine manufacturing.

Figure 7A:
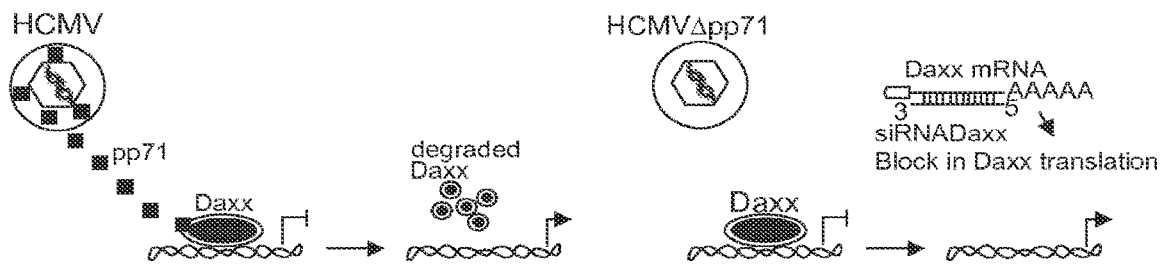
FIG. 7A is a drawing illustrating how, during infection with wildtype HCMV, the tegument protein pp71 degrades the cellular corepressor DAXX. In the absence of pp71, DAXX represses viral gene expression and thus lytic replication. However, viral gene expression can proceed normally even in the absence of pp71 when DAXX mRNA is eliminated by gene knockdown with DAXX-specific siRNA.
Figure 7B:
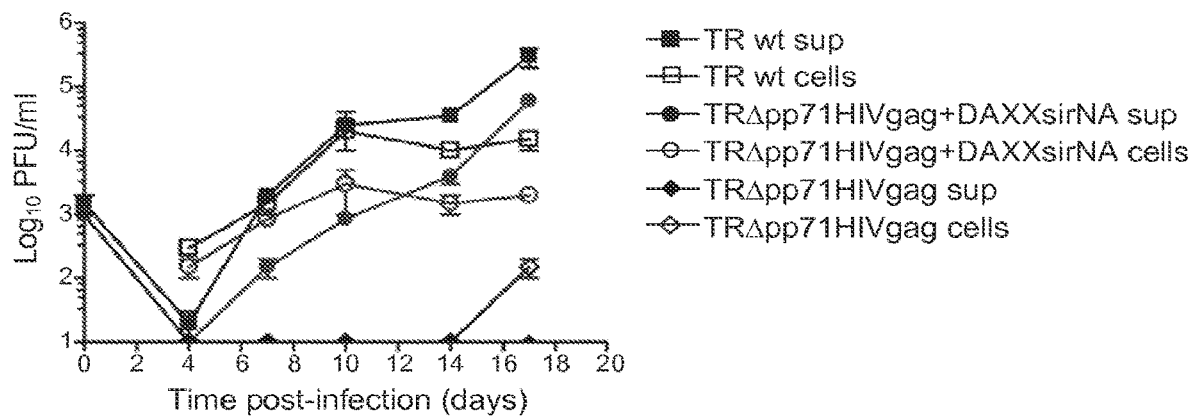
FIG. 7B is a plot of MRC-5 cells transfected with DAXX-specific siRNA and infected 24 hours (h) post-transfection with TR3 and TR3Δpp71HIVgag at MOI=0.05. At the indicated times post-infection, cells and supernatants were harvested separately and titered on complementing cells expressing pp71.
Figure 13:
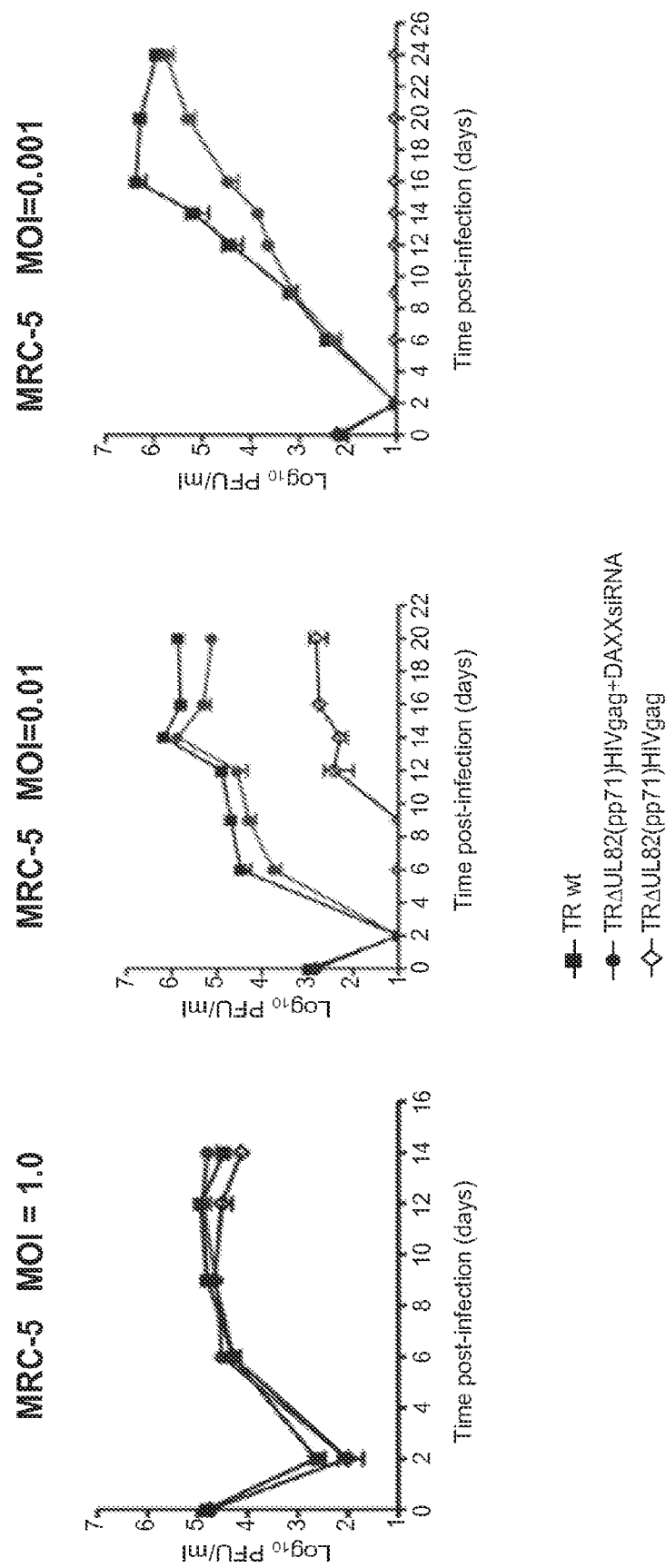
FIG. 13 is a plot comparing the growth kinetics of wild-type TR3 (squares) vs. ΔUL82(pp71)HIVgag in the presence (circles) or absence (diamonds) of DAXX siRNA over a range of infectious particles per cell. The growth defect becomes visible at clinically relevant low MOI, where MRC-5 cells transfected with DAXX-specific siRNA and infected 24 h post-transfection with TR3 and TR3Δpp71HIVgag are functionally complemented by siRNA or fail to replicate in the absence of DAXX siRNA. The lack of replication at low MOI indicates tha the virus is deficient in cell to cell spread. At the indicated times post-infection, supernatants were harvested and titered under pp71 complementing conditions (DAXX siRNA transfected MRC-5 cells).

One approach used in complementation is to fuse the essential gene to a degradation domain (such as FKBP), a strategy described in WO2013/036465 (incorporated by reference herein). While FKBP-fusions might be useful for the manufacturing of non-persistent vaccines that are replication deficient in vivo, in the case of the mutant HCMV described herein there is a risk that the degradation domain will be mutated and the attenuation will thus be lost, rendering the HCMV able to spread from host to host. Disclosed herein is an approach involving silencing an antiviral host cell factor using, for example, siRNA. The result is a cell line that does not require complementation because the mutant HCMV can be grown in vitro, even though it remains attenuated in vivo. An example of this process is illustrated in FIG. 7A. As described above, HCMV-TR3 lacking the UL82 gene that encodes phosphoprotein 71 (pp71) is unable to grow in fibroblasts. However, when expression of the antiviral protein DAXX is silenced by siRNA expressed in fibroblasts, HCMV-TR3ΔUL82 can be grown at high yield (FIG. 7B and FIG. 13).

Figure 8A:
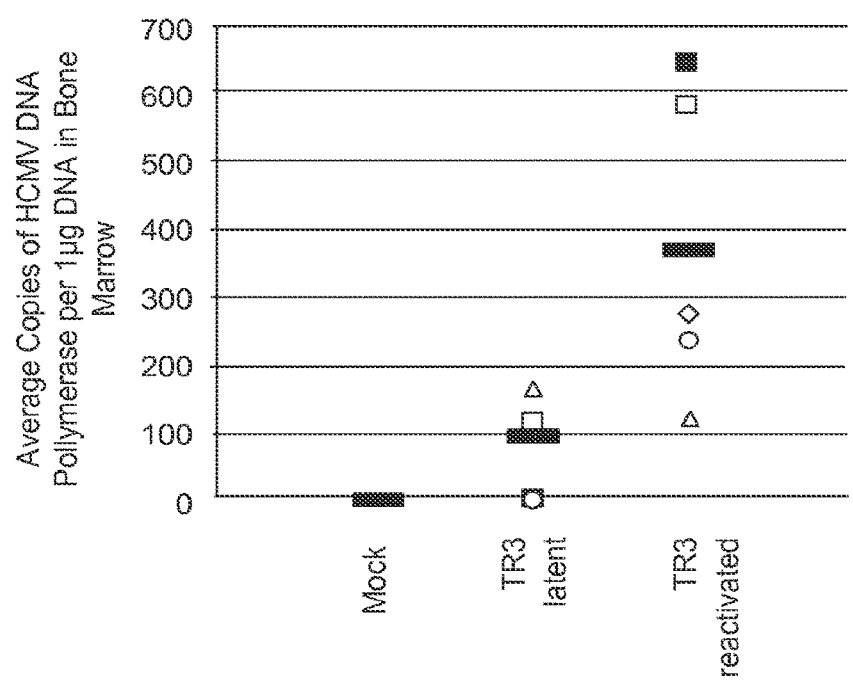
FIGS. 8A and 8B are plots showing that HCMVIR3ΔUL82 (Δpp71) establishes latency in humanized mice but is deficient in its ability to reactivate and disseminate. For both plots, NOD/SCID/IL2Rγ-null (NSG) mice engrafted with CD34+ stem cells were inoculated intraperitoneally with fibroblasts infected with TR3 or TR3ΔUL82 virus. Four weeks post-infection, human hematopoietic stem cells were mobilized by G-CSF treatment, and the viral load was measured in bone marrow (TR3, FIG. 8A) and liver (TR3ΔUL82, FIG. 8B) by quantitative PCR.
Figure 8B:
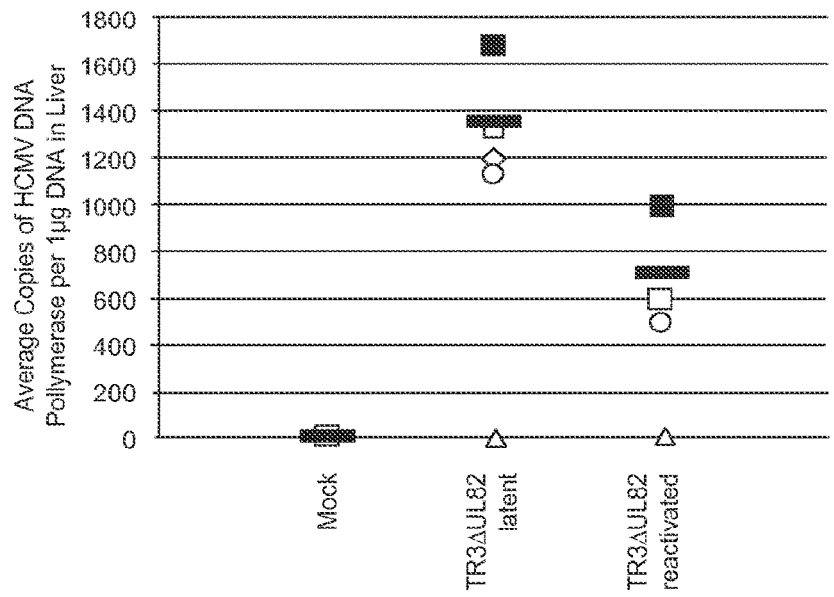
Figure 14:
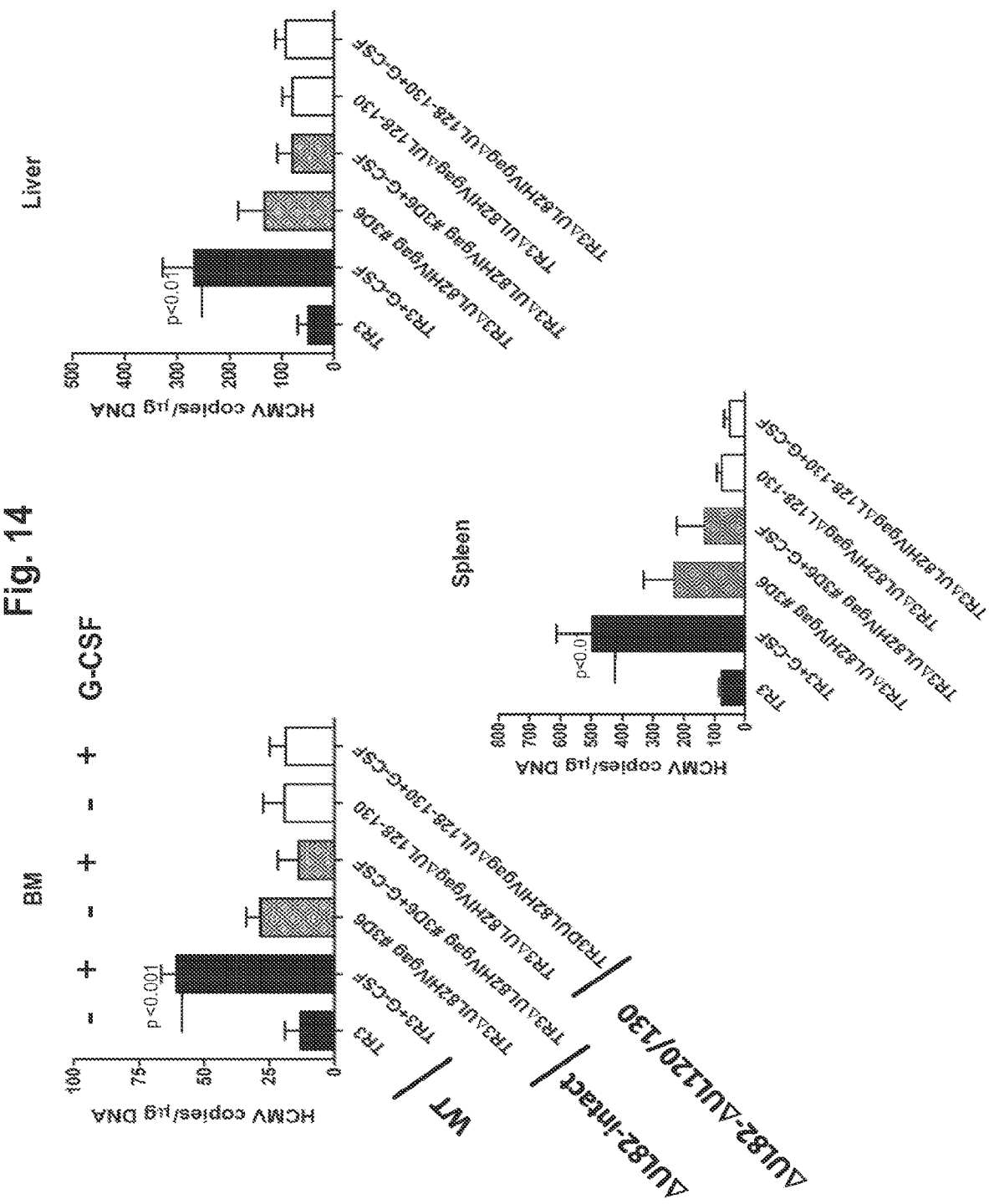
FIG. 14 is a set of three graphs demonstrating that HCMVlR3ΔUL82 (Δpp71) establishes latency in humanized mice but is deficient in its ability to reactivate and disseminate. NOD/SCID/IL2Rγ-null (NSG) mice engrafted with CD34+ stem cells were inoculated intra-peritoneally with fibroblasts infected with TR3, TR3ΔUL82, or TR3ΔUL82ΔUL128-130 virus. Four weeks post-infection, human hematopoietic stem cells were mobilized by G-CSF treatment and the viral load was measured in bone marrow (upper left panel), liver (upper right panel), and spleen (bottom panel). The relative virus copy number as a function of total micrograms of DNA are plotted based on quantitative PCR. Values in the absence of granulocyte colony stimulating factor (G-CSF) represent the latent viral load and values after G-CSF stimulation represent the reactivation of virus emerging from latency. Constructs deleted for pp71 establish latent infection but fail to respond to G-CSF stimulation as measured by copies of virus genomic DNA.

Example 8—HCMV-TR3 Lacking UL82(pp71) Maintains Persistence In Vivo but is Deficient in its Ability t Reactivate from Latency Human cytomegalovirus (HCMV) establishes latent infection in host cells that is regulated via temporal expression viral genes. HCMV pp71 is a tegument protein that counteracts the host intrinsic immunity degradation of the cellular protein Daxx (death domain associated protein) (Penkert, R R, and R F Kalejta, *Future Virol* 7, 855-869 (2012); incorporated by reference herein). Degradation of Daxx by pp71 is necessary for optimal immediate early gene expression and lytic replication. In vitro data suggests that HCMV prevents pp71-mediated degradation of Daxx during establishment of latency by sequestering pp71 in the cytoplasm of infected cells. However, the in vivo role of pp71 in HCMV persistence, maintenance of latency and reactivation remains unknown. We have previously shown that HCMV infection of human hematopoietic stem cells (HSCs) engrafted in immune deficient mice (HU-NSG) results in viral latency that can be reactivated following G-CSF treatment. While this model is important, HU NSG mice lack mature human T-cells. In contrast NSG mice transplanted with HSCs in conjunction with human fetal liver and thymus (BLT mice) develop all the human hematopoietic cell lineages necessary for a functional human immune system, including mature CD4 and CD8 T-cells. In this new humanized mouse model it is demonstrated that HCMV establishes latency and reactivation similar to HU-NSG mice. Latently infected mice also generate human IgG as well as HCMV-specific T-cell responses. Importantly, infection of BLT mice with a conditionally expressing pp71 (TR UL82-FKBP) or a pp71 knockout (TR(delta)UL82) resulted in the establishment of infection but failed to reactivate. These data indicate that pp71 plays an important role in HCMV reactivation and that replication deficient virus can generate a T-cell response. The ability to replicate in vitro is not a good predictor of whether a virus can establish latency, as shown in FIG. 1B. For example, AD169 replicates well in vitro, but cannot establish latency, as shown in FIG. 1B. However, HCMV-TR3ΔUL82 grown on DAXX siRNA expressing MRC-5 cells establishes latency in humanized mice, but does not reactivate or disseminate (FIG. 8). Similar results were obtained in NSG mice for HCMV-TR3ΔUL82 and HCMV-TR3ΔUL82ΔUL128-130 (FIG. 14).

Example 9—pp71-Deleted HCMV-TR3 Expressing HIVgag Maintains the Ability to Induce HIVgag Specific Effector Memory T Cells in In Vivo Due to its large genome, HCMV offers the opportunity to insert multiple heterologous antigens into a viral vector. The expression of multiple heterologous antigens by HCMV requires the identification of endogenous genes that can be used to insert foreign sequences without affecting vector function. Previously, transposon analysis identified all non-essential genes in the HCMV genome in vitro (Yu D et al., *Proc Natl Acad Sci USA* 100, 12396-12401 (2003); incorporated by reference herein.

Figure 9:
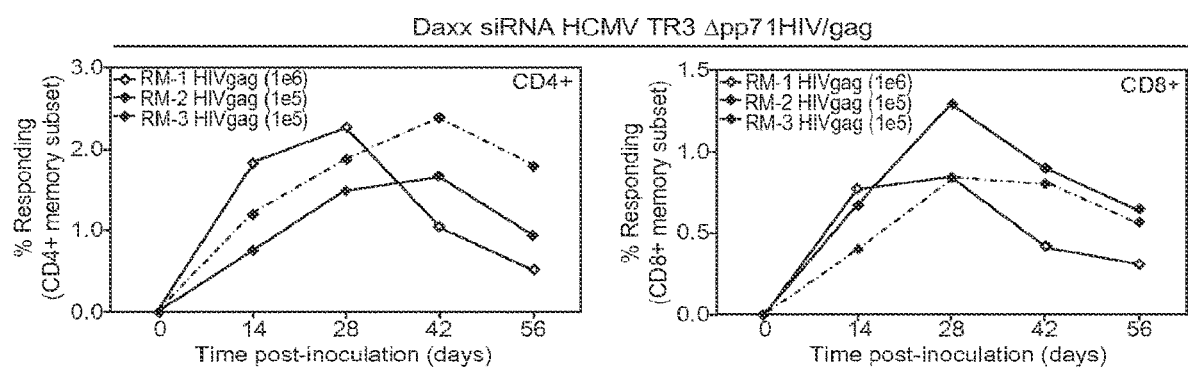
FIG. 9 is a set of plots showing that pp71-deleted HCMV-TR3 expressing HIVgag maintains the ability to induce HIVgag-specific effector memory T cells in non-human primates. HCMV expressing HIVgag but lacking pp71 was constructed by replacing the UL82(pp71) gene with HIVgag. The resulting virus was recovered using DAXX siRNA. $10^6$ or $10^5$ PFU of the resulting virus was inoculated subcutaneously into RM, and the T cell response to HIVgag was determined at the indicated days by intracellular cytokine staining. Shown is the percentage of CD4$^+$ (left) and CD8$^+$ (center) memory T cells in peripheral blood mononuclear cells (PMBC) responding to over-lapping HIVgag peptides. The right panel shows that the responding T cells display effector memory phenotype.
Figure 15:
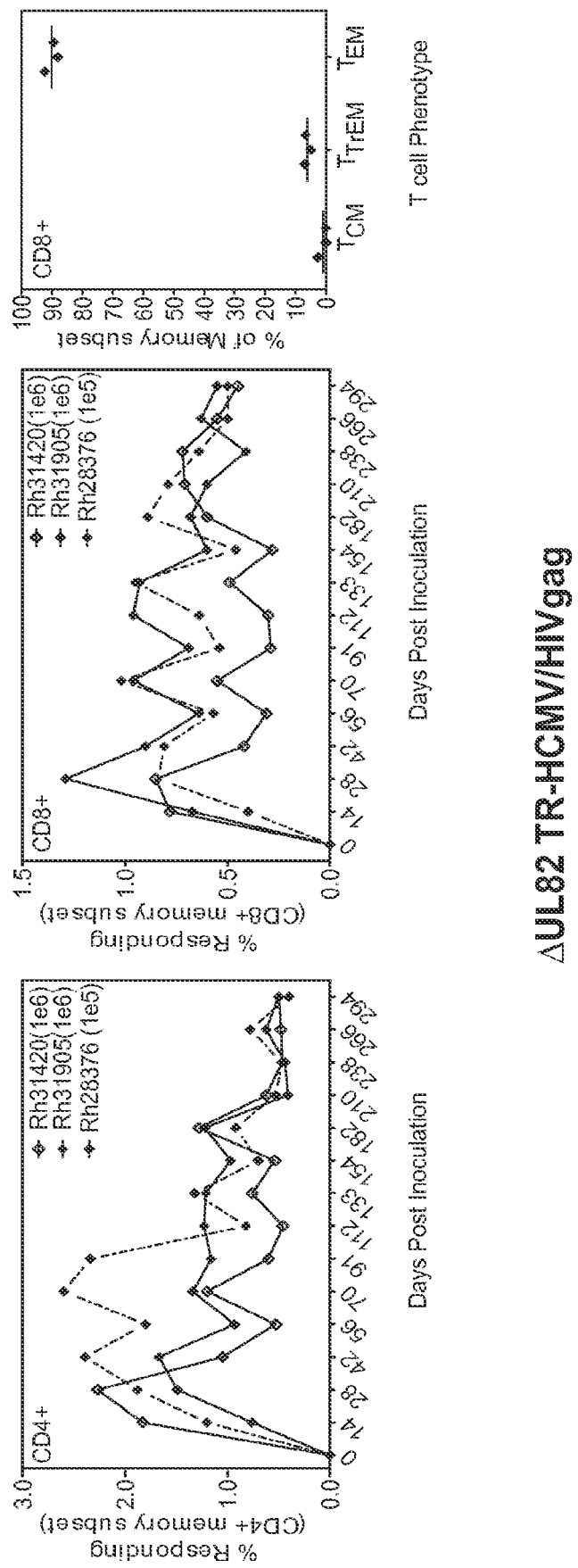
FIG. 15 is a set of three plots characterizing the immune response of three RM inoculated with the TR3/HCMV Δpp71(HIVgag) construct. The vector was grown and titered in the presence of siRNA and concentrated for subcutaneous inoculation. Shown is the percentage of CD4$^+$ (left panel) and CD8$^+$ (middle panel) memory T cells in peripheral blood mononuclear cells (PMBC) responding to over-lapping HIVgag peptides. Responses to different doses of the construct are graphed to 294 days post inoculum. The right panel demonstrates the CD8+ response of the Δpp71 (HIVgag) TR3/HCMV to be consistent with the T-effector memory phenotype.

However, this does not provide a prediction as to which non-essential genes in vitro would be non-essential in vivo and, further, whether or not the replacement of a viral gene with a gene encoding a heterologous antigen would induce an immune response when the expression of the heterologous antigen is driven by the promoter of the replaced gene. FIG. 9 and FIG. 15 show that replacement of UL82(pp71) with HIVgag elicits and maintains an effector memory type T cell immune response in vivo.

Figure 10A:
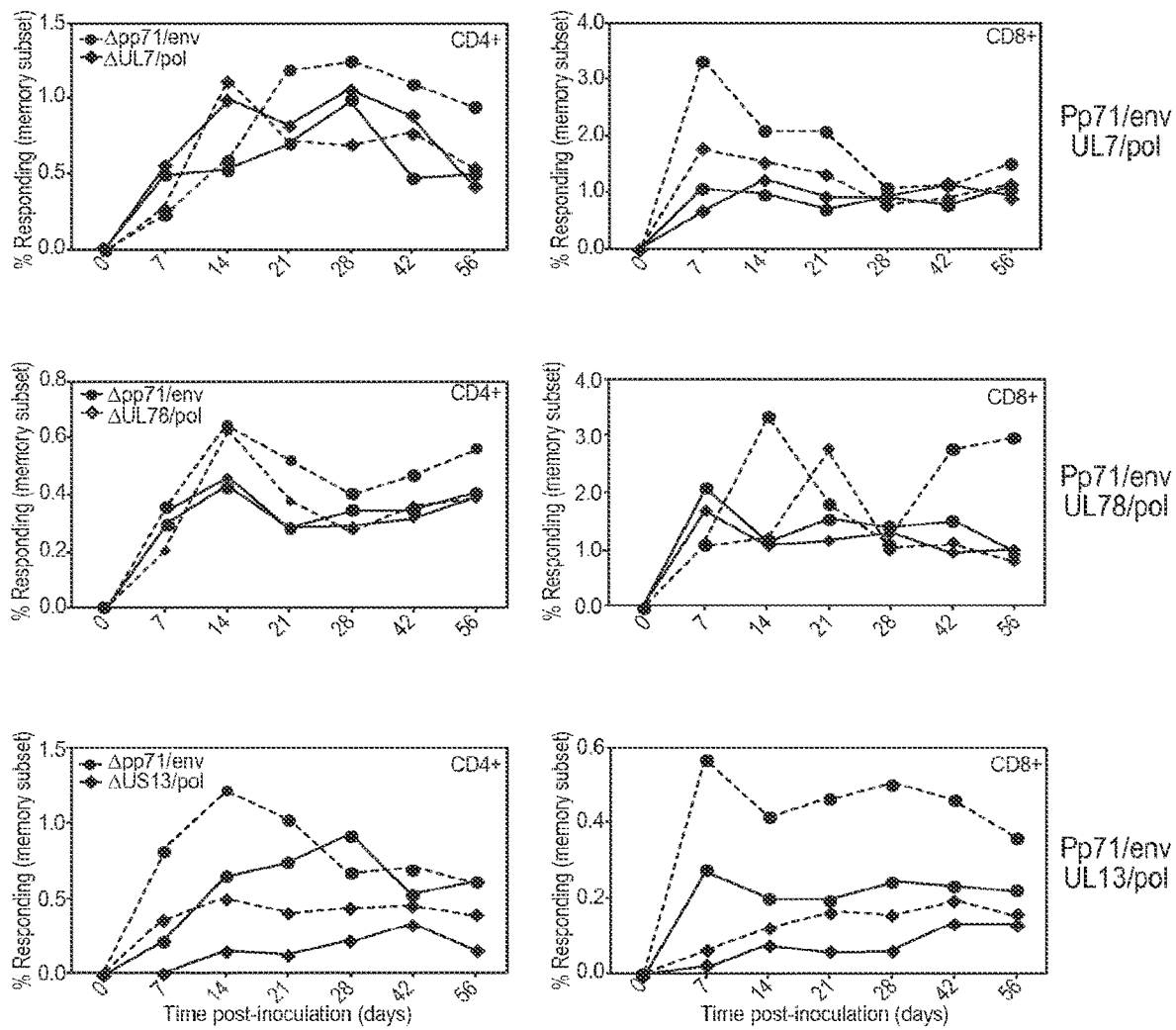
FIG. 10A is a set of six plots showing the results of dual RhCMV vectors expressing both SIVenv and SIVpol. The dual expression vectors were constructed by first replacing Rh110 (the RhCMV homologue of pp71) with SIVenv. Next, the homologs of HCMV genes UL7 (Rh19), UL78 (Rh107) or US13 (Rh191) were replaced with SIVpol. The resulting vectors were recovered in pp71-expressing rhesus fibroblasts. $5 \times 10^6$ PFU of each vector was inoculated into two RM each (one RM is shown as solid line, the other RM is shown as stippled line). The CD4$^+$ and CD8$^+$ T cell response was measured in PBMC at the indicated days using overlapping 15mer peptides corresponding to either SIVpol or SIVenv. The percent SIV-specific T cells within the T cell memory pool is shown.
Figure 10B:
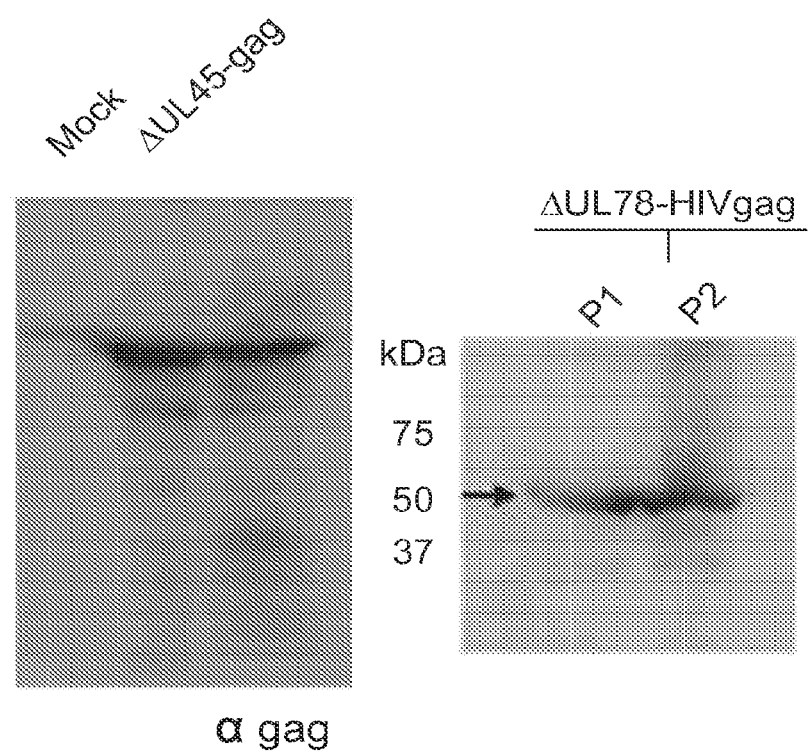
FIG. 10B is an image of an SDS-PAGE gel showing the results when MRC-5 cells were mock-infected or infected with TR3ΔUL7HIVgag, TR3ΔUL45HIVgag, or TR3ΔUL78HIVgag at MOI 0.5. Protein extracts were prepared 96 hours post-infection (hpi). 20 micrograms of proteins were separated on 10% SDS-PAGE, and the immunoblot was decorated with an anti-Gag (p24) antibody.

Additional sites for replacement with a heterologous antigen include HCMV UL7, UL78 and US13. When each of these is replaced with a heterologous antigen (SIVpol) in vectors that already carry a replacement of the pp71-ORF with antigen (SIVenv), immune responses were generated each time. The results are summarized in FIG. 10A. FIG. 10B shows that replacement of UL7, UL45 and UL78 with HIVgag in HCMV results in HIVgag expression in vitro.

Example 10—Stability of pp71 Deleted HCMV-TR3 through Growth and Production Under Conditional Complementation Previous work demonstrated that clinical isolates of HCMV undergo rapid adaptation in vitro when grown in fibroblasts. In particular, generation of frameshift mutations leading to premature stop codons in RL13 and loss of expression of one or more of the pentameric complex proteins (UL128, UL130 and UL131A) can occur after even a low number of passages in tissue culture (Stanton R J et al. *J Clin Invest* 120(9), 3191-3208 (2010); incorporated by reference herein). Reconstruction of the complete human cytomegalovirus genome in a BAC reveals RL13 to be a potent inhibitor of replication (Id.). As a consequence, all HCMV strains previously used in clinical studies (AD169, Towne, Toledo) display multiple rearrangements and deletions (Murphy, E D et al. *Proc Natl Acad Sci U.S.A.* 100(25), 14976-14981 (2003); incorporated by reference herein). These fibroblast-adaptations might result in the deletion of UL131A, as observed in AD169, thus rendering the virus non-infectious in vivo. To determine whether UL82-deleted HCMV-TR3/HIVgag grown in fibroblast cells treated with DAXX siRNA would similarly display instability upon multiple passages, we analyzed the viral genome by next generation sequencing (NGS).

Specifically, the recombinant bacterial artificial chromosome DNA was sequenced prior to introduction into fibroblasts, and, upon reconstitution in fibroblasts, viral DNA was isolated at passage 5 and passage 9. Genomic DNA was isolated from the supernatant of infected human fibroblasts by Hirt extraction (Hirt B. *J Mol Biol.* 26(2):365-369 (1967); incorporated by reference herein) after virus purification through a 20% sucrose cushion. DNA libraries were generated using the TruSeq DNA Sample Preparation kit and adapters with known primer binding sites were ligated to each end of the DNA fragments. Paired end sequencing, analyzing 150 bp on each end of the unknown DNA, was performed on an Illumina MiSeq NGS sequencer using the MiSeq Reagent Kits v2 for 300 cycles. The resulting sequence reads were imported into Geneious 8.1.4 and trimmed with the lowest possible error probability limit of 0.001, meaning that every base pair with a higher error probability of 0.1% is deleted. De novo sequence assembly was performed with 250.000 to 1.000.000 reads to determine the DNA sequence in an unbiased fashion. No major insertions, deletions or genomic rearrangements were observed compared to the predicted sequences. Next, a reference-guided assembly of all reads was performed using the de novo sequence as the reference to determine the full and correct majority sequence. The mean minimum coverage was >150 fold.

Figure 16:
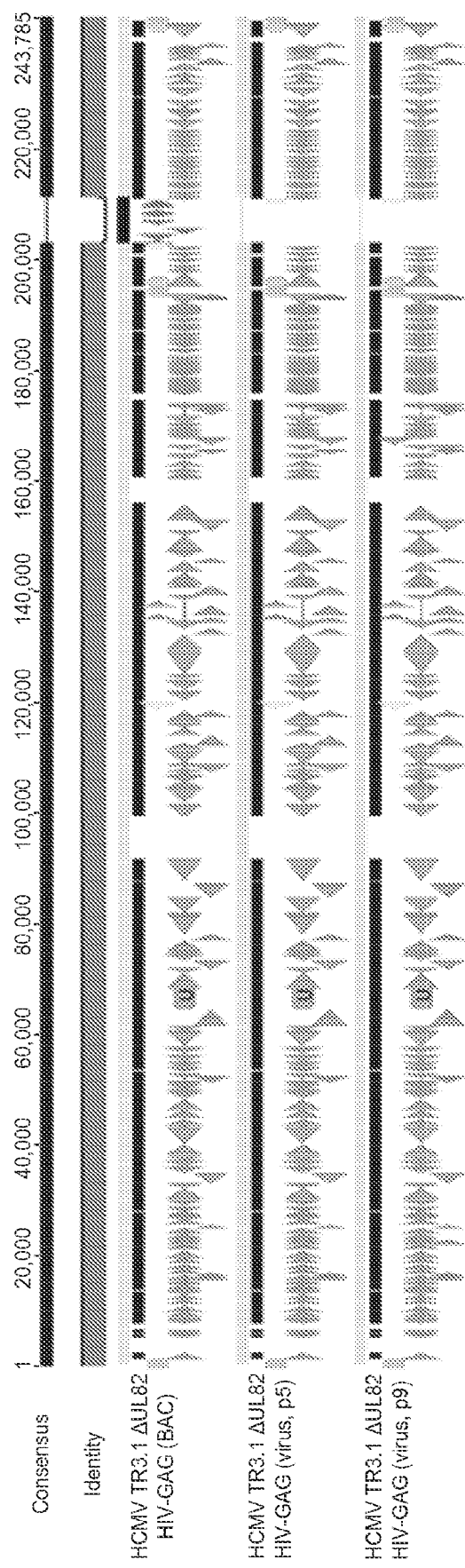
FIG. 16 graphically depicts the sequence alignment of HCMV/TR3 ΔUL82(pp71)HIVgag through passage 9 compared to the BAC clone sequence. The open reading frames (ORFs) are depicted as arrows, where the self-excising BAC is depicted with white arrows, the viral ORFs are depicted with grey arrows, and the HIVgag insert replacing the UL82 ORF is depicted with black arrows. Internal and terminal repeats are depicted with grey ovals. No significant polymorphisms were observed LOD 1%.

FIG. 16 shows an alignment of the resulting sequences. Open reading frames (ORFs) encoded in the self-excising BAC cassette are depicted with white arrows, and viral ORFs are depicted with grey arrows. Yellow arrows depict the HIVgag ORF replacing the UL82 ORF. Grey ovals depict internal and terminal repeats. Non-coding regions are shown as interruptions of the coding regions shown as black bars. As expected, the BAC cassette was excised upon viral reconstitution in tissue culture. However, all other nucleotides in the majority sequence were identical to the predicted sequence (consensus). Importantly, no changes of any amino acids were observed in the ORFs even through nine passages. This includes ORFs encoding the UL128-131A genes, RL13 as well as the AD169-derived genes UL97 and US2-7. These observations suggest a surprising stability of UL82-deleted HCMV-TR3 despite multiple passages in fibroblasts in the presence of DAXX siRNA.

Figure 17:
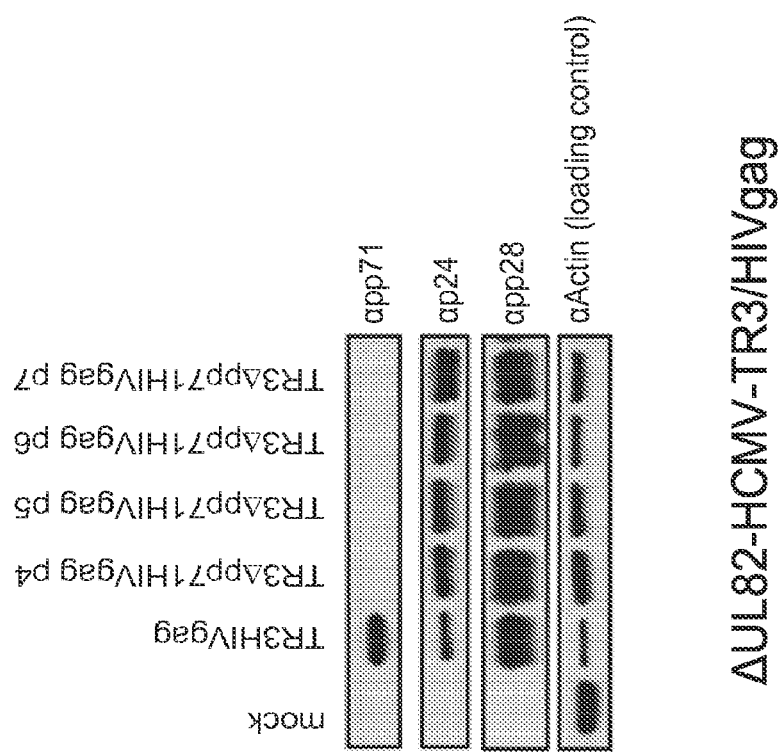
FIGS. 17a and 17b confirm the gag insert expression and homogeneity over several infectious cycles.

Importantly, there were no changes in the ORF encoding HIVgag expressed by the UL82 promoter. This was independently confirmed by immunoblot and Sanger-sequencing of the HIVgag insert at passages 5, 6 and 7 after reconstitution of UL82(pp71)-deleted HCMV-TR3. FIG. 17A shows an immunoblot of lysates from fibroblasts infected with the indicated viruses. Lysates were separated by SDS-PAGE, transferred onto nylon membranes and reacted with antibodies specific for pp71, HIVgag (p24) and the viral protein pp28 and the cellular protein actin. As expected, pp71 was present in the parental TR3 virus, but not in HIVgag-expressing vectors due to replacement of UL82 with HIVgag. Importantly, HIVgag was stably expressed upon each passage. FIG. 17B shows an alignment based on sequences analysis of PCR-fragments spanning the HIVgag gene and obtained from viral DNA at the indicated passage. No nucleotide changes were observed.

In contrast to the surprisingly stable expression of HIVgag expressed by the endogenous UL82 promoter, expression of heterologous antigens by heterologous promoters are routinely unstable upon multiple passages. For example, SIVgag expressed by the heterologous EF1α promoter in the RhCMV 68-1.2 vector displayed a premature disruption of the coding region due to a point mutation. FIG. 18 shows the frequency of single nucleotide polymorphisms (SNPs) compared to the reference sequence from a next generation sequencing analysis of a UL36-deleted RhCMV vector derived from a clone of RhCMV 68-1.2 that expresses SIVgag using the EF1α promoter. Approximately 38% of the genomes demonstrate a premature stop codon in the SIVgag sequence.

The invention claimed is:

1. A recombinant human cytomegalovirus (HCMV) comprising:
   (1) a first nucleic acid encoding at least one heterologous antigen;
   (2) an inactivating mutation in the UL78 gene; and
   (3) active US2, US3, US6, US7, UL97, and UL131A genes;

wherein the recombinant HCMV is a genetically modified TR strain of HCMV; and
   the recombinant HCMV is ganciclovir-sensitive.

2. The recombinant HCMV of claim 1, wherein the UL97 gene is derived from the AD169 strain of HCMV.

3. The recombinant HCMV of claim 1, wherein the active US2, US3, US6, and US7 genes are derived from the AD169 strain of HCMV.

4. The recombinant HCMV of claim 1, wherein expression of the at least one heterologous antigen is driven by the UL7 promoter, the UL45 promoter, the UL78 promoter, or the US13 promoter.

5. The recombinant HCMV of claim 1, wherein the inactivating mutation in the UL78 gene is a deletion of all or part of the UL78 gene.

6. The recombinant HCMV of claim 5, wherein the at least one heterologous antigen replaces all or part of the UL78 gene.

7. The recombinant HCMV of claim 6, wherein expression of the at least one heterologous antigen replacing all or part of the UL78 gene is driven by the UL78 promoter.

8. The recombinant HCMV of claim 1, further comprising an inactivating mutation in a HCMV gene selected from the group consisting of: UL7, UL38, UL45, and US13.

9. The recombinant HCMV of claim 8, wherein the inactivating mutation in the UL7, UL38, UL45, or US13 gene is a deletion of all or part of the UL7, UL38, UL45, or US13 gene.

10. The recombinant HCMV of claim 9, wherein the at least one heterologous antigen replaces all or part of the UL7, UL38, UL45, or US13 gene.

11. The recombinant HCMV of claim 10, wherein expression of the at least one heterologous antigen replacing all or part of the UL7, UL38, UL45, or US13 gene is driven by the UL7, UL38, UL45 , or US13 promoter.

12. The recombinant HCMV of claim 1, further comprising an inactivating mutation in the UL128 gene or the UL130 gene.

13. The recombinant HCMV of claim 12, wherein the recombinant HCMV comprises an inactivating mutation in the UL128 gene and the UL130 gene.

14. The recombinant HCMV of claim 1, wherein the at least one heterologous antigen is a pathogen specific antigen or tumor antigen.

15. The recombinant HCMV of claim 1, wherein the nucleic acid sequences encoding the recombinant HCMV genome and the at least one heterologous antigen are stable upon multiple passages through fibroblasts.

16. The recombinant HCMV of claim 1, further comprising a second heterologous antigen.

17. The recombinant HCMV of claim 16, wherein the first heterologous antigen replaces all or part of the UL78 gene, and wherein the second heterologous antigen replaces all or part of an HCMV gene selected from the group consisting of: UL7, UL45, and US13.

18. The recombinant HCMV of claim 17, wherein the expression of the first heterologous antigen is driven by the UL78 promoter, and wherein the expression of the second heterologous antigen is driven by the UL7 promoter, the UL45 promoter, or the US13 promoter.

19. The recombinant HCMV of claim 1, wherein the first heterologous antigen is a pathogen specific antigen or tumor antigen.

20. The recombinant HCMV of claim 19, wherein the second heterologous antigen is a pathogen specific or tumor antigen that is different from the first heterologous antigen.

21. The recombinant HCMV of claim 16, wherein the nucleic acid sequences encoding the recombinant HCMV genome and the first and second heterologous antigens are stable upon multiple passages through fibroblasts.

22. An immunogenic composition comprising the recombinant HCMV of claim 1 and a pharmaceutically acceptable carrier.

23. A method of inducing an immune response in a subject, the method comprising: administering an effective amount of the immunogenic composition of claim 22 to the subject.

24. The method of claim 23, wherein administration of the recombinant HCMV induces and maintains a long-term effector memory T cell response to the at least one heterologous antigen.

25. An immunogenic composition comprising the recombinant HCMV of claim 16 and a pharmaceutically acceptable carrier.

26. A method of inducing an immune response in a subject, the method comprising: administering an effective amount of the immunogenic composition of claim 25 to the subject.

27. The method of claim 26, wherein administration of the recombinant HCMV vector induces and maintains a long-term effector memory T cell response to the first and second heterologous antigens.

28. An isolated polynucleotide that encodes the recombinant HCMV vector of claim 1.

29. An isolated cell comprising the polynucleotide of claim 28.

30. The isolated cell of claim 29, wherein the isolated cell is a mammalian cell.

\* \* \* \* \*